US005670367A

United States Patent [19]
Dorner et al.

[11] Patent Number: 5,670,367
[45] Date of Patent: Sep. 23, 1997

[54] RECOMBINANT FOWLPOX VIRUS

[75] Inventors: Friedrich Dorner, Vienna; Friedrich Scheiflinger, Orth/Donau; Falko Gunter Falkner, Mannsdorf, all of Austria

[73] Assignee: Immuno Aktiengesellschaft, Vienna, Austria

[21] Appl. No.: 232,463

[22] Filed: Apr. 22, 1994

Related U.S. Application Data

[63] Continuation of Ser. No. 935,313, Aug. 26, 1992, abandoned.

[30] Foreign Application Priority Data

Aug. 26, 1991 [EP] European Pat. Off. ............... 91114300

[51] Int. Cl.[6] .......................... C12N 15/86; C07H 21/045

[52] U.S. Cl. .................................... 435/320.1; 435/172.1; 435/172.3; 435/235.1; 536/23.1; 536/223.72; 536/24.1

[58] Field of Search ................................ 435/69.1, 69.3, 435/172.1, 172.3, 235.1, 240.2, 320.1; 536/23.1, 23.72, 24.1, 24.2

[56] References Cited

U.S. PATENT DOCUMENTS

| | | | |
|---|---|---|---|
| 5,093,258 | 3/1992 | Cohen et al. | 435/235.1 |
| 5,174,993 | 12/1992 | Paoletti et al. | 424/199.1 |
| 5,180,675 | 1/1993 | Drillien et al. | 435/235.1 |
| 5,338,683 | 8/1994 | Paoletti et al. | 435/320.1 |

FOREIGN PATENT DOCUMENTS

| | | |
|---|---|---|
| 0 162 782 | 11/1985 | European Pat. Off. . |
| 0 284 416 | 9/1988 | European Pat. Off. . |
| 0 308 220 | 3/1989 | European Pat. Off. . |
| 0 314 569 | 5/1989 | European Pat. Off. . |
| 0 338 807 | 10/1989 | European Pat. Off. . |
| WO 86/05806 | 10/1986 | WIPO . |
| WO 88/02022 | 3/1988 | WIPO . |
| WO 89/03429 | 4/1989 | WIPO . |
| WO 89/12684 | 12/1989 | WIPO . |
| WO 90/02191 | 3/1990 | WIPO . |
| WO 90/04638 | 5/1990 | WIPO . |
| WO 90/12882 | 11/1990 | WIPO . |

OTHER PUBLICATIONS

Mackett et al. *Journal of General Virology*, 67:2067–2082 (1986).
Alexander et al. *Journal of Virology*, 66:2934–2942 (1992).
Kriajevska et al. *Journal of General Virology*, 74:47–53 (1993).
Jenkins et al. *AIDS Research and Human Retroviruses*, 7:991–998 (1991).
Piccini et al. *Methods in Enzymology*, 153:545–563 (1987).
De La Salle et al. *Nature*, 316:268–270 (1985).
Boyle et al. *Gene*, 35:169–177 (1985).
Wilson et al. *Nucleic Acids Research*, 15:4690 (1987).
Fuerst et al. *Proc. Nat'l. Acad. Sci. USA*, 83:8122–8126 (1986).
Fuerst et al. *Molecular & Cellular Biology*, 7:2538–2544 (1987).
Kumar et al., Mapping of a major early/late gene of fowlpox virus, *Virus Research*, 15 (1990) pp. 175–186.
Venkatesan et al., Distinctive Nucleotide Sequences Adjacent to Multiple Initiation and Termination Sites of an Early Vacinia Virus Gene, *Cell*, vol. 25, pp. 805–813 (Sep. 1981).
Drillien et al., "Similar Genetic Organization between a Region of Fowlpox Virus DNA and the Vaccine Virus HindIII J Fragment," *Virology*, 160:203–209 (1987).

Taylor et al., "Recombinant Fowlpox Virus Inducing Protective Immunity in Non–avian Species," *Vaccine*, 6: 497–503 (1988).

Boyle et al., "Construction of Recombinant Fowlpox Viruses As Vectors For Poultry Vaccines," *Virus Research*, 10: 343–356 (1988).

Davison et al., "Structure of Vaccinia Virus Early Promoters," *J. Mol. Biol.*, 210: 749–769 (1989).

Chakrabarti et al., "Vaccinia Virus Expression Vector," *Mol. and Cell. Biol.*, 5(12): 3403–3409 (1985).

Boyle et al., "Identification and Cloning of the Fowlpox Virus Thymidine Kinase Gene Using Vaccinia Virus," *J. Gen. Virol.*, 67: 1591–1600 (1986).

Spehner et al., "Construction of Fowlpox Virus with Intergenic Insertions: Expression of the B–Galactosidase Gene and the Measles Virus Fusion Gene," *J. Virol.*, 64(2): 527–533 (1990).

Kumar et al., "Activity of Fowlpox Virus Late Gene Promoter in Vaccinia and Fowlpox Virus Recombinants," *Arch. Virol.*, 112: 139–148 (1990).

Binns et al., "Prospects for a Novel Genetically Engineered Vaccine Against Infectious Bronchitis," *Isr. J. Vet. Med.*, 42(2): 124–127 (1986).

*Primary Examiner*—David Guzo

*Attorney, Agent, or Firm*—Foley & Lardner

[57] ABSTRACT

An improved method is described to prepare recombinant fowlpox virus for the expression of proteins or for use as a vaccine. The new method uses for the insertion of foreign DNA an intergenic region which is located between the FPV thymidine kinase (tk)gene and the 3'-open reading frame. Said intergenic region is enlarged to comprise one or more unique restriction sites, thereby allowing insertion of foreign DNA in such a way that the FPV tk-gene remains intact and codes for the entire thymidine kinase. New strong poxvirus promoters are presented and new FPV host virus strains carrying a vaccinia virus thymidine kinase gene and an *E. coli* lacZ gene as a novel non-essential site. The novel fowlpox virus host strains allow the use of any insertion plasmid carrying vaccinia virus tk-gene flanking regions.

9 Claims, 28 Drawing Sheets

*pFP-UV2*

*pFP-UV2-PT*

FIG. 3B
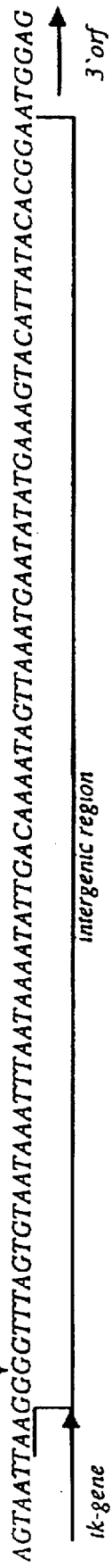
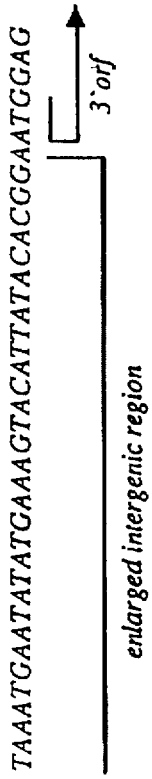
FPV-wildtype intergenic sequence
site directed mutagenesis
FPV-enlarged intergenic sequence

FIG. 10A

```
NsiI
ATGCATTTGT TAGAGCTTGG TATAGCGGAC AACTAAGTAA TTGTAAAGAA GAAAACGAAA CTATCAAAAC
   -125                                                                  
        -99   -95              -86                                    -42
CGTTTATGAA ATGATAGAAA AAAGAATATA AATAATCCTG TATTTTAGTT TAAGTAACAG TAAAATAATG
             -19                               -1 +1
AGTAGAAAAT ACTATTTTTA TAGCCTATAAATC ATG GAA AAG AAA CTG ATT CAA GAG TAT GAA
```

FIG. 10B

NsiI
ATGCATTTGT TAGAGCTTGG TATAGCGGAC AACTAAGTAA TTGTAAAGAA GAAAACGAAA CTATCAAAAC
         -99    -95                           -86                              -125
CGTTTATGAA ATGATAGAAA AAAGAATATA AATAATCCTG TATTTTAGTT TAAGTAACAG TAAAATAATG
          -19                                        -42
AGTAGAAAAT ACTATTTTTT TATAGCCTATA AATCATGGAA AAGAAACTGA TTCAAGAGTA TGAAAAACTC
                                  -1+1
AAAGGCCAAG AGGCCAAAGA TGTCTTTACC AGGCAGCTAC TTATCTGCCA CGAAGATATG CGTGGCAGAA
TGGACAACAT GACTAAGTTA ATTAGTGACG TATTTAGAAC ATGGCTGGAA GGTAGTAGCA AAGCACCCAC
CGAGAAGTCG GATATTGATA CGATGCCTCC TTCTAATGAT GCTGGTTCTG AGCCACAGCC CCAACCTAGC
GAAAGTAAAC CACCCGAGCA ACCCTCTCCC GAACCCGAAA AAGACTCTTC TAGTAAACCA TCAGATCAAC
CTACTCCCGA ACCCGAAAAA GGCTCTTCTA GCAAACCCCG TACAGATATC TTTAGTGGTT TACGTAATAA
AGAAATTAAT TTTGAAAGA ACTGTTGGAG CATTTATCCA ATATATTATT TTAATTTAAA TCAATTGAGT
TAATGTAATA ACTTTTTACA TATATTTGC TCTAGTCCGA AATAGGAAAT TAGCAAAAAA TAATGATTAT
TATATATTAA TGTTTTAACT TAATAATTAA TTTATAAAAT ATTTATTGTC CTTTTTGTAA TTTATCACGT
TATCGTACGT GGTAGGTAGT TATGGATGTT TTTATCATTA TGATAGTAAA TAGTATCACA
GCAGATTAA TTACTTCTGT GATATACAAT ACATGTATTA AGGATTACCC GCACCCAAAA ATATATCGT
GATCTGTAAT ATATAAAAAT AAATACCATA ATATCACCAA TCATGGTAAA AATAGTGTTT
EcoRI
GTGATGAATTC

FIG. 13B

Sequence of the multiple cloning site of pFSgpt

```
CATATG AGGCCT GGATCC CGGGTCGAC GCGGCCGC TAACTGACTGATTTTTCTCAATT
Nde I   Stu I  BamHI  Smal Sal I   Not I
```

FIG. 14B

ATGAATTC GGATCC CGGGTCGAC GCGGCCGC TAACTGACTGATTTTCTCAATT
         EcoRI   BamHI  SmaI SalI   NotI

FIG. 15A

5'-AATGAGTAGAAAATACTATTTTTATAGCCTATAAATC ATG GAA AAG...//...TCC TTA CAT ATG GTT CGT-3'

P2-gene/polylinker sequences → lacZ

FIG. 15B

5'-AATGAGTAGAAAATACTATTTTTATAGCCTATATAA ATG AAT TCC GTT CGT-3'

EcoRI → lacZ

FIG. 15C

5'-AATGAGTAGAAAATACTATTTTTATAGCCTATAAATC ATG AAT TCC GTT CGT-3'

EcoRI → lacZ

FIG. 15D

5'-AATGAGTAGAAAATACTATTTTGTTTATAGCCTATAAATC ATG AAT TCC GTT CGT-3' insertion / EcoRI → lacZ

FIG. 18A

5'-GAATATATGT ATGTAAAAAT ATAGTAGAAT TTCATTTTGT TTTTTTCTAT GCTATAAATGAATTCCTGCAGGTCGACTCTAGAGGATCCCGTC-3'
                                                                    EcoRI                          BamHI  lacZ

FIG. 18B

EcoRI       58bp   lacZ
5'-ATTTAGAAT ATATGTATGT AAAAATATAG TAGAATTCA TTTTGTTTTT TTCTATGCTATAAATAAAGAATTCCTGCAGGT...CATATG-3'

FIG. 18C

PstI   EcoRI       lacZ
5'-GGGTTAGAAT ATATGTATGT AAAAATATAG TAGAATTTCA TTTTGTTTTT TTCTATGCTA TAAATAGGCT GCAGGAATTCCTTACATATG-3'

FIG. 18D

PstI   EcoRI       lacZ
5'-GGGGTTACGT CTCTTTAGGT ACTTATTTTG ATACGTTACA AGTAAAAAAC TATCAAATAT AAATAGGCTG CAGGAATTCCTTACATATG-3'

FIG. 18E

PstI   EcoRI       lacZ
5'-GGGAAGCTTT TTTTTTTTT TTTTTTTGGC ATATAAATAG GCTGCAGGAATTCCTTACATATG-3'

RECOMBINANT FOWLPOX VIRUS

This application is a continuation of application Ser. No. 07/935,313, filed Aug. 26, 1992, abandoned.

The invention concerns recombinant fowlpox virus (FPV), specific vectors, new strong promoters, novel FPV host strains as well as a process for the recombinant production of proteins.

Fowlpox virus, the archetypal member of the arian pox viruses, possesses the typical pox virus structure. The viral genome has been estimated to be 200–240×10$^6$ daltons.

Pox of birds, though prevalent world-wide, is not considered a public health problem because the host-range of the arian pox viruses is limited to birds and excludes mammals. After infection of a host, viral DNA replication starts, after an early protein synthesis, between 60 and 96 hours post-infection and is followed by the synthesis of late proteins. The assembly of infectious virions occurs between 72 and 96 hours.

Growth of FPV in tissue culture cells has been achieved on chicken embryo fibroblast (CEF) cells, chicken embryo dermal (CED) cells as well as duck embryo fibroblast (DEF) cells. In tissue culture, the viral cycle is similar and appears to be quicker than in birds. In the CED cells DNA replication commences between 12 and 16 hours, and infectious virus particles first appear after 16 hours and continue to increase in number until 48 hours post-infection.

For vaccinia virus (VV), the archetypal member of the orthopox virus, Paniceli & Paoletti (Proc. Natl. Aced. Sci., 79, 4927–4931 (1982)) as well as Mackett et al (Proc. Natl. Aced. Sci., 79, 7415–7419 (1982)) have developed a technique known as in vivo recombination which allows the insertion of foreign DNA into the vaccinia virus genome by site-specific recombination. This technique has led to the use of vaccinia virus as a eukaryotic expression vector for creating live recombinant vaccines. The construction of recombinant pox viruses is usually done by insertion of foreign genes into regions of the viral genome that are non-essential for growth in cell culture. For recombinant vaccinia viruses the thymidine kinase (tk) gene is such a non-essential site (NES) that, in addition, allows selection of tk-negative recombinant viruses.

For the construction of recombinant FPV the same principles are applied as described for recombinant vaccinia virus. Several non-essential sites have been described including the fowlpox virus thymidine kinase gene in the strain FPV-M3 (Boyle & Coupar, PCT/AU87/00323; Boyle & Coupar, Virus Res., 10, 343 (1988)), a region present on a 900 bp PvuII fragment of the wild-type virus strain FP-1 (Taylor et al, Vaccine, 6, 497–503, 504–508 (1988)), and the intergenic region between the open reading frames orf 7 and orf 9 (Drillien et el, Virology, 160, 203–209 (1987); Spehner et al, J. Virol., 64, 527–533 (1990)).

Recently, several groups have described the construction of FPV recombinants. Noboru et al disclose in EP-284,416 a number of genomic insertion sites which are non-essential for FPV growth in tissue culture. Paoletti describes in PCT/WO-89/03429 vectors for producing FPV recombinants; they disclose the expression of genes encoding foreign antigens under the control of various vaccinie promoters.

Further, Binns et al disclose in PCT/WO-90/04638 a number of FPV promoters using a transient assay with β-galactosidase. Drillien and Spehner describe in EP-314,569 the construction of FPV recombinants containing a gene which encodes the measles F protein under the control of a vaccinia promoter. The gene was inserted into the FPV genome at a site non-essential for growth in tissue culture.

Cohen and Panicali describe in PCT/WO-90/02191 a recombinant fowlpox virus capable of expressing immunogenic protein of pathogens. This recombinant FPV provides a live vaccine for poultry and other animals.

The present inventors have realized that the presence of an intact thymidine kinase gene is required in the FPV strain HP1.441 to obtain stable recombinants with predictable genomes.

Up to date it has not been clarified scientifically to what an extent the tk-gene is essential for various FPV strains. To overcome this uncertainty, the inventors have searched for further locations to insert foreign DNA, and have found that the intergenic region between the intact tk-gene and the 3' open reading frame is a preferable insertion site. The present invention also provides novel FPV host strains, which have been modified to comprise a vaccinia virus thymidine kinase gene and an *E. coli* lacZ gene as a novel non-essential site, thereby allowing the use of any insertion plasmid which carries vaccinia virus tk flanking regions. The invention also provides new strong promoters as well as a number of preferred plasmid constructs.

To show the advantages according to the invention, FPV insertion plasmids were constructed which use as the site of insertion of the foreign marker gene either the interrupted viral thymidine kinase gene or the intergenic region between the intact tk-gene and the 3' open reading frame. The analysis of the genomic structures of the recombinants derived from both types of experiments revealed that only in the presence of an intact thymidine kinase gene stable recombinants with predictable genomes were obtained. This result strongly suggests that the FPV tk-gene is essential in its entirety for growth of the virus in cell culture.

Construction schemes of the fowlpox virus insertion plasmids pFP-UV2 and pFP-UV2-PT. The abbreviations have the following meaning:

FPV-tk=fowlpox virus thymidine kinase gene; VV-tk= vaccinia virus thymidine kinase gene; P11=promoter of the vaccinia virus major late 11 kDa polypeptide; P7.5= promoter of the vaccinia virus 7.5 kDa polypeptide; lacZ=*E. coli* gene encoding β-galactosidase (the arrows indicate the directions of transcription).

FIG. 2A–2C

Figure 2A:
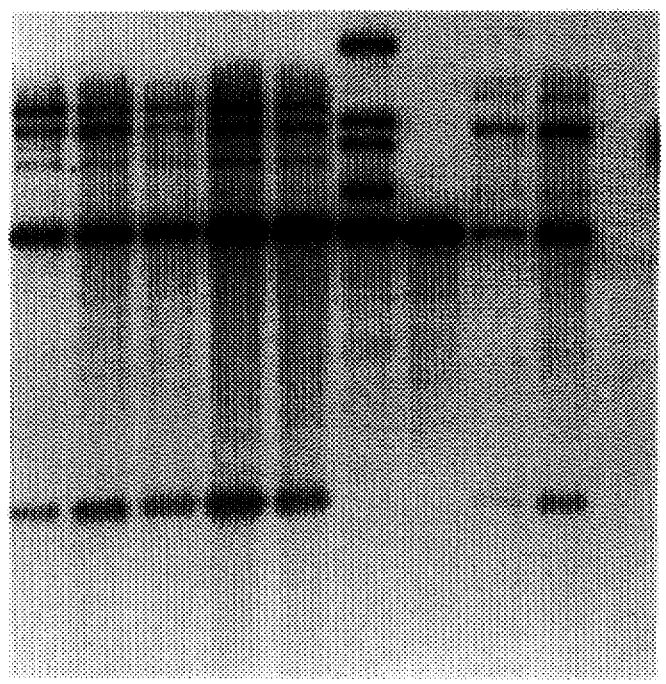
Figure 2B:
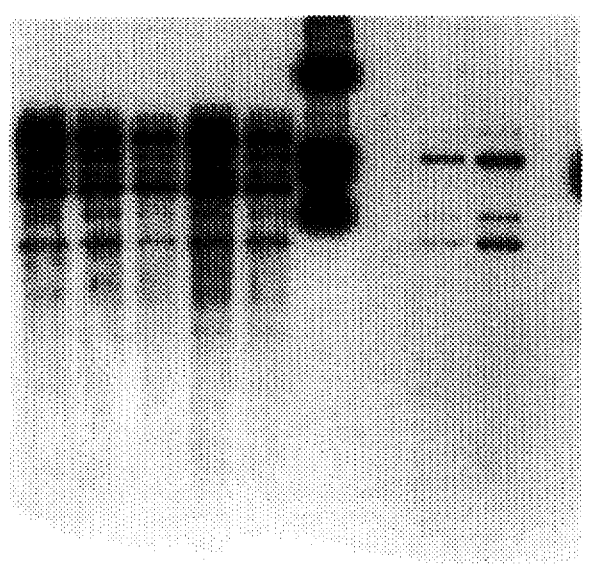
Figure 2C:
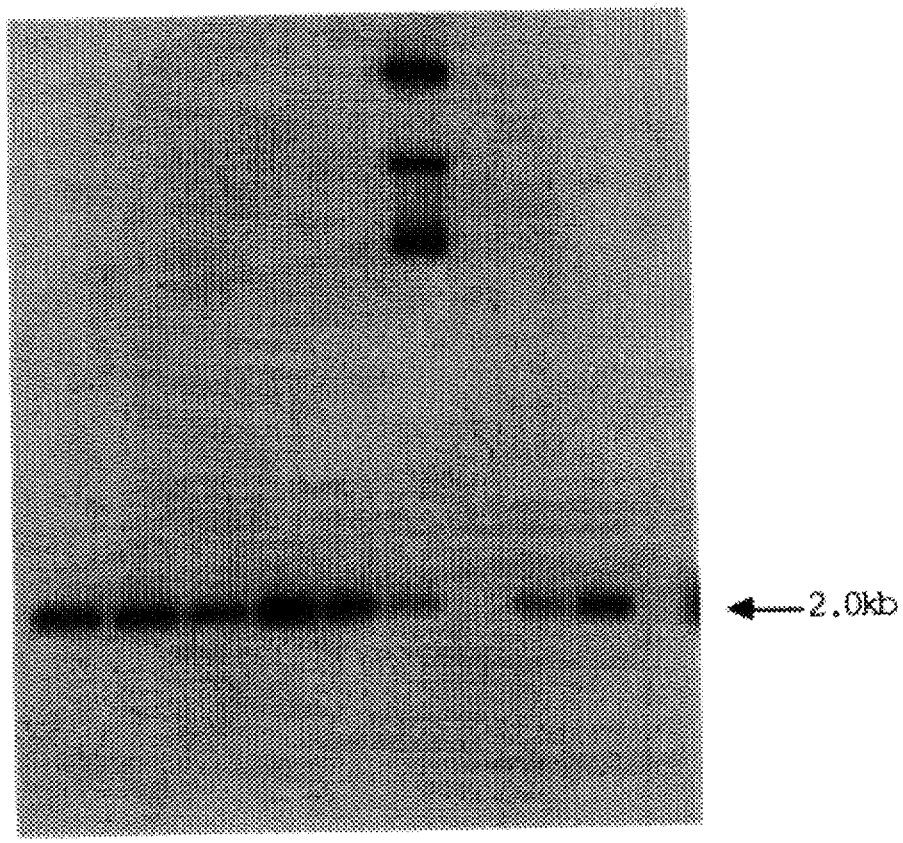
Figure 3A:
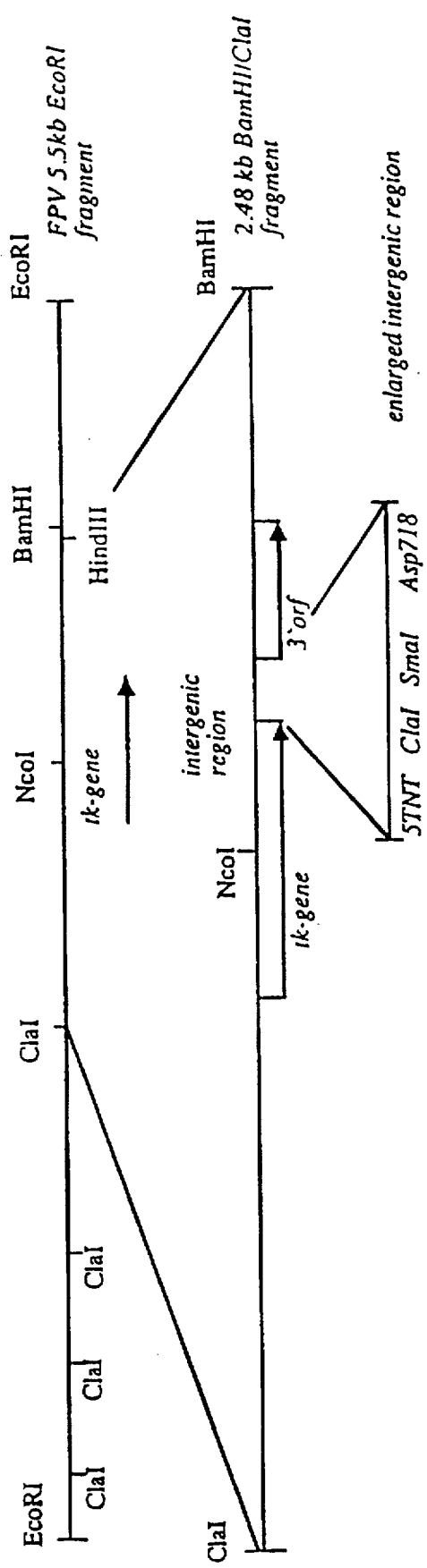

Southern blot analysis of FPV recombinants derived from the insertion plasmid pFP-UV2-PT. Total DNA was prepared from infected cells, digested with EcoRI, separated on a 1% agarose gel and transferred onto a nitrocellulose membrane. The membrane was hybridized to a $^{32}$P labeled FPV tk-gene probe (FIG. 2A), a lacZ gene probe (FIG. 2B) and a prothrombin gene probe (FIG. 2C). Lanes 1–5 in all figures represent DNAs from the FPV recombinant f-PT1-blue at different stages of plaque purification (3rd, 5th, 7th, 9th and 11th round, respectively). In lane 6 a different isolate, f-PT2-blue, is shown. Lanes 7, 8 and 9 represent FPV wild-type and two independent white plaque isolates (f-PT-white 1 and 2), respectively. As a negative control chicken embryo fibroblast DNA is shown in lane 10. The arrowhead in FIG. 2A points to the FPV wild-type tk-gene band. The values given on the right correspond to standards in kilo basepairs (kb).

FIG. 3A

Structure of the wild-type and the mutant fowlpox virus tk-locus. The locations of the FPV tk-gene in the 5.5 kb EcoRI fragment and in the 2.48 kb BamHI/ClaI fragment are shown. (The single NcoI site in the middle of the coding region of the tk-gene was used to construct the insertion vector pFP-UV2.)

Immediately downstream of the tk-gene, the intergenic region was modified and enlarged by oligonucleotide directed mutagenesis leaving the 3'orf and the tk-gene itself intact while introducing a transcription stop signal and several convenient restriction sites.

FIG. 3B

Sequence of the FPV wild-type (SEQ ID NO:42) and of the modified intergenic region (SEQ ID NO:20). The modified intergenic region is present in the recombination plasmid pTKm and its derivatives.

FIG. 4A and 4B

Construction of the FPV insertion plasmids pTKm-sP11-gpt, pTKm-VVtka (SEQ ID NO:3) and pTKm-VVtkb (SEQ ID NO:4). The details of the constructs are described in the Experimental Part. sP11=synthetic vaccinia virus late promoter derived from the promoter of the vaccinia major late 11 kDA polypeptide; 3'orf=open reading frame downstream of the fowlpox virus tk-gene; gpt=*E. coli* gene coding for the enzyme xanthine-guanine-phosphoribosyl transferase. Further abbreviations are the same as described in the legend of FIGS. 1A and 1B. Arrows indicate the direction of transcription.

FIG. 5

Southern blot analysis of EcoRI-digested DNA of the purified FPV recombinants f-sP11#1 and of FPV wild type virus DNA.

A) The blot was hybridized with the FPV tk-gene probe. Lane 1, DNA of the FPV recombinant f-sP11#1; lane 2, DNA of the FPV wild type virus HP1.441; lane 3, lambda DNA digested with Hind III.

B) The blot was hybridized with the gpt-gene probe; lane 1, lambda DNA digested with HindIII; lane 2, DNA of the FPV recombinant f-sP11#1; lane 3, DNA of the FPV wild type virus HP1.441.

C) The blot was hybridized with the lacZ gene and phage lambda DNA probes; lane 1, lambda DNA digested with Hind III, lane 2, DNA of the FPV recombinant f-sP11#1; lane 3, DNA of the FPV wild type virus HP1.441. (The values given on the right correspond to standards in kilo basepairs.)

FIG. 6A–6C

Southern blot analysis of DNA of the FPV recombinants f-TK2a and f-TK2b. The blots were hybridized with the FPV tk-gene probe (FIG. 6A), the VV-tk gene probe (FIG. 6B) and with lacZ gene and the lambda DNA probes (FIG. 6C). Lanes 1, FPV wild type DNA (HP1.441) digested with PstI; lanes 2, f-TK2a DNA digested with PstI; lanes 3, f-TK2b DNA digested with PstI; lanes 4, FPV wild type DNA (HP1.441) digested with ClaI; lanes 5, f-TK2a DNA digested with ClaI; lanes 6, f-TK2b DNA digested with ClaI; lanes 7, FPV wild type DNA (HP1.441) digested with EcoRI; lanes 8, f-TK2a DNA digested with EcoRI; lanes 9, f-TK2b DNA digested with EcoRI; lanes 10, marker DNA; lanes 11, pTKm-VVtka DNA digested with EcoRI; lanes 12, pTKm-VVtkb DNA digested with EcoRI; lanes 13, pTKm-VVtka DNA digested with ClaI; lanes 14, pTKm-VVtkb DNA digested with ClaI; lanes 15, pTKm-VVtka DNA digested with PstI.

FIG. 6D

The restriction enzyme cleavage maps of the fowlpox virus host strain f-TK2a with the enzymes EcoRI, PstI and ClaI are shown. The numbers indicate the predicted size of the fragments in kilo basepairs (kb). FPV-tk=fowlpox virus thymidine kinase gene; VV-tk=vaccinia virus thymidine kinase gene; sP11=synthetic P11 promoter; lacZ=*E. coli* lacZ gene; the arrows indicate the direction of transcription.

FIG. 6E

The restriction enzyme cleavage maps of the fowlpox virus host strain f-TK2b with the enzymes EcoRI, PstI and ClaI are shown. For further information and abbreviations see legend of FIG. 6D.

FIG. 7

Schematic presentation of the region around of the FPV thymidine kinase (tk) locus of the wild type virus and of the novel FPV host strains f-TK2a (ECAC accession number V93121601) and f-TK2b (ECAC accession number V93121602). The FPV host strains have inserted into the intergenic region between the FPV tk-gene and the 3'-open reading frame (orf) two new inserts, the vaccinia virus tk-gene (VV-tk) and the *E. coli* lacZ gene (lacZ). The arrows indicate the direction of transcription of the respective genes.

FIG. 8

Construction scheme of the "promoter trap" plasmids pFP-Z1 and pFP-Z21 (SEQ ID NO:5). The plasmids were constructed as outlined in the graph and as described in the Experimental Part. FPV-tk=fowlpox virus thymidine kinase gene; P7.5=promoter of the vaccinia virus 7.5 kDa protein gene; P11=promoter of the gene of the vaccinia virus 11 kDa polypeptide; ssDNA=single strand DNA; arrows indicate the direction of transcription.

FIG. 9

Construction scheme of the vaccinia virus insertion plasmids pTZgpt-P2a (SEQ ID NO:6) and pTZgpt-P2b (SEQ ID NO:7). Details of the construction are shown in the graph and described in the Experimental Part. Part of the abbreviations are described in the legend of FIGS. 1A and 1B; gpt=gene coding for the *E. coli* xanthine guanine phosphoribosyltransferase; arrows indicate the direction of transcription.

FIG. 10A

Sequence (bases 1–204 of SEQ ID NO:19) of the FPV P2 promoter and the first ten codons of the P2 gene. The A residue of the initiation codon (in bold type) was defined as position +1. At position −6 to −2 the vaccinia virus late promoter core sequence is present and at position −19 to −13 there is a vaccinia early RNA stop signal. Sequences that match in a minimum of 11 nucleotides to the 16 bp vaccinia early promoter critical region are underlined. The upstream region extends up to position −174. The downstream region (30 nucleotides coding sequence of the P2 gene) extends from +1 to +30.

FIG. 10B

Sequence (SEQ ID NO:19) of the NsiI-EcoRI fragment containing the FPV P2 promoter, the P2 gene and the downstream region. For underlined parts see legend to FIG. 10A. The upstream region extends up to position −174. The coding sequence of the P2 gene extends from +1 to +399 and codes for 133 amino acids. The calculated molecular mass of the P2 gene is 14 806 Da. The downstream region (415 bp) is A- and T-rich and does not contain open reading frames coding for proteins larger than 4 kDa.

FIG. 11

Comparison of the P2 promoter with other poxvirus promoters. The histogram shows the β-galactosidase expression levels induced by different poxvirus promoter-lacZ constructs. Cytoplasmic extracts of CV-1 cells infected with the indicated recombinant viruses were prepared and assayed for enzymatic activity as described in the Experimental Part. The expression levels of the different recombinants were compared with the standard level of vF1sβ (100%).

FIG. 12

SDS-PAGE analysis of CV-1 cells infected with different vaccinia recombinants. Cells were infected as described in the Experimental Part. Total soluble proteins were prepared and different amounts (5 µl and 10 µl) analyzed on a 10% polyacrylamide gel. Lanes 1 and 2: protein induced by vaccinia wild-type virus; lanes 3 and 4: proteins induced by the vaccinia recombinant vF1sβ; lanes 5 and 6: proteins induced by the virus vP2a; lanes 7 and 8: proteins induced by the VV recombinant vP2b; lanes 9 and 10: proteins induced by the VV recombinant vart. The reference virus vF1sβ (lanes 3 and 4) induces a novel protein in the 117 kDa range (lower arrow) that cannot be detected in wild-type virus infected cells (lanes 1 and 2). The β-galactosidase/P2-gene fusion protein obtained with the recombinants vP2a and vP2b (lanes 5 to 8) is about 130 kDa (upper FIG. 1.

FIG. 13A

Construction scheme of the insertion plasmid pFSgpt (SEQ ID NO:10). The plasmids were constructed as outlined in the figure. For abbreviations see legend of FIGS. 1A and 1B.

FIG. 13B

Sequence (bases 1514–1571 of SEQ ID NO:10) of the multiple cloning site of pFSgpt. The translational stop codons are in bold type; the poxvirus early transcription stop signal is underlined.

FIG. 14A

Construction of the insertion plasmids pP2mxgpt, containing mutated P2 promoter (mx) sequences. Oligonucleotides encoding either wild-type or mutant P2 promoter sequences were ligated into pFSgpt. The E. coli lacZ gene was placed downstream of the various promoters, thereby creating the promoter test plasmids pP2mxgpt-lacZ. P2mx.1 and P2mx.2=synthetic linker sequences encoding P2 promoter. For further abbreviations see legend of FIGS. 1A and 1B.

FIG. 14B

Sequence (bases 1677–1730 of SEQ ID NO:11) of the multiple cloning site of the insertion plasmid pP2mxgpt. The translational start and stop codons are in bold type; the poxvirus early transcription stop signal is underlined.

FIGS. 15A–15D

Structure of wild-type and mutant P2 promoters (the sequence of the P2-promoter wildtype sequence in the plasmid pTZgpt-P2a is also shown in SEQ ID NOs. 48 and 49; the sequence of P2 promoter mutant m0 in the plasmid pP2m0gpt-lacZ is also shown in SEQ ID NO:50; the sequence of P2 promoter mutant m1 in the plasmid pP2m1gpt-lacZ is also shown in SEQ ID NO:51; the sequence of P2 promoter mutant m2 in the plasmid pP2m2gpt-lacZ is also shown in SEQ ID NO:52).

Figure 16A:
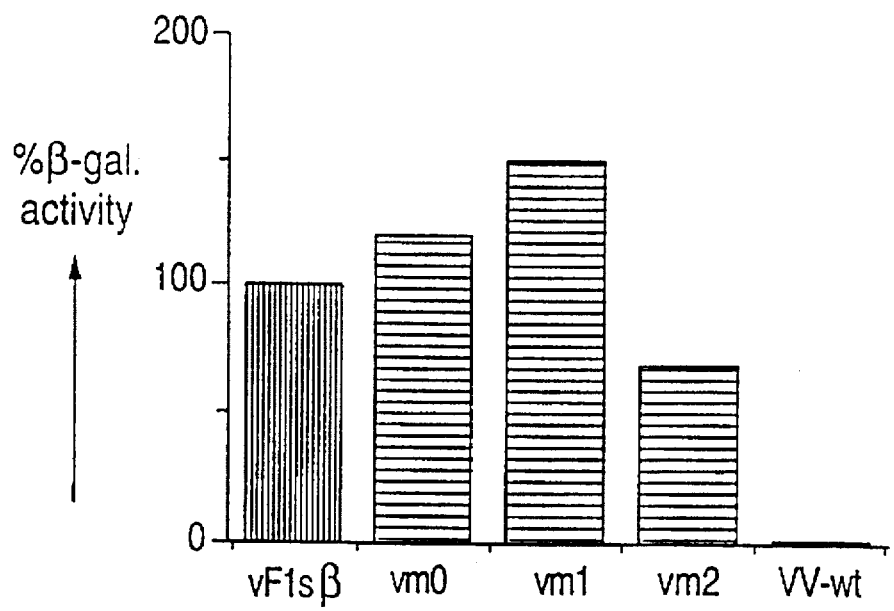
Figure 16B:
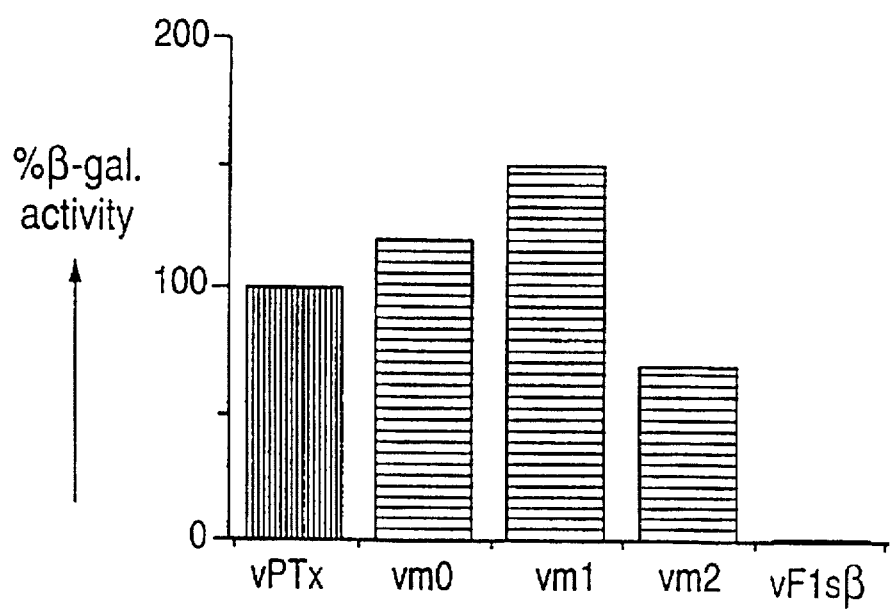

FIGS. 16A and 16B

Comparison of the β-galactosidase activities induced by the P2 promoter mutants in infected CV-1 cells.

a) late promoter activities
b) early promoter activities

FIG. 17A and 17B

A) Construction scheme of the vaccinia virus insertion plasmids pTZgpt-F1s (SEQ ID NO:14) and pTZgpt-P11M. The plasmids were constructed as described in the Experimental Part. tk=vaccinia virus thymidine kinase gene; P7.5= promoter of the gene of the vaccinia virus 7.5 kDa protein; P11=promoter of the gene of the vaccinia virus 11 kDa polypeptide; P11M=mutated P11 promoter; f1 ori=f1 origin of replication; gpt=E. coli gpt gene (coding for the enzyme xanthine guanine phosphoribosyl transferase); MCS= multiple cloning site.

B) Construction scheme of the promoter test vectors pTZgpt-sP11 (SEQ ID NO:16), pTZgpt-s4b (SEQ ID NO:17) and pTZgpt-sart (SEQ ID NO:18) (pTZgpt-sPx). FPV-tk=thymidine kinase gene of fowlpox virus; P7.5= promoter of the gene of the vaccinia virus 7.5 kD8 protein; -sPx designates the respective synthetic linker sequences sP11, S4b and sart used for construction of promoters; gpt=E. coli gpt gene coding for xanthine guanine phosphoribosyl transferase; arrows indicate the direction of transcription.

FIGS. 18A–18E

Structure of the promoter regions. The nucleotide sequence of the mutated promoter regions is shown. The vaccinia virus late promoter consensus sequence (thin line), the translation initiation codons (bold lines) and the position of several restriction sites are indicated. P11wt (SEQ ID NO:43), wild-type sequence of the P11 promoter; P11m (SEQ ID NO:44), mutated P11 sequence; sP11 (SEQ ID NO:45), synthetic mutated P11 sequence; s4b (SEQ ID NO:46), synthetic FPV 4b promoter; sart (SEQ ID NO:47), synthetic (artificial) late promoter.

FIG. 19

Comparison of β-galactosidase expression levels induced by the different pox virus promoter lacZ gene constructs. The expression levels of the different recombinants were compared with the standard level of vF1sβ (100%).

The present invention thus concerns a recombinant fowlpox virus (FPV) insertion plasmid, which is characterized in that the intergenic region between the FPV tk-gene and the 3' open reading frame (3' off) is enlarged to form one or more unique restriction sites so that by insertion of foreign DNA into this intergenic region the FPV tk-gene remains intact and codes for the entire thymidine kinase (TK).

Said enlarged intergenic region may e.g. comprise the following sequence (SEQ ID NO:20):

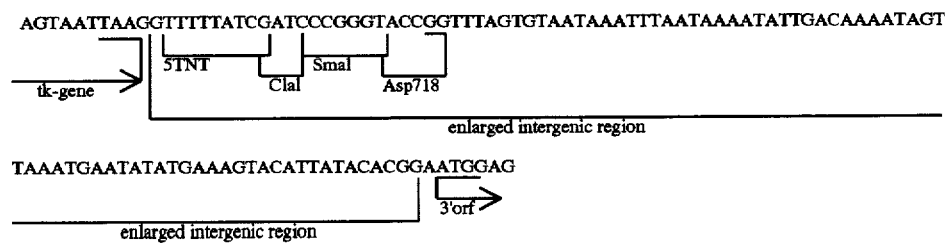

This modification of the wild type intergenic region may be obtained by site-specific mutagenesis.

A recombinant FPV capable of expressing foreign protein (s) is produced by integrating into the fowlpox viral genome a DNA sequence encoding foreign protein(s). This foreign DNA sequence is integrated into the FPV genome by an in vivo recombination event between the insertion plasmid carrying the foreign DNA sequence and flanking sequences of the FPV genome. This insertion plasmid comprises at least the foreign DNA sequence linked to a fowlpox or other pox virus promoter located between DNA sequences which are homologous to the above intergenic region and the flanking sequences. Thus, a selectable insertion plasmid comprises at least:

(a) a natural or synthetic poxvirus promoter linked to a foreign DNA sequence which is to be expressed;

(b) a second pox virus promoter linked to a gene encoding a marker or indicator for selection of recombinant FPV;

(c) DNA sequences of FPV flanking the construct of elements (a) and (b) at both 5' and 3' ends, said flanking DNA sequences being homologous to the sequences upstream and downstream of the enlarged intergenic region.

Above plasmid preferably comprises further a replicon for replication in a prokaryotic host, and a gene encoding a selectable marker or indicator for selection in a transformed prokaryotic host.

The promoters used in the above plasmid as well as in recombinant FPV are pox virus promoters, especially FPV promoters. For efficient expression of a foreign protein it is preferable that the promoter is immediately adjacent to the coding sequence of the foreign DNA sequences.

Most of the VV recombinants constructed so far use cloned VV promoters to drive the foreign gene of interest. In vivo recombination of a transcription unit consisting of a cloned VV promoter and a foreign gene into a non-essential site of the VV genome usually results in the duplication of the promoter elements and may give rise to secondary recombinations, segregation and instability of the recombinant. For the construction of genetically stable pox virus recombinants it is therefore desirable to use either non-homologous or short synthetic viral promoters that control the transcription of the foreign gene.

A preferred FVP promoter is the P2 promoter (FIG. 10B). This promoter contains in its upstream part several critical early regions followed by the late promoter consensus sequence. The functional analysis confirmed that the P2 promoter is active early and late in the viral life cycle.

The strength of the novel FPV promoter was compared with several known strong poxvirus promoters in vaccinia virus recombinants. It was found that the P2 promoter belongs to one of the strongest natural promoters in VV infected cells.

In an attempt to optimize the P2 promoter, a series of mutants was constructed (FIGS. 15A–15D and SEQ ID NOS.48–52). In all mutations the P2 gene fusion sequence is removed and the initiation codon of the lacZ gene is located adjacent to the late promoter signal TAAAT. In the mutation m0 (SEQ ID NO:21: TAAATG AAT TCC) the ATG of the lacZ gene is directly fused with the late promoter core sequence, thereby deleting the C residue at position −1 of the wild-type P2 sequence, a mutation that improves the efficiency of a late promoter. This structure is found in many late VV promoters and is thought to be the optimal context of the late promoter consensus and the initiation codon (Davidson, A. J. and Moss B., J. Mol. Biol. 210: 749, 1989).

The mutant m1 (SEQ ID NO:22: TAAACATG AAT TCC) has the ATG of the lacZ gene directly fused with the ATG of the putative P2 gene.

The mutation m2 was constructed in order to investigate the significance of the early promoter critical regions found upstream of the late promoter region. The mutant promoter m2 has the same structure as m1, except that the early RNA stop signal within the functionally important T-rich region upstream of the late promoter motif was inactivated by a TTG insertion at position −18.

Thus, preferred FPV promoters are the P2 promoter having a DNA sequence as derivable from FIG. 10A and functional equivalents thereof. Experimental data as to the promoter strength are shown in FIGS. 16A and 16B.

The promoter regions are preferably followed by a multiple cloning site (MCS) which allows the insertion of foreign genes.

The P2 gene and the downstream region were characterized by sequence analysis (FIG. 10B). The P2-gene codes for 133 amino acids; the calculated molecular mass is 14 806 Da. The downstream region (415 bp) is A and T rich and does not contain open reading frames coding for proteins larger than 4 kDa, i.e. this region of the genome is probably a non-coding region. The downstream region of the P2 gene is therefore a novel non-essential site that can be used for the insertion of foreign genes into the FPV genome.

Preferred plasmids contain genetic elements which allow selection of recombinant FPV. These elements comprise a gene encoding a selectable marker or indicator together with a poxvirus promoter which controls the expression of said gene in the recombinant virus. The promoter and the marker or indicator gene are located between the flanking FPV sequences so that the same are co-integrated into the FPV genome. Recombinant FPV can then be selected based upon expression of the marker or indicator.

A preferred gene for indentification is the E. coli lacZ gene which encodes the enzyme β-galactosidase. Methods for identification based upon expression of this enzyme are discussed in the literature. Selection methods include drug resistance selection, e.g. the selection by the gene encoding xanthine guanine phosphoribosyl transferase, the latter conferring resistance to mycophenolic acid.

The plasmids according to the invention also contain preferably a replicon for replication in a prokaryotic host as well as a gene encoding a selectable indicator or marker which allow selection and amplification in a prokaryotic host such as E. coli. The replicon can be obtained from any conventional prokaryotic plasmid such as pBR322. The selectable marker can be a gene conferring antibiotic resistance.

Specific plasmids acccording to the invention may be constructed by replacing the lacZ gene of insertion plasmid pTKm-sP11-gpt by a foreign gene of interest.

The DNA plasmids containing the DNA sequence to be expressed together with the marker or indicator genes are flanked by appropriate FPV sequences, the latter allowing recombination with FPV and integration of the flanked genes into the FPV genome. This recombination occurs in the cytoplasm of a eukaryotic host cell. Appropriate host cells for recombination require that they are (1) infectable by FPV and (2) transfectable by the DNA vector. Examples of such cells are chicken embryo fibroblast and chicken embryo dermal cells.

For in vivo recombination, the cells are first infected with FPV and then transfected with the insertion plasmid. Viral infection is accomplished by standard techniques for infection of eukaryotic cells with FPV. Subsequently, the cells are transfected with the insertion plasmid by means of any of the conventional transfection techniques.

After infection and subsequent transfection, the cells are incubated under standard conditions, and virus is allowed to replicate; during this time in vivo recombination occurs between the homologous FPV sequences of the insertion vector and FPV so that the foreign DNA sequences are inserted into the FPV genome.

Recombinant FPV is then selected by means of the inserted marker or indicator, e.g. the *E. coli* lacZ gene which expresses β-galactosidase. Using a chromogenic substrate for this enzyme, e.g.

5-bromo-4-chloro-3-indolyl-β-D-galactoside, recombinant viruses are detected as blue plaques.

According to another essential embodiment of the invention, the recombinant FPV comprises as insertion site within the above intergenic region a vaccinia virus tk-gene which can serve as non-essential site (NES) for the insertion of one or more foreign DNA sequences.

As a preferred modification, said recombinant FPV comprises in said enlarged intergenic region a selection marker and/or a reporter gene and the VV tk-gene in any desirable order.

Figure 7:
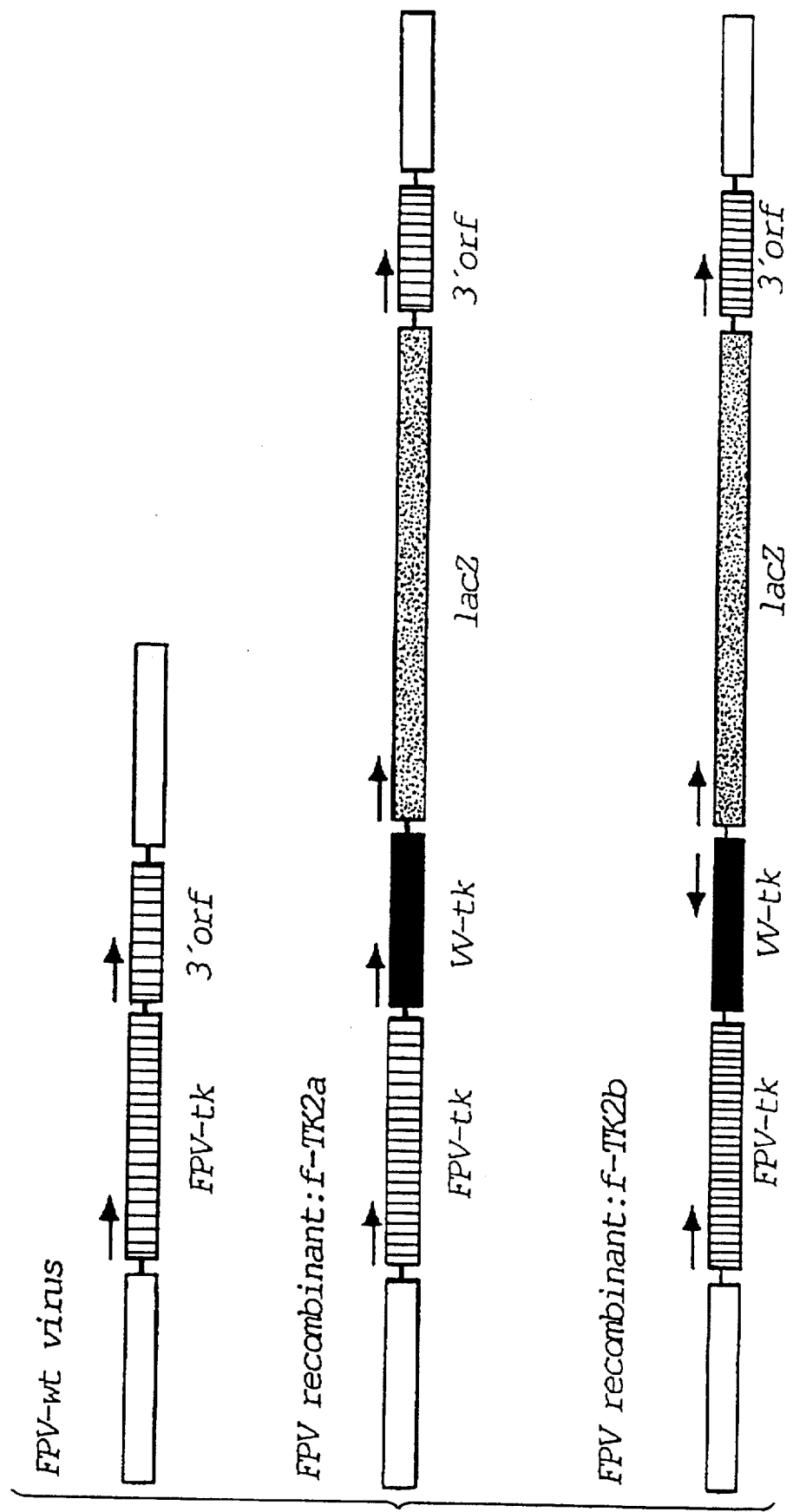

The most preferred modifications consist of recombinant fowlpox viruses which comprise within an enlarged intergenic region the insertion of the vaccinia virus tk-gene and of the lacZ gene. The genomic structures of such two novel host strains is shown in FIG. 7. Either the fowlpox virus or the vaccinia virus tk-gene may be used as non-essential sites to insert foreign genes. The strains f-TK2a and f-TK2b differ only in the orientation of the vaccinia virus tk-gene. This allows the insertion by homologous recombination of foreign genes of interest in two orientations. This may be advantageous to study transcriptional interference phenomena.

Since the above modification of a novel FPV host strain comprises two intact tk-genes, it is possible to use either one for the insertion of foreign DNA. This allows the application of an extended range of plasmids which possess either FPV tk or VV tk flanking sequences.

Thus the invention comprises recombinant FPV which has been obtained by homologous recombination of the above novel FPV host strain and any of the plasmids described here which allow insertion of a foreign DNA into either the FPV tk-gene or the VV tk-gene.

Figure 14A:
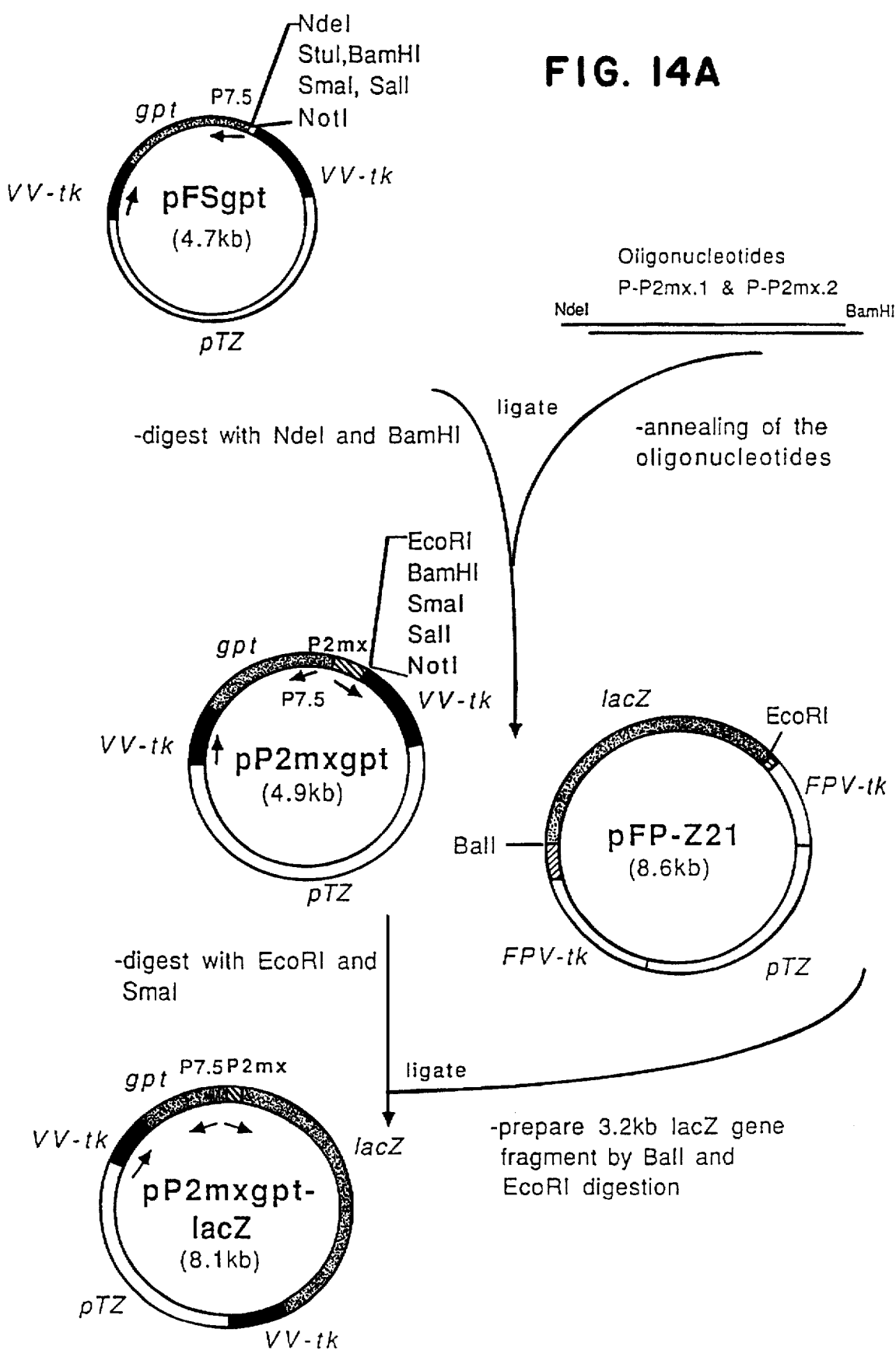
Figure 17A:
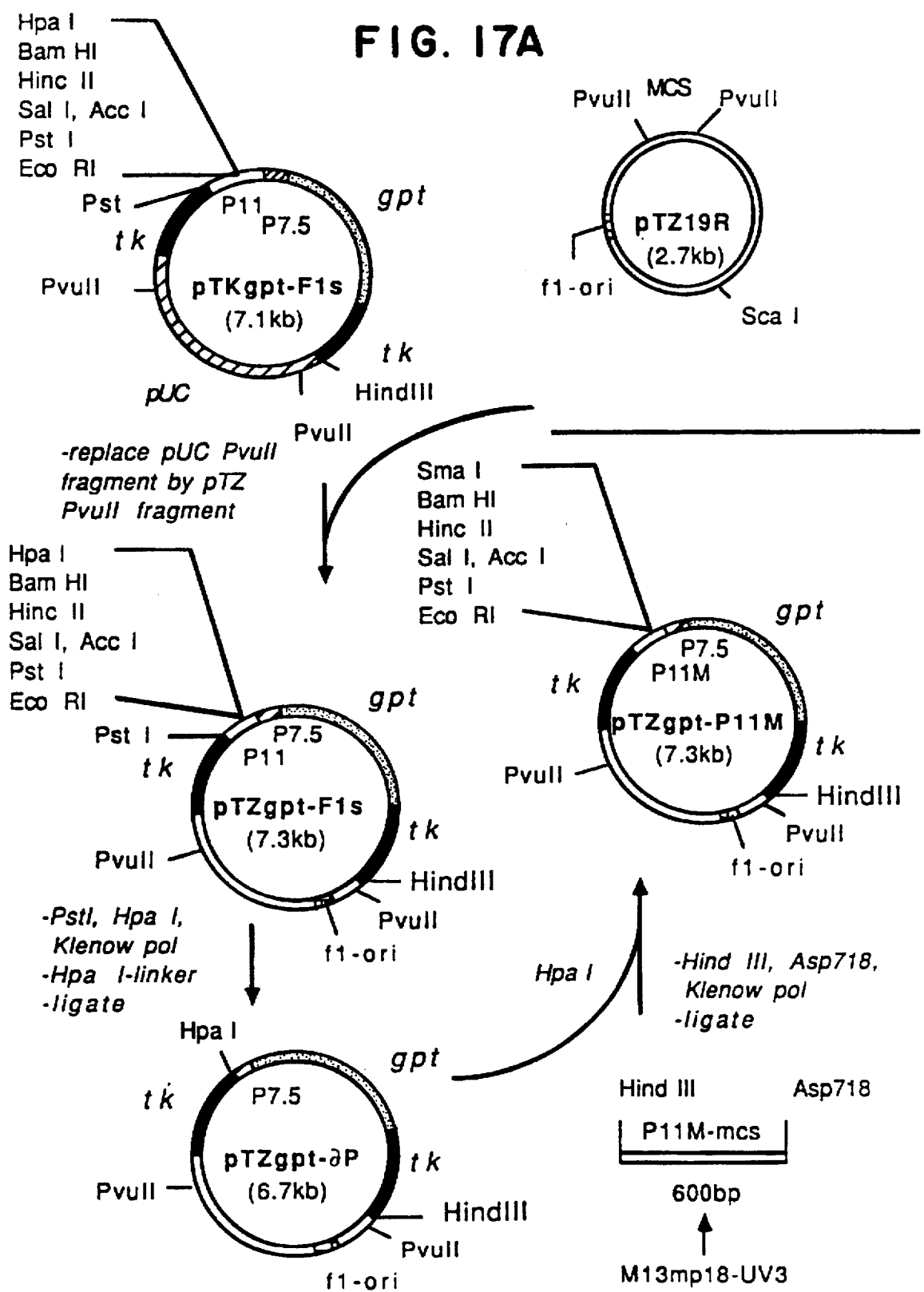

As described above, a recombinant FPV capable of expressing foreign protein(s) is produced by integrating into the FPV genome a DNA sequence encoding said foreign protein(s). This is done by in vivo recombination by means of an insertion vector as described above. Specific vectors according to the invention may be constructed by means of insertion plasmids pTZgpt-F1s or pTZgpt-P11M as shown in FIG. 17A, and pP2mxgpt as shown in FIG. 14A.

The construct pTZgpt-F1s (FIG. 17A and SEQ ID NO:14) presents a plasmid that is advantageous in comparison to the previously used plasmid pTKgpt-F1s (upper part of FIG. 17A) in that the f1 origin of replication (f1 ori) was introduced by substituting the pTZ portion in place of the pUC portion (PvuII fragments). Insertion of the f1 ori allows the production of a single-stranded DNA as required for sequencing and in vitro mutagenesis. In this way, time-consuming recloning experiments in M13 vectors are superfluous.

In the plasmid pTZgpt-P11M (FIG. 17A), the P11 "late promoter consensus region" (SEQ ID NO:23) TAAAT-GAATTC is mutated and converted to the following sequence (SEQ ID NO:24): TAAATAAAGAATTC. This construct has the advantage that the genes can be expressed under the control of their own translation-initiation codons (ATG).

The plasmid pTZgpt-dP (FIG. 17A and SEQ ID NO:15) comprises besides the flanking VV tk sequences and the gpt gene under the control of promoter P7.5 a single HpaI site. This site serves conveniently for the insertion of various promoter-foreign-gene cassettes.

The insertion plasmids pP2m0gpt (SEQ ID NO:11), pP2m1gpt (SEQ ID NO:12), pP2m2gpt (SEQ ID NO:13) (pP2mxgpt; FIG. 14A) direct the foreign gene of interest into the vaccina virus tk-gene of the novel fowlpox virus host strains (FIG. 7). The abbreviation P2mx stands for the mutated P2 promoters as described in FIGS. 15A–15D. These insertion plasmids are suited for the high level expression of open reading frames that lack their own translational initiation and termination codons. The translational stop codons that terminate translation in all three reading frames are provided by the plasmids. An additional feature of the multiple cloning sites of the insertion plasmids pP2m0gpt, pP2m1gpt, pP2m2gpt is a transcriptional stop signal, that terminates poxvirus early gene expression; the sequence (bases 1677–1730 of SEQ ID NO:11) of the multiple cloning site is shown in FIG. 14B.

Figure 13A:
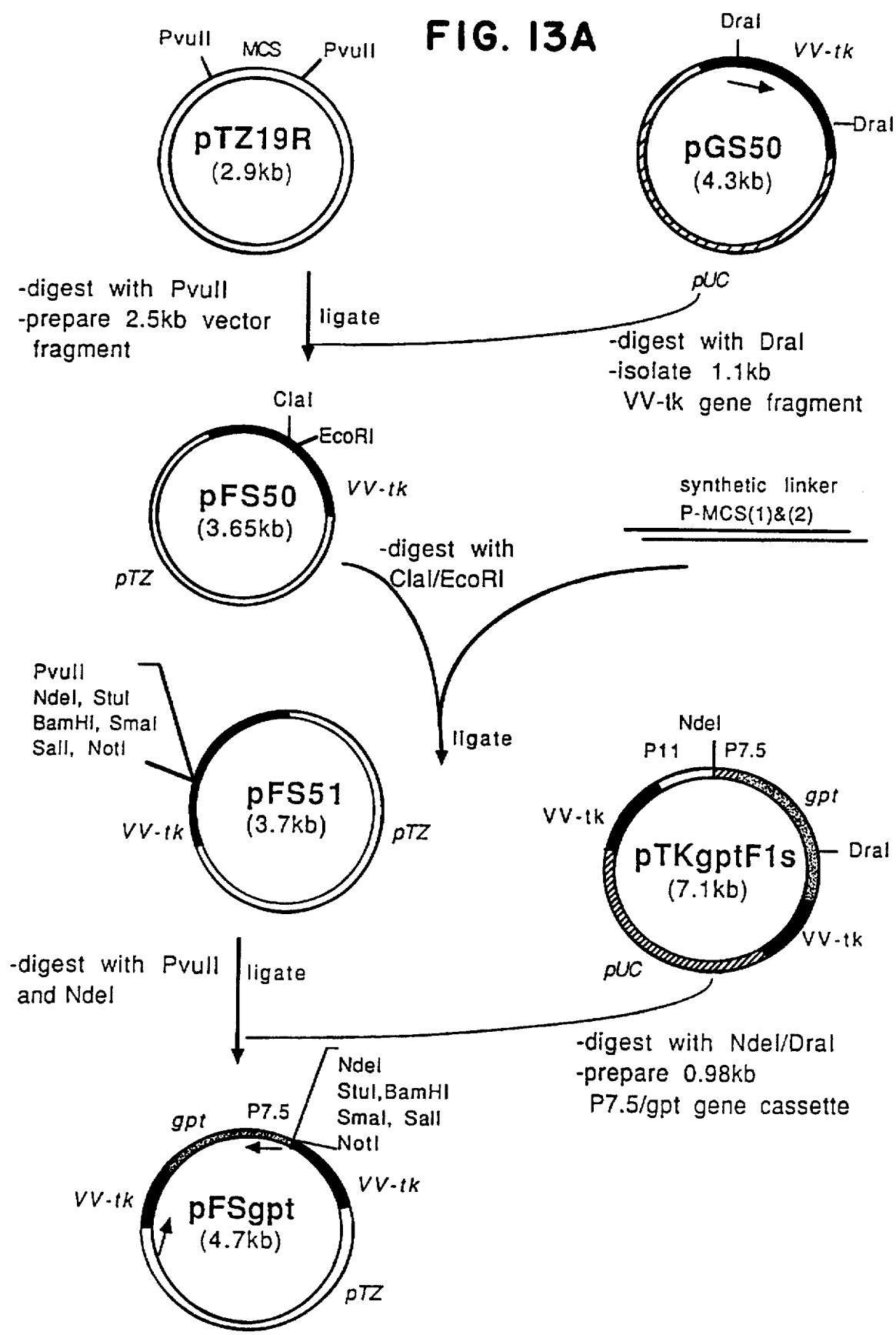

The plasmid pFSgpt (SEQ ID NO:10) (FIG. 13A) also directs the foreign gene of interest into the vaccinia virus tk-gene of the novel fowlpox virus host strains (FIG. 7). It may be used for the cloning of poxvirus-promoter foreign gene cassettes. The plasmid pFSgpt also provides translational stop codons and the poxvirus early transcription stop signal. The sequence of the multiple cloning site is shown in FIG. 13B.

Figure 17B:
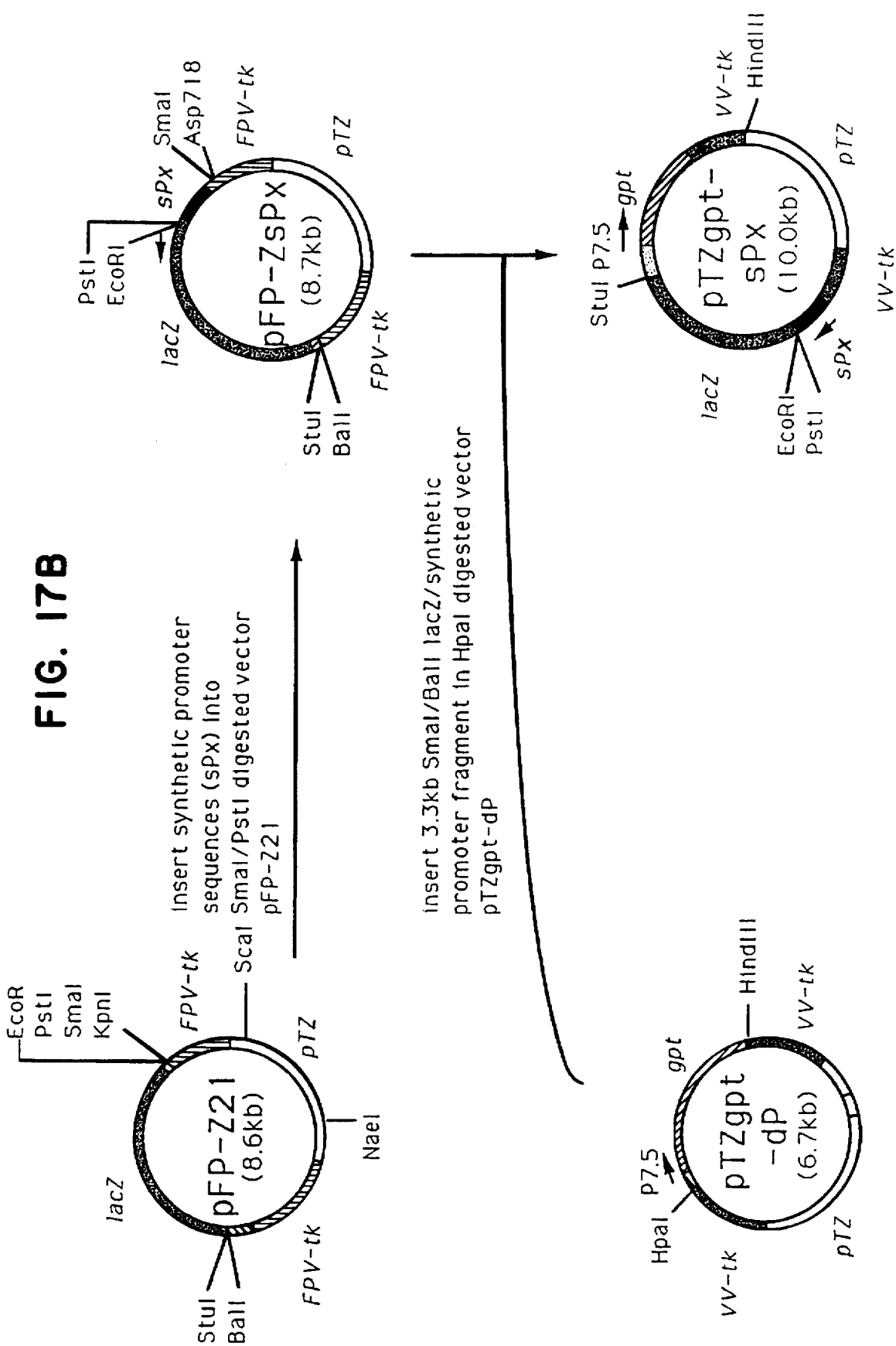
Figure 19:
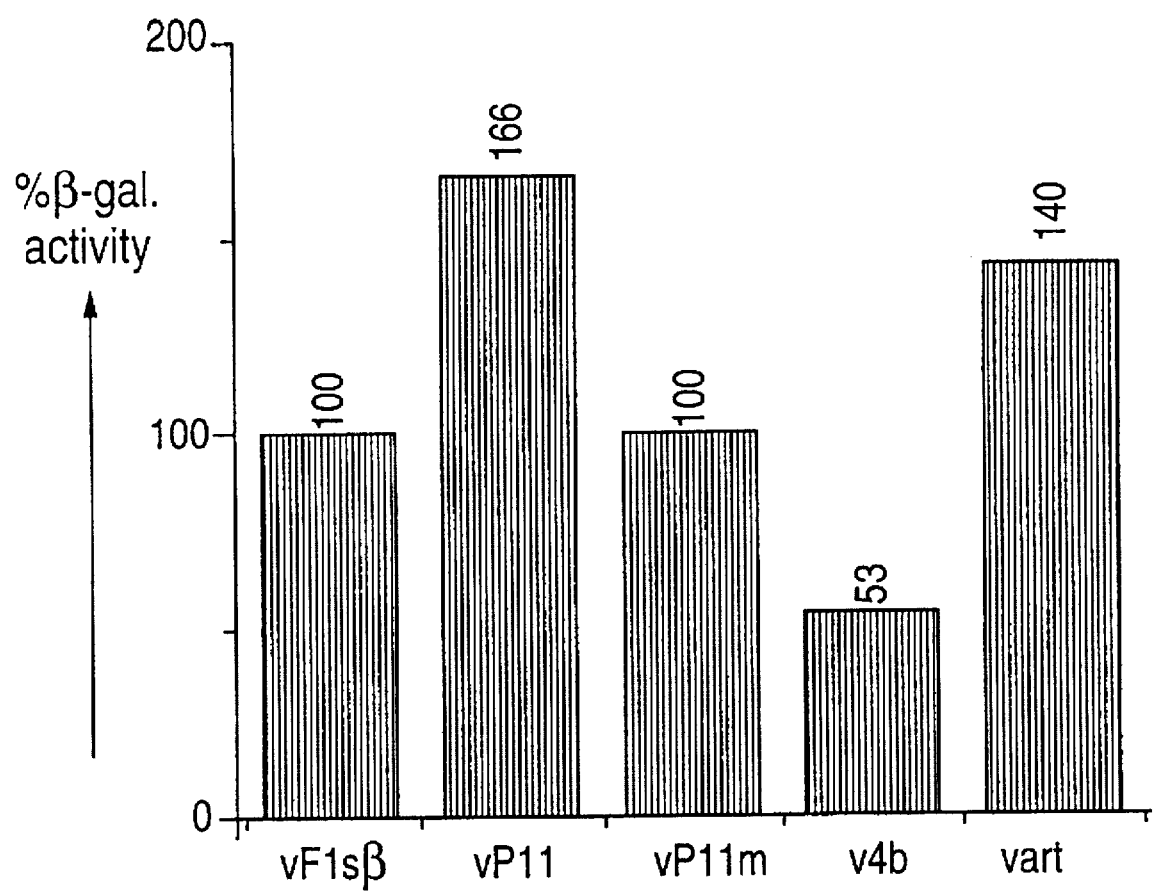

The plasmids pTZgpt-sPx (FIG. 17B) are "promoter test plasmids", which were constructed to test various synthetic promoters (here designated as sPx). The abbreviation sPx may have the following meaning:

a) sP11 (SEQ ID NO:16)=synthetic VV P11 promoter mutant;

b) s4b (SEQ ID NO:17)=synthetic FPV 4b promoter mutant;

c) sart (SEQ ID NO:18)=synthetic promoter mutant.

The above promoters comprise strong late promoters which are active in VV as well as FPV. These promoters may be excised with or without reporter gene (lacZ) and can thus be cloned into various vector systems. These additional promoters enlarge the available promoter pool and allow multiple expression. They also have the advantage that the regions which are homologous to the viral genome are restricted to rather short sequences, a fact that reduces the probability of recombinations and thus decreases instability of recombinant viruses.

As described above, a recombinant FPV which is used for the expression of foreign protein(s) is obtained by in vivo homologous recombination.

The invention comprises also a method for the expression of a foreign protein. This method consists of infecting appropriate host cells with a recombinant FPV according to the invention. The host cells are then cultured to allow expression of the desired protein, and the latter is recovered by means of conventional techniques.

Suitable cells or cell cultures are chicken embryo fibroblast cells or chicken dermal fibroblast cells.

Any desired protein may be expressed by use of the above recombinant FPV and obtained in sufficient quantities. It is of special interest to express proteins which require post-translational modification in a way as it is performed by the host cell. Such proteins are e.g. Factors II, V, VII, VIII, IX, X, XI, XII, XIII, protein C, protein S, von Willebrand-Factor, plasminogen and derivatives thereof, wherein one or more amino acid is replaced, deleted or inserted, partial sequences and activated forms thereof, apolipoproteins, such as apoAI and apoAII, and viral antigens such as hepatitis B-antigens, the antigens of hepatitis C-virus, the antigens of hepatitis E-virus, the antigens of tick-borne encephalitis (TBE) virus, the antigens of HIV, HSV and whole or partial sequences of such antigens which cause pertussis, tetanus, malaria, poultry diseases, Marek's disease, ILT, infectious, bronchitis, coccidiosis and Newcastle disease, the above antigens being useful as vaccines.

Experimental Part

In the descriptions which follow, the following abbreviations are used:

CDS=coding sequence rc=reverse complementary sequence rcCDS=reverse complementary coding sequence arabic numbers are the position of nucleotides ATG=translational start codon EMBL ID=Identifier in EMBL DATABANK 1.1 Virus and cells The fowlpox virus strain HP1 (Mayr & Malicki; Zentralblatt f. Veterinärmedizin, Reihe B, 13, 1–12 (1966)) and the attenuated strain HP1-441 (passage number 441 of HP1) were kindly provided by Prof. A. Mayr, Munich. Primary chicken embryo fibroblasts (CEF) were prepared as described in the European patent application publication No. 0 338 807. The cells were grown in tissue culture medium 199 (TCM 199; Gibco BRL) supplemented with 5% fetal calf serum, glutamine and antibiotics. Vaccinia virus (ATCC # VR 119, strain WR) was kindly provided by Dr. B. Moss. The virus was replicated in CV-1 cells and purified as reported by Mackett et al (in D. M. Glover (ed). (1985), DNA cloning: A practical approach; IRL Press, Oxford). The African Green Monkey kidney cell line CV-1 (ATCC # CCL 70) was obtained from the American Type Culture Collection, Rockville, Md.

1.2 Purification of fowlpox virus (FPV)

The purification was essentially done as described by Joklik (Virology, 18, 9–18 (1962)) with the following modifications: CEF monolayers (twenty 175 cm$^2$ cell culture flasks) were infected with 1 pfu(plaque forming unit)/cell and incubated for 4–5 days at +37° C. and 5% $CO_2$. The cells were scraped into the medium, spun down at 2,000 rpm for 20 minutes in a H6000A-rotor of a Sorvall RC3C centrifuge. The pellet was resuspended in 5 ml of 10 mM Tris pH 9, sonicated, supplemented with 1/10 volume of 2.5% trypsin and incubated at +37° C. for 30 minutes. To pellet the extracellular virus, the supernatent was centrifuged at 17,000 rpm for 2 hours at +4° C. in a Beckman type 19 rotor. The trypsinized cells and the virus pellet of the cell culture supernatant were pooled, loaded on a 36% sucrose cushion and centrifuged for 80 minutes at 13,500 rpm in a Beckman SW28 rotor at +4° C. The pellet was resuspended in 1 ml of 1 mM Tris pH 9, sonicated, layered onto a 20–40% sucrose gradient and centrifuged at 12,000 rpm for 50 minutes at +4° C. The two viral bands (the intra- and extracellular forms of the virus) were collected, pooled and 2 volumes of 10 mM Tris pH 9 were added. The viral pellet was collected after centrifugation at 15,500 rpm for 60 minutes and resuspended in 500 µl 1 mM Tris 1 mM NaCl pH 9.

1.3 Cell infection and plaque assays

The plaque assays were performed on confluent monolayers of CEFs (in tissue culture dishes; 60 cm$^2$, approximately 6×10$^6$ cells or in 6 well plates, 10 cm$^2$, 1×10$^6$ cells per well) or CV-1 cells in 6 well plates (10 cm$^2$; 1×10$^6$ cells per well) respectively. The virus suspension was allowed to adsorb to the cells in a volume of 0.6 ml TCM 199 with occasional rocking for 1 hour. The suspension was removed by aspiration and replaced by an overlay consisting of serumfree DMEM, antibiotics and 1% low melting agarose (LMA; Gibco BRL). FPV-plaques titrated on CEF-cells were stained with 30 µg/ml of neutral red (Sigma) on the 5th or 6th day of infection. Vaccinia virus plaques titrated on CV-1 cells were stained with 50 µg/ml of neutral red on the 3rd day of infection.

1.4 In vivo recombination

CEF cells or CV-1 cells (in 60 cm$^2$ tissue culture dishes) were infected with 1 plaque forming unit (pfu) per cell of HP1-441 or VV, respectively. The virus was adsorbed for 1 hour at +37° C. in 2.5 ml TCM 199. Subsequently the medium was aspirated and the infected monolayers were overlayed with a DNA-Ca-phosphate precipitate, consisting of 20 µg of plasmid DNA and 5 µg of HP1-441 or VV wild-type DNA in Hepes buffered saline in a final volume of 1 ml according to Graham & van der Eb (Virology, 52, 456–467 (1973)). After a 30 minutes incubation period at room temperature 9 ml of TCM 199 were added and the incubation was continued for another 4 hours at +37° C. The medium was replaced with 10 ml of fresh TCM 199 and the plates were incubated for 2 days. Then the cells were scraped into the medium and the pellets were lysed by three successive cycles of freezing and thawing. Progeny virus was then assayed for the presence of recombinants.

1.5 Selection and plaque purification of the recombinants 1.5.1 Blue plaque screening Viruses with lacZ gene inserts were identified by blue plaque screening as described by Chakrabarti et al (Mol. Cell. Biol., 5, 3403–3409 (1985)) with the following modifications: CEF-cells (in 60 cm$^2$ tissue culture dishes) or CV-1 cells (in 6 well plates) were infected with viral crude stocks derived from recombination experiments and overlayed with serumfree DMEM containing 1% LMA. After 5–6 days for CEF and 3 days for CV-1 the monolayers were stained with a second overlay consisting of 1% LMA in phosphate buffered saline (PBS) and 600 µg/ml of the chromogenic substrate 5-bromo-4-chloro-3-indolyl-β-D-galactoside (X-gal). Blue plaques appeared about 4–12 hours later.

1.5.2 gpt-selection

Recombinant FPV viruses with gpt-gene inserts were identified on the basis of their resistance to the drug mycophenolic acid (MPA) essentially as described by Falkner & Moss (J. Virol., 62, 1849–1854 (1988)) with the following modifications: monolayers of CEF cells were infected with recombinant virus and overlayed with DMEM supplemented with 125 µg/ml xanthine, 5–25 µg/ml MPA and 1% LMA. After 5–6 days the plaques were visualized by staining with a second overlay consisting of 1% LMA in PBS containing 30 µg/ml neutral red. In case of gpt- and lacZ positive recombinants the overlay contained in addition 600 µg/ml of X-gal. The plaques were subjected to several rounds of plaque purification.

Monolayers of CV-1 cells were infected with recombinant vaccinia virus and overlayed with DMEM supplemented with 250 µg/ml xanthine, 15 µg/ml hypoxanthine, 25 µg/ml MPA and 1% LMA. After 2–3 days the plaques were visualized by staining with a second overlay consisting of 1% MPA in PBS containing 50 µg/ml neutral red and 600 µg/ml X-gal. The plaques were subjected to several rounds of plaque purification.

1.6 Transient expression assays

The assay was essentially done as described by Cochran et al (Proc. Natl. Acad. Sci. USA, 82, 19–23 (1985)) and modified as follows: Confluent monolayers of CV-1 cells (about 1×10$^7$ cells) were infected with 5 or 10 plaque forming units of vaccinia wild-type virus and transfected with 30 μg plasmid DNA in the form of a DNA-Ca-precipitate prepared according to Graham & van der Eb (Virology, 52, 456–467 (1973)). Cells were harvested 24 hours post-infection by centrifugation and resuspended in 100 μl PBS. Cytoplasmic extracts of infected cells were prepared by sonication and assayed for β-galactosidase activity.

1.7 β-galactosidase assays

Confluent monolayers of CV-1 cells (8×10⁶ cells) were infected with 10 plaque forming units of vaccinia recombinants, harvested 24 hours post-infection by centrifugation and resuspended in 100 μl PBS. For the preparation of cytoplasmic extracts the cells were disrupted by three repeated cycles of freezing and thawing and by sonication. Protein extracts were quantified according to Bradford (Anal. Biochem., 72, 248–254 (1976)). The enzymatic assays were carried out essentially as described by Miller (in Experiments in molecular genetics, Cold Spring Harbor Laboratory, Cold Spring Harbor, N.Y.: 352–355 (1972)) and modified as follows: All reagents were prewarmed to 28° C., lysates were kept on ice. The reactions were carried out in 770 μl 1×Z buffer (0.6M $Na_2HPO_4$, 0.4M $NaH_2PO_4$, 0.1M KCl, 0.01M $MgSO_4$, 0.5M β-mercaptoethanol, pH 7), 200 μl of the chromogenic substrate o-nitrophenyl-β-D-galactopyranoside (ONPG; 4 mg/ml in 0.1M phosphate buffer pH 7.0) was added and the reaction was started by adding of 30 μl of diluted (1:100) cell extract. After 3 minutes at room temperature the assay was transferred to a Beckman DU8 photometer. Optical density was recorded at 420 μm for 15 minutes at 28° C. with reference to a PBS sample. Results were confirmed by scanning of polyacrylamide gels using a UV-Vis densitometer (Hirschmann).

1.8 Sequencing

The sequences were determined with the T7 polymerase sequencing kit (Pharmacia) by the dideoxy chain termination method (Sanger & Coulson; J. Mol. Biol., 94, 441 (1975)) with specific primers. The construction of the plasmids was performed according to standard techniques as described by Sambrook et al (Molecular cloning; Cold Spring Harbor Laboratory Press (1989)).

2. Construction of the insertion plasmids 2.1 pFPtk5

As a first step, the FPV thymidine kinase gene was cloned as follows: an EcoRI digest of fowlpox virus DNA (strain HP1 Munich) was cloned into the EcoRI site of the vector pTZ19R (Pharmacia). The tk-gene containing plasmid (designated pFPtk5) was identified by colony filter hybridization using the oligonucleotide probe (SEQ ID NO:25) 5'-CAG TTA TTG TGG CCG CGC TTA ACG GTG A-3'. The plasmid contained a 5.5 kb EcoRI fragment.

2.2 pFPtk10.4 pFPtk5 was cleaved with ClaI, BamHI and ScaI, treated with Klenow polymerase and ligated with the vector pTZ19R, which had been treated with PvuII, EcoRI and phosphatase. The resulting plasmid, pFPtk10.4, had the 2.48 kb BamHI-ClaI insert that contains the fowlpox virus tk-gene (Boyle et al; Virology, 156, 355–356 (1987)).

2.3 pFP-UV2i

Into the unique NcoI site within the tk-coding region of pFPtk10.4, the 2.3 kb SspI fragment from pUV1 (Falkner et al; Nucl. Acids Res., 15, 7192 (1987)) was inserted; the fragment contains the P11-promoter (Bertholet et al; Proc. Natl. Acad. Sci. U.S.A., 82, 2096–2100 (1985)), the P7.5 promoter (Cochran et al; J. Virol., 54, 30–37 (1985)) and the 5'-part of the lacZ gene.

2.4 pFP-UV2

The cloning of the plasmid pFP-UV2 was completed by inserting the 2.3 kb lacZ fragment (3' part of the lacZ gene) into the intermediate plasmid pFP-UV2i.

2.5 pFP-UV2-PT

In the following experiment the cDNA sequence for prothrombin was cloned into plasmid pFP-UV2. This experiment was carried out by excising the 2.0 kb EcoRI fragment from the plasmid pPt # 12, which is described in European patent application No. 90 101 623.8. The complete human prothrombin cDNA was then cloned into the EcoRI and phosphatase treated vector pFP-UV2. In this construct the translational start codon of the prothrombin cDNA is exactly fused with the naturally occurring start codon of the promoter of the vaccinia virus major late 11K polypeptide. The resulting plasmid was designated pFP-UV2-PT.

2.6 pTKm (SEQ ID NO:1)

This plasmid was constructed from pFPtk10.4 by oligonucleotide directed mutagenesis using a phosphorothioate-based mutagenesis procedure (Amersham, Inc.). The mutagenic primer used to enlarge and modify the intergenic region of the FPV thymidine kinase gene had the sequence (SEQ ID NO:26) 5'-TTA CAC TAA ACC GGT ACC CGG GAT CGA TAA AAA CCT TAA TTA CTA-3'. The structure of the mutation was confirmed by sequencing using the primer (SEQ ID NO:27) 5'-CCATTCCGTGTATAATGTAC-3' located 46 bp downstream of the altered sequence. Features of this plasmid are outlined in the table below.

| pTKm (4997bp) SEQ ID NO: 1 | |
|---|---|
| location | description |
| 1–2459 | pTZ19R (Pharmacia). Position 1 corresponds to the first nucleotide C starting with the motif: 5'-CTTCCGCTT-3'. |
| 60–3449 | Unsequenced portion of the fowlpox virus FPV-tk gene flanking region. |
| 3450–4631 | FPV-tk- sequence described in Boyle et al., Virology, 156: 355–356 (1987). (EMBL ID PXFPVTK) |
| 3558–4106 | CDS of FPV-tk gene |
| 4112–4132 | enlarged intergenic region |
| 4631–4943 | unsequenced portion of the FPV-tk gene flanking region including BamHI site. |
| 4944–4997 | pTZ19R–; |

2.7 pFP-ZsP11

In the plasmid pFP-Z21 (see 2.15), the lacZ gene is flanked by several restriction sites but does not contain promoter sequences. Into the PstI and SmaI sites of pFP-Z21 a synthetic promoter (a modified version of the vaccinia P11 promoter) was inserted upstream of the lacZ gene by ligation of a synthetic linker consisting of the annealed oligonucleotides I and II. (oligonucleotide I (SEQ ID NO:28), 5'-GCC TAT TTA TAG CAT AGA AAA AAA CAA AAT GAA ATT TTA CTA TAT TTT TAT ATA CAT ATA TTC TAA CCC-3'; oligonucleotide II (SEQ ID NO:29), 5'-GGG TTA GAA TAT ATG TAT GTA AAA ATA TAG TAG AAT TTC ATT TTG TTT TTT TCT ATG CTA TAA ATA GGC TGC A-3').

2.8 pTKm-sP11 (SEQ ID NO:2)

The 3.3 kb SmaI/BalI fragment, encompassing the E. coli lacZ gene regulated by the synthetic vaccinia late promoter was prepared from the plasmid pFP-ZsP11 and inserted into the vector pTKm linearized with SmaI. The resulting plasmid was designated pTKm-sP11. Features of this plasmid are outlined in the table below.

pTKm-sP11 (8313bv) SEQ ID NO: 2

| location | description |
|---|---|
| 1–2459 | pTZ19R (Pharmacia). Position 1 corresponds to the first nucleotide C starting with the motif: 5'-CTTCCGCTT-3'. |
| 2460–3449 | Unsequenced portion of the fowlpox virus FPV-tk gene flanking region. |
| 3450–4111 | left flanking region and FPV-tk sequence as described in Boyle et al., Virology 156:3SS-356 (1987). (EMBL ID PXFPVTK) |
| 3558–4106 | CDS of FPV-tk gene |
| 4112–4125 | enlarged intergenic region sequences |
| 4126–4198 | sP11-Promoter sequences corresponding to the oligonucleotide II (2.7 pFP-ZsP11) |
| 4213–7317 | CDS of the E. Coli lacz-gene |
| 7442–7448 | enlarged intergenic region sequences |
| 7449–7947 | right flanking region of the FPV-tk sequence as described in Boyle et al., 1987. (EMBL ID PXFPVTK) |
| 7948–8259 | unsequenced portion of the FPV-tk gene flanking region including BamHI site |
| 8260–8313 | pTZ19R–. |

2.9 pTKm-sP11-gpt pTKm-sP11 was linearized with SmaI and ligated with the 1.1 kb Hpa 1-Dra I P7.5-gpt gene cassette excised from the plasmid pTKgpt-F1s (Falkner & Moss; J. Virol., 62, 1849–1854 (1988)). The resulting plasmid was designated pTKm-sP11-gpt.

2.10 pTKm-VVtka and b (SEQ ID NOS. 3 and 4, respectively)

These palsmids were constructed by inserting the complete vaccinia virus thymidine kinase gene, prepared as a 1.1 b Dra I fragment from pGS50 (Mackett & Smith; J. Gen. Virol., 67, 2067–2082 (1986)) into the SmaI linearized vector pTKm-sP11. The resulting plasmids were designated pTKm-VVtka and b. Features of these plasmids are outlined in the tables below.

pTKm-Vvtka (9454bp SEQ ID NO: 3)

| location | description |
|---|---|
| 1–2459 | pTZ19R (Pharmacia). Position 1 corresponds to the first nucleotide C starting with the motif: 5'-CTTCCGCTT-3'. |
| 2460–3449 | Unsequenced portion of the fowlpox virus FPV-tk gene flanking region. |
| 3450–4111 | left flanking region and FPV-tk sequence as described in Boyle et al., Virology 156:355-356 (1987). (EMBL ID PXFPVTK) |
| 3558–4106 | CDS of FPV-tk gene |
| 4112–4125 | enlarged intergenic region sequences |
| 4126–4266 | VV tk-gene sequences derived as a 1.15kb DraI fragment from the plasmid pGS50 (Fuerst et al., 1987) |
| 4360–4890 | CDS VV tk-gene (EMBL ID PVHINLJ) |
| 5267–5339 | sP11-Promoter sequences corresponding to the oligonucleotide II (2.7 pFP-ZsP11) |
| 5354–8458 | CDS of the E. coli lacZ-gene |
| 8583–8589 | enlarged intergenic region sequences |
| 8590–9088 | right flanking region of the FPV-tk sequence as described in Boyle et al, 1987. (EMBL ID PXFPVTK) |
| 9089–9400 | unsequenced portion of the FPV-tk gene flanking region including BamHI site. |
| 9401–9454 | pTZ19R–. | pTKm-VVtkb (9454bp SEQ ID NO: 4)

| location | description |
|---|---|
| 1–2459 | pTZ19R (Pharmacia). Position 1 corresponds to the first nucleotide C starting with the motif: 5'-CTTCCGCTT-3'. |
| 2460–3449 | Unsequenced portion of the fowlpox virus FPV-tk gene flanking region. |
| 3450–4111 | left flanking region and FPV-tk sequence as described in Boyle et al., Virology 156:355-356 (1987). (EMBL ID PXFPVTK) |
| 3558–4106 | CDS of FPV-tk gene |
| 4112–4125 | enlarged intergenic region sequences |
| 4126–4266 | rc VV tk-gene sequences derived as a 1.15kb DraI fragment from the plasmid pGS50 (Fuerst et al., 1987) |
| 4502–5032 | rcCDS VV tk-gene (EMBL ID PVHINLJ) |
| 5267–5339 | sP11-Promoter sequences corresponding to the oligonuclectide II (2.7 pFP-ZsP11) |
| 5354–8458 | CDS of the E. coli lacZ-gene |
| 8583–8589 | enlarged intergenic region sequences |
| 8590–9088 | right flanking region cf the FPV-tk sequence as described in Boyle et al, 1987. (EMBL ID PXFPVTK) |
| 9089–9400 | unsequenced portion of the FPV-tk gene flanking region including BamHI site. |
| 9401–9454 | pTZ19R–. |

2.11 M13mp18-UV1

As a first step, the 1.2 kb PstI/SauI fragment derived from the insertion vector pFP-UV2 (see 2.4) was subcloned into M13mp18. This fragment encompasses the promoters of the vaccinia virus genes coding for the 11K (P11; Bertholet et al; Proc. Natl. Acad. Sci. U.S.A., 82, 2096–2100 (1985)) and 7.5K polypeptides (P7.5; Cochran et al; J. Virol., 54, 30–37 (1985)) and part of the lacZ gene. The resulting plasmid was designated M13mp18-UV1.

2.12 M13mp18-Eco2

Oligonucleotide directed mutagenesis (Amersham, Inc.) was used to introduce a second EcoRI site 7 bp upstream the ATG of the lacZ gene of M13mp18-UV1, creating the intermediate plasmid M13mp1S-Eco2. The mutagenic primer used to alter the lacZ upstream region had the sequence 5'-ACC ATA TGT AAG GAA TTC CTT AGA TAA-3'.

2.13 pFP-UV2-Eco2

The modified PstI/SauI promoter fragment prepared from M13mp18-Eco2 was inserted into PstI/SauI cut pFP-UV2 and the resulting vector was designated pFP-UV-2-Eco2.

2.14 pFP-Z1

The plasmid pFP-Z1 was constructed by deleting the 0.9 kb EcoRI P11/P7.5 fragment from pFP-UV2-Eco2, thereby placing the multiple cloning site immediately upstream the lacZ gene.

2.15 pFP-Z21 (SEQ ID NO:5)

The plasmid pFP-Z21 was constructed by introducing a synthetic linker sequence (SEQ ID NO:31) (5'-CGA TTG GCC AGG ATC CGT CGA CAG GCC TAT-3'; complementary strand (SEQ ID NO:32), 5'-CGA TAG GCC TGT CGA CGG ATC CTG GCC AAT-3') into the partially ClaI digested vector pFP-Z1. This modification allows the simple excision of the lacZ gene. Features of this plasmid are outlined in the table below.

pFP-Z21 (8775bp) SEQ ID NO: 5

| location | description |
|---|---|
| 1–2459 | pTZ19R (pharmacia). Position 1 corresponding to the first nucleotide C starting with the motif: 5'-CTTCCGCTT-3'. |
| 2460–3449 | Unsequenced portion of the fowlpox virus FPV-tk gene flanking region. |
| 3450–3866 | left portion of the FPV-tk (Boyle et al, 1987) (EMBL ID PXFPVTK), down to the unique Klenow Pol-treated NcoI site of the FPV-tk gene |
| 3558 | ATG of the FPV-tk gene |

| pFP-Z21 (8775bp) SEQ ID NO: 5 | |
|---|---|
| location | description |
| 3866 | G-residue of the unique Klenow Pol-treated NcoI site of the FPV-tk gene. |
| 3867–7661 | Sequences of the plasmid pUV1 (Falkner et al., nucl. Acids Res., 15: 7192 (1987). |
| 4402–7506 | rcCDS of *E. coli* lacZ-gene |
| 4401 | A residue of the rc stop codon ATT |
| 7506 | T residue of the rc start codon TAC |
| 7662–8409 | right portion of the FPV-tk (Boyle et al, 1987 (EMBL ID PXFPVTK), down from the unique Klenow Pol-treated NcoI site of the FPV-tk gene. |
| 7662 | C residue of the unique Klenow Pol-treated NcoI site |
| 7906 | T residue of the FPV-tk gene stop codon TAA |
| 8410–8721 | unsequenced portion of the FPV-tk gene flanking region including BamHI site. |
| 8722–8775 | pTZ19R--. |

2.16 pFP-2

The plasmid pFP-2 was isolated from a library constructed by inserting random fragments of SspI/EcoRV digested FPV-DNA (HP1-441) into the plasmid pFP-Z1 linearized with SmaI.

2.17 pFP-ZP2

The 0.6 kb EcoRI/NsiI fragment containing the P2 promoter activity was prepared from pFP-2. This fragment was ligated with the EcoRI/PstI linearized vector pFP-Z21.

2.18 pTZgpt-P2a (SEQ ID NO:6) and pTZgpt-P2b (SEQ ID NO:7)

These plasmids were constructed by inserting the P2-lacZ gene cassette derived from pFP-ZP2 (a 3.7 kb SmaI/StuI fragment) into the HpaI linearized plasmid pTZgpt-dP (see 2.27). The resulting vectors were designated pTZgpt-P2a and pTZgpt-P2b. Features of these plasmids are outlined in the tables below.

| pTZgpt-P2a (10408bp) SEQ ID NO: 6 | |
|---|---|
| location | description |
| 1–87 | pUC13 Position 1 corresponds to the first nucleotide C starting with the motif 5'-CAG CTG GCG ###GGG-3'. |
| 88–1028 | left portion of the rc VV-tk gene (EMBL ID PVHINLJ) and the flanking region down to the unique Klenow Pol-treated ScoRI site of the VV-tk gene. These sequences are derived from the plasmid pGS50 (Fuerst et al., Mol. Cell. Biol., 7: 2538–2544 (1987). |
| 771 | A-residue of the rc stop codon ATT of the VV-tk gene |
| 1028 | Second T-residue of the Klenow Pol-treated EcoRI site of the VV-tk gene |
| 1047 | second T-residue of HpaI-linker 5'-GGTTAACC-3'. |
| 1048–4854 | P2-lacZ-insert (3807bp) |
| 1154–4258 | rc CDS of lacz-gene |
| 4876–5158 | P7.5 promoter |
| 5357–5812 | CDS *E. coli* gpt gene |
| 6947–7715 | right portion of the rc VV-tk gene (EMBL ID PVHINLJ) and the flanking region up to the unique Klenow Pol-treated EcoRI site of the VV-tk gene. These sequences are derived from the plasmid pGS50 (Puerst et al, 1987) |
| 6947 | first A-residue of the Klenow Pol-treated EcoRI site of the VV-tk gene |
| 7224 | T residue of the rc start codon TAC of the VV-tk gene |
| 7716–7898 | pUC13 sequences |
| 7899–10408 | pTZ19R (Pharmacia) |

| PTZgpt-P2b (10408) SEQ ID NO: 7 | |
|---|---|
| 1–87 | pUC13 Position 1 corresponds to the first nucleotide C starting with the motif 5'-CAG CTG CCC-3'. |
| 8–1028 | left portion of the rc VV-tk gene (EMBL ID.PVHINLJ) and the flanking region down to the unique Klenow Pol-treated EcoRI site of the VV-tk gene. These sequences are derived from the plasmid pGS50 (Fuerst et al., Mol. Cell. Biol., 7: 2538–2544 (1987). |
| 771 | A residue of the rc stop codon ATT of the VV-tk gene |
| 1028 | second T residue of the Klenow Pol-treated EcoRi site of the VV-tk gene |
| 1047 | second T residue of HpaI-linker 5'-GGTTAACC-3'. |
| 1048–4854 | P2-lacZ insert (3807bp) |
| 1644–4748 | CDS of lacz-gene |
| 4876–5158 | P7.5 promoter |
| 5357–5812 | CDS *E. coli* gpt gene |
| 6947–7715 | right portion of the rc VV-tk gene (EMBL ID PVHINLJ) and the flanking region up to the unique Klenow Pol-treated EcoRI site of the VV-tk gene. These sequences are derived from the plasmed pGS50 (Fuerst et al., 1987) |
| 6947 | first A residue of the Klenow Pol-treated EcoRI site of the VV-tk gene |
| 7224 | T residue of the rc start codon TAC of the VV-tk gene |
| 7716–7898 | pUC13 sequences |
| 7899–10408 | pTZ19R (Pharmacia)--; |

2.19 pFS50 (SEQ ID NO:8)

In a first step, the plasmid pTZ19R (Pharmacia) was digested with PvuII to delete a 349 bp fragment containing the multiple cloning site and adjacent sequences. This vector fragment was ligated with a 1.1 kb vaccinia tk-gene fragment prepared from pGS50 by DraI digestion. The resulting plasmid was designated pFS50. Features of this plasmid are outlined in the table below.

| pFS50 (3656bp) SEQ ID NO: 8 | |
|---|---|
| location | description |
| 1–55 | pTZ19R (Pharmacia). Position 1 corresponds to the first nucleotide C starting with the motif: 5'-AGC GCC CAA-3'. |
| 56–1197 | VV-tk gene (EMBL ID PVHINLJ) sequences derived as a 1.15kb DraI from the plasmed pGS50 (Fuerst et al., Mol. Cell. Biol., 7: 2538–2544 (1987)). |
| 291–821 | CDS VV-tk gene |
| 1198–3656 | pTZ19R (Pharmacia)--. |

2.20 pFS51 (SEQ ID NO:9)

pFS50 was cut with ClaI and EcoRI and ligated with a synthetic linker (P-MCS1 and 2). This vector was designated pFS51. The oligonucleotides used for linker construction had the sequence: P-MCS1 (bases 533–596 of SEQ ID NO:9), 5'-CGA GCA GCTG CAT ATG AGG CCT GGA TCC CGG GTC GAC GCG GCC GCT AAC TGA CTG ATT TTT CTC-3' and P-MCS2 (SEQ ID NO:33), 5'-AAT TGA GAA AAA TCA GTC AGT TAG CGG CCG CGT CGA CCC GGG ATC CAG GCC TCA TAT GCA GCT GCT-3'. Features of this plasmid are outlined in the table below.

| pFS51 (3688bp) SEQ. ID NO: 9 | |
|---|---|
| location | description |
| 1–55 | pTZ19R (Pharmacia). Position 1 corresponds to the first nucleotide C starting with the motif: 5'-AGC GCC CAA-3'. |
| 56–532 | VV-tk gene (EMBL ID PVHINLJ) sequences and flanking region down to the destroyed ClaI site in the VV-tk |

-continued pFS51 (3688bp) SEQ. ID NO: 9

| location | description |
|---|---|
| | gene. [plasmid pGS50 (Fuerst et al., Mol. Cell. Biol., 7: 2538–2544 (1987) sequences] |
| 291 | A residue of the initiation codon ATG of the VV-tk gene |
| 533–596 | multiple cloning site corresponding to the oligonucleotide P-MCS1(2.20 construction pFS51) |
| 597–1229 | VV-tk gene (EMBL ID PVHINLJ) sequences and flanking region down from the destroyed EcoRI site in the VV-tk gene. (plasmid pGS50 (Fuerst et al., 1987) sequences) |
| 597 | first A residue of the destroyed EcoRI site in the VV-tk gene. |
| 854 | T residue in the VV-tk gene stop codon TAA |
| 1230–3688 | pTZ19R (Pharmacia)–; |

2.21 pFSgpt (SEQ ID NO:10)

The plasmid pFSgpt was generated by subcloning a 0.98 kb P7.5-gpt gene cassette, prepared from pTKgpt-F1s (Falkner & Moss; J. Virol., 62, 1849–1854 (1988)) by digestion with NdeI and DraI, into the PvuII/NdeI cut plasmid pFS51. Features of this plasmid pFSgpt are outlined in the table below.

pFSgpt (4659bp) SEQ ID NO: 10

| location | description |
|---|---|
| 1–55 | pTZ19R Pharmacia). Position 1 corresponds to the first nucleotide C starting with the motif: 5'-AGC GCC CAA-3'. |
| 56–532 | VV-tk gene (EMBL ID PVHINLJ) sequences and flanking region down to the destroyed ClaI site in the VV-tk gene. [plasmid pGS50 (Fuerst et al., Mol. Cell. Biol., 7: 2538–2544 (1987)) sequences] |
| 291 | A residue of the initiation codon ATG of the VV-tk gene |
| 679–1134 | rcCDS of the E. coli gpt gene |
| 1329–1515 | rc P7.5 |
| 1516–1567 | multiple cloning site |
| 1568–2200 | VV-tk gene (EMBL ID PVHINLJ) sequences and flanking region down from the destroyed EcoRI site in the VV-tk gene. (plasmid pGS50 (Fuerst et al., 1987) sequences) |
| 1568 | first A residue of the destroyed EcoRI Bile ionquthe VV-tk gene. |
| 1825 | T residue in the VV-tk gene stop codon TAA |
| 2201–4659 | pTZ19R (Pharmacia)–; |

2.22 pP2m0gpt (SEQ ID NO:11)

Synthetic oligonucleotides encoding the mutant m0 P2 promoter were annealed and inserted by forced cloning into the NdeI/BamHI linearized vector pFSgpt. The nucleotide sequences of these oligonucleotides are as follows: m0.1 (bases 1516–1685 of SEQ ID NO:11): 5'-TAC GGC TTG GTA TAG CGG ACA ACT AAG TAA TTG TAA AGA AGA AAA CGA AAC TAT CAA AAC CGT TTA TGA AAT GAT AGA AAA AAG AAT ATA AAT AAT CCT GTA TTT TAG TTT AAG TAA CAG TAA AAT AAT GAG TAG AAA ATA CTA TTT TTT ATA GCC TAT AAA TCA TGA ATT CG-3'. m0.2 (SEQ ID NO:34): 5'-GATC CGA ATT CAT TTA TAG GCT ATA AAA AAT AGT ATT TTC TAC TCA TTA TTT TAC TGT TAC TTA AAC TAA AAT ACA GGA TTA TTT ATA TTC TTT TTT CTA TCA TTT CAT AAA CGG TTT TGA TAG TTT CGT TTT CTT CTT TAC AAT TAC TTA GTT GTC CGC TAT ACC AAG CCG-3'. The resulting plasmid was designated pP2m0gpt. Features of this plasmid are outlined in the table below.

pP2m0gpt (4818bp) SEQ ID NO: 11

| location | description |
|---|---|
| 1–55 | pTZ19R (Pharmacia). Position 1 corresponds to the first nucleotide C starting with the motif: 5'-AGc GCC CAA-3'. |
| 56–532 | VV-tk gene (EMBL ID PVHINLJ) sequences and flanking region down to the destroyed ClaI site in the VV-tk gene. (plasmid PGSSO (Puerat et al., Mol. Cell. Biol., 7: 2538–2544 (1987)) sequences) |
| 291 | A residue of the initiation codon ATG of the VV-tk gene |
| 679–1234 | rcCDS of the E. coli gpt gene |
| 1329–1515 | rc P7.5 |
| 1516–1685 | P2m0 promoter sequence corresponding to the oligonucleotide m0.1 (2.22 construction of the plasmid pP2m0gpt) |
| 1678 | second T residue of the TAAAT promoter motif |
| 1727–2359 | VV-tk gene (EMBL ID PVHINLJ) sequences and flanking region down from the destroyed EcoRI Bite in the Vv-tk gene. (plasmid pGS50 (Fuerat et al., 1987) sequences) |
| 1727 | first A residue of the destroyed EcoRI site in the Vv-tk gene. |
| 1984 | T residue in the VV-tk gene stop codon TAA |
| 2360–4818 | pTZ19R (Pharmacia)–. |

2.23 pP2m1gpt (SEQ ID NO:12)

To construct pP2m1gpt the synthetic linker sequences m1.1 and m1.2 were annealed and ligated with the NdeI/BamHI linearized vector pFSgpt. The oligonucleotides had the following sequences: m1.1 (bases 1516–1688 of SEQ ID NO:12): 5'-TAC GGC TTG GTA TAG CGG ACA ACT AAG TAA TTG TAA AGA AGA AAA CGA AAC TAT CAA AAC CGT TTA TGA AAT GAT AGA AAA AAG AAT ATA AAT AAT CCT GTA TTT TAG TTT AAG TAA CAG TAA AAT AAT GAG TAG AAA ATA CTA TTT TTT ATA GCC TAT AAA TCA TGA ATT CG-3'. m1.2 (SEQ ID NO:35): 5'-GAT CCG AAT TCA TGA TTT ATA GGC TAT AAA AAA TAG TAT TTT CTA CTC ATT ATT TTA CTG TTA CTT AAA CTA AAA TAC AGG ATT ATT TAT ATT CTT TTT TCT ATC ATT TCA TAA ACG GTT TTG ATA GTT TCG TTT TCT TCT TTA CAA TTA CTT AGT TGT CCG CTA TAC CAA GCC G-3'. The resulting plasmid was designated pP2m1gpt. Features of this plasmid are outlined in the table below.

pP2m1gpt (4821bp) SEQ ID NO: 12

| location | description |
|---|---|
| 1–55 | pTZ19R (Pharmacia). Position 1 corresponds to the first nucleotide C starting with the motif: 5,-ACC GCC CAA-3'. |
| 56–532 | VV-tk gene (EMBL ID PVHINLJ) sequences and flanking region down to the destroyed ClaI site in the vv-tk gene. [plasmid pGS50 (Fuerst et al., Mol. Cell. Biol., 7: 2538–2544, (1987)) sequences] |
| | A residue of the initiation codon ATG of the VV-tk gene |
| 679–1134 | rcCDS of the E. coli gpt gene |
| 1329–1515 | rc P7.5 |
| 1516–1678 | P2ml promoter sequence |
| 1678 | second T residue of the TAAAT promoter motif |
| 1730–2362 | VV-tk gene (EMBL ID PVHINLJ) sequence and flanking region down from the destroyed EcoRI site in the Vv-tk gene. (plasmid pGS50 (Fuerat et al., 1987) sequences) |
| 1730 | first A residue of the destroyed EcoRI site in the vv-tk gene. |
| 1987 | T residue in the VV-tk gene stop codon TAA |
| 2363–4821 | pTZ19R (Pharmacia)–; |

2.24 pP2m2gpt (SEQ ID NO:13)

The vector pP2m2gpt was created by ligation of annealed oligonucleotides m2.1 and m2.2 with the NdeI/BamHI cut plasmid pFSgpt. The oligonucleotides used for cloning had the following sequences: m2.1 (bases 1516–1691 of SEQ ID NO:13): 5'-TAC GGC TTG GTA TAG CGG ACA ACT AAG TAA TTG TAA AGA AGA AAA CGA AAC TAT CAA AAC CGT TTA TGA AAT GAT AGA AAA AAG AAT ATA AAT AAT CCT GTA TTT TAG TTT AAG TAA CAG TAA AAT AAT GAG TAG AAA ATA CTA TTT TGT TTT ATA GCC TAT AAA TCA TGA ATT CG-3'. m2.2 (SEQ ID NO:36): 5'-GATC CGA ATT CAT GAT TTA TAG GCT ATA AAA CAA AAT AGT ATT TTC TAC TCA TTA TTT TAC TGT TAC TTA AAC TAA AAT ACA GGA TTA TTT ATA TTC TTT TTT CTA TCA TTT CAT AAA CGG TTT TGA TAG TTT CGT TTT CTT CTT TAC AAT TAC TTA GTT GTC CGC TAT ACC AAG CCG-3'. The resulting plasmid was designated pP2m2gpt. Features of this plasmid are outlined in the table below.

| \_\_\_pP2m2gpt (4824bp) SEQ ID NO: 13\_\_\_ | |
|---|---|
| location | description |
| 1–55 | pTZ19R (Pharmacia). Position 1 corresponds to the first nucleotide C starting with the motif: 5'-AGC GCC CAA-3'. |
| 56–532 | VV-tk gene (EMBL ID PVHINLJ) sequences and flanking region down to the destroyed ClaI site in the vv-tk gene. [plasmid pGS50 (Fuerat et al., Mol. Cell. Biol., 7: 2538–2544, (1987)) sequences) |
| 291 | A residue of the initiation codon ATG of the Vv-tk gene |
| 679–1134 | rcCDS of the E. coli gpt gene |
| 1329–1515 | rc P7.5 |
| 1516–1681 | P2m2 promoter sequence |
| 1681 | second T-residue of the TAAAT promoter-motif |
| 1733–2365 | VV-tk gene (EMBL ID PVHINLJ) sequences and flanking region down from the destroyed EcoRI site in the Vv-tk gene. (plasmid pGS50 (Fuerst et al., 1987) sequences) |
| 1733 | first A residue of the destroyed EcoRI site in the Vv-tk gene. |
| 1990 | T residue in the VV-tk gene stop codon TAA |
| 2366–4824 | pTZ19R (Pharmacia)–. |

2.25 pP2m0gpt-lacZ, pP2m1gpt-lacZ and pP2m2gpt-LacZ/ pP2mxgpt-lacZ)

The construction of pP2m0gpt-lacZ, pP2m1gpt-lacZ and pP2m2gpt-lacZ was done by inserting the E. coli lacZ gene as a 3.2 kb EcoRI/BalII fragment (derived from plasmid pFP-Z21) into the EcoRI/SmaI linearized vectors pP2m0gpt-lacZ, pP2m1gpt and pP2m2gpt, respectively.

2.26 pTZgpt-F1s (SEQ ID NO:14)

The vaccinia virus insertion vector pTZgpt-F1s was constructed by replacing the 2.4 kb PvuII fragment (originally derived from the plasmid pUC 18) of pTKgpt-F1s (Falkner & Moss; J. Virol., 62, 1849–1854 (1988)) by the 2.5 kb PvuII fragment from the plasmid pTZ19R (Pharmacia, Inc.). In addition to the ampicillin resistance gene and the plasmid origin of replication (also present on the 2.4 kb pUC PvuII fragment) the bacteriophage f1 origin of replication was introduced into pTKgpt-F1s by this cloning step. Features of this plasmid are outlined in the table below.

| \_\_\_pTgpt-F1s (7218bp) SEQ ID NO: 14\_\_\_ | |
|---|---|
| location | description |
| 1–87 | pUC13 Position 1 corresponds to the first nucleotide C starting with the motif 5'-CAG CTG GCG-3'. |
| 88–4708 | Sequences derived from the plasmid pTKgpt-F1o (Falkner et al. J. Virol., 62:1849-1854 (1988)) |
| 88–1028 | left portion of the rc VV-tk gene (EMBL ID PVHINLJ) |

| \_\_\_pTgpt-F1s (7218bp) SEQ ID NO: 14\_\_\_ | |
|---|---|
| location | description |
| | and the flanking region down to the unique Klenow Pol-treated EcoRI site of the VV-tk gene. These sequences are derived from the plasmid pGS50 (Fuerst et al., Mol. cell. Biol., 7: 2538–2544, (1987)). |
| 771 | A residue of the rc stop codon ATT of the vv-tk gene |
| 1028 | Second T residue of the Klenow Pol-treated EcoRI site of the VV-tk gene |
| 1029–1630 | PII promoter sequences |
| 1630 | G residue in the P11 motif 5'-TAAATG-3'. |
| 1631–1685 | multiple cloning site |
| 1686–1968 | P7.5 promoter |
| 2167–2622 | CDS E. coli gpt gene |
| 3757–4525 | right portion of the rc VV-tk gene (EMBL ID PVHINLJ) and the flanking region up to the unique Klenow Pol-treated EcoRI site of the VV-tk gene. These sequences are derived from the plasmid pGS50 (Puerst et al., 1987) |
| 3757 | first A residue of the Klenow #Pol-treated EcoRI site of the VV-tk gene |
| 4034 | T residue of the rc start codon TAC of the Vv-tk gene |
| 4526–4708 | pUC13 sequences |
| 4709–7218 | pTZ19R (Pharmacia)–; |

2.27 pTZgpt-dP (SEQ ID NO:15)

The P11 promoter of pTZgpt-F1s was deleted by digestion of PstI and HpaI and the large vector fragment ligated with HpaI linkers (5'-GGTTAACC-3', Pharmacia Inc.). The resulting plasmid was designated pTZgpt-dP. Features of this plasmid are outlined in the table below.

| \_\_\_pTZgpt-dP (6596bp) SEQ ID NO: 15\_\_\_ | |
|---|---|
| location | description |
| 1–87 | pUC13 Position 1 corresponds to the first nucleotide C starting with the motif 5'-CAG CTG GCG-3'. |
| 88–1028 | left portion of the re VV-tk gene (EMBL ID PVHINLJ) and the flanking region down to the unique Klenow Pol-treated EcoRI site of the Vv-tk gene. These sequences are derived from the plasmid PGSSO (Fuerst et al., Sol. Cel.Z. Biol., 7: 2538–2544 (1987)) |
| 771 | A residue of the rc stop codon ATT of the Vv-tk gene |
| 1028 | second T residue of the Klenow Pol-treated EcoRI site of the VV-tk gene |
| 1043 | C residue of former PstI site |
| 1047 | Second T residue of HpaI-linker 5'-GGTTAACC-3'. |
| 1069–1351 | P7.5 promoter |
| 1550–2005 | CDS E. coli gpt gene |
| 3140–3908 | right portion of the rc VV-tk gene (EMBL ID PVHINLJ) and the flanking region up to the unique Klenow Pol-treated EcoRI site of the VV-tk gene. These sequences are derived from the plasmid pGS50 (Fuerat et al., 1987) |
| 3140 | first A residue of the Klenow Pol-treated EcoRI site of the VV-tk gene |
| 3417 | T residue of the rc start codon TAC of the Vv-tk gene |
| 3909–4091 | pUC13 sequences |
| 4092–6601 | pTZ19R (Pharmacia)–. |

2.28 M13mp18-UV3

The plasmid M13mp18-UV3 was constructed by oligonucleotide directed in vitro mutagenesis (Pharmacia, Inc.) of the P11 promoter in the vector M13mp18-UV1 (see 2.11). The oligonucleotide used to alter the promoter region had the sequence (SEQ ID NO:37): 5'-TAGCTATAA ATAAA-GAATT CCTGCAG-3'-.

2.29 pTZgpt-P11M

The vaccinia virus recombination plasmid pTZgpt-P11M was constructed by inserting a 600 bp HindIII/Asp718 Klenow polymerase treated fragment derived from M13mp18-UV3 into the HpaI digested pTZgpt-dP plasmid. This fragment contains the mutated P11 promoter (P11M).

2.30 pFP-ZsP11

The oligonucleotides sP11(3) and sP11(4) were annealed and cloned into the SmaI/PstI cut vector pFP-Z21 (see 2.15). The sequences of sP11(3) (bases 4295–4363 of SEQ ID NO:16) and of sP11(4) (SEQ ID NO:38) were 5'-GCCTATTTAT AGCATAGAAA AAAACAAAAT GAAATTCTAC TATATTTTTA CATACATATA TTCTAACCC-3' and 5'-GGGTTAGAAT ATATGTATGT AAAAATATAG TAGAATTTCA TTTTGTTTTT TTCTAT- GCTA TAAATAGGCT GCA-3', respectively. The resulting plasmid was designated pFP-ZsP11.

2.31 pTZgpt-sP11 (SEQ ID NO:16)

pFP-ZsP11 was digested with SmaI/BalI and the 3.3 kb fragment containing the synthetic promoter sequence linked to the lacZ gene was cloned into the vaccinia virus insertion vector pTZgpt-dP (see 2.27). The resulting plasmid was designated pTZgpt-sP11. Features of this plasmid are outlined in the table below.

| pTZgpt-sP11 (9917bp) SEQ ID NO: 16 | |
|---|---|
| location | description |
| 1–87 | pUC13 Position I corresponds to the first nucleotide C starting with the motif 5'-CAG CTG GCG-3'. |
| 88–1028 | left portion of the rc VV-tk gene (EMBL ID PVHINLJ) and the flanking region down to the unique Klenow Pol-treated EcoRI site of the VV-tk gene. These sequences are derived from the plasmid PGSSO (Fuerst et al., Mol. Cell. Biol., 7: 2538–2544 (1987)) |
| 771 | A residue of the rc stop codon ATT of the VV-tk gene |
| 1028 | second T residue of the Klenow Pol-treated EcoRI site of the VV-tk gene |
| 1043 | C residue of former PatI site |
| 1047 | Second T residue of HpaI-linker 5'-GGTTAACC-3'. |
| 1048 | first C residue of defective BalII site |
| 1172–4276 | rcCDS of E. coli lacz-gene |
| 4363 | third C residue of defective SmaI site |
| 4385–4667 | P7.5 promoter |
| 4866–5321 | CDS E. coli gpt gene |
| 6456–7224 | right portion of the rc VV-tk gene (EMBL ID PVHINLJ) and the flanking region up to the unique Klenow Pol-treated EcoRI site of the VV-tk gene. These sequences are derived from the plasmid PGSSO (Fuerst et al., 1987) |
| 6456 | first A residue of the Klenow Pol-treated EcoRI site of the VV-tk gene |
| 6733 | T residue of the rc start codon TAC of the VV-tk gene |
| 7225–7407 | pUC13 sequences |
| 7408–9917 | pTZ19R (Pharmacia)–; |

2.32 pFP-Zs4b

The oligonucleotides s4b(3) and s4b(4) were annealed and cloned into the SmaI/PstI cut vector pFP-Z21 (see 2.15). The sequences of s4b(3) (bases 4295–4362 of SEQ ID NO:17) and of s4b(4) (SEQ ID NO:39) were 5'-GCCTATTTAT ATTTGATAGT TTTTTACTTG TAACGTATCA AAATAAGTAC CTAAAGAGAC CTAACCCC-3' and 5'-GGGGTTACGT CTCTTTAGGT ACTTATTTTG ATACGTTACA AGTAAAAAAC TAT- CAAATAT AAATAGGCTG CA-3', respectively. The resulting plasmid was designated pFP-Zs4b.

2.33 pTZgpt-s4b (SEQ ID NO:17)

pFP-Zs4b was digested with SmaI/BalI and the 3.3 kb fragment containing the synthetic promoter sequence linked to the lacZ gene was cloned into the vaccinia virus insertion vector pTZgpt-dP (see 2.27). The resulting plasmid was designated pTZgpt-s4b. Features of this plasmid are outlined in the table below.

| pTZgpt-s4b (9916bp) SEQ ID NO: 17 | |
|---|---|
| location | description |
| 1–87 | pUC13 Position 1 corresponds to the first nucleotide C starting with the motif 5'-CAG CTG GCG-3'. |
| 88–1028 | left portion of the rc VV-tk gene (EMBL ID PVHINLJ) and the flanking region down_to the unique Klenow Pol-treated EcoRI site of the VV tk gene. These sequences are derived from the plasmid PGSSO (Fuerst et al., Mol. Cell. Biol., 7: 2538–2544 (1987)). |
| 771 | A residue of the rc stop codon ATT of the VV-tk gene |
| 1028 | second T residue of the Klenow Pol-treated EcoRI site of the VV-tk gene |
| 1043 | C residue of former PatI site |
| 1047 | second T residue of HpaI-linker 5#-GGTTAACC-3'. |
| 1048 | first C residue of defective BalI site |
| 1172–4276 | rcCDS of E. coli lacz-gene |
| 4362 | third C residue of defective SmaI site |
| 4384–4666 | P7.5 promoter |
| 4865–5320 | CDS E. coli gpt gene |
| 6455–7223 | right portion of the rc VV-tk gene (EMBL ID PVHINLJ) and the flanking region up to the unique Klenow Pol-treated EcoRI site of the VV-tk gene. These sequences are derived from the plasmid pGS50 (Fuerst et al., 1987) |
| 6455 | first A residue of the Klenow Pol-treated EcoRI site of the VV-tk gene |
| 6732 | T residue of the rc start codon TAC of the VV-tk gene |
| 7224–7406 | pUC13 sequences |
| 7407–9916 | pTZ19R (Pharmacia)– |

2.34 pFP-Zsart

The oligonucleotides sart(3) and sart(4) were annealed and cloned into the SmaI/PstI cut vector pFP-Z21 (see 2.15). The sequences of sart(3) (bases 4295–4366 of SEQ ID NO:18) and sart(4) (SEQ ID NO:40) were 5'-GCCTATTTAT ATGCCAAAAA AAAAAAAAAA AAAAAGCTTC CC-3' and 5'-GGGAAGCTTT TTTTTTTTTT TTTTTTTGGC ATATAAATAG GCTGCA-3', respectively. The resulting plasmid was designated pFP-Zsart.

2.35 pTZgpt-sart (SEQ ID NO:18)

pFP-Zsart was digested with SmaI/BalI and the 3.3 kb fragment containing the synthetic promoter sequence linked to the lacZ gene was cloned into the vaccinia virus insertion vector pTZgpt-dP (see 2.27). The resulting plasmid was designated pTZgpt-sart. Features of this plasmid are outlined in the table below.

| pTZgpt-sart (9890bp) SEQ ID NO: 18 | |
|---|---|
| location | description |
| 1–87 | pUC13 Position 1 corresponds to the first nucleotide C starting with the motif 5'-CAG CTG GCG AAA GGG-3'. |
| 88–1028 | left portion of the rc VV-tk gene (EMBL ID PVHINLJ) and the flanking region down to the unique Klenow Pol-treated EcoRI site of the VV-tk gene. TheBe sequences are derived from the plasmid PGSSO (Puerst et al., Mol. Cell. Biol., 7: 2538–2544 (1987)). |
| 771 | A residue of the rc stop codon ATT of the VV-tk gene |
| 1028 | second T residue of the Klenow Pol-treated EcoRI site of the VV-tk gene |
| 1043 | C residue of former PstI site |
| 1047 | second T residue of HpaI-linker 5'-GGTTAACC-3'. |
| 1048 | first C residue of defective BalI site |
| 1172–4276 | rcCDS of E. coli lacz-gene |
| 4336 | third C residue of defective SmaI site |
| 4358–4640 | P7.5 promoter |
| 4839–5294 | CDS E. coli gpt gene |
| 6429–7197 | right portion of the rc VV-tk gene (EMBL ID PVHINLJ) and the flanking region up to the unique Klenow Pol-treated EcoRI site of the VV-tk gene. These sequences are derived from the plasmid PGSSO (Fuerst et al., |

-continued

| | pTZgpt-sart (9890bp) SEQ ID NO: 18 |
|---|---|
| location | description |
| | 1987) |
| 6429 | first A residue of the Klenow Pol-treated EcoRI site of the VV-tk gene |
| 6706 | T residue of the rc start codon TAC of the VV-tk gene |
| 7198–7380 | pUC13 sequences |
| 7381–9890 | pTZ19R (Pharmacia)-. |

Recombinant viruses vf1sβ, vP11, vP11m, v4b and vart were derived from recombination plasmids pTKgptF1β (Falkner & Moss; J. Virol., 62, 1849–1854 (1988)), pTZgpt-sP11, pP11m-lacZ (T. Langmann, Diplomarbeit, Universit at Wien 1991), pTZgpt-s4b and pTZgpt-sart, respectively.

Figure 1A:
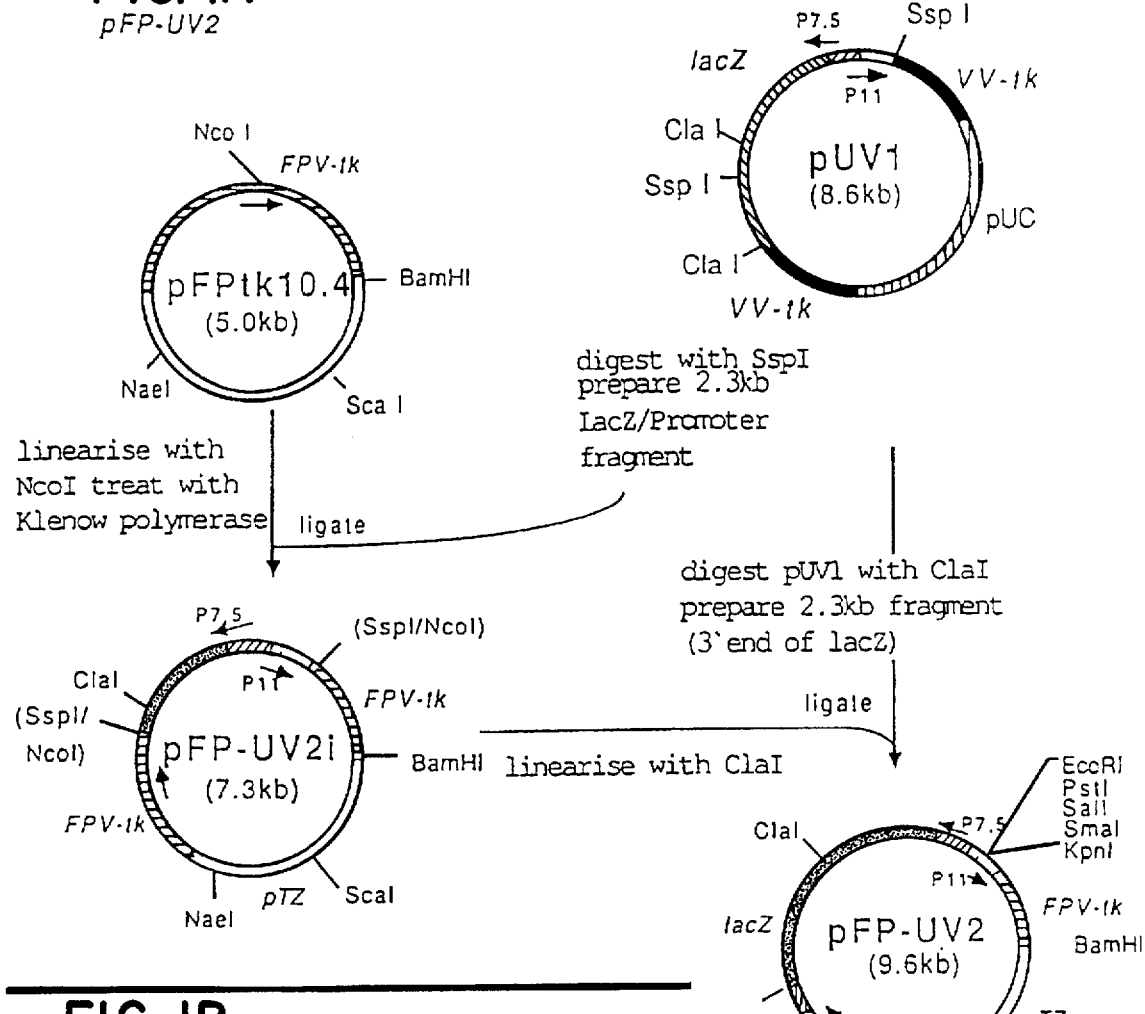
FIGS. 1A and 1B
Figure 1B:
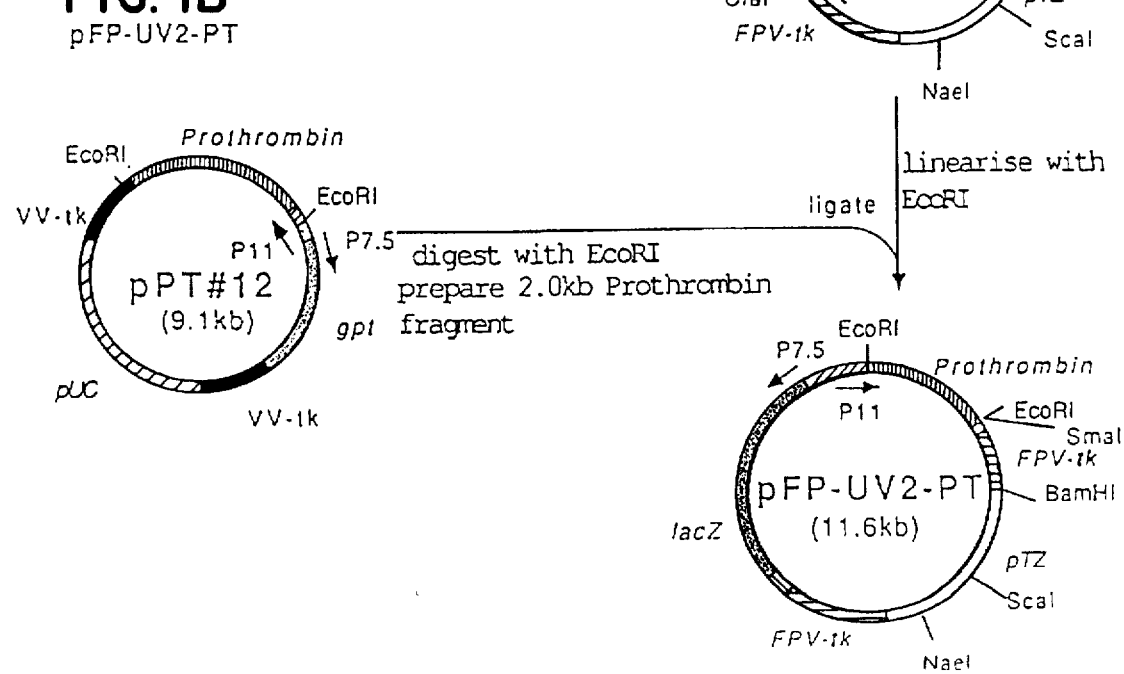

3. Relevance of the fowlpox virus thymidine kinase gene for growth in the cell culture 3.1 Construction of the FPV insertion plasmid pFP-UV2 and pFP-UV2-PT In the first type of plasmids constructed, pFP-UV2 and pFP-UV2-PT, the coding sequence of the fowlpox virus tk-gene is split into two fragments by the foreign gene inserts. The plasmid pFP-UV2 has a similar structure as the vaccinia virus insertion plasmid pUV1 (Falkner et al; Nucl. Acids Res., 15, 7192 (1987)). In pUV1 the *E. coli* lacZ reporter gene is driven by the vaccinia virus early/late P7.5 promoter (Cochran et al; J. Virol., 54, 30–37 (1985)). The promoter of the vaccinia virus major late 11K polypeptide (Bertholet et al; Proc. Natl. Acad. Sci. U.S.A., 82; 2096–2100 (1985)) is followed by the multiple cloning site and serves as the regulatory element of the foreign gene to be inserted. Both components are flanked by sequences of the vaccinia tk-gene (FIGS. 1A and 1B). The plasmid pFP-UV2 has the same arrangement of the lacZ reporter gene and the promoters. It is flanked, however, by fowlpox virus tk-gene sequences (FIGS. 1A and 1B). Insertion of pFP-UV2 into the genomic tk-locus of FPV by in vivo recombination will, as in the case of pUV1, result in the inactivation of the viral tk-gene. To construct this plasmid, the promoter-lacZ gene cassette of pUV1 was cloned in two steps into the unique NcoI site within the FPV tk-gene as outlined in FIG. 1A. To construct the recombination plasmid pFP-UV2-PT the human prothrombin cDNA was inserted into the vector pFP-UV2 downstream of the vaccinia 11K promoter. The plasmid pFP-UV2-PT was used for the construction of the first series of FPV recombinants.

3.2 Genomic characterization of FPV recombinants derived from pFP-UV2-PT

In order to investigate the functional properties of the plasmid pFP-UV2-PT, an in vivo recombination experiment in chicken embryo fibroblasts was carried out. Due to the lacZ reporter gene, recombinant virus could be identified by blue plaque screening. Several blue plaques were picked and plaque purified three times. Southern hybridizations of total DNA from cells infected with the FPV recombinants with the FPV tk-gene and the lacZ gene probes, however, revealed that the predicted banding pattern of the restriction fragments (one novel band of about 8.3 kb with the lacZ gene and two bands of about 1.9 and 8.3 kb with the FPV tk-gene probe) could not be observed. Instead a complex pattern of bands was seen, including the wild-type tk-gene band. One typical viral isolate, designated f-PT1 blue, was chosen for further rounds of plaque purification and Southern analysis. Beginning with the three times plaque purified isolate, a total of 11 rounds of plaque purification did not change the complex banding pattern significantly. In lanes 1–5 of FIG. 2A and 2B, the Southern analysis of viral DNAs of the 3rd, 5th, 7th, 9th and 11th round of plaque purification as visualized with the FPV tk-gene probe (FIG. 2A) and the lacZ gene probe (FIG. 2B) is shown. Another isolate, f-PT2 blue, showed a similar but not identical DNA banding pattern (FIG. 2A and 2B, lane 6).

During all rounds of plaque purification frequently white plaques were observed. Two white plaques, f-PT1 and 2 white, were analyzed together with the f-PT blue isolates. They hybridized with the lacZ gene probe but failed to develop the blue colour (FIG. 2B, lanes 8 and 9). Hybridization with the FPV tk-gene probe revealed in all cases the presence of the wild-type tk-gene (FIG. 2A, lanes 1 to 9, arrowhead). The FPV wild-type control is seen in lane 7 and the negative control (chicken embryo fibrolast DNA) in lane 10. To demonstrate that these unexpected findings were not due to a partial EcoRI digest the same blot as shown in FIG. 2A was hybridized to a prothrombin gene probe. As shown in FIG. 2C in all cases (except in lane 6; these larger bands may be due to a more complex recombination event in the f-PT2 blue genome) only one band, the 2.0 kb prothrombin band, was detected, indicating that the restriction digest was complete. The complex bands seen in FIG. 2A and 2B are therefore not artifacts due to a partial digest of the viral DNA, but reflect that the inactiviation of the viral tk-gene with the insertion plasmid pFP-UV2-PT a genomically monoclonal fowlpox recombinant could not be obtained.

3.3 Construction of the FPV insertion plasmid pTKm-sP11-gpt

In order to check the hypothesis, that the tk-gene is essential in FPV strain HP1.441, a novel insertion plasmid, pTKm, was constructed. The site of insertion of a foreign gene in this plasmid is located in the intergenic region between the tk-gene and the open reading frame downstream of the tk-gene (3'off). The wild-type intergenic region between the tk-gene and the 3'orf does not contain unique restriction sites for inserting foreign genes. This region was therefore modified as shown in FIG. 3. Immediately downstream of the stop codon of the tk-gene a vaccinia early transcription stop signal (Rohrmann G. et al, Cell 46:1029 (1986)) and the unique restriction sites ClaI, SmaI and Asp718 were introduced by site directed mutagenesis. Into the modified enlarged intergenic region of the plasmid pTKm the synthetic P11 promoter-lacZ gene cassette and the P7.5-gpt gene cassette were inserted in two steps. The plasmid finally obtained was designated pTKm-sP11-gpt (FIG. 4); it contains the lacZ gene for blue plaque screening and the gpt-gene as a selective marker. Upon integration into the viral genome, it will not split and inactivate the FPV tk-gene.

3.4 Recombinant fowlpox viruses with intact FPV tk-gene

The plasmid pTKm-sP11-gpt was subsequently used to construct FPV recombinants by in vivo recombination in chicken embryo fibroblasts. All plaques obtained under gpt-selection also stained blue in the presence of X-gal in the overlay. Only two rounds of plaque purification (under gpt-selection) were necessary to obtain the viral isolates.

Subsequently, one of the isolates, designated f-sP11#1, was grown to large scale and purified. Viral DNA of the recombinant and of wild-type virus was digested with EcoRI, separated on an agarose gel and analyzed by Southern blotting. In FIG. 5A–C different probes were used; the individual lanes represent the following:

A) Hybridization with the FPV tk-gene probe. Lane 1 represents DNA of FPV recombinant f-sP11#1, lane 2 represents DNA of the FPV wild type virus HP1.441; lane 3 represents lambda DNA digested with HindIII.

B) Hybridization with the gpt-gene probe. Lane 1 reresents lambda DNA digested with HindIII; lane 2 is DNA of FPV recombinant f-sP11#1; lane 3 is DNA of the FPV wild type virus HP 1.441.

C) Hybridization with the lacZ gene and phage lambda DNA probes. Lane 1 represents lambda DNA digested with HindIII; lane 2 is DNA of the FPV recombinant f-sP11#1; lane 3 is DNA of the FPV wild type virus HP1.441. The values given on the right for comparison correspond to standards in kilo basepairs.

Figure 5:
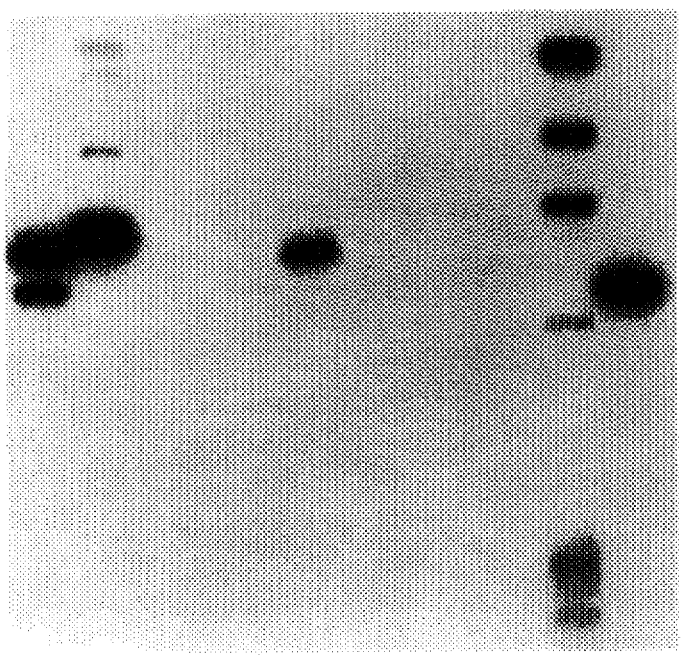

In FIG. 5A the restriction fragments were hybridized with the FPV tk-gene probe. In the recombinant DNA two novel fragments of 5.2 kb and 4.7 kb are visible (lane 1); in the control DNA the 5.5 kb wild-type tk-band can be seen. After hybridization with the gpt-gene probe (FIG. 5B), the 5.2 kb fragment that contains part of the tk-gene and the gpt sequences lights up (lane 2) while with the wild-type virus (lane 3) no signal is obtained. Finally, hybridization with the lacZ gene and the phage lambda probes (FIG. 5C) reveals the 4.7 kb lacZ gene containing fragment of the recombinant virus (lane 2) and the marker bands (lane 1). Again the wild-type virus (lane 3) does not hybridize.

It is concluded from this experiment that the intergenic region between the FPV tk-gene and the 3'orf is non-essential and that an intact tk-gene allows the purification of legitimate FPV recombinants.

3.5 Novel FPV host strains: f-TK2a and F-TK2b

Figure 4A:
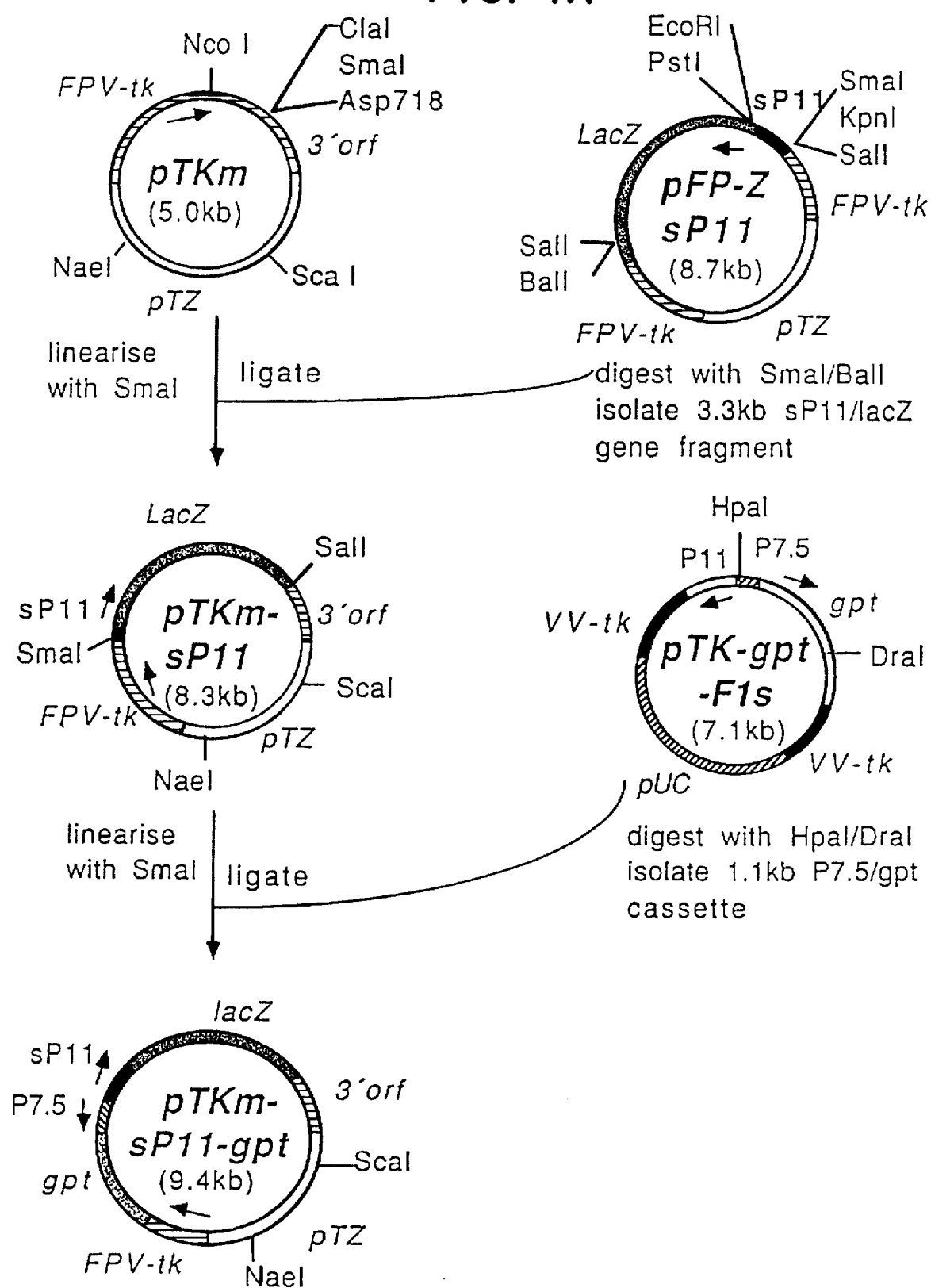
Figure 4B:
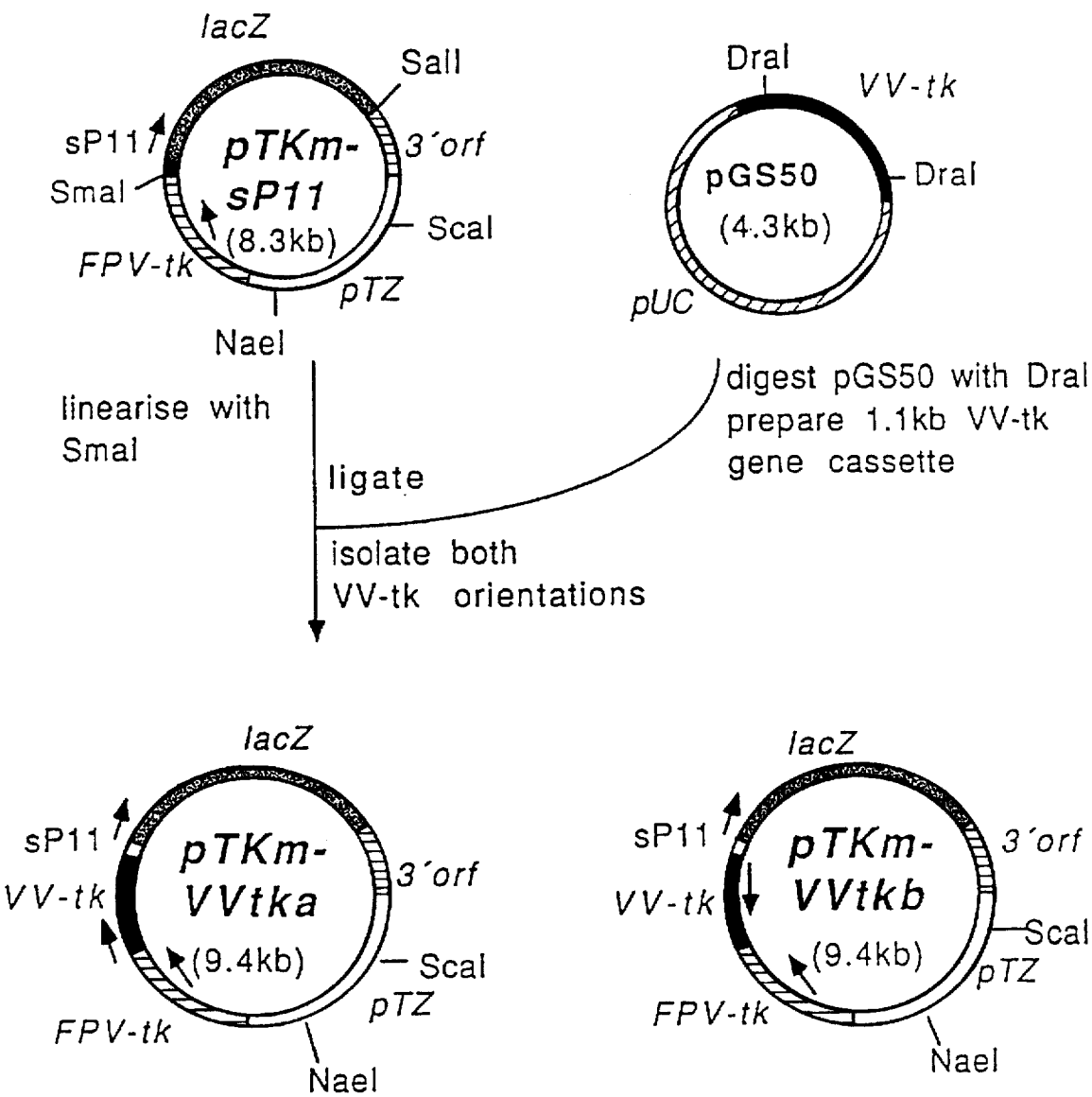
Figure 6A:
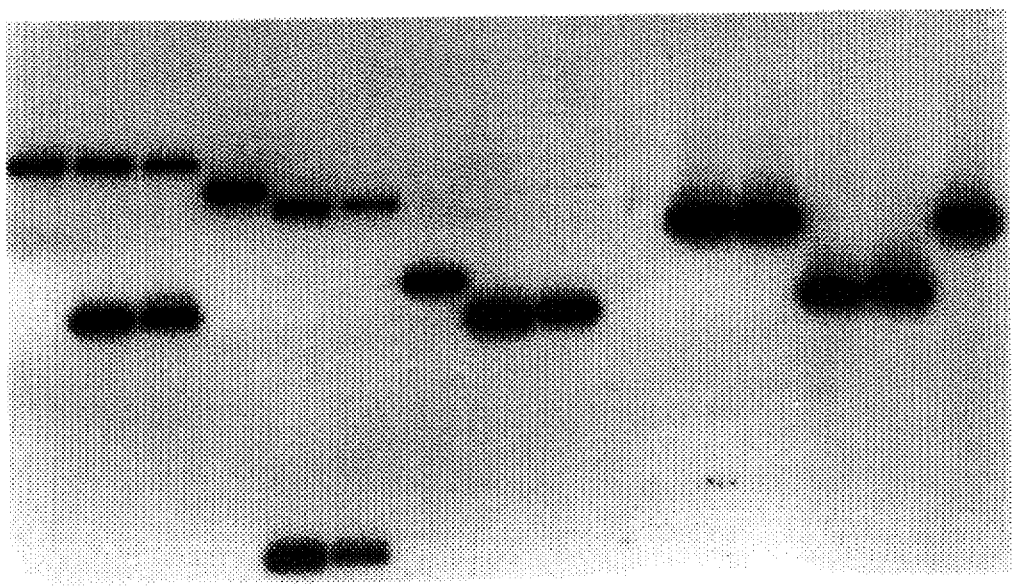
Figure 6B:
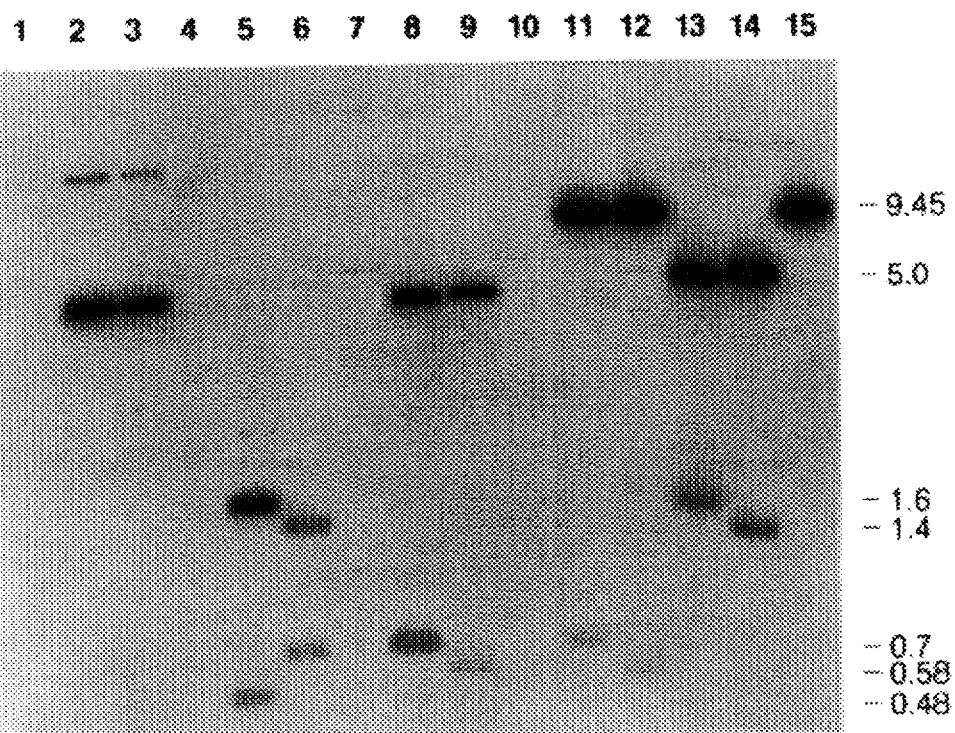
Figure 6C:
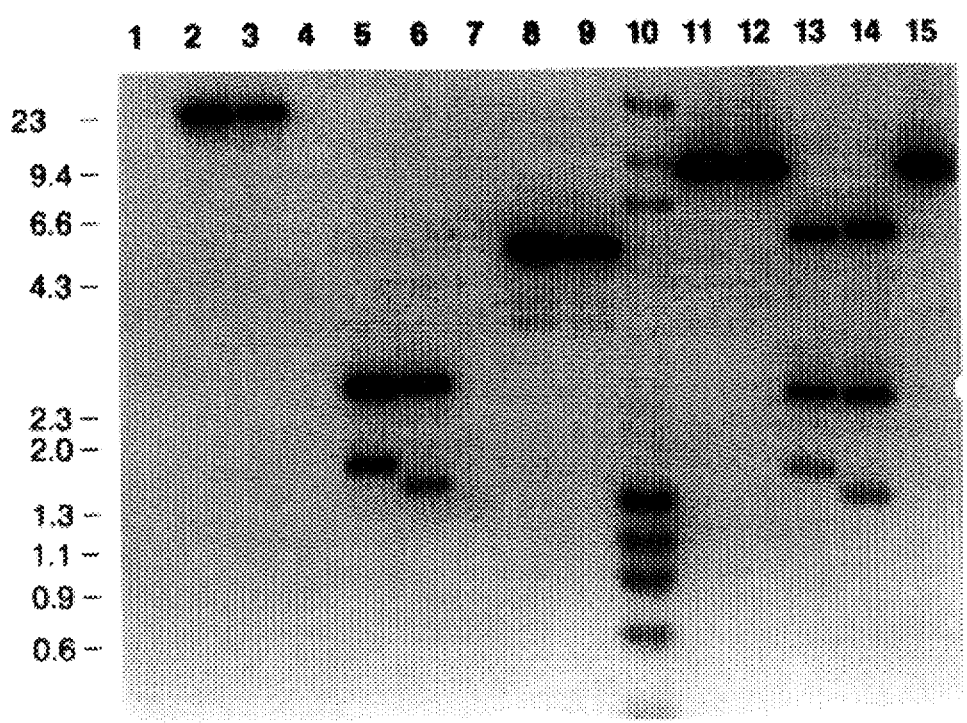
Figure 6D:
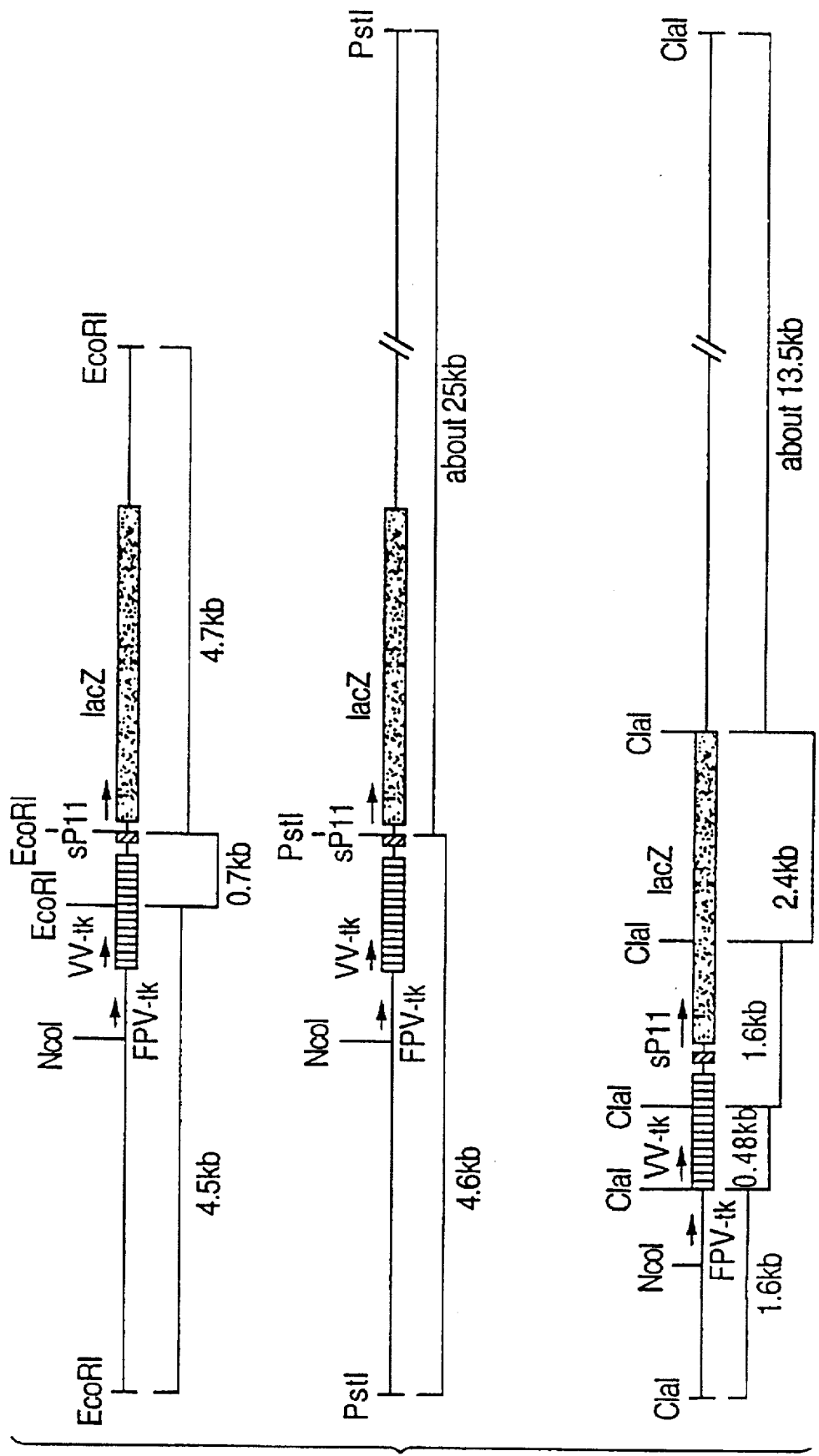
Figure 6E:
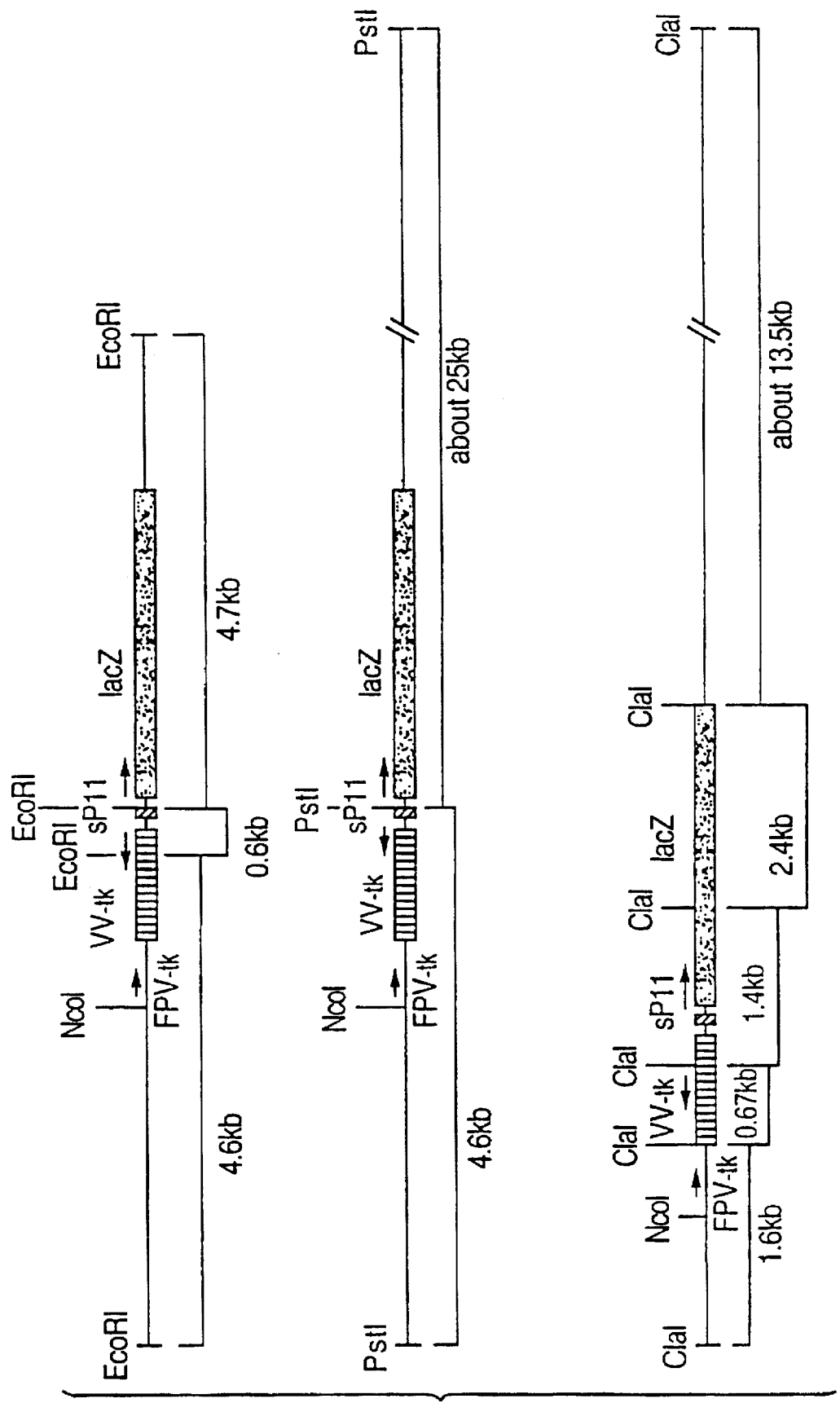

For technical and biological reasons it is more difficult and more time-consuming to construct recombinant FPV. Therefore, prior to inserting a gene of interest into FPV, a similar vaccinia virus recombinant was usually constructed to study the function of the respective gene. To be able to use the same vaccinia insertion plasmids also for the construction of fowlpox recombinants, the vaccinia virus tk-gene, together with the $E.$ $coli$ lacZ gene was inserted into the intergenic region of the tk-gene and the 3'off of fowlpox virus. The plasmids pTKm-VVtka and pTKM-VVtkb were constructed by cloning the functional VV tk-gene into the intermediate plasmid pTKm-sP11 (FIG. 4). Upon recombination of pTKm-VVtka and b with FPV-wild-type virus two novel FPV host strain (termed f-TK2a and f-TK2b) were created. The novel host strain thus contains two functional tk-genes and the lacZ gene, all of which can be used as novel non-essential sites with the appropriate insertion plasmids as recombination substrates. The Southern blot analysis of the novel strains is shown in FIG. 6A–C. The DNA's of the wild type virus HP1.441, the two FPV recombinants and the plasmids pTKm-VVtka and pTKm-VVtkb were digested with the restriction enzymes PstI, ClaI and EcoRI, separated on a 1% agarose gel, transferred onto nitrocellulose. The blots in FIGS. 6A–C were hybridized with the FPV-tk-gene probe (6A), with the vaccinia virus tk-gene probe (FIG. 6B) and with the lacZ gene and the lambda DNA probes (FIG. 6C). In all digests the predicted banding pattern (see also FIGS. 6D and 6E) could be observed. In case of the ClaI digests the small hybridizing fragments of about 0.5 and 0.7 kb in lanes 5 and 6 of FIG. 6B cannot be seen in the ClaI digested parental plasmids (lanes 13 and 14 of FIG. 6B). This is due to the fact that the plasmid DNAs were isolated from the $E.$ $coli$ strain HB101, a strain that methylates the respective ClaI site. In a control experiment this site was cleavable when the DNA was prepared from a Dam methylation negative $E.$ $coli$ strain.

4. Fowlpox virus early/late promoter in vaccinia virus recombinants 4.1 Identification of the fowlpox promoters A transcription unit consisting of a vaccinia virus promoter and the coding sequence of the lacZ gene is active in $E.$ $coli$ cells resultings in a β-galactosidase positive phenotype of the bacterial colonies grown in the presence of the chromogenic substrate X-gal. This phenomenon has been observed when working with vaccinia insertion plasmids containing the $E.$ $coli$ lacZ gene in lacZ negative $E.$ $coli$ strains (Chakrabarti et al; Mol. Cell. Biol., 5, 3403–3409 (1985)). Since the promoter sequences of FPV and vaccinia are functionally equivalent (Boyle & Coupar; J. Gen. Virol., 67, 1591–1600 (1986); Taylor et al; Vaccine, 6, 497–503 (1988)) also fowlpox promoters should be active in $E.$ $coli$. Based on these considerations a strategy was worked out for the identification of promoter elements in fowlpox virus DNA.

Figure 8:
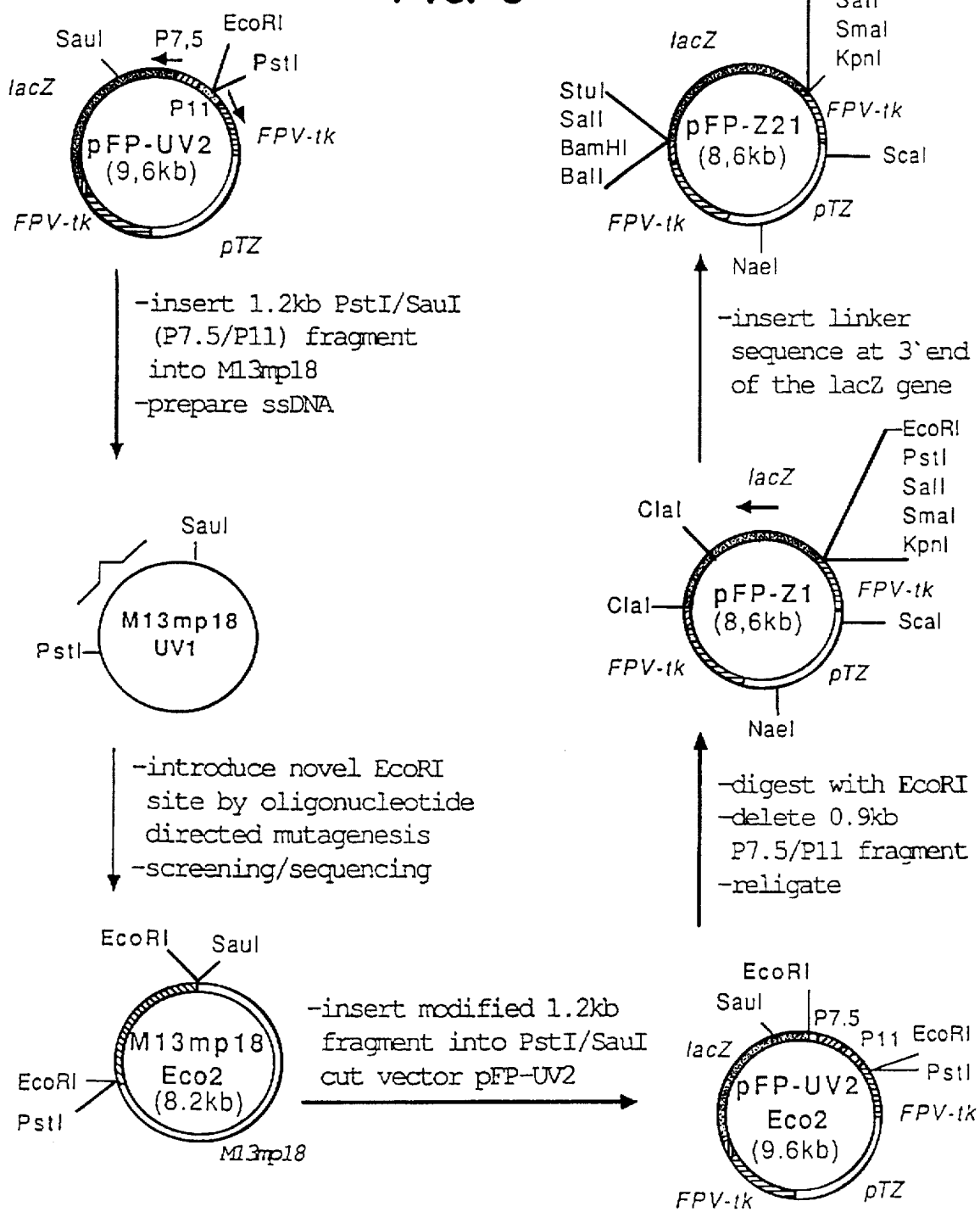
Figure 9:
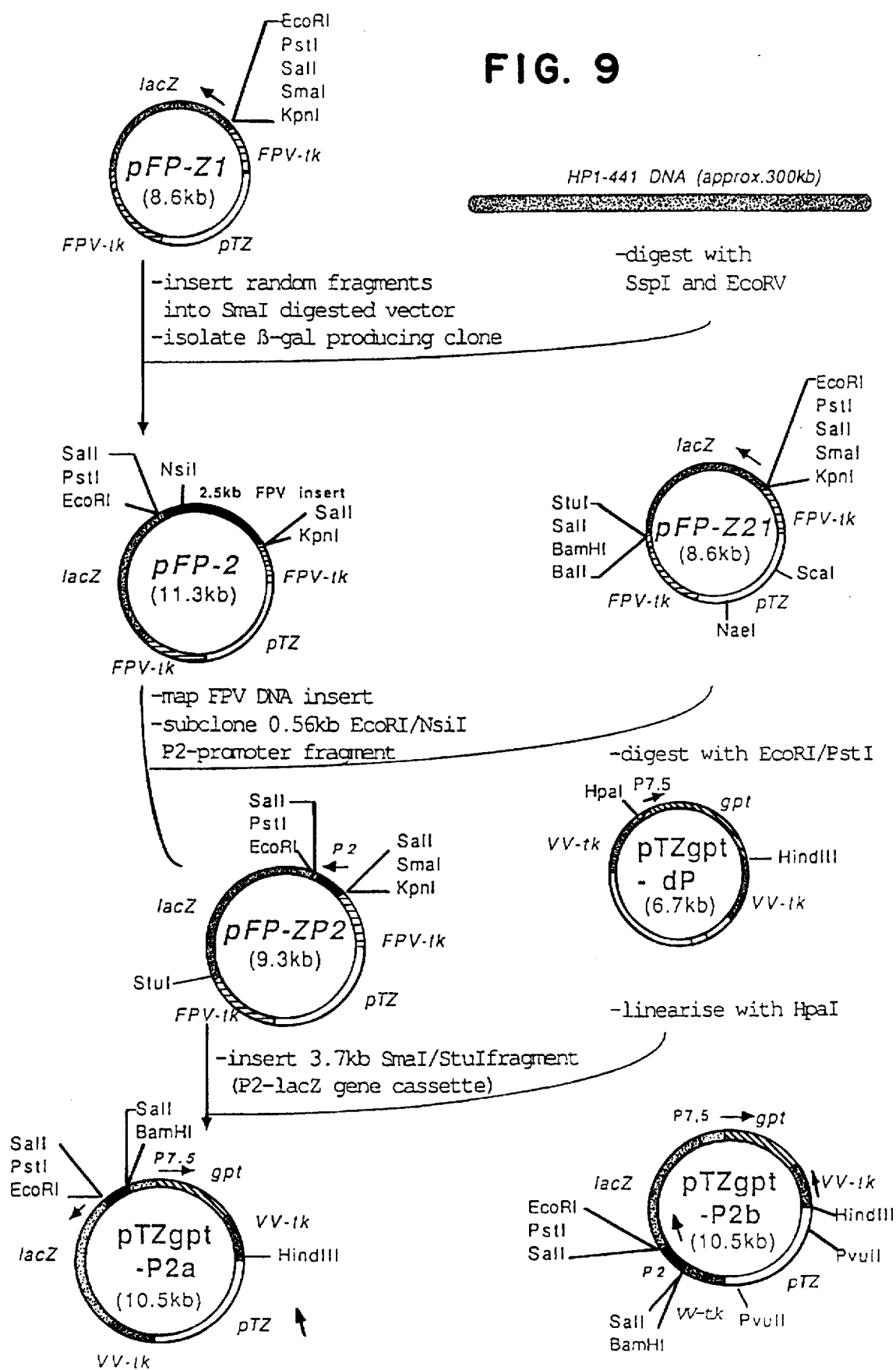

As the first step the plasmids pFP-Z1 and pFP-Z21 were constructed (FIG. 8); both plasmids contain a promoterless lacZ gene. As the parental plasmid, pFP-UV2 was chosen. It contains the $E.$ $coli$ lacZ gene controlled by the vaccinia virus P 7.5 promoter, the P11 promoter and a multiple cloning site for cloning purposes and is flanked by fowlpox virus tk-sequences. In order to delete the vaccinia promoters a novel EcoRI site was introduced 7 bp upstream of the initiation codon of the lacZ gene. Cleavage with EcoRI and religation resulted in the plasmid pFP-Z1 that contains unique restriction sites adjacent to the promoterless lacZ gene. In the next step the DNA of the fowlpox virus strain HP1-441 was digested with the restriction endonucleases SspI and EcoRV and cloned into the unique SmaI site adjacent to the lacZ gene of the plasmid pFP-Z1 (FIG. 9). The plasmids were transfected into the β-galactosidase negative $E.$ $coli$ strain NM 522 and plated onto agar-dishes containing ampicillin and X-gal. After overnight growth, a small percentage of the colonies developed a blue color. Several colonies were picked and the plasmid DNAs were assayed in a transient expression assay in CV-1 cells for vaccinia virus specific gene expression (data not shown). The plasmid DNAs induced varying amounts of β-galactosidase activity in the vaccinia transient expression assay. For further analysis the clone that gave the highest activity (clone #2) was chosen, the promoter was designated "P2" and the plasmid pFP-2 (FIG. 9).

4.2 Structure of the fowlpox virus promoter P2

The DNA of the 2.5 kb P2 promoter insert of the plasmid pFP-2 was analyzed by restriction mapping. The 560 bp EcoRI-NsiI fragment was found to be proximal to the lacZ gene and would therefore contain the promoter sequences. This fragment was inserted into the plasmid pFP-Z21, a derivative of pFP-Z1 that has at the 3' end of the lacZ gene a polylinker insert (FIG. 8). The promoter lacZ gene cassette was then excised and cloned into the single HpaI site of the plasmid pTZgpt-dP resulting in the plasmids pTZgpt-P2a and pTZgpt-P2b (FIG. 9). Since the orientation of the promoter foreign gene transcription unit may influence the level of transcription both plasmids were used for further investigation. Sequencing of the promoter insert was carried out using the plasmid pTZgpt-P2a as the template. The primary structure of the promoter and the first ten codons of the P2 gene is shown in FIG. 10A and bases 1–204 of SEQ ID NO:19. The 5' untranslated region is 174 bp long starting with a NsiI site. Upstream of the initiation codon the conserved poxvirus promoter consensus sequence TAAAT is present (FIG. 10A, pos. −6 to −2) that is typical for late promoters, but is also found in some early promoters. Within the first 174 bp of the upstream region also several "critical early regions" followed by an early transcription stop signal (TTTTTNT) are present. The early transcription stop signal overlaps with the functional important T-rich region of the late promoters.

The P2-lacZ transcription unit in the plasmid pTZgpt-P2a was a fusion gene. The initiation codon was followed by 360 bp of the P2-gene fused in frame with 39 nucleotides of the 5' untranslated region and the coding region lacZ gene (data not shown). The calculated molecular weight of the fusion gene is 133 kD.

4.3 Comparison of the strength of the P2 promoter with other pox virus promoters The plasmids pTZgpt-P2a and pTZgpt-P2b were used for the construction of the vaccinia virus recombinants vP2a and vP2b. The strength of the P2 promoter in both recombinants was compared with other strong pox virus promoters. The vaccinia recombinant vF1sβ (Falkner & Moss; J. Virol., 62, 1849–1854 (1988)) contains the wild-type version of the vaccinia P11 promoter. The vaccinia recombinant vart contains a modified version of the synthetic late promoter that is 1.4 fold stronger than the P11 wild-type promoter. In all viruses the lacZ reporter gene is immediately adjacent to the respective pox virus promoters.

Figure 11:
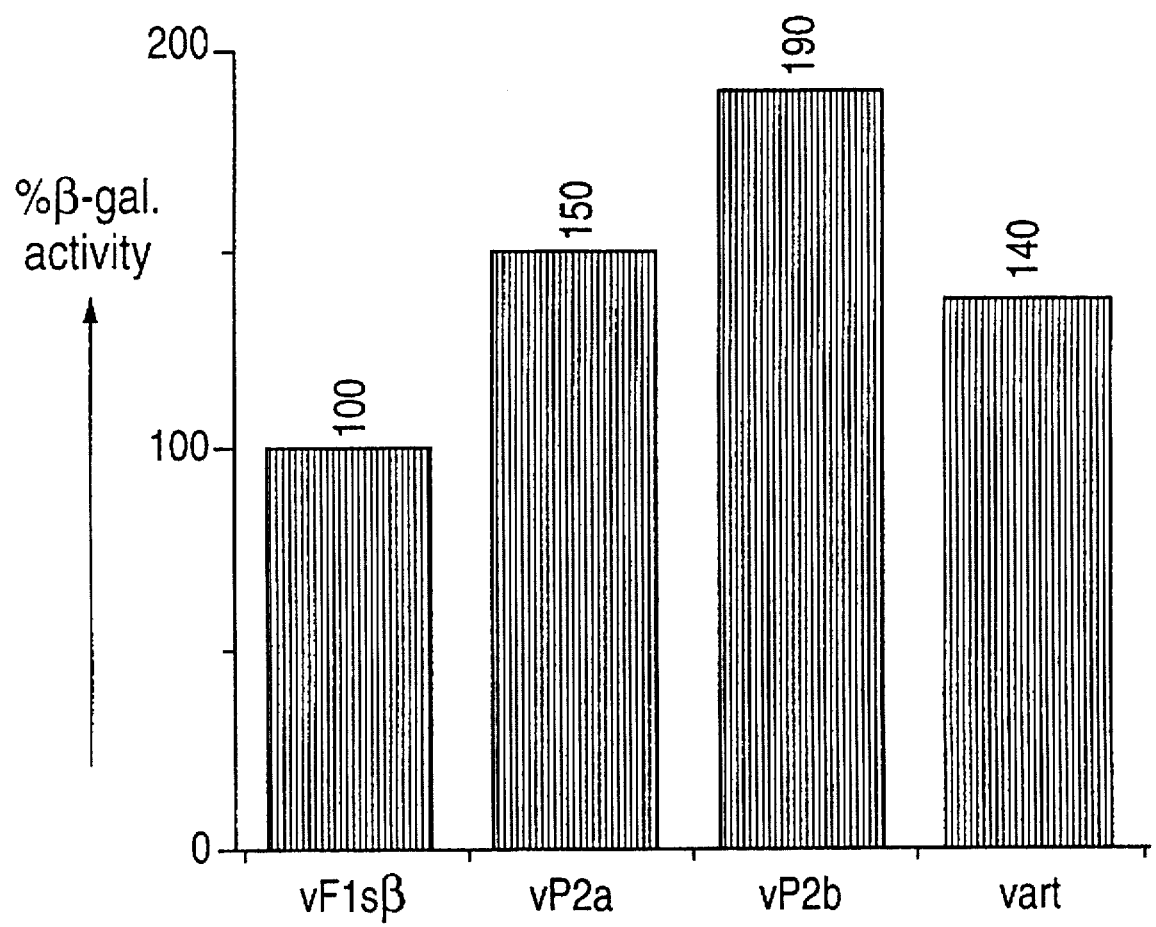

For the β-galactosidase activity assays CV-1 cells were infected with the viruses as described in the Methods part. FIG. 11 shows the enzymatic activities induced by the different viral constructs in CV-1 cells. The activity of the wild-type P11 promoter in vF1sβ was defined as 100%. Remarkably, the "b"-orientation of the FPV P2 promoter induced an activity of 190%, indicating that the P2 promoter belongs to the strongest pox virus promoters. After a 24 hour incubation period, the β-galactosidase is one of the most abundant proteins and accounts for about 6.3% of the total soluble cellular proteins. The recombinant virus having the "a"-orientation of the P2 promoter induced a β-galactosidase activity of 150% which accounts for about 5% of the soluble cellular protein. The virus vart was found to induce 140% of β-galactosidase activity as compared to the standard value induced by vF1sβ. The β-galactosidase activity measurements are mean values of three independent experiments. In order to confirm these values by an independant second method the 24 hour extracts of infected CV-1 cells were separated on 10% polyacrylamide gels and scanned with a densitometer. The β-galactosidase peaks were quantified relative to the 42 kDa actin band as an internal standard. The value obtained for vF1sβ again served as the 100% standard. The scanning data are in good agreement with the enzymatically determined activity data as shown in the following table.

TABLE

| Virus | Relative β-galactosidase expression (% β-galactosidase of soluble protein) | |
|---|---|---|
| | % Activity | % Scanning |
| vF1sβ | 100 (3.3%) | 100 |
| vP2a | 150 (5.0%) | 150 |
| vP2b | 190 (6.3%) | 195 |
| vart | 140 (4.6% | n.d. |

Figure 12:
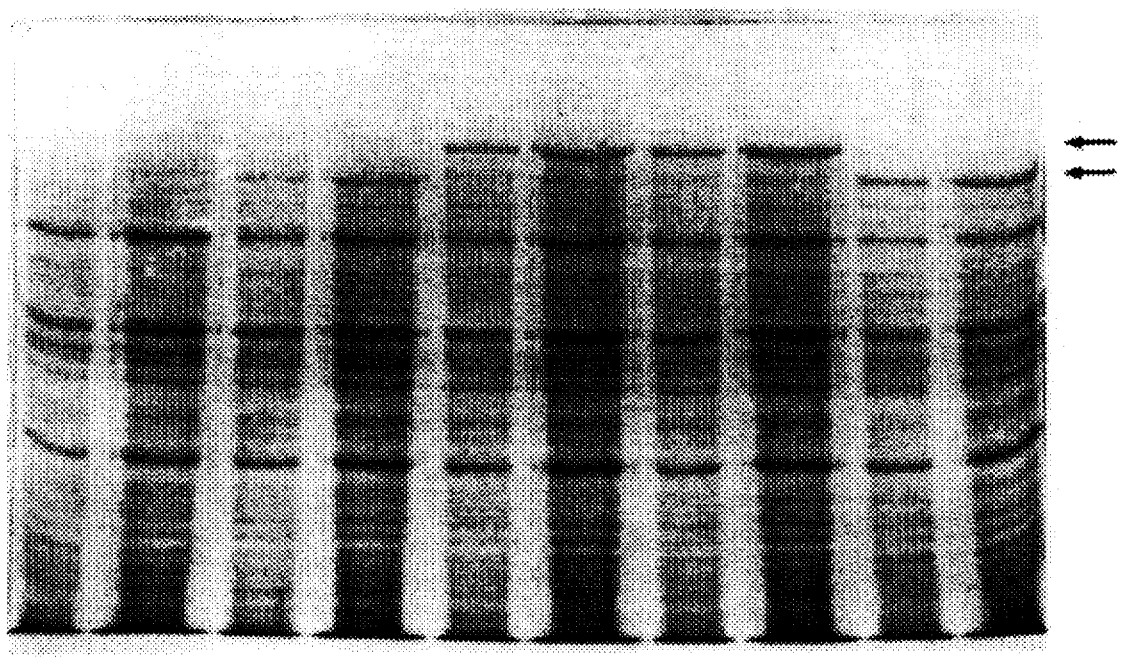

To illustrate the abundance of the β-galactosidase in the cell extracts 24 hours post-infection, a commassie blue stained polyacrylamide gel of the total soluble proteins is shown in FIG. 12. The reference virus, vF1sβ, and the recombinant vart induce a novel band in the 117 kD size range (lanes 3, 4, 9 and 10; lower arrow) that cannot be seen in the wild-type virus control (lanes 1 and 2). As suggested by the sequence analysis, the β-galactosidase fusion protein induced by the viruses vP2a and vP2b is larger than the native enzyme, proving its fusion gene character (lanes 5 to 8; upper arrow).

4.4 Optimization of the P2 promoter

In an attempt to optimize the P2 gene promoter a panel of novel insertion plasmids were constructed, that contain mutated P2 promoter regions linked with the lacZ gene. As the first step a plasmid was generated that allows the simple insertion of double stranded promoter oligonucleotides and contains a minimal P7.5-gpt gene cassette for selection purposes. The construction of this plasmid, pFSgpt, is shown in FIG. 13. Into the unique NdeI and BamHI sites of this plasmid, the different mutant promoter oligonucleotides m0, m1 and m2 were inserted. The resulting plasmids were designated pP2m0gpt, pP2m1gpt and pP2m2gpt (pP2mxgpt, FIG. 14). In the next step the E. coli lacZ gene was placed downstream of the promoter sequences resulting in the plasmids pP2m0gpt-lacZ, pP2m1gpt-lacZ and pP2m2gpt-lacZ (pP2mxgpt-lacZ, FIG. 14).

In the mutant promoter m0 (SEQ ID NO:21) (TAAATG AAT TCC) the ATG of the lacZ gene is directly fused with the late promoter core sequence thereby deleting the C-residue at position -1 of the wild-type P2 sequence, a mutation that should improve the efficiency of a late promoter (FIG. 15). This structure is found in many vaccinia late promoters and is thought to be the optimal context of the late promoter consensus and the initiation codon.

In the mutant m1 (SEQ ID NO:22) (TAAACATG AAT TCC) the second codon of the lacZ gene is directly fused with the ATG of the putative P2 gene. In this mutant the lacZ gene is driven by the P2 wild-type promoter (FIG. 15).

The mutation m2 was constructed in order to investigate the role of the early promoter critical regions found in the upstream region of the P2 gene. The mutant promoter m2 has the same structure as m1 except that the early RNA stop signal within the functional important T-rich region upstream the late promoter motif was inactivated by a TTG insertion at position -18 (FIG. 15).

4.5 Effect of the mutations on early and late β-gal expression

The plasmids were used to construct vaccinia virus recombinants and to infect CV-1 cells. Cytoplasmic extracts were assayed for β-galactosidase activity. Results are shown in FIGS. 16A and 16B.

We claim:

1. Recombinant fowlpox virus, wherein the 3'-region downstream of the fowlpox virus P2 gene is used as a non-essential site for the insertion of foreign DNA.

2. A recombinant fowlpox virus having a thymidine kinase gene and an adjacent, downstream open reading frame separated from said thymidine kinase gene by an intergenic region, wherein said recombinant fowlpox virus has inserted into said intergenic region a foreign DNA sequence and a poxvirus promoter to cause expression of said foreign DNA sequence, wherein said poxvirus promoter is a fowlpox P2 promoter.

3. A plasmid comprising the fowlpox P2 promoter.

4. A plasmid comprising the FPV P2 promoter, the P2 gene and the 3'-sequence as shown in SEQ ID NO:19 or a functional equivalent thereof.

5. A plasmid comprising a fowlpox thymidine kinase gene, a downstream intergenic region adjacent to said thymidine kinase gene and a downstream fowlpox open reading frame adjacent to said downstream intergenic region, such that said downstream intergenic region is located between said thymidine kinase gene and said downstream fowlpox open reading frame, wherein said intergenic region comprises at least one site for insertion of foreign DNA into said intergenic region, wherein said plasmid further comprises:

(a) a fowlpox P2 promoter linked to a foreign DNA sequence to be expressed;

(b) a poxvirus promoter linked to a gene encoding a marker or indicator for selection of recombinant fowlpox virus, wherein element (a) and element (b) form a construct; and (c) DNA sequences of fowlpox virus flanking said construct of elements (a) and (b), wherein said flanking sequences have homology with sequences upstream and downstream of the intergenic region or within the intergenic region to permit insertion of said construct into fowlpox.

6. Plasmid pTZgpt-P2a of FIG. 9.

7. Plasmid pTZgpt-P2b of FIG. 9.

8. Isolated fowlpox promoter P2.

9. An isolated fowlpox promoter according to claim 8, wherein said promoter comprises a sequence set forth at bases 1–174 of SEQ ID NO:19.

* * * * *

SEQUENCE LISTING ( 1 ) GENERAL INFORMATION:

( i i i ) NUMBER OF SEQUENCES: 52

( 2 ) INFORMATION FOR SEQ ID NO:1:

( i ) SEQUENCE CHARACTERISTICS:
      ( A ) LENGTH: 4997 base pairs
      ( B ) TYPE: nucleic acid
      ( C ) STRANDEDNESS: single
      ( D ) TOPOLOGY: linear ( v i i ) IMMEDIATE SOURCE:
      ( B ) CLONE: pTKm ( x i ) SEQUENCE DESCRIPTION: SEQ ID NO:1:

```
CTTCCGCTTC CTCGCTCACT GACTCGCTGC GCTCGGTCGT TCGGCTGCGG CGAGCGGTAT        60
CAGCTCACTC AAAGGCGGTA ATACGGTTAT CCACAGAATC AGGGGATAAC GCAGGAAAGA       120
ACATGTGAGC AAAAGGCCAG CAAAAGGCCA GGAACCGTAA AAAGGCCGCG TTGCTGGCGT       180
TTTTCCATAG GCTCCGCCCC CCTGACGAGC ATCACAAAAA TCGACGCTCA AGTCAGAGGT       240
GGCGAAACCC GACAGGACTA TAAAGATACC AGGCGTTTCC CCCTGGAAGC TCCCTCGTGC       300
GCTCTCCTGT TCCGACCCTG CCGCTTACCG GATACCTGTC CGCCTTTCTC CCTTCGGGAA       360
GCGTGGCGCT TTCTCAATGC TCACGCTGTA GGTATCTCAG TTCGGTGTAG GTCGTTCGCT       420
CCAAGCTGGG CTGTGTGCAC GAACCCCCCG TTCAGCCCGA CCGCTGCGCC TTATCCGGTA       480
ACTATCGTCT TGAGTCCAAC CCGGTAAGAC ACGACTTATC GCCACTGGCA GCAGCCACTG       540
GTAACAGGAT TAGCAGAGCG AGGTATGTAG GCGGTGCTAC AGAGTTCTTG AAGTGGTGGC       600
CTAACTACGG CTACACTAGA AGGACAGTAT TTGGTATCTG CGCTCTGCTG AAGCCAGTTA       660
CCTTCGGAAA AAGAGTTGGT AGCTCTTGAT CCGGCAAACA AACCACCGCT GGTAGCGGTG       720
GTTTTTTTGT TTGCAAGCAG CAGATTACGC GCAGAAAAAA AGGATCTCAA GAAGATCCTT       780
TGATCTTTTC TACGGGGTCT GACGCTCAGT GGAACGAAAA CTCACGTTAA GGGATTTTGG       840
TCATGAGATT ATCAAAAAGG ATCTTCACCT AGATCCTTTT AAATTAAAAA TGAAGTTTTA       900
AATCAATCTA AAGTATATAT GAGTAAACTT GGTCTGACAG TTACCAATGC TTAATCAGTG       960
AGGCACCTAT CTCAGCGATC TGTCTATTTC GTTCATCCAT AGTTGCCTGA CTCCCCGTCG      1020
TGTAGATAAC TACGATACGG GAGGGCTTAC CATCTGGCCC CAGTGCTGCA ATGATACCGC      1080
GAGACCCACG CTCACCGGCT CCAGATTTAT CAGCAATAAA CCAGCCAGCC GGAAGGGCCG      1140
AGCGCAGAAG TGGTCCTGCA ACTTTATCCG CCTCCATCCA GTCTATTAAT TGTTGCCGGG      1200
AAGCTAGAGT AAGTAGTTCG CCAGTTAATA GTTTGCGCAA CGTTGTTGCC ATTGCTGCAG      1260
GCATCGTGGT GTCACGCTCG TCGTTTGGTA TGGCTTCATT CAGCTCCGGT TCCCAACGAT      1320
CAAGGCGAGT TACATGATCC CCCATGTTGT GCAAAAAAGC GGTTAGCTCC TTCGGTCCTC      1380
CGATCGTTGT CAGAAGTAAG TTGGCCGCAG TGTTATCACT CATGGTTATG GCAGCACTGC      1440
ATAATTCTCT TACTGTCATG CCATCCGTAA GATGCTTTTC TGTGACTGGT GAGTACTCAA      1500
CCAAGTCATT CTGAGAATAG TGTATGCGGC GACCGAGTTG CTCTTGCCCG GCGTCAACAC      1560
GGGATAATAC CGCGCCACAT AGCAGAACTT TAAAAGTGCT CATCATTGGA AAACGTTCTT      1620
CGGGGCGAAA ACTCTCAAGG ATCTTACCGC TGTTGAGATC CAGTTCGATG TAACCCACTC      1680
GTGCACCCAA CTGATCTTCA GCATCTTTTA CTTTCACCAG CGTTTCTGGG TGAGCAAAAA      1740
CAGGAAGGCA AAATGCCGCA AAAAAGGGAA TAAGGGCGAC ACGGAAATGT TGAATACTCA      1800
```

```
TACTCTTCCT TTTTCAATAT TATTGAAGCA TTTATCAGGG TTATTGTCTC ATGAGCGGAT   1860
ACATATTTGA ATGTATTTAG AAAAATAAAC AAATAGGGGT TCCGCGCACA TTTCCCCGAA   1920
AAGTGCCACC TGACGCGCCC TGTAGCGGCG CATTAAGCGC GGCGGGTGTG GTGGTTACGC   1980
GCAGCGTGAC CGCTACACTT GCCAGCGCCC TAGCGCCCGC TCCTTTCGCT TTCTTCCCTT   2040
CCTTTCTCGC CACGTTCGCC GGCTTTCCCC GTCAAGCTCT AAATCGGGGG CTCCCTTTAG   2100
GGTTCCGATT TAGTGCTTTA CGGCACCTCG ACCCCAAAAA ACTTGATTAG GGTGATGGTT   2160
CACGTAGTGG GCCATCGCCC TGATAGACGG TTTTTCGCCC TTTGACGTTG GAGTCCACGT   2220
TCTTTAATAG TGGACTCTTG TTCCAAACTG GAACAACACT CAACCCTATC TCGGTCTATT   2280
CTTTTGATTT ATAAGGGATT TTGCCGATTT CGGCCTATTG GTTAAAAAAT GAGCTGATTT   2340
AACAAAAATT TAACGCGAAT TTTAACAAAA TATTAACGTT TACAATTTCC CATTCGCCAT   2400
TCAGGCTGCG CAACTGTTGG GAAGGGCGAT CGGTGCGGGC CTCTTCGCTA TTACGCCAGC   2460
GATNNNNNNN NNNNNNNNNN NNNNNNNNNN NNNNNNNNNN NNNNNNNNNN NNNNNNNNNN   2520
NNNNNNNNNN NNNNNNNNNN NNNNNNNNNN NNNNNNNNNN NNNNNNNNNN NNNNNNNNNN   2580
NNNNNNNNNN NNNNNNNNNN NNNNNNNNNN NNNNNNNNNN NNNNNNNNNN NNNNNNNNNN   2640
NNNNNNNNNN NNNNNNNNNN NNNNNNNNNN NNNNNNNNNN NNNNNNNNNN NNNNNNNNNN   2700
NNNNNNNNNN NNNNNNNNNN NNNNNNNNNN NNNNNNNNNN NNNNNNNNNN NNNNNNNNNN   2760
NNNNNNNNNN NNNNNNNNNN NNNNNNNNNN NNNNNNNNNN NNNNNNNNNN NNNNNNNNNN   2820
NNNNNNNNNN NNNNNNNNNN NNNNNNNNNN NNNNNNNNNN NNNNNNNNNN NNNNNNNNNN   2880
NNNNNNNNNN NNNNNNNNNN NNNNNNNNNN NNNNNNNNNN NNNNNNNNNN NNNNNNNNNN   2940
NNNNNNNNNN NNNNNNNNNN NNNNNNNNNN NNNNNNNNNN NNNNNNNNNN NNNNNNNNNN   3000
NNNNNNNNNN NNNNNNNNNN NNNNNNNNNN NNNNNNNNNN NNNNNNNNNN NNNNNNNNNN   3060
NNNNNNNNNN NNNNNNNNNN NNNNNNNNNN NNNNNNNNNN NNNNNNNNNN NNNNNNNNNN   3120
NNNNNNNNNN NNNNNNNNNN NNNNNNNNNN NNNNNNNNNN NNNNNNNNNN NNNNNNNNNN   3180
NNNNNNNNNN NNNNNNNNNN NNNNNNNNNN NNNNNNNNNN NNNNNNNNNN NNNNNNNNNN   3240
NNNNNNNNNN NNNNNNNNNN NNNNNNNNNN NNNNNNNNNN NNNNNNNNNN NNNNNNNNNN   3300
NNNNNNNNNN NNNNNNNNNN NNNNNNNNNN NNNNNNNNNN NNNNNNNNNN NNNNNNNNNN   3360
NNNNNNNNNN NNNNNNNNNN NNNNNNNNNN NNNNNNNNNN NNNNNNNNNN NNNNNNNNNN   3420
NNNNNNNNNN NNNNNNNNNN NNNNNNNNNC TCCGTTTTAT GGAAATATTT TCTACTATTA   3480
TGTTTATTCC TGGAATAATT ATATTGTACG CTGCTTATAT AAGAAAAATT AAAATGAAAA   3540
ATAATTAGAA TCTGAAAATG TCTTCTGGAA GCATCCATGT TATTACAGGC CCTATGTTTT   3600
CCGGTAAAAC ATCGGAGCTA GTAAGAAGAA TAAAAGATT  TATGCTATCT AACTTTAAAT   3660
GTATTATTAT TAAACATTGT GGAGATAATA GATATAATGA GGATGATATA AACAAAGTAT   3720
ATACTCATGA TCTATTGTTT ATGGAGGCTA CGGCATCTTC TAATCTATCT GTATTAGTAC   3780
CTACGCTATT AAATGATGGA GTTCAGGTAA TAGGTATAGA CGAGGCTCAA TTCTTTCTAG   3840
ACATAGTAGA ATTTAGTGAA TCCATGGCTA ATTTAGGTAA AACAGTTATT GTGGCCGCGC   3900
TTAACGGTGA TTTTAAACGC GAATTATTCG GTAACGTATA TAAGTTATTA TCATTAGCTG   3960
AAACAGTGTC CAGTTTGACA GCTATTTGCG TGAAATGCTA TTGCGACGCT TCGTTTTCTA   4020
AACGAGTTAC AGAAAATAAA GAAGTAATGG ATATAGGTGG TAAAGATAAA TACATAGCCG   4080
TGTGTAGGAA ATGTTTTTTT AGTAATTAAG GTTTTTATCG ATCCCGGGTA CCGGTTTAGT   4140
GTAATAAATT TAATAAAATA TTGACAAAAT AGTTAAATGA ATATATGAAA GTACATTATA   4200
```

-continued

```
CACGGAATGG AGTTCGATAT TAGTTCTTGC AGAATGATAT ATTCTGTTCT CGAACAATAT    4260
CACTTTGTTT CTGATAATCG TTATAACAAT CAAAATTTA GAATTATATT ATACTGTTTA     4320
AAAGATTCTA CGATAAAGAA ATATCCGTAC AGGTTTGTTT CTGAAATTCA CTTTGTAAGA    4380
TACATAATTA ACAAATTCAG GGGGAAAAAT CTTTACAAAA TTAGTATAGA AGCTATAGAT    4440
ATATCAAAAG GTAGACAACA AATAATCAGA ACCTAATTTT TTTATCAAAA AATTAAAATA    4500
TAAATAAAAT GAAAAATAAC TTGTATGAAG AAAAAATGAA CATGAGTAAG AAACAAGTAA    4560
AAACTCAAAG TAAATGTAAT AATAACGCAT CTAGATTTAC ATGCTTGGAT GCGGTGCAAT    4620
ACGCTAAGCT TNNNNNNNNN NNNNNNNNNN NNNNNNNNNN NNNNNNNNNN NNNNNNNNNN    4680
NNNNNNNNNN NNNNNNNNNN NNNNNNNNNN NNNNNNNNNN NNNNNNNNNN NNNNNNNNNN    4740
NNNNNNNNNN NNNNNNNNNN NNNNNNNNNN NNNNNNNNNN NNNNNNNNNN NNNNNNNNNN    4800
NNNNNNNNNN NNNNNNNNNN NNNNNNNNNN NNNNNNNNNN NNNNNNNNNN NNNNNNNNNN    4860
NNNNNNNNNN NNNNNNNNNN NNNNNNNNNN NNNNNNNNNN NNNNNNNNNN NNNNNNNNNN    4920
NNNNNNNNNN NNNNNNGGA TCCTGCATTA ATGAATCGGC CAACGCGCGG GGAGAGGCGG     4980
TTTGCGTATT GGGCGCT                                                   4997
```

( 2 ) INFORMATION FOR SEQ ID NO:2:

( i ) SEQUENCE CHARACTERISTICS:
        ( A ) LENGTH: 8313 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pTKm-sP11

( x i ) SEQUENCE DESCRIPTION: SEQ ID NO:2:

```
CTTCCGCTTC CTCGCTCACT GACTCGCTGC GCTCGGTCGT TCGGCTGCGG CGAGCGGTAT     60
CAGCTCACTC AAAGGCGGTA ATACGGTTAT CCACAGAATC AGGGGATAAC GCAGGAAAGA    120
ACATGTGAGC AAAAGGCCAG CAAAAGGCCA GGAACCGTAA AAAGGCCGCG TTGCTGGCGT    180
TTTTCCATAG GCTCCGCCCC CCTGACGAGC ATCACAAAAA TCGACGCTCA AGTCAGAGGT    240
GGCGAAACCC GACAGGACTA TAAAGATACC AGGCGTTTCC CCCTGGAAGC TCCCTCGTGC    300
GCTCTCCTGT TCCGACCCTG CCGCTTACCG GATACCTGTC CGCCTTTCTC CCTTCGGGAA    360
GCGTGGCGCT TTCTCAATGC TCACGCTGTA GGTATCTCAG TTCGGTGTAG GTCGTTCGCT    420
CCAAGCTGGG CTGTGTGCAC GAACCCCCCG TTCAGCCCGA CCGCTGCGCC TTATCCGGTA    480
ACTATCGTCT TGAGTCCAAC CCGGTAAGAC ACGACTTATC GCCACTGGCA GCAGCCACTG    540
GTAACAGGAT TAGCAGAGCG AGGTATGTAG GCGGTGCTAC AGAGTTCTTG AAGTGGTGGC    600
CTAACTACGG CTACACTAGA AGGACAGTAT TTGGTATCTG CGCTCTGCTG AAGCCAGTTA    660
CCTTCGGAAA AAGAGTTGGT AGCTCTTGAT CCGGCAAACA AACCACCGCT GGTAGCGGTG    720
GTTTTTTTGT TTGCAAGCAG CAGATTACGC GCAGAAAAAA AGGATCTCAA GAAGATCCTT    780
TGATCTTTTC TACGGGGTCT GACGCTCAGT GGAACGAAAA CTCACGTTAA GGGATTTTGG    840
TCATGAGATT ATCAAAAAGG ATCTTCACCT AGATCCTTTT AAATTAAAAA TGAAGTTTTA    900
AATCAATCTA AAGTATATAT GAGTAAACTT GGTCTGACAG TTACCAATGC TTAATCAGTG    960
AGGCACCTAT CTCAGCGATC TGTCTATTTC GTTCATCCAT AGTTGCCTGA CTCCCCGTCG   1020
TGTAGATAAC TACGATACGG GAGGGCTTAC CATCTGGCCC CAGTGCTGCA ATGATACCGC   1080
GAGACCCACG CTCACCGGCT CCAGATTTAT CAGCAATAAA CCAGCCAGCC GGAAGGGCCG   1140
```

```
AGCGCAGAAG TGGTCCTGCA ACTTTATCCG CCTCCATCCA GTCTATTAAT TGTTGCCGGG    1200
AAGCTAGAGT AAGTAGTTCG CCAGTTAATA GTTGCGCAA CGTTGTTGCC ATTGCTGCAG     1260
GCATCGTGGT GTCACGCTCG TCGTTTGGTA TGGCTTCATT CAGCTCCGGT TCCCAACGAT    1320
CAAGGCGAGT TACATGATCC CCCATGTTGT GCAAAAAGC GGTTAGCTCC TTCGGTCCTC    1380
CGATCGTTGT CAGAAGTAAG TTGGCCGCAG TGTTATCACT CATGGTTATG GCAGCACTGC   1440
ATAATTCTCT TACTGTCATG CCATCCGTAA GATGCTTTC TGTGACTGGT GAGTACTCAA    1500
CCAAGTCATT CTGAGAATAG TGTATGCGGC GACCGAGTTG CTCTTGCCCG GCGTCAACAC    1560
GGGATAATAC CGCGCCACAT AGCAGAACTT TAAAAGTGCT CATCATTGGA AAACGTTCTT    1620
CGGGGCGAAA ACTCTCAAGG ATCTTACCGC TGTTGAGATC CAGTTCGATG TAACCCACTC    1680
GTGCACCCAA CTGATCTTCA GCATCTTTTA CTTTCACCAG CGTTTCTGGG TGAGCAAAAA    1740
CAGGAAGGCA AAATGCCGCA AAAAAGGGAA TAAGGGCGAC ACGGAAATGT TGAATACTCA    1800
TACTCTTCCT TTTTCAATAT TATTGAAGCA TTTATCAGGG TTATTGTCTC ATGAGCGGAT    1860
ACATATTTGA ATGTATTTAG AAAAATAAAC AAATAGGGGT TCCGCGCACA TTTCCCCGAA    1920
AAGTGCCACC TGACGCGCCC TGTAGCGGCG CATTAAGCGC GGCGGGTGTG GTGGTTACGC    1980
GCAGCGTGAC CGCTACACTT GCCAGCGCCC TAGCGCCCGC TCCTTTCGCT TTCTTCCCTT    2040
CCTTTCTCGC CACGTTCGCC GGCTTTCCCC GTCAAGCTCT AAATCGGGGG CTCCCTTTAG    2100
GGTTCCGATT TAGTGCTTTA CGGCACCTCG ACCCCAAAAA ACTTGATTAG GGTGATGGTT    2160
CACGTAGTGG GCCATCGCCC TGATAGACGG TTTTTCGCCC TTTGACGTTG GAGTCCACGT    2220
TCTTTAATAG TGGACTCTTG TTCCAAACTG GAACAACACT CAACCCTATC TCGGTCTATT    2280
CTTTTGATTT ATAAGGGATT TGCCGATTT CGGCCTATTG GTTAAAAAAT GAGCTGATTT    2340
AACAAAAATT TAACGCGAAT TTAACAAAA TATTAACGTT TACAATTTCC CATTCGCCAT    2400
TCAGGCTGCG CAACTGTTGG GAAGGGCGAT CGGTGCGGGC CTCTTCGCTA TTACGCCAGC    2460
GATNNNNNNN NNNNNNNNNN NNNNNNNNNN NNNNNNNNNN NNNNNNNNNN NNNNNNNNNN    2520
NNNNNNNNNN NNNNNNNNNN NNNNNNNNNN NNNNNNNNNN NNNNNNNNNN NNNNNNNNNN    2580
NNNNNNNNNN NNNNNNNNNN NNNNNNNNNN NNNNNNNNNN NNNNNNNNNN NNNNNNNNNN    2640
NNNNNNNNNN NNNNNNNNNN NNNNNNNNNN NNNNNNNNNN NNNNNNNNNN NNNNNNNNNN    2700
NNNNNNNNNN NNNNNNNNNN NNNNNNNNNN NNNNNNNNNN NNNNNNNNNN NNNNNNNNNN    2760
NNNNNNNNNN NNNNNNNNNN NNNNNNNNNN NNNNNNNNNN NNNNNNNNNN NNNNNNNNNN    2820
NNNNNNNNNN NNNNNNNNNN NNNNNNNNNN NNNNNNNNNN NNNNNNNNNN NNNNNNNNNN    2880
NNNNNNNNNN NNNNNNNNNN NNNNNNNNNN NNNNNNNNNN NNNNNNNNNN NNNNNNNNNN    2940
NNNNNNNNNN NNNNNNNNNN NNNNNNNNNN NNNNNNNNNN NNNNNNNNNN NNNNNNNNNN    3000
NNNNNNNNNN NNNNNNNNNN NNNNNNNNNN NNNNNNNNNN NNNNNNNNNN NNNNNNNNNN    3060
NNNNNNNNNN NNNNNNNNNN NNNNNNNNNN NNNNNNNNNN NNNNNNNNNN NNNNNNNNNN    3120
NNNNNNNNNN NNNNNNNNNN NNNNNNNNNN NNNNNNNNNN NNNNNNNNNN NNNNNNNNNN    3180
NNNNNNNNNN NNNNNNNNNN NNNNNNNNNN NNNNNNNNNN NNNNNNNNNN NNNNNNNNNN    3240
NNNNNNNNNN NNNNNNNNNN NNNNNNNNNN NNNNNNNNNN NNNNNNNNNN NNNNNNNNNN    3300
NNNNNNNNNN NNNNNNNNNN NNNNNNNNNN NNNNNNNNNN NNNNNNNNNN NNNNNNNNNN    3360
NNNNNNNNNN NNNNNNNNNN NNNNNNNNNN NNNNNNNNNN NNNNNNNNNN NNNNNNNNNN    3420
NNNNNNNNNN NNNNNNNNNN NNNNNNNNNC TCCGTTTTAT GGAAATATTT TCTACTATTA    3480
TGTTTATTCC TGGAATAATT ATATTGTACG CTGCTTATAT AAGAAAAATT AAAATGAAAA    3540
```

```
ATAATTAGAA TCTGAAAATG TCTTCTGGAA GCATCCATGT TATTACAGGC CCTATGTTTT    3600
CCGGTAAAAC ATCGGAGCTA GTAAGAAGAA TAAAAAGATT TATGCTATCT AACTTTAAAT    3660
GTATTATTAT TAAACATTGT GGAGATAATA GATATAATGA GGATGATATA AACAAAGTAT    3720
ATACTCATGA TCTATTGTTT ATGGAGGCTA CGGCATCTTC TAATCTATCT GTATTAGTAC    3780
CTACGCTATT AAATGATGGA GTCAGGTAA TAGGTATAGA CGAGGCTCAA TTCTTCTAG      3840
ACATAGTAGA ATTTAGTGAA TCCATGGCTA ATTTAGGTAA AACAGTTATT GTGGCCGCGC    3900
TTAACGGTGA TTTTAAACGC GAATTATTCG GTAACGTATA TAAGTTATTA TCATTAGCTG    3960
AAACAGTGTC CAGTTTGACA GCTATTGCG TGAAATGCTA TTGCGACGCT TCGTTTCTA      4020
AACGAGTTAC AGAAAATAAA GAAGTAATGG ATATAGGTGG TAAAGATAAA TACATAGCCG    4080
TGTGTAGGAA ATGTTTTTTT AGTAATTAAG GTTTTATCG ATCCCGGGTT AGAATATATG     4140
TATGTAAAAA TATAGTAGAA TTTCATTTTG TTTTTTTCTA TGCTATAAAT AGGCTGCAGG    4200
AATTCCTTAC ATATGGTTCG TGCTAACAAA CGCAACGAGG CTCTACGAAT CGGGGATCGC    4260
GGCCGCGATC CCGTCGTTTT ACAACGTCGT GACTGGGAAA ACCCTGGCGT TACCCAACTT    4320
AATCGCCTTG CAGCACATCC CCCTTTCGCC AGCTGGCGTA ATAGCGAAGA GGCCCGCACC    4380
GATCGCCCTT CCCAACAGTT GCGCAGCCTG AATGGCGAAT GGCGCTTTGC CTGGTTTCCG    4440
GCACCAGAAG CGGTGCCGGA AAGCTGGCTG GAGTGCGATC TTCCTGAGGC CGATACTGTC    4500
GTCGTCCCCT CAAACTGGCA GATGCACGGT TACGATGCGC CCATCTACAC CAACGTAACC    4560
TATCCCATTA CGGTCAATCC GCCGTTTGTT CCCACGGAGA ATCCGACGGG TTGTTACTCG    4620
CTCACATTTA ATGTTGATGA AAGCTGGCTA CAGGAAGGCC AGACGCGAAT TATTTTTGAT    4680
GGCGTTAACT CGGCGTTTCA TCTGTGGTGC AACGGGCGCT GGGTCGGTTA CGGCCAGGAC    4740
AGTCGTTTGC CGTCTGAATT TGACCTGAGC GCATTTTTAC GCGCCGGAGA AAACCGCCTC    4800
GCGGTGATGG TGCTGCGTTG GAGTGACGGC AGTTATCTGG AAGATCAGGA TATGTGGCGG    4860
ATGAGCGGCA TTTTCCGTGA CGTCTCGTTG CTGCATAAAC CGACTACACA AATCAGCGAT    4920
TTCCATGTTG CCACTCGCTT TAATGATGAT TTCAGCCGCG CTGTACTGGA GGCTGAAGTT    4980
CAGATGTGCG GCGAGTTGCG TGACTACCTA CGGGTAACAG TTTCTTTATG CAGGGTGAA    5040
ACGCAGGTCG CCAGCGGCAC CGCGCCTTTC GGCGGTGAAA TTATCGATGA GCGTGGTGGT    5100
TATGCCGATC GCGTCACACT ACGTCTGAAC GTCGAAAACC GAAACTGTG GAGCGCCGAA     5160
ATCCCGAATC TCTATCGTGC GGTGGTTGAA CTGCACACCG CCGACGGCAC GCTGATTGAA    5220
GCAGAAGCCT GCGATGTCGG TTTCCGCGAG GTGCGGATTG AAAATGGTCT GCTGCTGCTG    5280
AACGGCAAGC CGTTGCTGAT TCGAGGCGTT AACCGTCACG AGCATCATCC TCTGCATGGT    5340
CAGGTCATGG ATGAGCAGAC GATGGTGCAG GATATCCTGC TGATGAAGCA GAACAACTTT    5400
AACGCCGTGC GCTGTTCGCA TTATCCGAAC CATCCGCTGT GGTACACGCT GTGCGACCGC    5460
TACGGCCTGT ATGTGGTGGA TGAAGCCAAT ATTGAAACCC ACGGCATGGT GCCAATGAAT    5520
CGTCTGACCG ATGATCCGCG CTGGCTACCG GCGATGAGCG AACGCGTAAC GCGAATGGTG    5580
CAGCGCGATC GTAATCACCC GAGTGTGATC ATCTGGTCGC TGGGGAATGA ATCAGGCCAC    5640
GGCGCTAATC ACGACGCGCT GTATCGCTGG ATCAAATCTG TCGATCCTTC CCGCCCGGTG    5700
CAGTATGAAG GCGGCGGAGC CGACACCACG GCCACCGATA TTATTTGCCC GATGTACGCG    5760
CGCGTGGATG AAGACCAGCC CTTCCCGGCT GTGCCGAAAT GGTCCATCAA AAAATGGCTT    5820
TCGCTACCTG GAGAGACGCG CCCGCTGATC CTTTGCGAAT ACGCCCACGC GATGGGTAAC    5880
AGTCTTGGCG GTTTCGCTAA ATACTGGCAG GCGTTTCGTC AGTATCCCCG TTTACAGGGC    5940
```

```
GGCTTCGTCT GGGACTGGGT GGATCAGTCG CTGATTAAAT ATGATGAAAA CGGCAACCCG    6000
TGGTCGGCTT ACGGCGGTGA TTTTGGCGAT ACGCCGAACG ATCGCCAGTT CTGTATGAAC    6060
GGTCTGGTCT TTGCCGACCG CACGCCGCAT CCAGCGCTGA CGGAAGCAAA ACACCAGCAG    6120
CAGTTTTTCC AGTTCCGTTT ATCCGGGCAA ACCATCGAAG TGACCAGCGA ATACCTGTTC    6180
CGTCATAGCG ATAACGAGCT CCTGCACTGG ATGGTGGCGC TGGATGGTAA GCCGCTGGCA    6240
AGCGGTGAAG TGCCTCTGGA TGTCGCTCCA CAAGGTAAAC AGTTGATTGA ACTGCCTGAA    6300
CTACCGCAGC CGGAGAGCGC CGGGCAACTC TGGCTCACAG TACGCGTAGT GCAACCGAAC    6360
GCGACCGCAT GGTCAGAAGC CGGGCACATC AGCGCCTGGC AGCAGTGGCG TCTGGCGGAA    6420
AACCTCAGTG TGACGCTCCC CGCCGCGTCC CACGCCATCC GCATCTGAC CACCAGCGAA     6480
ATGGATTTTT GCATCGAGCT GGGTAATAAG CGTTGGCAAT TTAACCGCCA GTCAGGCTTT    6540
CTTTCACAGA TGTGGATTGG CGATAAAAAA CAACTGCTGA CGCCGCTGCG CGATCAGTTC    6600
ACCCGTGCAC CGCTGGATAA CGACATTGGC GTAAGTGAAG CGACCCGCAT TGACCCTAAC    6660
GCCTGGGTCG AACGCTGGAA GGCGGCGGGC CATTACCAGG CCGAAGCAGC GTTGTTGCAG    6720
TGCACGGCAG ATACACTTGC TGATGCGGTG CTGATTACGA CCGCTCACGC GTGGCAGCAT    6780
CAGGGGAAAA CCTTATTTAT CAGCCGGAAA ACCTACCGGA TTGATGGTAG TGGTCAAATG    6840
GCGATTACCG TTGATGTTGA AGTGGCGAGC GATACACCGC ATCCGGCGCG GATTGGCCTG    6900
AACTGCCAGC TGGCGCAGGT AGCAGAGCGG GTAAACTGGC TCGGATTAGG GCCGCAAGAA    6960
AACTATCCCG ACCGCCTTAC TGCCGCCTGT TTTGACCGCT GGGATCTGCC ATTGTCAGAC    7020
ATGTATACCC CGTACGTCTT CCCGAGCGAA AACGGTCTGC GCTGCGGGAC GCGCGAATTG    7080
AATTATGGCC CACACCAGTG GCGCGGCGAC TTCCAGTTCA ACATCAGCCG CTACAGTCAA    7140
CAGCAACTGA TGGAAACCAG CCATCGCCAT CTGCTGCACG CGGAAGAAGG CACATGGCTG    7200
AATATCGACG GTTTCCATAT GGGGATTGGT GGCGACGACT CCTGGAGCCC GTCAGTATCG    7260
GCGGAATTAC AGCTGAGCGC CGGTCGCTAC CATTACCAGT TGGTCTGGTG TCAAAAATAA    7320
TAATAACCGG GCAGGCCATG TCTGCCCGTA TTTCGCGTAA GGAAATCCAT TATGTACTAT    7380
TTAATCCAAC AATGTCTGGA AAGAACTGTC CTTCATCGAT AGGCCTGTCG ACGGATCCTG    7440
GGGGTACCGG TTTAGTGTAA TAAATTTAAT AAAATATTGA CAAAATAGTT AAATGAATAT    7500
ATGAAAGTAC ATTATACACG GAATGGAGTT CGATATTAGT TCTTGCAGAA TGATATATTC    7560
TGTTCTCGAA CAATATCACT TTGTTTCTGA TAATCGTTAT AACAATCAAA AATTTAGAAT    7620
TATATTATAC TGTTTAAAAG ATTCTACGAT AAAGAAATAT CCGTACAGGT TTGTTTCTGA    7680
AATTCACTTT GTAAGATACA TAATTAACAA ATTCAGGGGG AAAAATCTTT ACAAAATTAG    7740
TATAGAAGCT ATAGATATAT CAAAAGGTAG ACAACAAATA ATCAGAACCT AATTTTTTA    7800
TCAAAAAATT AAAATATAAA TAAAATGAAA AATAACTTGT ATGAAGAAAA AATGAACATG    7860
AGTAAGAAAC AAGTAAAAAC TCAAAGTAAA TGTAATAATA ACGCATCTAG ATTTACATGC    7920
TTGGATGCGG TGCAATACGC TAAGCTTNNN NNNNNNNNNN NNNNNNNNNN NNNNNNNNNN    7980
NNNNNNNNNN NNNNNNNNNN NNNNNNNNNN NNNNNNNNNN NNNNNNNNNN NNNNNNNNNN    8040
NNNNNNNNNN NNNNNNNNNN NNNNNNNNNN NNNNNNNNNN NNNNNNNNNN NNNNNNNNNN    8100
NNNNNNNNNN NNNNNNNNNN NNNNNNNNNN NNNNNNNNNN NNNNNNNNNN NNNNNNNNNN    8160
NNNNNNNNNN NNNNNNNNNN NNNNNNNNNN NNNNNNNNNN NNNNNNNNNN NNNNNNNNNN    8220
NNNNNNNNNN NNNNNNNNNN NNNNNNNNNN NNNGGATCCT GCATTAATGA ATCGGCCAAC    8280
GCGCGGGGAG AGGCGGTTTG CGTATTGGGC GCT                                 8313
```

( 2 ) INFORMATION FOR SEQ ID NO:3:

( i ) SEQUENCE CHARACTERISTICS:
        ( A ) LENGTH: 9454 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pTKm-VVtka ( x i ) SEQUENCE DESCRIPTION: SEQ ID NO:3:

```
CTTCCGCTTC CTCGCTCACT GACTCGCTGC GCTCGGTCGT TCGGCTGCGG CGAGCGGTAT        60

CAGCTCACTC AAAGGCGGTA ATACGGTTAT CCACAGAATC AGGGGATAAC GCAGGAAAGA       120

ACATGTGAGC AAAAGGCCAG CAAAAGGCCA GGAACCGTAA AAAGGCCGCG TTGCTGGCGT       180

TTTTCCATAG GCTCCGCCCC CCTGACGAGC ATCACAAAAA TCGACGCTCA AGTCAGAGGT       240

GGCGAAACCC GACAGGACTA TAAAGATACC AGGCGTTTCC CCCTGGAAGC TCCCTCGTGC       300

GCTCTCCTGT TCCGACCCTG CCGCTTACCG GATACCTGTC CGCCTTTCTC CCTTCGGGAA       360

GCGTGGCGCT TTCTCAATGC TCACGCTGTA GGTATCTCAG TTCGGTGTAG GTCGTTCGCT       420

CCAAGCTGGG CTGTGTGCAC GAACCCCCCG TTCAGCCCGA CCGCTGCGCC TTATCCGGTA       480

ACTATCGTCT TGAGTCCAAC CCGGTAAGAC ACGACTTATC GCCACTGGCA GCAGCCACTG       540

GTAACAGGAT TAGCAGAGCG AGGTATGTAG GCGGTGCTAC AGAGTTCTTG AAGTGGTGGC       600

CTAACTACGG CTACACTAGA AGGACAGTAT TTGGTATCTG CGCTCTGCTG AAGCCAGTTA       660

CCTTCGGAAA AAGAGTTGGT AGCTCTTGAT CCGGCAAACA AACCACCGCT GGTAGCGGTG       720

GTTTTTTTGT TTGCAAGCAG CAGATTACGC GCAGAAAAAA AGGATCTCAA GAAGATCCTT       780

TGATCTTTTC TACGGGGTCT GACGCTCAGT GGAACGAAAA CTCACGTTAA GGGATTTTGG       840

TCATGAGATT ATCAAAAAGG ATCTTCACCT AGATCCTTTT AAATTAAAAA TGAAGTTTTA       900

AATCAATCTA AAGTATATAT GAGTAAACTT GGTCTGACAG TTACCAATGC TTAATCAGTG       960

AGGCACCTAT CTCAGCGATC TGTCTATTTC GTTCATCCAT AGTTGCCTGA CTCCCCGTCG      1020

TGTAGATAAC TACGATACGG GAGGGCTTAC CATCTGGCCC CAGTGCTGCA ATGATACCGC      1080

GAGACCCACG CTCACCGGCT CCAGATTTAT CAGCAATAAA CCAGCCAGCC GGAAGGGCCG      1140

AGCGCAGAAG TGGTCCTGCA ACTTTATCCG CCTCCATCCA GTCTATTAAT TGTTGCCGGG      1200

AAGCTAGAGT AAGTAGTTCG CCAGTTAATA GTTTGCGCAA CGTTGTTGCC ATTGCTGGAG      1260

GCATCGTGGT GTCACGCTCG TCGTTTGGTA TGGCTTCATT CAGCTCCGGT TCCCAACGAT      1320

CAAGGCGAGT TACATGATCC CCCATGTTGT GCAAAAAAGC GGTTAGCTCC TTCGGTCCTC      1380

CGATCGTTGT CAGAAGTAAG TTGGCCGCAG TGTTATCACT CATGGTTATG GCAGCACTGC      1440

ATAATTCTCT TACTGTCATG CCATCCGTAA GATGCTTTTC TGTGACTGGT GAGTACTCAA      1500

CCAAGTCATT CTGAGAATAG TGTATGCGGC GACCGAGTTG CTCTTGCCCG GCGTCAACAC      1560

GGGATAATAC CGCGCCACAT AGCAGAACTT TAAAAGTGCT CATCATTGGA AAACGTTCTT      1620

CGGGGCGAAA ACTCTCAAGG ATCTTACCGC TGTTGAGATC CAGTTCGATG TAACCCACTC      1680

GTGCACCCAA CTGATCTTCA GCATCTTTTA CTTTCACCAG CGTTCTGGG TGAGCAAAAA       1740

CAGGAAGGCA AAATGCCGCA AAAAAGGGAA TAAGGGCGAC ACGGAAATGT TGAATACTCA      1800

TACTCTTCCT TTTTCAATAT TATTGAAGCA TTTATCAGGG TTATTGTCTC ATGAGCGGAT      1860

ACATATTTGA ATGTATTTAG AAAAATAAAC AAATAGGGGT TCCGCGCACA TTTCCCCGAA      1920

AAGTGCCACC TGACGCGCCC TGTAGCGGCG CATTAAGCGC GGCGGGTGTG GTGGTTACGC      1980
```

| | | | | | |
|---|---|---|---|---|---|
| GCAGCGTGAC | CGCTACACTT | GCCAGCGCCC | TAGCGCCCGC | TCCTTTCGCT | TTCTTCCCTT | 2040
| CCTTTCTCGC | CACGTTCGCC | GGCTTTCCCC | GTCAAGCTCT | AAATCGGGGG | CTCCCTTTAG | 2100
| GGTTCCGATT | TAGTGCTTTA | CGGCACCTCG | ACCCCAAAAA | ACTTGATTAG | GGTGATGGTT | 2160
| CACGTAGTGG | GCCATCGCCC | TGATAGACGG | TTTTTCGCCC | TTTGACGTTG | GAGTCCACGT | 2220
| TCTTTAATAG | TGGACTCTTG | TTCCAAACTG | GAACAACACT | CAACCCTATC | TCGGTCTATT | 2280
| CTTTTGATTT | ATAAGGGATT | TTGCCGATTT | CGGCCTATTG | GTTAAAAAAT | GAGCTGATTT | 2340
| AACAAAAATT | TAACGCGAAT | TTTAACAAAA | TATTAACGTT | TACAATTTCC | CATTCGCCAT | 2400
| TCAGGCTGCG | CAACTGTTGG | GAAGGGCGAT | CGGTGCGGGC | CTCTTCGCTA | TTACGCCAGC | 2460
| GATNNNNNNN | NNNNNNNNNN | NNNNNNNNNN | NNNNNNNNNN | NNNNNNNNNN | NNNNNNNNNN | 2520
| NNNNNNNNNN | NNNNNNNNNN | NNNNNNNNNN | NNNNNNNNNN | NNNNNNNNNN | NNNNNNNNNN | 2580
| NNNNNNNNNN | NNNNNNNNNN | NNNNNNNNNN | NNNNNNNNNN | NNNNNNNNNN | NNNNNNNNNN | 2640
| NNNNNNNNNN | NNNNNNNNNN | NNNNNNNNNN | NNNNNNNNNN | NNNNNNNNNN | NNNNNNNNNN | 2700
| NNNNNNNNNN | NNNNNNNNNN | NNNNNNNNNN | NNNNNNNNNN | NNNNNNNNNN | NNNNNNNNNN | 2760
| NNNNNNNNNN | NNNNNNNNNN | NNNNNNNNNN | NNNNNNNNNN | NNNNNNNNNN | NNNNNNNNNN | 2820
| NNNNNNNNNN | NNNNNNNNNN | NNNNNNNNNN | NNNNNNNNNN | NNNNNNNNNN | NNNNNNNNNN | 2880
| NNNNNNNNNN | NNNNNNNNNN | NNNNNNNNNN | NNNNNNNNNN | NNNNNNNNNN | NNNNNNNNNN | 2940
| NNNNNNNNNN | NNNNNNNNNN | NNNNNNNNNN | NNNNNNNNNN | NNNNNNNNNN | NNNNNNNNNN | 3000
| NNNNNNNNNN | NNNNNNNNNN | NNNNNNNNNN | NNNNNNNNNN | NNNNNNNNNN | NNNNNNNNNN | 3060
| NNNNNNNNNN | NNNNNNNNNN | NNNNNNNNNN | NNNNNNNNNN | NNNNNNNNNN | NNNNNNNNNN | 3120
| NNNNNNNNNN | NNNNNNNNNN | NNNNNNNNNN | NNNNNNNNNN | NNNNNNNNNN | NNNNNNNNNN | 3180
| NNNNNNNNNN | NNNNNNNNNN | NNNNNNNNNN | NNNNNNNNNN | NNNNNNNNNN | NNNNNNNNNN | 3240
| NNNNNNNNNN | NNNNNNNNNN | NNNNNNNNNN | NNNNNNNNNN | NNNNNNNNNN | NNNNNNNNNN | 3300
| NNNNNNNNNN | NNNNNNNNNN | NNNNNNNNNN | NNNNNNNNNN | NNNNNNNNNN | NNNNNNNNNN | 3360
| NNNNNNNNNN | NNNNNNNNNN | NNNNNNNNNN | NNNNNNNNNN | NNNNNNNNNN | NNNNNNNNNN | 3420
| NNNNNNNNNN | NNNNNNNNNN | NNNNNNNNNC | TCCGTTTTAT | GGAAATATTT | TCTACTATTA | 3480
| TGTTTATTCC | TGGAATAATT | ATATTGTACG | CTGCTTATAT | AAGAAAAATT | AAAATGAAAA | 3540
| ATAATTAGAA | TCTGAAAATG | TCTTCTGGAA | GCATCCATGT | TATTACAGGC | CCTATGTTTT | 3600
| CCGGTAAAAC | ATCGGAGCTA | GTAAGAAGAA | TAAAAAGATT | TATGCTATCT | AACTTTAAAT | 3660
| GTATTATTAT | TAAACATTGT | GGAGATAATA | GATATAATGA | GGATGATATA | AACAAAGTAT | 3720
| ATACTCATGA | TCTATTGTTT | ATGGAGGCTA | CGGCATCTTC | TAATCTATCT | GTATTAGTAC | 3780
| CTACGCTATT | AAATGATGGA | GTTCAGGTAA | TAGGTATAGA | CGAGGCTCAA | TTCTTTCTAG | 3840
| ACATAGTAGA | ATTTAGTGAA | TCCATGGCTA | ATTTAGGTAA | AACAGTTATT | GTGGCCGCGC | 3900
| TTAACGGTGA | TTTTAAACGC | GAATTATTCG | GTAACGTATA | TAAGTTATTA | TCATTAGCTG | 3960
| AAACAGTGTC | CAGTTTGACA | GCTATTTGCG | TGAAATGCTA | TTGCGACGCT | TCGTTTTCTA | 4020
| AACGAGTTAC | AGAAAATAAA | GAAGTAATGG | ATATAGGTGG | TAAAGATAAA | TACATAGCCG | 4080
| TGTGTAGGAA | ATGTTTTTTT | AGTAATTAAG | GTTTTATCG | ATCCCAAAAA | ACTGTTAAC | 4140
| AAGGTCCCTA | TTGTTACAGA | TGGAAGGGTC | AAACTTAATA | AAGGATATTT | GTTCGACTTT | 4200
| GTGATTAGTT | TGATGCGATT | CAAAAAGAA | TCCTCTCTAG | CTACCACCGC | AATAGATCCT | 4260
| GTTAGATACA | TAGATCCTCG | TCGCAATATC | GCATTTTCTA | ACGTGATGGA | TATATTAAAG | 4320
| TCGAATAAAG | TGAACAATAA | TTAATTCTTT | ATTGTCATCA | TGAACGGCGG | ACATATTCAG | 4380

```
TTGATAATCG GCCCCATGTT TTCAGGTAAA AGTACAGAAT TAATTAGACG AGTTAGACGT    4440
TATCAAATAG CTCAATATAA ATGCGTGACT ATAAATATT  CTAACGATAA TAGATACGGA    4500
ACGGGACTAT GGACGCATGA TAAGAATAAT TTTGAAGCAT GGAAGCAAC  TAAACTATGT    4560
GATGTCTTGG AATCAATTAC AGATTTCTCC GTGATAGGTA TCGATGAAGG ACAGTTCTTT    4620
CCAGACATTG TTGAATTCTG TGAGCGTATG GCAAACGAAG GAAAATAGT  TATAGTAGCC    4680
GCACTCGATG GGACATTTCA ACGTAAACCG TTTAATAATA TTTGAATCT  TATTCCATTA    4740
TCTGAAATGG TGGTAAAACT AACTGCTGTG TGTATGAAAT GCTTAAGGA  GGCTTCCTTT    4800
TCTAAACGAT TGGGTGAGGA AACCGAGATA GAAATAATAG GAGGTAATGA TATGTATCAA    4860
TCGGTGTGTA GAAAGTGTTA CATCGACTCA TAATATTATA TTTTTATCT  AAAAAACTAA    4920
AAATAAACAT TGATTAAATT TTAATATAAT ACTTAAAAAT GGATGTTGTG TCGTTAGATA    4980
AACCGTTTAT GTATTTGAG  GAAATTGATA ATGAGTTAGA TTACGAACCA GAAAGTGCAA    5040
ATGAGGTCGC AAAAAAACTG CCGTATCAAG GACAGTTAAA ACTATTACTA GGAGAATTAT    5100
TTTTTCTTAG TAAGTTACAG CGACACGGTA TATTAGATGG TGCCACCGTA GTGTATATAG    5160
GATCTGCTCC CGGTACACAT ATACGTTATT TGAGAGATCA TTTCTATAAT TTAGGAGTGA    5220
TCATCAAATG GATGCTAATT GACGGCCGCC ATCATGATCC TATTTTGGGT TAGAATATAT    5280
GTATGTAAAA ATATAGTAGA ATTTCATTTT GTTTTTTCT  ATGCTATAAA TAGGCTGCAG    5340
GAATTCCTTA CATATGGTTC GTGCTAACAA ACGCAACGAG GCTCTACGAA TCGGGATCG    5400
CGGCCGCGAT CCCGTCGTTT TACAACGTCG TGACTGGGAA AACCCTGGCG TTACCCAACT    5460
TAATCGCCTT GCAGCACATC CCCCTTTCGC CAGCTGGCGT AATAGCGAAG AGGCCCGCAC    5520
CGATCGCCCT TCCCAACAGT TGCGCAGCCT GAATGGCGAA TGGCGCTTTG CCTGGTTTCC    5580
GGCACCAGAA GCGGTGCCGG AAAGCTGGCT GGAGTGCGAT CTTCCTGAGG CCGATACTGT    5640
CGTCGTCCCC TCAAACTGGC AGATGCACGG TTACGATGCG CCCATCTACA CCAACGTAAC    5700
CTATCCCATT ACGGTCAATC CGCCGTTTGT TCCCACGGAG AATCCGACGG GTTGTTACTC    5760
GCTCACATTT AATGTTGATG AAAGCTGGCT ACAGGAAGGC CAGACGCGAA TTATTTTTGA    5820
TGGCGTTAAC TCGGCGTTTC ATCTGTGGTG CAACGGGCGC TGGGTCGGTT ACGGCCAGGA    5880
CAGTCGTTTG CCGTCTGAAT TTGACCTGAG CGCATTTTTA CGCGCCGGAG AAAACCGCCT    5940
CGCGGTGATG GTGCTGCGTT GGAGTGACGG CAGTTATCTG GAAGATCAGG ATATGTGGCG    6000
GATGAGCGGC ATTTTCCGTG ACGTCTCGTT GCTGCATAAA CCGACTACAC AAATCAGCGA    6060
TTTCCATGTT GCCACTCGCT TTAATGATGA TTTCAGCCGC GCTGTACTGG AGGCTGAAGT    6120
TCAGATGTGC GGCGAGTTGC GTGACTACCT ACGGGTAACA GTTTCTTTAT GGCAGGGTGA    6180
AACGCAGGTC GCCAGCGGCA CCGCGCCTTT CGGCGGTGAA ATTATCGATG AGCGTGGTGG    6240
TTATGCCGAT CGCGTCACAC TACGTCTGAA CGTCGAAAAC CCGAAACTGT GGAGCGCCGA    6300
AATCCCGAAT CTCTATCGTG CGGTGGTTGA ACTGCACACC GCCGACGGCA CGCTGATTGA    6360
AGCAGAAGCC TGCGATGTCG GTTTCCGCGA GGTGCGGATT GAAAATGGTC TGCTGCTGCT    6420
GAACGGCAAG CCGTTGCTGA TTCGAGGCGT TAACCGTCAC GAGCATCATC CTCTGCATGG    6480
TCAGGTCATG GATGAGCAGA CGATGGTGCA GGATATCCTG CTGATGAAGC AGAACAACTT    6540
TAACGCCGTG CGCTGTTCGC ATTATCCGAA CCATCCGCTG TGGTACACGC TGTGCGACCG    6600
CTACGGCCTG TATGTGGTGG ATGAAGCCAA TATTGAAACC CACGGCATGG TGCCAATGAA    6660
TCGTCTGACC GATGATCCGC GCTGGCTACC GGCGATGAGC GAACGCGTAA CGCGAATGGT    6720
GCAGCGCGAT CGTAATCACC CGAGTGTGAT CATCTGGTCG CTGGGGAATG AATCAGGCCA    6780
```

```
CGGCGCTAAT CACGACGCGC TGTATCGCTG GATCAAATCT GTCGATCCTT CCCGCCCGGT    6840
GCAGTATGAA GGCGGCGGAG CCGACACCAC GGCCACCGAT ATTATTTGCC CGATGTACGC    6900
GCGCGTGGAT GAAGACCAGC CCTTCCGGC  TGTGCCGAAA TGGTCCATCA AAAAATGGCT    6960
TTCGCTACCT GGAGAGACGC GCCCGCTGAT CCTTTGCGAA TACGCCCACG CGATGGGTAA    7020
CAGTCTTGGC GGTTTCGCTA AATACTGGCA GGCGTTTCGT CAGTATCCCC GTTACAGGG     7080
CGGCTTCGTC TGGGACTGGG TGGATCAGTC GCTGATTAAA TATGATGAAA ACGGCAACCC    7140
GTGGTCGGCT TACGGCGGTG ATTTTGGCGA TACGCCGAAC GATCGCCAGT TCTGTATGAA    7200
CGGTCTGGTC TTTGCCGACC GCACGCCGCA TCCAGCGCTG ACGGAAGCAA AACACCAGCA    7260
GCAGTTTTTC CAGTTCCGTT TATCCGGGCA AACCATCGAA GTGACCAGCG AATACCTGTT    7320
CCGTCATAGC GATAACGAGC TCCTGCACTG GATGGTGGCG CTGGATGGTA AGCCGCTGGC    7380
AAGCGGTGAA GTGCCTCTGG ATGTCGCTCC ACAAGGTAAA CAGTTGATTG AACTGCCTGA    7440
ACTACCGCAG CCGGAGAGCG CCGGGCAACT CTGGCTCACA GTACGCGTAG TGCAACCGAA    7500
CGCGACCGCA TGGTCAGAAG CCGGGCACAT CAGCGCCTGG CAGCAGTGGC GTCTGGCGGA    7560
AAACCTCAGT GTGACGCTCC CCGCCGCGTC CCACGCCATC CCGCATCTGA CCACCAGCGA    7620
AATGGATTTT TGCATCGAGC TGGGTAATAA GCGTTGGCAA TTTAACCGCC AGTCAGGCTT    7680
TCTTTCACAG ATGTGGATTG GCGATAAAAA ACAACTGCTG ACGCCGCTGC GCGATCAGTT    7740
CACCCGTGCA CCGCTGGATA CGACATTGG  CGTAAGTGAA GCGACCCGCA TTGACCCTAA    7800
CGCCTGGGTC GAACGCTGGA AGGCGGCGGG CCATTACCAG GCCGAAGCAG CGTTGTTGCA    7860
GTGCACGGCA GATACACTTG CTGATGCGGT GCTGATTACG ACCGCTCACG CGTGGCAGCA    7920
TCAGGGGAAA ACCTTATTTA TCAGCCGGAA AACCTACCGG ATTGATGGTA GTGGTCAAAT    7980
GGCGATTACC GTTGATGTTG AAGTGGCGAG CGATACACCG CATCCGGCGC GGATTGGCCT    8040
GAACTGCCAG CTGGCGCAGG TAGCAGAGCG GGTAAACTGG CTCGGATTAG GCCGCAAGA    8100
AAACTATCCC GACCGCCTTA CTGCCGCCTG TTTTGACCGC TGGGATCTGC CATTGTCAGA    8160
CATGTATACC CCGTACGTCT TCCCGAGCGA AAACGGTCTG CGCTGCGGGA CGCGCGAATT    8220
GAATTATGGC CCACACCAGT GGCGCGGCGA CTTCCAGTTC AACATCAGCC GCTACAGTCA    8280
ACAGCAACTG ATGGAAACCA GCCATCGCCA TCTGCTGCAC GCGGAAGAAG GCACATGGCT    8340
GAATATCGAC GGTTTCCATA TGGGGATTGG TGGCGACGAC TCCTGGAGCC CGTCAGTATC    8400
GGCGGAATTA CAGCTGAGCG CCGGTCGCTA CCATTACCAG TTGGTCTGGT GTCAAAAATA    8460
ATAATAACCG GGCAGGCCAT GTCTGCCCGT ATTTCGCGTA AGGAAATCCA TTATGTACTA    8520
TTTAATCCAA CAATGTCTGG AAAGAACTGT CCTTCATCGA TAGGCCTGTC GACGGATCCT    8580
GGGGGTACCG GTTAGTGTA  ATAAATTTAA TAAATATTG  ACAAATAGT  TAAATGAATA    8640
TATGAAAGTA CATTATACAC GGAATGGAGT TCGATATTAG TTCTTGCAGA ATGATATATT    8700
CTGTTCTCGA ACAATATCAC TTTGTTTCTG ATAATCGTTA TAACAATCAA AAATTTAGAA    8760
TTATATTATA CTGTTTAAAA GATTCTACGA TAAAGAAATA TCCGTACAGG TTTGTTTCTG    8820
AAATTCACTT TGTAAGATAC ATAATTAACA AATTCAGGGG GAAAAATCTT TACAAAATTA    8880
GTATAGAAGC TATAGATATA TCAAAGGTA  GACAACAAAT AATCAGAACC TAATTTTTTT    8940
ATCAAAAAAT TAAAATATAA ATAAAATGAA AAATAACTTG TATGAAGAAA AAATGAACAT    9000
GAGTAAGAAA CAAGTAAAAA CTCAAAGTAA ATGTAATAAT AACGCATCTA GATTACATG     9060
CTTGGATGCG GTGCAATACG CTAAGCTTNN NNNNNNNNNN NNNNNNNNNN NNNNNNNNNN    9120
NNNNNNNNNN NNNNNNNNNN NNNNNNNNNN NNNNNNNNNN NNNNNNNNNN NNNNNNNNNN    9180
```

| | | | | | | |
|---|---|---|---|---|---|---|
| NNNNNNNNNN | NNNNNNNNNN | NNNNNNNNNN | NNNNNNNNNN | NNNNNNNNNN | NNNNNNNNNN | 9240 |
| NNNNNNNNNN | NNNNNNNNNN | NNNNNNNNNN | NNNNNNNNNN | NNNNNNNNNN | NNNNNNNNNN | 9300 |
| NNNNNNNNNN | NNNNNNNNNN | NNNNNNNNNN | NNNNNNNNNN | NNNNNNNNNN | NNNNNNNNNN | 9360 |
| NNNNNNNNNN | NNNNNNNNNN | NNNNNNNNNN | NNNNGGATCC | TGCATTAATG | AATCGGCCAA | 9420 |
| CGCGCGGGGA | GAGGCGGTTT | GCGTATTGGG | CGCT | | | 9454 |

( 2 ) INFORMATION FOR SEQ ID NO:4:

( i ) SEQUENCE CHARACTERISTICS:
        ( A ) LENGTH: 9454 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pTKm-VVtkb ( x i ) SEQUENCE DESCRIPTION: SEQ ID NO:4:

| | | | | | | |
|---|---|---|---|---|---|---|
| CTTCCGCTTC | CTCGCTCACT | GACTCGCTGC | GCTCGGTCGT | TCGGCTGCGG | CGAGCGGTAT | 60 |
| CAGCTCACTC | AAAGGCGGTA | ATACGGTTAT | CCACAGAATC | AGGGGATAAC | GCAGGAAAGA | 120 |
| ACATGTGAGC | AAAAGGCCAG | CAAAAGGCCA | GGAACCGTAA | AAAGGCCGCG | TTGCTGGCGT | 180 |
| TTTTCCATAG | GCTCCGCCCC | CCTGACGAGC | ATCACAAAAA | TCGACGCTCA | AGTCAGAGGT | 240 |
| GGCGAAACCC | GACAGGACTA | TAAAGATACC | AGGCGTTTCC | CCCTGGAAGC | TCCCTCGTGC | 300 |
| GCTCTCCTGT | TCCGACCCTG | CCGCTTACCG | GATACCTGTC | CGCCTTTCTC | CCTTCGGGAA | 360 |
| GCGTGGCGCT | TTCTCAATGC | TCACGCTGTA | GGTATCTCAG | TTCGGTGTAG | GTCGTTCGCT | 420 |
| CCAAGCTGGG | CTGTGTGCAC | GAACCCCCCG | TTCAGCCCGA | CCGCTGCGCC | TTATCCGGTA | 480 |
| ACTATCGTCT | TGAGTCCAAC | CCGGTAAGAC | ACGACTTATC | GCCACTGGCA | GCAGCCACTG | 540 |
| GTAACAGGAT | TAGCAGAGCG | AGGTATGTAG | GCGGTGCTAC | AGAGTTCTTG | AAGTGGTGGC | 600 |
| CTAACTACGG | CTACACTAGA | AGGACAGTAT | TTGGTATCTG | CGCTCTGCTG | AAGCCAGTTA | 660 |
| CCTTCGGAAA | AAGAGTTGGT | AGCTCTTGAT | CCGGCAAACA | AACCACCGCT | GGTAGCGGTG | 720 |
| GTTTTTTTGT | TTGCAAGCAG | CAGATTACGC | GCAGAAAAAA | AGGATCTCAA | GAAGATCCTT | 780 |
| TGATCTTTTC | TACGGGGTCT | GACGCTCAGT | GGAACGAAAA | CTCACGTTAA | GGGATTTTGG | 840 |
| TCATGAGATT | ATCAAAAAGG | ATCTTCACCT | AGATCCTTTT | AAATTAAAAA | TGAAGTTTTA | 900 |
| AATCAATCTA | AAGTATATAT | GAGTAAACTT | GGTCTGACAG | TTACCAATGC | TTAATCAGTG | 960 |
| AGGCACCTAT | CTCAGCGATC | TGTCTATTTC | GTTCATCCAT | AGTTGCCTGA | CTCCCCGTCG | 1020 |
| TGTAGATAAC | TACGATACGG | GAGGGCTTAC | CATCTGGCCC | CAGTGCTGCA | ATGATACCGC | 1080 |
| GAGACCCACG | CTCACCGGCT | CCAGATTTAT | CAGCAATAAA | CCAGCCAGCC | GGAAGGGCCG | 1140 |
| AGCGCAGAAG | TGGTCCTGCA | ACTTTATCCG | CCTCCATCCA | GTCTATTAAT | TGTTGCCGGG | 1200 |
| AAGCTAGAGT | AAGTAGTTCG | CCAGTTAATA | GTTTGCGCAA | CGTTGTTGCC | ATTGCTGGAG | 1260 |
| GCATCGTGGT | GTCACGCTCG | TCGTTTGGTA | TGGCTTCATT | CAGCTCCGGT | TCCCAACGAT | 1320 |
| CAAGGCGAGT | TACATGATCC | CCCATGTTGT | GCAAAAAGC | GGTTAGCTCC | TTCGGTCCTC | 1380 |
| CGATCGTTGT | CAGAAGTAAG | TTGGCCGCAG | TGTTATCACT | CATGGTTATG | GCAGCACTGC | 1440 |
| ATAATTCTCT | TACTGTCATG | CCATCCGTAA | GATGCTTTTC | TGTGACTGGT | GAGTACTCAA | 1500 |
| CCAAGTCATT | CTGAGAATAG | TGTATGCGGC | GACCGAGTTG | CTCTTGCCCG | GCGTCAACAC | 1560 |
| GGGATAATAC | CGCGCCACAT | AGCAGAACTT | TAAAAGTGCT | CATCATTGGA | AAACGTTCTT | 1620 |
| CGGGGCGAAA | ACTCTCAAGG | ATCTTACCGC | TGTTGAGATC | CAGTTCGATG | TAACCCACTC | 1680 |

| | | | | | | |
|---|---|---|---|---|---|---|
| GTGCACCCAA | CTGATCTTCA | GCATCTTTTA | CTTTCACCAG | CGTTTCTGGG | TGAGCAAAAA | 1740 |
| CAGGAAGGCA | AAATGCCGCA | AAAAAGGGAA | TAAGGGCGAC | ACGGAAATGT | TGAATACTCA | 1800 |
| TACTCTTCCT | TTTTCAATAT | TATTGAAGCA | TTTATCAGGG | TTATTGTCTC | ATGAGCGGAT | 1860 |
| ACATATTTGA | ATGTATTTAG | AAAAATAAAC | AAATAGGGGT | TCCGCGCACA | TTTCCCCGAA | 1920 |
| AAGTGCCACC | TGACGCGCCC | TGTAGCGGCG | CATTAAGCGC | GGCGGGTGTG | GTGGTTACGC | 1980 |
| GCAGCGTGAC | CGCTACACTT | GCCAGCGCCC | TAGCGCCCGC | TCCTTTCGCT | TTCTTCCCTT | 2040 |
| CCTTTCTCGC | CACGTTCGCC | GGCTTTCCCC | GTCAAGCTCT | AAATCGGGGG | CTCCCTTTAG | 2100 |
| GGTTCCGATT | TAGTGCTTTA | CGGCACCTCG | ACCCCAAAAA | ACTTGATTAG | GGTGATGGTT | 2160 |
| CACGTAGTGG | GCCATCGCCC | TGATAGACGG | TTTTTCGCCC | TTTGACGTTG | GAGTCCACGT | 2220 |
| TCTTTAATAG | TGGACTCTTG | TTCCAAACTG | GAACAACACT | CAACCCTATC | TCGGTCTATT | 2280 |
| CTTTTGATTT | ATAAGGGATT | TTGCCGATTT | CGGCCTATTG | GTTAAAAAAT | GAGCTGATTT | 2340 |
| AACAAAAATT | TAACGCGAAT | TTTAACAAAA | TATTAACGTT | TACAATTTCC | CATTCGCCAT | 2400 |
| TCAGGCTGCG | CAACTGTTGG | GAAGGGCGAT | CGGTGCGGGC | CTCTTCGCTA | TTACGCCAGC | 2460 |
| GATNNNNNNN | NNNNNNNNNN | NNNNNNNNNN | NNNNNNNNNN | NNNNNNNNNN | NNNNNNNNNN | 2520 |
| NNNNNNNNNN | NNNNNNNNNN | NNNNNNNNNN | NNNNNNNNNN | NNNNNNNNNN | NNNNNNNNNN | 2580 |
| NNNNNNNNNN | NNNNNNNNNN | NNNNNNNNNN | NNNNNNNNNN | NNNNNNNNNN | NNNNNNNNNN | 2640 |
| NNNNNNNNNN | NNNNNNNNNN | NNNNNNNNNN | NNNNNNNNNN | NNNNNNNNNN | NNNNNNNNNN | 2700 |
| NNNNNNNNNN | NNNNNNNNNN | NNNNNNNNNN | NNNNNNNNNN | NNNNNNNNNN | NNNNNNNNNN | 2760 |
| NNNNNNNNNN | NNNNNNNNNN | NNNNNNNNNN | NNNNNNNNNN | NNNNNNNNNN | NNNNNNNNNN | 2820 |
| NNNNNNNNNN | NNNNNNNNNN | NNNNNNNNNN | NNNNNNNNNN | NNNNNNNNNN | NNNNNNNNNN | 2880 |
| NNNNNNNNNN | NNNNNNNNNN | NNNNNNNNNN | NNNNNNNNNN | NNNNNNNNNN | NNNNNNNNNN | 2940 |
| NNNNNNNNNN | NNNNNNNNNN | NNNNNNNNNN | NNNNNNNNNN | NNNNNNNNNN | NNNNNNNNNN | 3000 |
| NNNNNNNNNN | NNNNNNNNNN | NNNNNNNNNN | NNNNNNNNNN | NNNNNNNNNN | NNNNNNNNNN | 3060 |
| NNNNNNNNNN | NNNNNNNNNN | NNNNNNNNNN | NNNNNNNNNN | NNNNNNNNNN | NNNNNNNNNN | 3120 |
| NNNNNNNNNN | NNNNNNNNNN | NNNNNNNNNN | NNNNNNNNNN | NNNNNNNNNN | NNNNNNNNNN | 3180 |
| NNNNNNNNNN | NNNNNNNNNN | NNNNNNNNNN | NNNNNNNNNN | NNNNNNNNNN | NNNNNNNNNN | 3240 |
| NNNNNNNNNN | NNNNNNNNNN | NNNNNNNNNN | NNNNNNNNNN | NNNNNNNNNN | NNNNNNNNNN | 3300 |
| NNNNNNNNNN | NNNNNNNNNN | NNNNNNNNNN | NNNNNNNNNN | NNNNNNNNNN | NNNNNNNNNN | 3360 |
| NNNNNNNNNN | NNNNNNNNNN | NNNNNNNNNN | NNNNNNNNNN | NNNNNNNNNN | NNNNNNNNNN | 3420 |
| NNNNNNNNNN | NNNNNNNNNN | NNNNNNNNNC | TCCGTTTTAT | GGAAATATTT | TCTACTATTA | 3480 |
| TGTTTATTCC | TGGAATAATT | ATATTGTACG | CTGCTTATAT | AAGAAAAATT | AAAATGAAAA | 3540 |
| ATAATTAGAA | TCTGAAAATG | TCTTCTGGAA | GCATCCATGT | TATTACAGGC | CCTATGTTTT | 3600 |
| CCGGTAAAAC | ATCGGAGCTA | GTAAGAAGAA | TAAAAAGATT | TATGCTATCT | AACTTTAAAT | 3660 |
| GTATTATTAT | TAAACATTGT | GGAGATAATA | GATATAATGA | GGATGATATA | AACAAAGTAT | 3720 |
| ATACTCATGA | TCTATTGTTT | ATGGAGGCTA | CGGCATCTTC | TAATCTATCT | GTATTAGTAC | 3780 |
| CTACGCTATT | AAATGATGGA | GTTCAGGTAA | TAGGTATAGA | CGAGGCTCAA | TTCTTTCTAG | 3840 |
| ACATAGTAGA | ATTTAGTGAA | TCCATGGCTA | ATTTAGGTAA | AACAGTTATT | GTGGCCGCGC | 3900 |
| TTAACGGTGA | TTTTAAACGC | GAATTATTCG | GTAACGTATA | TAAGTTATTA | TCATTAGCTG | 3960 |
| AAACAGTGTC | CAGTTTGACA | GCTATTTGCG | TGAAATGCTA | TTGCGACGCT | TCGTTTCTA | 4020 |
| AACGAGTTAC | AGAAAATAAA | GAAGTAATGG | ATATAGGTGG | TAAAGATAAA | TACATAGCCG | 4080 |

```
TGTGTAGGAA ATGTTTTTTT AGTAATTAAG GTTTTTATCG ATCCCAAAAT AGGATCATGA  4140
TGGCGGCCGT CAATTAGCAT CCATTTGATG ATCACTCCTA AATTATAGAA ATGATCTCTC  4200
AAATAACGTA TATGTGTACC GGGAGCAGAT CCTATATACA CTACGGTGGC ACCATCTAAT  4260
ATACCGTGTC GCTGTAACTT ACTAAGAAAA AATAATTCTC CTAGTAATAG TTTTAACTGT  4320
CCTTGATACG GCAGTTTTTT TGCGACCTCA TTTGCACTTT CTGGTTCGTA ATCTAACTCA  4380
TTATCAATTT CCTCAAAATA CATAAACGGT TTATCTAACG ACACAACATC CATTTTAAG   4440
TATTATATTA AAATTTAATC AATGTTTATT TTTAGTTTTT TAGATAAAAA ATATAATATT  4500
ATGAGTCGAT GTAACACTTT CTACACACCG ATTGATACAT ATCATTACCT CCTATTATTT  4560
CTATCTCGGT TTCCTCACCC AATCGTTTAG AAAAGGAAGC CTCCTTAAAG CATTTCATAC  4620
ACACAGCAGT TAGTTTTACC ACCATTTCAG ATAATGGAAT AAGATTCAAA ATATTATTAA  4680
ACGGTTTACG TTGAAATGTC CCATCGAGTG CGGCTACTAT AACTATTTTT CCTTCGTTTG  4740
CCATACGCTC ACAGAATTCA ACAATGTCTG GAAAGAACTG TCCTTCATCG ATACCTATCA  4800
CGGAGAAATC TGTAATTGAT TCCAAGACAT CACATAGTTT AGTTGCTTCC AATGCTTCAA  4860
AATTATTCTT ATCATGCGTC CATAGTCCCG TTCCGTATCT ATTATCGTTA GAATATTTA   4920
TAGTCACGCA TTTATATTGA GCTATTTGAT AACGTCTAAC TCGTCTAATT AATTCTGTAC  4980
TTTTACCTGA AAACATGGGG CCGATTATCA ACTGAATATG TCCGCCGTTC ATGATGACAA  5040
TAAAGAATTA ATTATTGTTC ACTTTATTCG ACTTTAATAT ATCCATCACG TTAGAAAATG  5100
CGATATTGCG ACGAGGATCT ATGTATCTAA CAGGATCTAT TGCGGTGGTA GCTAGAGAGG  5160
ATTCTTTTTT GAATCGCATC AAACTAATCA CAAAGTCGAA CAAATATCCT TTATTAAGTT  5220
TGACCCTTCC ATCTGTAACA ATAGGGACCT TGTTAAACAG TTTTTGGGT TAGAATATAT   5280
GTATGTAAAA ATATAGTAGA ATTTCATTTT GTTTTTTTCT ATGCTATAAA TAGGCTGCAG  5340
GAATTCCTTA CATATGGTTC GTGCTAACAA ACGCAACGAG GCTCTACGAA TCGGGATCG   5400
CGGCCGCGAT CCCGTCGTTT TACAACGTCG TGACTGGGAA AACCCTGGCG TTACCCAACT  5460
TAATCGCCTT GCAGCACATC CCCCTTTCGC CAGCTGGCGT AATAGCGAAG AGGCCCGCAC  5520
CGATCGCCCT TCCCAACAGT TGCGCAGCCT GAATGGCGAA TGGCGCTTTG CCTGGTTTCC  5580
GGCACCAGAA GCGGTGCCGG AAAGCTGGCT GGAGTGCGAT CTTCCTGAGG CCGATACTGT  5640
CGTCGTCCCC TCAAACTGGC AGATGCACGG TTACGATGCG CCCATCTACA CCAACGTAAC  5700
CTATCCCATT ACGGTCAATC CGCCGTTTGT TCCCACGGAG AATCCGACGG GTTGTTACTC  5760
GCTCACATTT AATGTTGATG AAAGCTGGCT ACAGGAAGGC CAGACGCGAA TTATTTTTGA  5820
TGGCGTTAAC TCGGCGTTTC ATCTGTGGTG CAACGGGCGC TGGGTCGGTT ACGGCCAGGA  5880
CAGTCGTTTG CCGTCTGAAT TTGACCTGAG CGCATTTTTA CGCGCCGGAG AAAACCGCCT  5940
CGCGGTGATG GTGCTGCGTT GGAGTGACGG CAGTTATCTG GAAGATCAGG ATATGTGGCG  6000
GATGAGCGGC ATTTTCCGTG ACGTCTCGTT GCTGCATAAA CCGACTACAC AAATCAGCGA  6060
TTTCCATGTT GCCACTCGCT TTAATGATGA TTTCAGCCGC GCTGTACTGG AGGCTGAAGT  6120
TCAGATGTGC GGCGAGTTGC GTGACTACCT ACGGGTAACA GTTTCTTTAT GGCAGGGTGA  6180
AACGCAGGTC GCCAGCGGCA CCGCGCCTTT CGGCGGTGAA ATTATCGATG AGCGTGGTGG  6240
TTATGCCGAT CGCGTCACAC TACGTCTGAA CGTCGAAAAC CCGAAACTGT GGAGCGCCGA  6300
AATCCCGAAT CTCTATCGTG CGGTGGTTGA ACTGCACACC GCCGACGGCA CGCTGATTGA  6360
AGCAGAAGCC TGCGATGTCG GTTTCCGCGA GGTGCGGATT GAAAATGGTC TGCTGCTGCT  6420
GAACGGCAAG CCGTTGCTGA TTCGAGGCGT TAACCGTCAC GAGCATCATC CTCTGCATGG  6480
```

```
TCAGGTCATG GATGAGCAGA CGATGGTGCA GGATATCCTG CTGATGAAGC AGAACAACTT    6540
TAACGCCGTG CGCTGTTCGC ATTATCCGAA CCATCCGCTG TGGTACACGC TGTGCGACCG    6600
CTACGGCCTG TATGTGGTGG ATGAAGCCAA TATTGAAACC CACGGCATGG TGCCAATGAA    6660
TCGTCTGACC GATGATCCGC GCTGGCTACC GGCGATGAGC GAACGCGTAA CGCGAATGGT    6720
GCAGCGCGAT CGTAATCACC CGAGTGTGAT CATCTGGTCG CTGGGGAATG AATCAGGCCA    6780
CGGCGCTAAT CACGACGCGC TGTATCGCTG GATCAAATCT GTCGATCCTT CCCGCCCGGT    6840
GCAGTATGAA GGCGGCGGAG CCGACACCAC GGCCACCGAT ATTATTTGCC CGATGTACGC    6900
GCGCGTGGAT GAAGACCAGC CCTTCCCGGC TGTGCCGAAA TGGTCCATCA AAAATGGCT    6960
TTCGCTACCT GGAGAGACGC GCCCGCTGAT CCTTTGCGAA TACGCCCACG CGATGGGTAA    7020
CAGTCTTGGC GGTTTCGCTA ATACTGGCA GGCGTTTCGT CAGTATCCCC GTTACAGGG     7080
CGGCTTCGTC TGGGACTGGG TGGATCAGTC GCTGATTAAA TATGATGAAA CGGCAACCC    7140
GTGGTCGGCT TACGGCGGTG ATTTTGGCGA TACGCCGAAC GATCGCCAGT TCTGTATGAA    7200
CGGTCTGGTC TTTGCCGACC GCACGCCGCA TCCAGCGCTG ACGGAAGCAA AACACCAGCA    7260
GCAGTTTTTC CAGTTCCGTT TATCCGGGCA AACCATCGAA GTGACCAGCG AATACCTGTT    7320
CCGTCATAGC GATAACGAGC TCCTGCACTG GATGGTGGCG CTGGATGGTA AGCCGCTGGC    7380
AAGCGGTGAA GTGCCTCTGG ATGTCGCTCC ACAAGGTAAA CAGTTGATTG AACTGCCTGA    7440
ACTACCGCAG CCGGAGAGCG CCGGGCAACT CTGGCTCACA GTACGCGTAG TGCAACCGAA    7500
CGCGACCGCA TGGTCAGAAG CCGGGCACAT CAGCGCCTGG CAGCAGTGGC GTCTGGCGGA    7560
AAACCTCAGT GTGACGCTCC CCGCCGCGTC CACGCCATC CCGCATCTGA CCACCAGCGA    7620
AATGGATTTT TGCATCGAGC TGGGTAATAA GCGTTGGCAA TTTAACCGCC AGTCAGGCTT    7680
TCTTTCACAG ATGTGGATTG GCGATAAAAA ACAACTGCTG ACGCCGCTGC GCGATCAGTT    7740
CACCCGTGCA CCGCTGGATA CGACATTGG CGTAAGTGAA GCGACCCGCA TTGACCCTAA    7800
CGCCTGGGTC GAACGCTGGA AGGCGGCGGG CCATTACCAG GCCGAAGCAG CGTTGTTGCA    7860
GTGCACGGCA GATACACTTG CTGATGCGGT GCTGATTACG ACCGCTCACG CGTGGCAGCA    7920
TCAGGGGAAA ACCTTATTTA TCAGCCGGAA AACCTACCGG ATTGATGGTA GTGGTCAAAT    7980
GGCGATTACC GTTGATGTTG AAGTGGCGAG CGATACACCG CATCCGGCGC GGATTGGCCT    8040
GAACTGCCAG CTGGCGCAGG TAGCAGAGCG GGTAAACTGG CTCGGATTAG GGCCGCAAGA    8100
AAACTATCCC GACCGCCTTA CTGCCGCCTG TTTTGACCGC TGGGATCTGC CATTGTCAGA    8160
CATGTATACC CCGTACGTCT TCCCGAGCGA AAACGGTCTG CGCTGCGGGA CGCGCGAATT    8220
GAATTATGGC CCACACCAGT GGCGCGGCGA CTTCCAGTTC AACATCAGCC GCTACAGTCA    8280
ACAGCAACTG ATGGAAACCA GCCATCGCCA TCTGCTGCAC GCGGAAGAAG GCACATGGCT    8340
GAATATCGAC GGTTTCCATA TGGGGATTGG TGGCGACGAC TCCTGGAGCC CGTCAGTATC    8400
GGCGGAATTA CAGCTGAGCG CCGGTCGCTA CCATTACCAG TTGGTCTGGT GTCAAAAATA    8460
ATAATAACCG GCAGGCCAT GTCTGCCCGT ATTTCGCGTA AGGAAATCCA TTATGTACTA    8520
TTTAATCCAA CAATGTCTGG AAAGAACTGT CCTTCATCGA TAGGCCTGTC GACGGATCCT    8580
GGGGGTACCG GTTAGTGTA ATAAATTTAA TAAATATTG ACAAAATAGT TAAATGAATA     8640
TATGAAAGTA CATTATACAC GGAATGGAGT TCGATATTAG TTCTTGCAGA ATGATATATT    8700
CTGTTCTCGA ACAATATCAC TTTGTTTCTG ATAATCGTTA TAACAATCAA AAATTTAGAA    8760
TTATATTATA CTGTTTAAAA GATTCTACGA TAAAGAAATA TCCGTACAGG TTTGTTTCTG    8820
AAATTCACTT TGTAAGATAC ATAATTAACA AATTCAGGGG GAAAAATCTT TACAAAATTA    8880
```

-continued

| | | | | | |
|---|---|---|---|---|---|
| GTATAGAAGC | TATAGATATA | TCAAAAGGTA | GACAACAAAT | AATCAGAACC | TAATTTTTTT | 8940 |
| ATCAAAAAAT | TAAAATATAA | ATAAAATGAA | AAATAACTTG | TATGAAGAAA | AAATGAACAT | 9000 |
| GAGTAAGAAA | CAAGTAAAAA | CTCAAAGTAA | ATGTAATAAT | AACGCATCTA | GATTACATG | 9060 |
| CTTGGATGCG | GTGCAATACG | CTAAGCTTNN | NNNNNNNNNN | NNNNNNNNNN | NNNNNNNNNN | 9120 |
| NNNNNNNNNN | NNNNNNNNNN | NNNNNNNNNN | NNNNNNNNNN | NNNNNNNNNN | NNNNNNNNNN | 9180 |
| NNNNNNNNNN | NNNNNNNNNN | NNNNNNNNNN | NNNNNNNNNN | NNNNNNNNNN | NNNNNNNNNN | 9240 |
| NNNNNNNNNN | NNNNNNNNNN | NNNNNNNNNN | NNNNNNNNNN | NNNNNNNNNN | NNNNNNNNNN | 9300 |
| NNNNNNNNNN | NNNNNNNNNN | NNNNNNNNNN | NNNNNNNNNN | NNNNNNNNNN | NNNNNNNNNN | 9360 |
| NNNNNNNNNN | NNNNNNNNNN | NNNNNNNNNN | NNNNGGATCC | TGCATTAATG | AATCGGCCAA | 9420 |
| CGCGCGGGGA | GAGGCGGTTT | GCGTATTGGG | CGCT | | | 9454 |

( 2 ) INFORMATION FOR SEQ ID NO:5:

( i ) SEQUENCE CHARACTERISTICS:
        ( A ) LENGTH: 8775 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pFP-Z21

( x i ) SEQUENCE DESCRIPTION: SEQ ID NO:5:

| | | | | | |
|---|---|---|---|---|---|
| CTTCCGCTTC | CTCGCTCACT | GACTCGCTGC | GCTCGGTCGT | TCGGCTGCGG | CGAGCGGTAT | 60 |
| CAGCTCACTC | AAAGGCGGTA | ATACGGTTAT | CCACAGAATC | AGGGGATAAC | GCAGGAAAGA | 120 |
| ACATGTGAGC | AAAAGGCCAG | CAAAAGGCCA | GGAACCGTAA | AAAGGCCGCG | TTGCTGGCGT | 180 |
| TTTTCCATAG | GCTCCGCCCC | CCTGACGAGC | ATCACAAAAA | TCGACGCTCA | AGTCAGAGGT | 240 |
| GGCGAAACCC | GACAGGACTA | TAAAGATACC | AGGCGTTTCC | CCCTGGAAGC | TCCCTCGTGC | 300 |
| GCTCTCCTGT | TCCGACCCTG | CCGCTTACCG | GATACCTGTC | CGCCTTTCTC | CCTTCGGGAA | 360 |
| GCGTGGCGCT | TTCTCAATGC | TCACGCTGTA | GGTATCTCAG | TTCGGTGTAG | GTCGTTCGCT | 420 |
| CCAAGCTGGG | CTGTGTGCAC | GAACCCCCCG | TTCAGCCCGA | CCGCTGCGCC | TTATCCGGTA | 480 |
| ACTATCGTCT | TGAGTCCAAC | CCGGTAAGAC | ACGACTTATC | GCCACTGGCA | GCAGCCACTG | 540 |
| GTAACAGGAT | TAGCAGAGCG | AGGTATGTAG | GCGGTGCTAC | AGAGTTCTTG | AAGTGGTGGC | 600 |
| CTAACTACGG | CTACACTAGA | AGGACAGTAT | TTGGTATCTG | CGCTCTGCTG | AAGCCAGTTA | 660 |
| CCTTCGGAAA | AAGAGTTGGT | AGCTCTTGAT | CCGGCAAACA | AACCACCGCT | GGTAGCGGTG | 720 |
| GTTTTTTTGT | TTGCAAGCAG | CAGATTACGC | GCAGAAAAAA | AGGATCTCAA | GAAGATCCTT | 780 |
| TGATCTTTTC | TACGGGGTCT | GACGCTCAGT | GGAACGAAAA | CTCACGTTAA | GGGATTTTGG | 840 |
| TCATGAGATT | ATCAAAAAGG | ATCTTCACCT | AGATCCTTTT | AAATTAAAAA | TGAAGTTTTA | 900 |
| AATCAATCTA | AAGTATATAT | GAGTAAACTT | GGTCTGACAG | TTACCAATGC | TTAATCAGTG | 960 |
| AGGCACCTAT | CTCAGCGATC | TGTCTATTTC | GTTCATCCAT | AGTTGCCTGA | CTCCCCGTCG | 1020 |
| TGTAGATAAC | TACGATACGG | GAGGGCTTAC | CATCTGGCCC | CAGTGCTGCA | ATGATACCGC | 1080 |
| GAGACCCACG | CTCACCGGCT | CCAGATTTAT | CAGCAATAAA | CCAGCCAGCC | GGAAGGGCCG | 1140 |
| AGCGCAGAAG | TGGTCCTGCA | ACTTTATCCG | CCTCCATCCA | GTCTATTAAT | TGTTGCCGGG | 1200 |
| AAGCTAGAGT | AAGTAGTTCG | CCAGTTAATA | GTTTGCGCAA | CGTTGTTGCC | ATTGCTCCAG | 1260 |
| GCATCGTGGT | GTCACGCTCG | TCGTTTGGTA | TGGCTTCATT | CAGCTCCGGT | TCCCAACGAT | 1320 |
| CAAGGCGAGT | TACATGATCC | CCCATGTTGT | GCAAAAAAGC | GGTTAGCTCC | TTCGGTCCTC | 1380 |

```
CGATCGTTGT CAGAAGTAAG TTGGCCGCAG TGTTATCACT CATGGTTATG GCAGCACTGC   1440
ATAATTCTCT TACTGTCATG CCATCCGTAA GATGCTTTTC TGTGACTGGT GAGTACTCAA   1500
CCAAGTCATT CTGAGAATAG TGTATGCGGC GACCGAGTTG CTCTTGCCCG GCGTCAACAC   1560
GGGATAATAC CGCGCCACAT AGCAGAACTT TAAAAGTGCT CATCATTGGA AAACGTTCTT   1620
CGGGGCGAAA ACTCTCAAGG ATCTTACCGC TGTTGAGATC CAGTTCGATG TAACCCACTC   1680
GTGCACCCAA CTGATCTTCA GCATCTTTTA CTTTCACCAG CGTTTCTGGG TGAGCAAAAA   1740
CAGGAAGGCA AAATGCCGCA AAAAAGGGAA TAAGGGCGAC ACGGAAATGT TGAATACTCA   1800
TACTCTTCCT TTTTCAATAT TATTGAAGCA TTTATCAGGG TTATTGTCTC ATGAGCGGAT   1860
ACATATTTGA ATGTATTTAG AAAAATAAAC AAATAGGGGT TCCGCGCACA TTTCCCCGAA   1920
AAGTGCCACC TGACGCGCCC TGTAGCGGCG CATTAAGCGC GGCGGGTGTG GTGGTTACGC   1980
GCAGCGTGAC CGCTACACTT GCCAGCGCCC TAGCGCCCGC TCCTTTCGCT TTCTTCCCTT   2040
CCTTTCTCGC CACGTTCGCC GGCTTTCCCC GTCAAGCTCT AAATCGGGGG CTCCCTTTAG   2100
GGTTCCGATT TAGTGCTTTA CGGCACCTCG ACCCCAAAAA ACTTGATTAG GGTGATGGTT   2160
CACGTAGTGG GCCATCGCCC TGATAGACGG TTTTTCGCCC TTTGACGTTG GAGTCCACGT   2220
TCTTTAATAG TGGACTCTTG TTCCAAACTG GAACAACACT CAACCCTATC TCGGTCTATT   2280
CTTTTGATTT ATAAGGGATT TGCCGATTT CGGCCTATTG GTTAAAAAAT GAGCTGATTT   2340
AACAAAAATT TAACGCGAAT TTTAACAAAA TATTAACGTT ACAATTTCC CATTCGCCAT   2400
TCAGGCTGCG CAACTGTTGG GAAGGGCGAT CGGTGCGGGC CTCTTCGCTA TTACGCCAGC   2460
GATNNNNNNN NNNNNNNNNN NNNNNNNNNN NNNNNNNNNN NNNNNNNNNN NNNNNNNNNN   2520
NNNNNNNNNN NNNNNNNNNN NNNNNNNNNN NNNNNNNNNN NNNNNNNNNN NNNNNNNNNN   2580
NNNNNNNNNN NNNNNNNNNN NNNNNNNNNN NNNNNNNNNN NNNNNNNNNN NNNNNNNNNN   2640
NNNNNNNNNN NNNNNNNNNN NNNNNNNNNN NNNNNNNNNN NNNNNNNNNN NNNNNNNNNN   2700
NNNNNNNNNN NNNNNNNNNN NNNNNNNNNN NNNNNNNNNN NNNNNNNNNN NNNNNNNNNN   2760
NNNNNNNNNN NNNNNNNNNN NNNNNNNNNN NNNNNNNNNN NNNNNNNNNN NNNNNNNNNN   2820
NNNNNNNNNN NNNNNNNNNN NNNNNNNNNN NNNNNNNNNN NNNNNNNNNN NNNNNNNNNN   2880
NNNNNNNNNN NNNNNNNNNN NNNNNNNNNN NNNNNNNNNN NNNNNNNNNN NNNNNNNNNN   2940
NNNNNNNNNN NNNNNNNNNN NNNNNNNNNN NNNNNNNNNN NNNNNNNNNN NNNNNNNNNN   3000
NNNNNNNNNN NNNNNNNNNN NNNNNNNNNN NNNNNNNNNN NNNNNNNNNN NNNNNNNNNN   3060
NNNNNNNNNN NNNNNNNNNN NNNNNNNNNN NNNNNNNNNN NNNNNNNNNN NNNNNNNNNN   3120
NNNNNNNNNN NNNNNNNNNN NNNNNNNNNN NNNNNNNNNN NNNNNNNNNN NNNNNNNNNN   3180
NNNNNNNNNN NNNNNNNNNN NNNNNNNNNN NNNNNNNNNN NNNNNNNNNN NNNNNNNNNN   3240
NNNNNNNNNN NNNNNNNNNN NNNNNNNNNN NNNNNNNNNN NNNNNNNNNN NNNNNNNNNN   3300
NNNNNNNNNN NNNNNNNNNN NNNNNNNNNN NNNNNNNNNN NNNNNNNNNN NNNNNNNNNN   3360
NNNNNNNNNN NNNNNNNNNN NNNNNNNNNN NNNNNNNNNN NNNNNNNNNN NNNNNNNNNN   3420
NNNNNNNNNN NNNNNNNNNN NNNNNNNNNC TCCGTTTTAT GGAAATATTT TCTACTATTA   3480
TGTTTATTCC TGGAATAATT ATATTGTACG CTGCTTATAT AAGAAAAATT AAAATGAAAA   3540
ATAATTAGAA TCTGAAAATG TCTTCTGGAA GCATCCATGT TATTACAGGC CTATGTTTT   3600
CCGGTAAAAC ATCGGAGCTA GTAAGAAGAA TAAAAAGATT TATGCTATCT AACTTTAAAT   3660
GTATTATTAT TAAACATTGT GGAGATAATA GATATAATGA GGATGATATA AACAAAGTAT   3720
ATACTCATGA TCTATTGTTT ATGGAGGCTA CGGCATCTTC TAATCTATCT GTATTAGTAC   3780
```

```
CTACGCTATT AAATGATGGA GTTCAGGTAA TAGGTATAGA CGAGGCTCAA TTCTTTCTAG   3840
ACATAGTAGA ATTTAGTGAA TCCATGATTG GCTTCATCCA CCACATACAG GCCGTAGCGG   3900
TCGCACAGCG TGTACCACAG CGGATGGTTC GGATAATGCG AACAGCGCAC GGCGTTAAAG   3960
TTGTTCTGCT TCATCAGCAG GATATCCTGC ACCATCGTCT GCTCATCCAT GACCTGACCA   4020
TGCAGAGGAT GATGCTCGTG ACGGTAACG CCTCGAATCA GCAACGGCTT GCCGTTCAGC    4080
AGCAGCAGAC CATTTTCAAT CCGCACCTCG CGGAAACCGA CATCGCAGGC TTCTGCTTCA   4140
ATCAGCGTGC CGTCGGCGGT GTGCAGTTCA ACCACCGCAC GATAGAGATT CGGGATTTCG   4200
GCGCTCCACA GTTTCGGGTT TTCGACGTTC AGACGTAGTG TGACGCGATC GGCATAACCA   4260
CCACGCTCAT CGATTGGCCA GGATCCGTCG ACAGGCCTAT CGATGAAGGA CAGTTCTTTC   4320
CAGACATTGT TGGATTAAAT AGTACATAAT GGATTTCCTT ACGCGAAATA CGGGCAGACA   4380
TGGCCTGCCC GGTTATTATT ATTTTTGACA CCAGACCAAC TGGTAATGGT AGCGACCGGC   4440
GCTCAGCTGT AATTCCGCCG ATACTGACGG GCTCCAGGAG TCGTCGCCAC CAATCCCCAT   4500
ATGGAAACCG TCGATATTCA GCCATGTGCC TTCTTCCGCG TGCAGCAGAT GGCGATGGCT   4560
GGTTTCCATC AGTTGCTGTT GACTGTAGCG GCTGATGTTG AACTGGAAGT CGCCGCGCCA   4620
CTGGTGTGGG CCATAATTCA ATTCGCGCGT CCCGCAGCGC AGACCGTTTT CGCTCGGGAA   4680
GACGTACGGG GTATACATGT CTGACAATGG CAGATCCCAG CGGTCAAAAC AGGCGGCAGT   4740
AAGGCGGTCG GGATAGTTTT CTTGCGGCCC TAATCCGAGC CAGTTTACCC GCTCTGCTAC   4800
CTGCGCCAGC TGGCAGTTCA GGCCAATCCG CGCCGGATGC GGTGTATCGC TCGCCACTTC   4860
AACATCAACG GTAATCGCCA TTTGACCACT ACCATCAATC CGGTAGGTTT TCCGGCTGAT   4920
AAATAAGGTT TTCCCCTGAT GCTGCCACGC GTGAGCGGTC GTAATCAGCA CCGCATCAGC   4980
AAGTGTATCT GCCGTGCACT GCAACAACGC TGCTTCGGCC TGGTAATGGC CCGCCGCCTT   5040
CCAGCGTTCG ACCCAGGCGT TAGGGTCAAT GCGGGTCGCT TCACTTACGC CAATGTCGTT   5100
ATCCAGCGGT GCACGGGTGA ACTGATCGCG CAGCGGCGTC AGCAGTTGTT TTTTATCGCC   5160
AATCCACATC TGTGAAAGAA AGCCTGACTG GCGGTTAAAT TGCCAACGCT TATTACCCAG   5220
CTCGATGCAA AAATCCATTT CGCTGGTGGT CAGATGCGGG ATGGCGTGGG ACGCGGCGGG   5280
GAGCGTCACA CTGAGGTTTT CCGCCAGACG CCACTGCTGC CAGGCGCTGA TGTGCCCGGC   5340
TTCTGACCAT GCGGTCGCGT TCGGTTGCAC TACGCGTACT GTGAGCCAGA GTTGCCCGGC   5400
GCTCTCCGGC TGCGGTAGTT CAGGCAGTTC AATCAACTGT TTACCTTGTG GAGCGACATC   5460
CAGAGGCACT TCACCGCTTG CCAGCGGCTT ACCATCCAGC GCCACCATCC AGTGCAGGAG   5520
CTCGTTATCG CTATGACGGA ACAGGTATTC GCTGGTCACT TCGATGGTTT GCCCGGATAA   5580
ACGGAACTGG AAAAACTGCT GCTGGTGTTT TGCTTCCGTC AGCGCTGGAT GCGGCGTGCG   5640
GTCGGCAAAG ACCAGACCGT TCATACAGAA CTGGCGATCG TTCGGCGTAT CGCCAAAATC   5700
ACCGCCGTAA GCCGACCACG GGTTGCCGTT TTCATCATAT TAATCAGCG ACTGATCCAC    5760
CCAGTCCCAG ACGAAGCCGC CCTGTAAACG GGATACTGA CGAAACGCCT GCCAGTATTT    5820
AGCGAAACCG CCAAGACTGT TACCCATCGC GTGGGCGTAT CGCAAAGGA TCAGCGGGCG    5880
CGTCTCTCCA GGTAGCGAAA GCCATTTTTT GATGGACCAT TTCGGCACAG CCGGGAAGGG   5940
CTGGTCTTCA TCCACGCGCG CGTACATCGG GCAAATAATA TCGGTGGCCG TGGTGTCGGC   6000
TCCGCCGCCT TCATACTGCA CCGGGCGGGA AGGATCGACA GATTTGATCC AGCGATACAG   6060
CGCGTCGTGA TTAGCGCCGT GGCCTGATTC ATTCCCCAGC GACCAGATGA TCACACTCGG   6120
GTGATTACGA TCGCGCTGCA CCATTCGCGT TACGCGTTCG CTCATCGCCG GTAGCCAGCG   6180
```

```
CGGATCATCG GTCAGACGAT TCATTGGCAC CATGCCGTGG GTTTCAATAT TGGCTTCATC    6240
CACCACATAC AGGCCGTAGC GGTCGCACAG CGTGTACCAC AGCGGATGGT TCGGATAATG    6300
CGAACAGCGC ACGGCGTTAA AGTTGTTCTG CTTCATCAGC AGGATATCCT GCACCATCGT    6360
CTGCTCATCC ATGACCTGAC CATGCAGAGG ATGATGCTCG TGACGGTTAA CGCCTCGAAT    6420
CAGCAACGGC TTGCCGTTCA GCAGCAGCAG ACCATTTTCA ATCCGCACCT CGCGGAAACC    6480
GACATCGCAG GCTTCTGCTT CAATCAGCGT GCCGTCGGCG GTGTGCAGTT CAACCACCGC    6540
ACGATAGAGA TTCGGGATTT CGGCGCTCCA CAGTTTCGGG TTTTCGACGT TCAGACGTAG    6600
TGTGACGCGA TCGGCATAAC CACCACGCTC ATCGATAATT TCACCGCCGA AAGGCGCGGT    6660
GCCGCTGGCG ACCTGCGTTT CACCCTGCCA TAAAGAAACT GTTACCCGTA GGTAGTCACG    6720
CAACTCGCCG CACATCTGAA CTTCAGCCTC CAGTACAGCG CGGCTGAAAT CATCATTAAA    6780
GCGAGTGGCA ACATGGAAAT CGCTGATTTG TGTAGTCGGT TTATGCAGCA ACGAGACGTC    6840
ACGGAAAATG CCGCTCATCC GCCACATATC CTGATCTTCC AGATAACTGC CGTCACTCCA    6900
ACGCAGCACC ATCACCGCGA GGCGGTTTTC TCCGGCGCGT AAAAATGCGC TCAGGTCAAA    6960
TTCAGACGGC AAACGACTGT CCTGGCCGTA ACCGACCCAG CGCCCGTTGC ACCACAGATG    7020
AAACGCCGAG TTAACGCCAT CAAAAATAAT TCGCGTCTGG CCTTCCTGTA GCCAGCTTTC    7080
ATCAACATTA AATGTGAGCG AGTAACAACC CGTCGGATTC TCCGTGGGAA CAAACGGCGG    7140
ATTGACCGTA ATGGGATAGG TTACGTTGGT GTAGATGGGC GCATCGTAAC CGTGCATCTG    7200
CCAGTTTGAG GGGACGACGA CAGTATCGGC CTCAGGAAGA TCGCACTCCA GCCAGCTTTC    7260
CGGCACCGCT TCTGGTGCCG GAAACCAGGC AAAGCGCCAT TCGCCATTCA GGCTGCGCAA    7320
CTGTTGGGAA GGGCGATCGG TGCGGGCCTC TTCGCTATTA CGCCAGCTGG CGAAAGGGGG    7380
ATGTGCTGCA AGGCGATTAA GTTGGGTAAC GCCAGGGTTT TCCCAGTCAC GACGTTGTAA    7440
AACGACGGGA TCGCGGCCGC GATCCCCGAT TCGTAGAGCC TCGTTGCGTT TGTTAGCACG    7500
AACCATATGT AAGGAATTCC TGCAGGTCGA CTCTAGAGGA TCCCCGGGTA CCGTCGACCG    7560
CCAAGCTCGG AATTAATTCT GTGAGCGTAT GGCAAACGAA GGAAAAATTA GTTATAGTAG    7620
CCGCACTCGA TGGGACATTT CAACGTAAAC CGTTTAATAA TCATGGCTAA TTTAGGTAAA    7680
ACAGTTATTG TGGCCGCGCT TAACGGTGAT TTTAAACGCG AATTATTCGG TAACGTATAT    7740
AAGTTATTAT CATTAGCTGA AACAGTGTCC AGTTTGACAG CTATTTGCGT GAAATGCTAT    7800
TGCGACGCTT CGTTTCTAA ACGAGTTACA GAAAATAAAG AAGTAATGGA TATAGGTGGT    7860
AAAGATAAAT ACATAGCCGT GTGTAGGAAA TGTTTTTTTA GTAATTAAGG GGTTTAGTGT    7920
AATAAATTTA ATAAAATATT GACAAAATAG TTAATGAAT ATATGAAAGT ACATTATACA    7980
CGGAATGGAG TTCGATATTA GTTCTTGCAG AATGATATAT TCTGTTCTCG AACAATATCA    8040
CTTTGTTTCT GATAATCGTT ATAACAATCA AAAATTTAGA ATTATATTAT ACTGTTTAAA    8100
AGATTCTACG ATAAAGAAAT ATCCGTACAG GTTTGTTTCT GAAATTCACT TTGTAAGATA    8160
CATAATTAAC AAATTCAGGG GGAAAAATCT TTACAAAATT AGTATAGAAG CTATAGATAT    8220
ATCAAAAGGT AGACAACAAA TAATCAGAAC CTAATTTTTT TATCAAAAAA TTAAAATATA    8280
AATAAAATGA AAAATAACTT GTATGAAGAA AAAATGAACA TGAGTAAGAA ACAAGTAAAA    8340
ACTCAAAGTA AATGTAATAA TAACGCATCT AGATTTACAT GCTTGGATGC GGTGCAATAC    8400
GCTAAGCTTN NNNNNNNNN NNNNNNNNNN NNNNNNNNNN NNNNNNNNNN NNNNNNNNNN    8460
NNNNNNNNNN NNNNNNNNNN NNNNNNNNNN NNNNNNNNNN NNNNNNNNNN NNNNNNNNNN    8520
NNNNNNNNNN NNNNNNNNNN NNNNNNNNNN NNNNNNNNNN NNNNNNNNNN NNNNNNNNNN    8580
```

| | | | | | | |
|---|---|---|---|---|---|---|
| NNNNNNNNNN | NNNNNNNNNN | NNNNNNNNNN | NNNNNNNNNN | NNNNNNNNNN | NNNNNNNNNN | 8640 |
| NNNNNNNNNN | NNNNNNNNNN | NNNNNNNNNN | NNNNNNNNNN | NNNNNNNNNN | NNNNNNNNNN | 8700 |
| NNNNNNNNNN | NNNNNGGATC | CTGCATTAAT | GAATCGGCCA | ACGCGCGGGG | AGAGGCGGTT | 8760 |
| TGCGTATTGG | GCGCT | | | | | 8775 |

( 2 ) INFORMATION FOR SEQ ID NO:6:

( i ) SEQUENCE CHARACTERISTICS:
        ( A ) LENGTH: 10408 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pTZgpt-P2a ( x i ) SEQUENCE DESCRIPTION: SEQ ID NO:6:

| | | | | | | |
|---|---|---|---|---|---|---|
| CAGCTGGCGA | AAGGGGGATG | TGCTGCAAGG | CGATTAAGTT | GGGTAACGCC | AGGGTTTTCC | 60 |
| CAGTCACGAC | GTTGTAAAAC | GACGGCCCTG | AATATGAAGG | AGCAAAAGGT | TGTAACATTT | 120 |
| TATTACCGTG | TGGGATATAA | AAGTCCTTGA | TCCATTGATC | TGGAAACGGG | CATCTCCATT | 180 |
| TAAGACTAGA | CGCCACGGGG | TTTAAAATAC | TAATCATGAC | ATTTTGTAGA | GCGTAATTAC | 240 |
| TTAGTAAATC | CGCCGTACTA | GGTTCATTTC | CTCCTCGTTT | GGATCTCACA | TCAGAAATTA | 300 |
| AAATAATCTT | AGAAGGATGC | AGTTGTTTTT | TGATGGATCG | TAGATATTCC | TCATCAACGA | 360 |
| ACCGAGTCAC | TAGAGTCACA | TCACGCAATC | CATTTAAAAT | AGGATCATGA | TGGCGGCCGT | 420 |
| CAATTAGCAT | CCATTTGATG | ATCACTCCTA | AATTATAGAA | ATGATCTCTC | AAATAACGTA | 480 |
| TATGTGTACC | GGGAGCAGAT | CCTATATACA | CTACGGTGGC | ACCATCTAAT | ATACCGTGTC | 540 |
| GCTGTAACTT | ACTAAGAAAA | AATAATTCTC | CTAGTAATAG | TTTAACTGT | CCTTGATACG | 600 |
| GCAGTTTTTT | TGCGACCTCA | TTTGCACTTT | CTGGTTCGTA | ATCTAACTCA | TTATCAATTT | 660 |
| CCTCAAAATA | CATAAACGGT | TTATCTAACG | ACACAACATC | CATTTTAAG | TATTATATTA | 720 |
| AAATTTAATC | AATGTTTATT | TTTAGTTTTT | TAGATAAAAA | ATATAATATT | ATGAGTCGAT | 780 |
| GTAACACTTT | CTACACACCG | ATTGATACAT | ATCATTACCT | CCTATTATTT | CTATCTCGGT | 840 |
| TTCCTCACCC | AATCGTTTAG | AAAAGGAAGC | CTCCTTAAAG | CATTTCATAC | ACACAGCAGT | 900 |
| TAGTTTTACC | ACCATTTCAG | ATAATGGAAT | AAGATTCAAA | ATATTATTAA | ACGGTTTACG | 960 |
| TTGAAATGTC | CCATCGAGTG | CGGCTACTAT | AACTATTTTT | CCTTCGTTTG | CCATACGCTC | 1020 |
| ACAGAATTAA | TTCCGAGCTT | GGCGGTTCCT | ATCGATGAAG | GACAGTTCTT | TCCAGACATT | 1080 |
| GTTGGATTAA | ATAGTACATA | ATGGATTTCC | TTACGCGAAA | TACGGGCAGA | CATGGCCTGC | 1140 |
| CCGGTTATTA | TTATTTTTGA | CACCAGACCA | ACTGGTAATG | GTAGCGACCG | GCGCTCAGCT | 1200 |
| GTAATTCCGC | CGATACTGAC | GGGCTCCAGG | AGTCGTCGCC | ACCAATCCCC | ATATGGAAAC | 1260 |
| CGTCGATATT | CAGCCATGTG | CCTTCTTCCG | CGTGCAGCAG | ATGGCGATGG | CTGGTTTCCA | 1320 |
| TCAGTTGCTG | TTGACTGTAG | CGGCTGATGT | TGAACTGGAA | GTCGCCGCGC | CACTGGTGTG | 1380 |
| GGCCATAATT | CAATTCGCGC | GTCCGCAGC | GCAGACCGTT | TTCGCTCGGG | AAGACGTACG | 1440 |
| GGGTATACAT | GTCTGACAAT | GGCAGATCCC | AGCGGTCAAA | ACAGGCGGCA | GTAAGGCGGT | 1500 |
| CGGGATAGTT | TTCTTGCGGC | CCTAATCCGA | GCCAGTTTAC | CCGCTCTGCT | ACCTGCGCCA | 1560 |
| GCTGGCAGTT | CAGGCCAATC | CGCGCCGGAT | GCGGTGTATC | GCTCGCCACT | TCAACATCAA | 1620 |
| CGGTAATCGC | CATTTGACCA | CTACCATCAA | TCCGGTAGGT | TTTCCGGCTG | ATAAATAAGG | 1680 |
| TTTTCCCCTG | ATGCTGCCAC | GCGTGAGCGG | TCGTAATCAG | CACCGCATCA | GCAAGTGTAT | 1740 |

-continued

```
CTGCCGTGCA CTGCAACAAC GCTGCTTCGG CCTGGTAATG GCCCGCCGCC TTCCAGCGTT   1800
CGACCCAGGC GTTAGGGTCA ATGCGGGTCG CTTCACTTAC GCCAATGTCG TTATCCAGCG   1860
GTGCACGGGT GAACTGATCG CGCAGCGGCG TCAGCAGTTG TTTTTTATCG CCAATCCACA   1920
TCTGTGAAAG AAAGCCTGAC TGGCGGTTAA ATTGCCAACG CTTATTACCC AGCTCGATGC   1980
AAAAATCCAT TTCGCTGGTG GTCAGATGCG GGATGGCGTG GGACGCGGCG GGAGCGTCA    2040
CACTGAGGTT TTCCGCCAGA CGCCACTGCT GCCAGGCGCT GATGTGCCCG GCTTCTGACC   2100
ATGCGGTCGC GTTCGGTTGC ACTACGCGTA CTGTGAGCCA GAGTTGCCCG GCGCTCTCCG   2160
GCTGCGGTAG TTCAGGCAGT TCAATCAACT GTTACCTTG TGGAGCGACA TCCAGAGGCA    2220
CTTCACCGCT TGCCAGCGGC TTACCATCCA GCGCCACCAT CCAGTGCAGG AGCTCGTTAT   2280
CGCTATGACG GAACAGGTAT CGCTGGTCA CTTCGATGGT TTGCCCGGAT AAACGGAACT    2340
GGAAAAACTG CTGCTGGTGT TTGCTTCCG TCAGCGCTGG ATGCGGCGTG CGGTCGGCAA    2400
AGACCAGACC GTTCATACAG AACTGGCGAT CGTTCGGCGT ATCGCCAAAA TCACCGCCGT   2460
AAGCCGACCA CGGGTTGCCG TTTTCATCAT ATTTAATCAG CGACTGATCC ACCCAGTCCC   2520
AGACGAAGCC GCCCTGTAAA CGGGGATACT GACGAAACGC CTGCCAGTAT TTAGCGAAAC   2580
CGCCAAGACT GTTACCCATC GCGTGGGCGT ATTCGCAAAG GATCAGCGGG CGCGTCTCTC   2640
CAGGTAGCGA AAGCCATTTT TTGATGGACC ATTTCGGCAC AGCCGGGAAG GGCTGGTCTT   2700
CATCCACGCG CGCGTACATC GGGCAAATAA TATCGGTGGC CGTGGTGTCG GCTCCGCCGC   2760
CTTCATACTG CACCGGGCGG GAAGGATCGA CAGATTTGAT CCAGCGATAC AGCGCGTCGT   2820
GATTAGCGCC GTGGCCTGAT TCATTCCCCA GCGACCAGAT GATCACACTC GGGTGATTAC   2880
GATCGCGCTG CACCATTCGC GTTACGCGTT CGCTCATCGC CGGTAGCCAG CGCGGATCAT   2940
CGGTCAGACG ATTCATTGGC ACCATGCCGT GGGTTTCAAT ATTGGCTTCA TCCACCACAT   3000
ACAGGCCGTA GCGGTCGCAC AGCGTGTACC ACAGCGGATG GTTCGGATAA TGCGAACAGC   3060
GCACGGCGTT AAAGTTGTTC TGCTTCATCA GCAGGATATC CTGCACCATC GTCTGCTCAT   3120
CCATGACCTG ACCATGCAGA GGATGATGCT CGTGACGGTT AACGCCTCGA ATCAGCAACG   3180
GCTTGCCGTT CAGCAGCAGC AGACCATTTT CAATCCGCAC CTCGCGGAAA CCGACATCGC   3240
AGGCTTCTGC TTCAATCAGC GTGCCGTCGG CGGTGTGCAG TTCAACCACC GCACGATAGA   3300
GATTCGGGAT TTCGGCGCTC CACAGTTTCG GGTTTTCGAC GTTCAGACGT AGTGTGACGC   3360
GATCGGCATA ACCACCACGC TCATCGATAA TTTCACCGCC GAAAGGCGCG GTGCCGCTGG   3420
CGACCTGCGT TTCACCCTGC CATAAAGAAA CTGTTACCCG TAGGTAGTCA CGCAACTCGC   3480
CGCACATCTG AACTTCAGCC TCCAGTACAG CGCGGCTGAA ATCATCATTA AAGCGAGTGG   3540
CAACATGGAA ATCGCTGATT TGTGTAGTCG GTTTATGCAG CAACGAGACG TCACGGAAAA   3600
TGCCGCTCAT CCGCCACATA TCCTGATCTT CCAGATAACT GCCGTCACTC CAACGCAGCA   3660
CCATCACCGC GAGGCGGTTT TCTCCGGCGC GTAAAAATGC GCTCAGGTCA AATTCAGACG   3720
GCAAACGACT GTCCTGGCCG TAACCGACCC AGCGCCCGTT GCACCACAGA TGAAACGCCG   3780
AGTTAACGCC ATCAAAAATA ATTCGCGTCT GGCCTTCCTG TAGCCAGCTT TCATCAACAT   3840
TAAATGTGAG CGAGTAACAA CCCGTCGGAT TCTCCGTGGG AACAAACGGC GGATTGACCG   3900
TAATGGGATA GGTTACGTTG GTGTAGATGG GCGCATCGTA ACCGTGCATC TGCCAGTTTG   3960
AGGGGACGAC GACAGTATCG GCCTCAGGAA GATCGCACTC CAGCCAGCTT TCCGGCACCG   4020
CTTCTGGTGC CGGAAACCAG GCAAAGCGCC ATTCGCCATT CAGGCTGCGC AACTGTTGGG   4080
AAGGGCGATC GGTGCGGGCC TCTTCGCTAT TACGCCAGCT GGCGAAAGGG GGATGTGCTG   4140
```

```
CAAGGCGATT AAGTTGGGTA ACGCCAGGGT TTTCCCAGTC ACGACGTTGT AAAACGACGG    4200
GATCGCGGCC GCGATCCCCG ATTCGTAGAG CCTCGTTGCG TTTGTTAGCA CGAACCATAT    4260
GTAAGGAATT CCTGCAGGTC GACTCTAGAG GATCCCCATC TGTACGGGGT TTGCTAGAAG    4320
AGCCTTTTTC GGGTTCGGGA GTAGGTTGAT CTGATGGTTT ACTAGAAGAG TCTTTTTCGG    4380
GTTCGGGAGA GGGTTGCTCG GGTGGTTTAC TTTCGCTAGG TTGGGCTGT GGCTCAGAAC    4440
CAGCATCATT AGAAGGAGGC ATCGTATCAA TATCCGACTT CTCGGTGGGT GCTTTGCTAC    4500
TACCTCCAGC CAATGTTCTA AATACGTCAC TAATTAACTT AGTCATGTTG TCCATTCTGC    4560
CACGCATATC TTCGTGGCAG ATAAGTAGCT GCCTGGTAAA GACATCTTTG GCCTCTTGGC    4620
CTTTGAGTTT TTCATACTCT TGAATCAGTT TCTTTTCCAT GATTTATAGG CTATAAAAAA    4680
TAGTATTTTC TACTCATTAT TTTACTGTTA CTTAAACTAA AATACAGGAT TATTTATATT    4740
CTTTTTTCTA TCATTTCATA AACGGTTTTG ATAGTTTCGT TTTCTTCTTT ACAATTACTT    4800
AGTTGTCCGC TATACCAAGC TCTAACAAAT GCAGGTCGAC TCTAGAGGAT CCCCAACCAA    4860
CTTAAGGGTA CCGCCTCGAC ATCTATATAC TATATAGTAA TACCAATACT CAAGACTACG    4920
AAACTGATAC AATCTCTTAT CATGTGGGTA ATGTTCTCGA TGTCGAATAG CCATATGCCG    4980
GTAGTTGCGA TATACATAAA CTGATCACTA ATTCCAAACC CACCCGCTTT TTATAGTAAG    5040
TTTTTCACCC ATAAATAATA AATACAATAA TTAATTTCTC GTAAAAGTAG AAAATATATT    5100
CTAATTTATT GCACGGTAAG GAAGTAGAAT CATAAAGAAC AGTGACGGAT GATCCCCAAG    5160
CTTGGACACA AGACAGGCTT GCGAGATATG TTTGAGAATA CCACTTTATC CCGCGTCAGG    5220
GAGAGGCAGT GCGTAAAAAG ACGCGGACTC ATGTGAAATA CTGGTTTTTA GTGCGCCAGA    5280
TCTCTATAAT CTCGCGCAAC CTATTTTCCC CTCGAACACT TTTTAAGCCG TAGATAAACA    5340
GGCTGGGACA CTTCACATGA GCGAAAAATA CATCGTCACC TGGGACATGT TGCAGATCCA    5400
TGCACGTAAA CTCGCAAGCC GACTGATGCC TTCTGAACAA TGGAAAGGCA TTATTGCCGT    5460
AAGCCGTGGC GGTCTGGTAC CGGGTGCGTT ACTGGCGCGT GAACTGGGTA TTCGTCATGT    5520
CGATACCGTT TGTATTTCCA GCTACGATCA CGACAACCAG CGCGAGCTTA AAGTGCTGAA    5580
ACGCGCAGAA GGCGATGGCG AAGGCTTCAT CGTTATTGAT GACCTGGTGG ATACCGGTGG    5640
TACTGCGGTT GCGATTCGTG AAATGTATCC AAAAGCGCAC TTTGTCACCA TCTTCGCAAA    5700
ACCGGCTGGT CGTCCGCTGG TTGATGACTA TGTTGTTGAT ATCCCGCAAG ATACCTGGAT    5760
TGAACAGCCG TGGGATATGG GCGTCGTATT CGTCCCGCCA ATCTCCGGTC GCTAATCTTT    5820
TCAACGCCTG GCACTGCCGG GCGTTGTTCT TTTTAACTTC AGGCGGGTTA CAATAGTTTC    5880
CAGTAAGTAT TCTGGAGGCT GCATCCATGA CACAGGCAAA CCTGAGCGAA ACCCTGTTCA    5940
AACCCCGCTT TAAACATCCT GAAACCTCGA CGCTAGTCCG CCGCTTTAAT CACGGCGCAC    6000
AACCGCCTGT GCAGTCGGCC CTTGATGGTA AAACCATCCC TCACTGGTAT CGCATGATTA    6060
ACCGTCTGAT GTGGATCTGG CGCGGCATTG ACCCACGCGA AATCCTCGAC GTCCAGGCAC    6120
GTATTGTGAT GAGCGATGCC GAACGTACCG ACGATGATTT ATACGATACG GTGATTGGCT    6180
ACCGTGGCGG CAACTGGATT TATGAGTGGG CCCCGGATCT TGTGAAGGA ACCTTACTTC    6240
TGTGGTGTGA CATAATTGGA CAAACTACCT ACAGAGATTT AAAGCTCTAA GGTAAATATA    6300
AAATTTTTAA GTGTATAATG TGTTAAACTA CTGATTCTAA TTGTTTGTGT ATTTAGATT    6360
CCAACCTATG GAACTGATGA ATGGGAGCAG TGGTGGAATG CCTTTAATGA GGAAAACCTG    6420
TTTTGCTCAG AAGAAATGCC ATCTAGTGAT GATGAGGCTA CTGCTGACTC TCAACATTCT    6480
ACTCCTCCAA AAAAGAAGAG AAAGGTAGAA GACCCCAAGG ACTTTCCTTC AGAATTGCTA    6540
```

```
AGTTTTTTGA GTCATGCTGT GTTAGTAAT  AGAACTCTTG CTTGCTTTGC TATTTACACC    6600
ACAAAGGAAA AAGCTGCACT GCTATACAAG AAAATTATGG AAAAATATTC TGTAACCTTT    6660
ATAAGTAGGC ATAACAGTTA TAATCATAAC ATACTGTTTT TTCTTACTCC ACACAGGCAT    6720
AGAGTGTCTG CTATTAATAA CTATGCTCAA AAATTGTGTA CCTTTAGCTT TTTAATTTGT    6780
AAAGGGGTTA ATAAGGAATA TTTGATGTAT AGTGCCTTGA CTAGAGATCA TAATCAGCCA    6840
TACCACATTT GTAGAGGTTT TACTTGCTTT AAAAAACCTC CCACACCTCC CCCTGAACCT    6900
GAAACATAAA ATGAATGCAA TTGTTGTTGT TAAGCTTGGG GGAATTAATT CAACAATGTC    6960
TGGAAAGAAC TGTCCTTCAT CGATACCTAT CACGGAGAAA TCTGTAATTG ATTCCAAGAC    7020
ATCACATAGT TTAGTTGCTT CCAATGCTTC AAAATTATTC TTATCATGCG TCCATAGTCC    7080
CGTTCCGTAT CTATTATCGT TAGAATATTT TATAGTCACG CATTTATATT GAGCTATTTG    7140
ATAACGTCTA ACTCGTCTAA TTAATTCTGT ACTTTTACCT GAAACATGG  GGCCGATTAT    7200
CAACTGAATA TGTCCGCCGT TCATGATGAC AATAAAGAAT TAATTATTGT TCACTTTATT    7260
CGACTTTAAT ATATCCATCA CGTTAGAAAA TGCGATATTG CGACGAGGAT CTATGTATCT    7320
AACAGGATCT ATTGCGGTGG TAGCTAGAGA GGATTCTTTT TTGAATCGCA TCAAACTAAT    7380
CACAAAGTCG ACAAATATC  CTTTATTAAG TTTGACCCTT CCATCTGTAA CAATAGGGAC    7440
CTTGTTAAAC AGTTTTTTAA AATCTTGAAA GTCTGTGAAT TTTGTCAATT GTCTGTATTC    7500
CTCTGAAAGA GATTCATAAC AATGACCCAC GGCTTCTAAT TTATTTTTG  ATTGGATCAA    7560
TAATAATAAC AGAAAGTCTA GATATTGAGT GATTTGCAAT ATATCAGATA ATGAAGATTC    7620
ATCATCTTGA CTAGCCAAAT ACTTAAAAAA TGAATCATCA TCTGCGAAGA ACATCGTTAA    7680
GAGATACTGG TTGTGATCCA TTTATTGATC GCAAAAGCTT GGCGTAATCA TGGTCATAGC    7740
TGTTTCCTGT GTGAAATTGT TATCCGCTCA CAATTCCACA CAACATACGA GCCGGAAGCA    7800
TAAAGTGTAA AGCCTGGGGT GCCTAATGAG TGAGCTAACT CACATTAATT GCGTTGCGCT    7860
CACTGCCCGC TTTCCAGTCG GGAAACCTGT CGTGCCAGCT GGCGTAATAG CGAAGAGGCC    7920
CGCACCGATC GCCCTTCCCA ACAGTTGCGC AGCCTGAATG GCGAATGGGA AATTGTAAAC    7980
GTTAATATTT TGTTAAAATT CGCGTTAAAT TTTTGTTAAA TCAGCTCATT TTTTAACCAA    8040
TAGGCCGAAA TCGGCAAAAT CCCTTATAAA TCAAAAGAAT AGACCGAGAT AGGGTTGAGT    8100
GTTGTTCCAG TTTGGAACAA GAGTCCACTA TTAAAGAACG TGGACTCCAA CGTCAAAGGG    8160
CGAAAAACCG TCTATCAGGG CGATGGCCCA CTACGTGAAC CATCACCCTA ATCAAGTTTT    8220
TTGGGGTCGA GGTGCCGTAA AGCACTAAAT CGGAACCCTA AAGGGAGCCC CCGATTTAGA    8280
GCTTGACGGG GAAAGCCGGC GAACGTGGCG AGAAAGGAAG GGAAGAAAGC GAAAGGAGCG    8340
GGCGCTAGGG CGCTGGCAAG TGTAGCGGTC ACGCTGCGCG TAACCACCAC ACCCGCCGCG    8400
CTTAATGCGC CGCTACAGGG CGCGTCAGGT GGCACTTTTC GGGGAAATGT GCGCGGAACC    8460
CCTATTTGTT TATTTTTCTA AATACATTCA AATATGTATC CGCTCATGAG ACAATAACCC    8520
TGATAAATGC TTCAATAATA TTGAAAAGG  AAGAGTATGA GTATTCAACA TTTCCGTGTC    8580
GCCCTTATTC CCTTTTTTGC GGCATTTTGC CTTCCTGTTT TTGCTCACCC AGAAACGCTG    8640
GTGAAAGTAA AAGATGCTGA AGATCAGTTG GGTGCACGAG TGGGTTACAT CGAACTGGAT    8700
CTCAACAGCG GTAAGATCCT TGAGAGTTTT CGCCCCGAAG AACGTTTTCC AATGATGAGC    8760
ACTTTTAAAG TTCTGCTATG TGGCGCGGTA TTATCCCGTG TTGACGCCGG GCAAGAGCAA    8820
CTCGGTCGCC GCATACACTA TTCTCAGAAT GACTTGGTTG AGTACTCACC AGTCACAGAA    8880
AAGCATCTTA CGGATGGCAT GACAGTAAGA GAATTATGCA GTGCTGCCAT AACCATGAGT    8940
```

```
GATAACACTG CGGCCAACTT ACTTCTGACA ACGATCGGAG GACCGAAGGA GCTAACCGCT        9000

TTTTTGCACA ACATGGGGGA TCATGTAACT CGCCTTGATC GTTGGGAACC GGAGCTGAAT        9060

GAAGCCATAC CAAACGACGA GCGTGACACC ACGATGCCTC AGCAATGGCA ACAACGTTGC        9120

GCAAACTATT AACTGGCGAA CTACTTACTC TAGCTTCCCG GCAACAATTA ATAGACTGGA        9180

TGGAGGCGGA TAAAGTTGCA GGACCACTTC TGCGCTCGGC CCTTCCGGCT GGCTGGTTTA        9240

TTGCTGATAA ATCGGAGCC GGTGAGCGTG GGTCTCGCGG TATCATTGCA GCACTGGGGC        9300

CAGATGGTAA GCCCTCCCGT ATCGTAGTTA TCTACACGAC GGGGAGTCAG GCAACTATGG        9360

ATGAACGAAA TAGACAGATC GCTGAGATAG GTGCCTCACT GATTAAGCAT TGGTAACTGT        9420

CAGACCAAGT TTACTCATAT ATACTTTAGA TTGATTTAAA ACTTCATTTT TAATTTAAAA        9480

GGATCTAGGT GAAGATCCTT TTTGATAATC TCATGACCAA AATCCCTTAA CGTGAGTTTT        9540

CGTTCCACTG AGCGTCAGAC CCCGTAGAAA AGATCAAAGG ATCTTCTTGA GATCCTTTTT        9600

TTCTGCGCGT AATCTGCTGC TTGCAAACAA AAAAACCACC GCTACCAGCG GTGGTTTGTT        9660

TGCCGGATCA AGAGCTACCA ACTCTTTTTC CGAAGGTAAC TGGCTTCAGC AGAGCGCAGA        9720

TACCAAATAC TGTCCTTCTA GTGTAGCCGT AGTTAGGCCA CCACTTCAAG AACTCTGTAG        9780

CACCGCCTAC ATACCTCGCT CTGCTAATCC TGTTACCAGT GGCTGCTGCC AGTGGCGATA        9840

AGTCGTGTCT TACCGGGTTG GACTCAAGAC GATAGTTACC GGATAAGGCG CAGCGGTCGG        9900

GCTGAACGGG GGGTTCGTGC ACACAGCCCA GCTTGGAGCG AACGACCTAC ACCGAACTGA        9960

GATACCTACA GCGTGAGCAT TGAGAAAGCG CCACGCTTCC CGAAGGGAGA AAGGCGGACA        10020

GGTATCCGGT AAGCGGCAGG GTCGGAACAG GAGAGCGCAC GAGGGAGCTT CCAGGGGGAA        10080

ACGCCTGGTA TCTTTATAGT CCTGTCGGGT TTCGCCACCT CTGACTTGAG CGTCGATTTT        10140

TGTGATGCTC GTCAGGGGGG CGGAGCCTAT GGAAAAACGC CAGCAACGCG GCCTTTTTAC        10200

GGTTCCTGGC CTTTTGCTGG CCTTTTGCTC ACATGTTCTT TCCTGCGTTA TCCCCTGATT        10260

CTGTGGATAA CCGTATTACC GCCTTTGAGT GAGCTGATAC CGCTCGCCGC AGCCGAACGA        10320

CCGAGCGCAG CGAGTCAGTG AGCGAGGAAG CGGAAGAGCG CCCAATACGC AAACCGCCTC        10380

TCCCCGCGCG TTGGCCGATT CATTAATG                                          10408
```

( 2 ) INFORMATION FOR SEQ ID NO:7:

( i ) SEQUENCE CHARACTERISTICS:
        ( A ) LENGTH: 10408 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pTZgpt-P2b ( x i ) SEQUENCE DESCRIPTION: SEQ ID NO:7:

```
CAGCTGGCGA AAGGGGGATG TGCTGCAAGG CGATTAAGTT GGGTAACGCC AGGGTTTTCC          60

CAGTCACGAC GTTGTAAAAC GACGGCCCTG AATATGAAGG AGCAAAAGGT TGTAACATTT         120

TATTACCGTG TGGGATATAA AAGTCCTTGA TCCATTGATC TGGAACGGG CATCTCCATT         180

TAAGACTAGA CGCCACGGGG TTTAAAATAC TAATCATGAC ATTTTGTAGA GCGTAATTAC         240

TTAGTAAATC CGCCGTACTA GGTTCATTTC CTCCTCGTTT GGATCTCACA TCAGAAATTA         300

AAATAATCTT AGAAGGATGC AGTTGTTTTT TGATGGATCG TAGATATTCC TCATCAACGA         360

ACCGAGTCAC TAGAGTCACA TCACGCAATC CATTTAAAAT AGGATCATGA TGGCGGCCGT         420

CAATTAGCAT CCATTTGATG ATCACTCCTA AATTATAGAA ATGATCTCTC AAATAACGTA         480
```

-continued

```
TATGTGTACC GGGAGCAGAT CCTATATACA CTACGGTGGC ACCATCTAAT ATACCGTGTC    540
GCTGTAACTT ACTAAGAAAA AATAATTCTC CTAGTAATAG TTTTAACTGT CCTTGATACG    600
GCAGTTTTTT TGCGACCTCA TTTGCACTTT CTGGTTCGTA ATCTAACTCA TTATCAATTT    660
CCTCAAAATA CATAAACGGT TTATCTAACG ACACAACATC CATTTTAAG TATTATATTA     720
AAATTTAATC AATGTTTATT TTAGTTTTT TAGATAAAAA ATATAATATT ATGAGTCGAT     780
GTAACACTTT CTACACACCG ATTGATACAT ATCATTACCT CCTATTATTT CTATCTCGGT    840
TTCCTCACCC AATCGTTTAG AAAAGGAAGC CTCCTTAAAG CATTTCATAC ACACAGCAGT    900
TAGTTTTACC ACCATTTCAG ATAATGGAAT AAGATTCAAA ATATTATTAA ACGGTTTACG    960
TTGAAATGTC CCATCGAGTG CGGCTACTAT AACTATTTTT CCTTCGTTTG CCATACGCTC   1020
ACAGAATTAA TTCCGAGCTT GGCGGTTGGG GATCCTCTAG AGTCGACCTG CATTTGTTAG   1080
AGCTTGGTAT AGCGGACAAC TAAGTAATTG TAAAGAAGAA AACGAAACTA TCAAAACCGT   1140
TTATGAAATG ATAGAAAAAA GAATATAAAT AATCCTGTAT TTTAGTTTAA GTAACAGTAA   1200
AATAATGAGT AGAAAATACT ATTTTTATA GCCTATAAAT CATGGAAAAG AAACTGATTC    1260
AAGAGTATGA AAAACTCAAA GGCCAAGAGG CCAAAGATGT CTTTACCAGG CAGCTACTTA   1320
TCTGCCACGA AGATATGCGT GGCAGAATGG ACAACATGAC TAAGTTAATT AGTGACGTAT   1380
TTAGAACATT GGCTGGAGGT AGTAGCAAAG CACCCACCGA GAAGTCGGAT ATTGATACGA   1440
TGCCTCCTTC TAATGATGCT GGTTCTGAGC CACAGCCCCA ACCTAGCGAA AGTAAACCAC   1500
CCGAGCAACC CTCTCCCGAA CCCGAAAAAG ACTCTTCTAG TAAACCATCA GATCAACCTA   1560
CTCCCGAACC CGAAAAGGC TCTTCTAGCA AACCCCGTAC AGATGGGGAT CCTCTAGAGT    1620
CGACCTGCAG GAATTCCTTA CATATGGTTC GTGCTAACAA ACGCAACGAG GCTCTACGAA   1680
TCGGGGATCG CGGCCGCGAT CCCGTCGTTT TACAACGTCG TGACTGGGAA AACCCTGGCG   1740
TTACCCAACT TAATCGCCTT GCAGCACATC CCCCTTTCGC CAGCTGGCGT AATAGCGAAG   1800
AGGCCCGCAC CGATCGCCCT TCCCAACAGT TGCGCAGCCT GAATGGCGAA TGGCGCTTTG   1860
CCTGGTTTCC GGCACCAGAA GCGGTGCCGG AAAGCTGGCT GGAGTGCGAT CTTCCTGAGG   1920
CCGATACTGT CGTCGTCCCC TCAAACTGGC AGATGCACGG TTACGATGCG CCCATCTACA   1980
CCAACGTAAC CTATCCCATT ACGGTCAATC CGCCGTTTGT TCCCACGGAG AATCCGACGG   2040
GTTGTTACTC GCTCACATTT AATGTTGATG AAAGCTGGCT ACAGGAAGGC CAGACGCGAA   2100
TTATTTTTGA TGGCGTTAAC TCGGCGTTTC ATCTGTGGTG CAACGGGCGC TGGGTCGGTT   2160
ACGGCCAGGA CAGTCGTTTG CCGTCTGAAT TTGACCTGAG CGCATTTTTA CGCGCCGGAG   2220
AAAACCGCCT CGCGGTGATG GTGCTGCGTT GGAGTGACGG CAGTTATCTG GAAGATCAGG   2280
ATATGTGGCG GATGAGCGGC ATTTTCCGTG ACGTCTCGTT GCTGCATAAA CCGACTACAC   2340
AAATCAGCGA TTTCCATGTT GCCACTCGCT TTAATGATGA TTTCAGCCGC GCTGTACTGG   2400
AGGCTGAAGT TCAGATGTGC GGCGAGTTGC GTGACTACCT ACGGGTAACA GTTTCTTTAT   2460
GGCAGGGTGA AACGCAGGTC GCCAGCGGCA CCGCGCCTTT CGGCGGTGAA ATTATCGATG   2520
AGCGTGGTGG TTATGCCGAT CGCGTCACAC TACGTCTGAA CGTCGAAAAC CGAAACTGT    2580
GGAGCGCCGA AATCCCGAAT CTCTATCGTG CGGTGGTTGA ACTGCACACC GCCGACGGCA   2640
CGCTGATTGA AGCAGAAGCC TGCGATGTCG GTTTCCGCGA GGTGCGGATT GAAAATGGTC   2700
TGCTGCTGCT GAACGGCAAG CCGTTGCTGA TTCGAGGCGT TAACCGTCAC GAGCATCATC   2760
CTCTGCATGG TCAGGTCATG GATGAGCAGA CGATGGTGCA GGATATCCTG CTGATGAAGC   2820
AGAACAACTT TAACGCCGTG CGCTGTTCGC ATTATCCGAA CCATCCGCTG TGGTACACGC   2880
```

```
TGTGCGACCG CTACGGCCTG TATGTGGTGG ATGAAGCCAA TATTGAAACC CACGGCATGG  2940
TGCCAATGAA TCGTCTGACC GATGATCCGC GCTGGCTACC GGCGATGAGC GAACGCGTAA  3000
CGCGAATGGT GCAGCGCGAT CGTAATCACC GAGTGTGAT  CATCTGGTCG CTGGGGAATG  3060
AATCAGGCCA CGGCGCTAAT CACGACGCGC TGTATCGCTG GATCAAATCT GTCGATCCTT  3120
CCCGCCCGGT GCAGTATGAA GGCGGCGGAG CCGACACCAC GGCCACCGAT ATTATTTGCC  3180
CGATGTACGC GCGCGTGGAT GAAGACCAGC CCTTCCCGGC TGTGCCGAAA TGGTCCATCA  3240
AAAAATGGCT TTCGCTACCT GGAGAGACGC GCCCGCTGAT CCTTTGCGAA TACGCCCACG  3300
CGATGGGTAA CAGTCTTGGC GGTTTCGCTA AATACTGGCA GGCGTTTCGT CAGTATCCCC  3360
GTTACAGGG  CGGCTTCGTC TGGGACTGGG TGGATCAGTC GCTGATTAAA TATGATGAAA  3420
ACGGCAACCC GTGGTCGGCT TACGGCGGTG ATTTTGGCGA TACGCCGAAC GATCGCCAGT  3480
TCTGTATGAA CGGTCTGGTC TTTGCCGACC GCACGCCGCA TCCAGCGCTG ACGGAAGCAA  3540
AACACCAGCA GCAGTTTTTC CAGTTCCGTT TATCCGGGCA AACCATCGAA GTGACCAGCG  3600
AATACCTGTT CCGTCATAGC GATAACGAGC TCCTGCACTG GATGGTGGCG CTGGATGGTA  3660
AGCCGCTGGC AAGCGGTGAA GTGCCTCTGG ATGTCGCTCC ACAAGGTAAA CAGTTGATTG  3720
AACTGCCTGA ACTACCGCAG CCGGAGAGCG CCGGGCAACT CTGGCTCACA GTACGCGTAG  3780
TGCAACCGAA CGCGACCGCA TGGTCAGAAG CCGGGCACAT CAGCGCCTGG CAGCAGTGGC  3840
GTCTGGCGGA AAACCTCAGT GTGACGCTCC CCGCCGCGTC CCACGCCATC CCGCATCTGA  3900
CCACCAGCGA AATGGATTTT TGCATCGAGC TGGGTAATAA GCGTTGGCAA TTTAACCGCC  3960
AGTCAGGCTT TCTTTCACAG ATGTGGATTG GCGATAAAAA ACAACTGCTG ACGCCGCTGC  4020
GCGATCAGTT CACCCGTGCA CCGCTGGATA ACGACATTGG CGTAAGTGAA GCGACCCGCA  4080
TTGACCCTAA CGCCTGGGTC GAACGCTGGA AGGCGGCGGG CCATTACCAG GCCGAAGCAG  4140
CGTTGTTGCA GTGCACGGCA GATACACTTG CTGATGCGGT GCTGATTACG ACCGCTCACG  4200
CGTGGCAGCA TCAGGGGAAA ACCTTATTTA TCAGCCGGAA AACCTACCGG ATTGATGGTA  4260
GTGGTCAAAT GGCGATTACC GTTGATGTTG AAGTGGCGAG CGATACACCG CATCCGGCGC  4320
GGATTGGCCT GAACTGCCAG CTGGCGCAGG TAGCAGAGCG GGTAAACTGG CTCGGATTAG  4380
GGCCGCAAGA AAACTATCCC GACCGCCTTA CTGCCGCCTG TTTTGACCGC TGGGATCTGC  4440
CATTGTCAGA CATGTATACC CCGTACGTCT TCCCGAGCGA AAACGGTCTG CGCTGCGGGA  4500
CGCGCGAATT GAATTATGGC CCACACCAGT GGCGCGGCGA CTTCCAGTTC AACATCAGCC  4560
GCTACAGTCA ACAGCAACTG ATGGAAACCA GCCATCGCCA TCTGCTGCAC GCGGAAGAAG  4620
GCACATGGCT GAATATCGAC GGTTTCCATA TGGGGATTGG TGGCGACGAC TCCTGGAGCC  4680
CGTCAGTATC GGCGGAATTA CAGCTGAGCG CCGGTCGCTA CCATTACCAG TTGGTCTGGT  4740
GTCAAAAATA ATAATAACCG GCAGGCCAT  GTCTGCCCGT ATTTCGCGTA AGGAAATCCA  4800
TTATGTACTA TTTAATCCAA CAATGTCTGG AAAGAACTGT CCTTCATCGA TAGGAACCAA  4860
CTTAAGGGTA CCGCCTCGAC ATCTATATAC TATATAGTAA TACCAATACT CAAGACTACG  4920
AAACTGATAC AATCTCTTAT CATGTGGGTA ATGTTCTCGA TGTCGAATAG CCATATGCCG  4980
GTAGTTGCGA TATACATAAA CTGATCACTA ATTCCAAACC CACCCGCTTT TTATAGTAAG  5040
TTTTTCACCC ATAAATAATA AATACAATAA TTAATTTCTC GTAAAAGTAG AAAATATATT  5100
CTAATTTATT GCACGGTAAG GAAGTAGAAT CATAAAGAAC AGTGACGGAT GATCCCCAAG  5160
CTTGGACACA AGACAGGCTT GCGAGATATG TTTGAGAATA CCACTTTATC CCGCGTCAGG  5220
GAGAGGCAGT GCGTAAAAAG ACGCGGACTC ATGTGAAATA CTGGTTTTTA GTGCGCCAGA  5280
```

-continued

```
TCTCTATAAT CTCGCGCAAC CTATTTTCCC CTCGAACACT TTTTAAGCCG TAGATAAACA    5340
GGCTGGGACA CTTCACATGA GCGAAAAATA CATCGTCACC TGGGACATGT TGCAGATCCA    5400
TGCACGTAAA CTCGCAAGCC GACTGATGCC TTCTGAACAA TGGAAGGCA  TTATTGCCGT    5460
AAGCCGTGGC GGTCTGGTAC CGGGTGCGTT ACTGGCGCGT GAACTGGGTA TTCGTCATGT    5520
CGATACCGTT TGTATTTCCA GCTACGATCA CGACAACCAG CGCGAGCTTA AAGTGCTGAA    5580
ACGCGCAGAA GGCGATGGCG AAGGCTTCAT CGTTATTGAT GACCTGGTGG ATACCGGTGG    5640
TACTGCGGTT GCGATTCGTG AAATGTATCC AAAAGCGCAC TTTGTCACCA TCTTCGCAAA    5700
ACCGGCTGGT CGTCCGCTGG TTGATGACTA TGTTGTTGAT ATCCCGCAAG ATACCTGGAT    5760
TGAACAGCCG TGGGATATGG GCGTCGTATT CGTCCCGCCA ATCTCCGGTC GCTAATCTTT    5820
TCAACGCCTG GCACTGCCGG GCGTTGTTCT TTTTAACTTC AGGCGGGTTA CAATAGTTTC    5880
CAGTAAGTAT TCTGGAGGCT GCATCCATGA CACAGGCAAA CCTGAGCGAA ACCCTGTTCA    5940
AACCCCGCTT TAAACATCCT GAAACCTCGA CGCTAGTCCG CCGCTTTAAT CACGGCGCAC    6000
AACCGCCTGT GCAGTCGGCC CTTGATGGTA AAACCATCCC TCACTGGTAT CGCATGATTA    6060
ACCGTCTGAT GTGGATCTGG CGCGGCATTG ACCCACGCGA AATCCTCGAC GTCCAGGCAC    6120
GTATTGTGAT GAGCGATGCC GAACGTACCG ACGATGATTT ATACGATACG GTGATTGGCT    6180
ACCGTGGCGG CAACTGGATT TATGAGTGGG CCCCGGATCT TTGTGAAGGA ACCTTACTTC    6240
TGTGGTGTGA CATAATTGGA CAAACTACCT ACAGAGATTT AAAGCTCTAA GGTAAATATA    6300
AAATTTTTAA GTGTATAATG TGTTAAACTA CTGATTCTAA TTGTTTGTGT ATTTTAGATT    6360
CCAACCTATG GAACTGATGA ATGGGAGCAG TGGTGGAATG CCTTTAATGA GGAAAACCTG    6420
TTTTGCTCAG AAGAAATGCC ATCTAGTGAT GATGAGGCTA CTGCTGACTC TCAACATTCT    6480
ACTCCTCCAA AAAGAAGAG  AAAGGTAGAA GACCCCAAGG ACTTTCCTTC AGAATTGCTA    6540
AGTTTTTTGA GTCATGCTGT GTTAGTAAT  AGAACTCTTG CTTGCTTTGC TATTTACACC    6600
ACAAAGGAAA AAGCTGCACT GCTATACAAG AAAATTATGG AAAAATATTC TGTAACCTTT    6660
ATAAGTAGGC ATAACAGTTA TAATCATAAC ATACTGTTTT TCTTACTCC  ACACAGGCAT    6720
AGAGTGTCTG CTATTAATAA CTATGCTCAA AAATTGTGTA CCTTTAGCTT TTTAATTTGT    6780
AAAGGGGTTA ATAAGGAATA TTTGATGTAT AGTGCCTTGA CTAGAGATCA TAATCAGCCA    6840
TACCACATTT GTAGAGGTTT TACTTGCTTT AAAAAACCTC CCACACCTCC CCCTGAACCT    6900
GAAACATAAA ATGAATGCAA TTGTTGTTGT TAAGCTTGGG GGAATTAATT CAACAATGTC    6960
TGGAAAGAAC TGTCCTTCAT CGATACCTAT CACGGAGAAA TCTGTAATTG ATTCCAAGAC    7020
ATCACATAGT TTAGTTGCTT CCAATGCTTC AAAATTATTC TTATCATGCG TCCATAGTCC    7080
CGTTCCGTAT CTATTATCGT TAGAATATTT TATAGTCACG CATTTATATT GAGCTATTTG    7140
ATAACGTCTA ACTCGTCTAA TTAATTCTGT ACTTTTACCT GAAAACATGG GGCCGATTAT    7200
CAACTGAATA TGTCCGCCGT TCATGATGAC AATAAAGAAT TAATTATTGT TCACTTTATT    7260
CGACTTTAAT ATATCCATCA CGTTAGAAAA TGCGATATTG CGACGAGGAT CTATGTATCT    7320
AACAGGATCT ATTGCGGTGG TAGCTAGAGA GGATTCTTTT TTGAATCGCA TCAAACTAAT    7380
CACAAAGTCG AACAAATATC CTTTATTAAG TTTGACCCTT CCATCTGTAA CAATAGGGAC    7440
CTTGTTAAAC AGTTTTTTAA AATCTTGAAA GTCTGTGAAT TTTGTCAATT GTCTGTATTC    7500
CTCTGAAAGA GATTCATAAC AATGACCCAC GGCTTCTAAT TTATTTTTTG ATTGGATCAA    7560
TAATAATAAC AGAAAGTCTA GATATTGAGT GATTTGCAAT ATATCAGATA ATGAAGATTC    7620
ATCATCTTGA CTAGCCAAAT ACTTAAAAAA TGAATCATCA TCTGCGAAGA ACATCGTTAA    7680
```

```
GAGATACTGG TTGTGATCCA TTTATTGATC GCAAAAGCTT GGCGTAATCA TGGTCATAGC    7740
TGTTTCCTGT GTGAAATTGT TATCCGCTCA CAATTCCACA CAACATACGA GCCGGAAGCA    7800
TAAAGTGTAA AGCCTGGGGT GCCTAATGAG TGAGCTAACT CACATTAATT GCGTTGCGCT    7860
CACTGCCCGC TTTCCAGTCG GGAAACCTGT CGTGCCAGCT GGCGTAATAG CGAAGAGGCC    7920
CGCACCGATC GCCCTTCCCA ACAGTTGCGC AGCCTGAATG GCGAATGGGA AATTGTAAAC    7980
GTTAATATTT TGTTAAAATT CGCGTTAAAT TTTTGTTAAA TCAGCTCATT TTTTAACCAA    8040
TAGGCCGAAA TCGGCAAAAT CCCTTATAAA TCAAAAGAAT AGACCGAGAT AGGGTTGAGT    8100
GTTGTTCCAG TTTGGAACAA GAGTCCACTA TTAAAGAACG TGGACTCCAA CGTCAAAGGG    8160
CGAAAAACCG TCTATCAGGG CGATGGCCCA CTACGTGAAC CATCACCCTA ATCAAGTTTT    8220
TTGGGGTCGA GGTGCCGTAA AGCACTAAAT CGGAACCCTA AAGGGAGCCC CCGATTTAGA    8280
GCTTGACGGG GAAAGCCGGC GAACGTGGCG AGAAAGGAAG GGAAGAAAGC GAAAGGAGCG    8340
GGCGCTAGGG CGCTGGCAAG TGTAGCGGTC ACGCTGCGCG TAACCACCAC ACCCGCCGCG    8400
CTTAATGCGC CGCTACAGGG CGCGTCAGGT GGCACTTTTC GGGGAAATGT GCGCGGAACC    8460
CCTATTTGTT TATTTTTCTA AATACATTCA AATATGTATC CGCTCATGAG ACAATAACCC    8520
TGATAAATGC TTCAATAATA TTGAAAAAGG AAGAGTATGA GTATTCAACA TTTCCGTGTC    8580
GCCCTTATTC CCTTTTTTGC GGCATTTTGC CTTCCTGTTT TTGCTCACCC AGAAACGCTG    8640
GTGAAAGTAA AAGATGCTGA AGATCAGTTG GGTGCACGAG TGGGTTACAT CGAACTGGAT    8700
CTCAACAGCG GTAAGATCCT TGAGAGTTTT CGCCCCGAAG AACGTTTTCC AATGATGAGC    8760
ACTTTTAAAG TTCTGCTATG TGGCGCGGTA TTATCCCGTG TTGACGCCGG GCAAGAGCAA    8820
CTCGGTCGCC GCATACACTA TTCTCAGAAT GACTTGGTTG AGTACTCACC AGTCACAGAA    8880
AAGCATCTTA CGGATGGCAT GACAGTAAGA GAATTATGCA GTGCTGCCAT AACCATGAGT    8940
GATAACACTG CGGCCAACTT ACTTCTGACA ACGATCGGAG GACCGAAGGA GCTAACCGCT    9000
TTTTTGCACA ACATGGGGGA TCATGTAACT CGCCTTGATC GTTGGGAACC GGAGCTGAAT    9060
GAAGCCATAC CAAACGACGA GCGTGACACC ACGATGCCTC AGCAATGGCA ACAACGTTGC    9120
GCAAACTATT AACTGGCGAA CTACTTACTC TAGCTTCCCG GCAACAATTA ATAGACTGGA    9180
TGGAGGCGGA TAAAGTTGCA GGACCACTTC TGCGCTCGGC CCTTCCGGCT GGCTGGTTTA    9240
TTGCTGATAA ATCTGGAGCC GGTGAGCGTG GGTCTCGCGG TATCATTGCA GCACTGGGGC    9300
CAGATGGTAA GCCCTCCCGT ATCGTAGTTA TCTACACGAC GGGGAGTCAG GCAACTATGG    9360
ATGAACGAAA TAGACAGATC GCTGAGATAG GTGCCTCACT GATTAAGCAT TGGTAACTGT    9420
CAGACCAAGT TTACTCATAT ATACTTTAGA TTGATTTAAA ACTTCATTTT TAATTTAAAA    9480
GGATCTAGGT GAAGATCCTT TTTGATAATC TCATGACCAA AATCCCTTAA CGTGAGTTTT    9540
CGTTCCACTG AGCGTCAGAC CCCGTAGAAA AGATCAAAGG ATCTTCTTGA GATCCTTTTT    9600
TTCTGCGCGT AATCTGCTGC TTGCAAACAA AAAAACCACC GCTACCAGCG GTGGTTTGTT    9660
TGCCGGATCA AGAGCTACCA ACTCTTTTTC CGAAGGTAAC TGGCTTCAGC AGAGCGCAGA    9720
TACCAAATAC TGTCCTTCTA GTGTAGCCGT AGTTAGGCCA CCACTTCAAG AACTCTGTAG    9780
CACCGCCTAC ATACCTCGCT CTGCTAATCC TGTTACCAGT GGCTGCTGCC AGTGGCGATA    9840
AGTCGTGTCT TACCGGGTTG GACTCAAGAC GATAGTTACC GGATAAGGCG CAGCGGTCGG    9900
GCTGAACGGG GGGTTCGTGC ACACAGCCCA GCTTGGAGCG AACGACCTAC ACCGAACTGA    9960
GATACCTACA GCGTGAGCAT TGAGAAAGCG CCACGCTTCC CGAAGGGAGA AAGGCGGACA   10020
GGTATCCGGT AAGCGGCAGG GTCGGAACAG GAGAGCGCAC GAGGGAGCTT CCAGGGGGAA   10080
```

-continued

| | | | | | |
|---|---|---|---|---|---|
| ACGCCTGGTA | TCTTTATAGT | CCTGTCGGGT | TTCGCCACCT | CTGACTTGAG | CGTCGATTTT | 10140 |
| TGTGATGCTC | GTCAGGGGGG | CGGAGCCTAT | GGAAAAACGC | CAGCAACGCG | GCCTTTTTAC | 10200 |
| GGTTCCTGGC | CTTTGCTGG | CCTTTTGCTC | ACATGTTCTT | TCCTGCGTTA | TCCCCTGATT | 10260 |
| CTGTGGATAA | CCGTATTACC | GCCTTTGAGT | GAGCTGATAC | CGCTCGCCGC | AGCCGAACGA | 10320 |
| CCGAGCGCAG | CGAGTCAGTG | AGCGAGGAAG | CGGAAGAGCG | CCCAATACGC | AAACCGCCTC | 10380 |
| TCCCCGCGCG | TTGGCCGATT | CATTAATG | | | | 10408 |

( 2 ) INFORMATION FOR SEQ ID NO:8:

( i ) SEQUENCE CHARACTERISTICS:
        ( A ) LENGTH: 3656 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pFS50

( x i ) SEQUENCE DESCRIPTION: SEQ ID NO:8:

| | | | | | |
|---|---|---|---|---|---|
| AGCGCCCAAT | ACGCAAACCG | CCTCTCCCCG | CGCGTTGGCC | GATTCATTAA | TGCAGAAAAA | 60 |
| ACTGTTTAAC | AAGGTCCCTA | TTGTTACAGA | TGGAAGGGTC | AAACTTAATA | AGGATATTT | 120 |
| GTTCGACTTT | GTGATTAGTT | TGATGCGATT | CAAAAAAGAA | TCCTCTCTAG | CTACCACCGC | 180 |
| AATAGATCCT | GTTAGATATC | ATAGATCCTC | GTCGCAATAT | CGCATTTTCT | AACGTGATGG | 240 |
| ATATATTAAA | GTCGAATAAA | GTGAACAATA | ATTAATTCTT | TATTGTCATC | ATGAACGGCG | 300 |
| GACATATTCA | GTTGATAATC | GGCCCCATGT | TTTCAGGTAA | AAGTACAGAA | TTAATTAGAC | 360 |
| GAGTTAGACG | TTATCAAATA | GCTCAATATA | AATGCGTGAC | TATAAAATAT | TCTAACGATA | 420 |
| ATAGATACGG | AACGGGACTA | TGGACGCATG | ATAAGAATAA | TTTTGAAGCA | TTGGAAGCAA | 480 |
| CTAAACTATG | TGATGTCTTG | GAATCAATTA | CAGATTTCTC | CGTGATAGGT | ATCGATGAAG | 540 |
| GACAGTTCTT | TCCAGACATT | GTTGAATTCT | GTGAGCGTAT | GGCAAACGAA | GGAAAAATAG | 600 |
| TTATAGTAGC | CGCACTCGAT | GGGACATTTC | AACGTAAACC | GTTAATAAT | ATTTGAATC | 660 |
| TTATTCCATT | ATCTGAAATG | GTGGTAAAAC | TAACTGCTGT | GTGTATGAAA | TGCTTTAAGG | 720 |
| AGGCTTCCTT | TTCTAAACGA | TTGGGTGAGG | AAACCGAGAT | AGAAATAATA | GGAGGTAATG | 780 |
| ATATGTATCA | ATCGGTGTGT | AGAAAGTGTT | ACATCGACTC | ATAATATTAT | ATTTTTATC | 840 |
| TAAAAAACTA | AAAATAAACA | TTGATTAAAT | TTAATATAA | TACTTAAAAA | TGGATGTTGT | 900 |
| GTCGTTAGAT | AAACCGTTTA | TGTATTTTGA | GGAAATTGAT | AATGAGTTAG | ATTACGAACC | 960 |
| AGAAAGTGCA | AATGAGGTCG | CAAAAAAACT | GCCGTATCAA | GGACAGTTAA | AACTATTACT | 1020 |
| AGGAGAATTA | TTTTTTCTTA | GTAAGTTACA | GCGACACGGT | ATATTAGATG | GTGCCACCGT | 1080 |
| AGTGTATATA | GGATCTGCTC | CCGGTACACA | TATACGTTAT | TTGAGAGATC | ATTTCTATAA | 1140 |
| TTTAGGAGTG | ATCATCAAAT | GGATGCTAAT | TGACGGCCGC | CATCATGATC | CTATTTTCTG | 1200 |
| GCGTAATAGC | GAAGAGGCCC | GCACCGATCG | CCCTTCCCAA | CAGTTGCGCA | GCCTGAATGG | 1260 |
| CGAATGGGAA | ATTGTAAACG | TTAATATTTT | GTTAAAATTC | GCGTTAAATT | TTTGTTAAAT | 1320 |
| CAGCTCATTT | TTTAACCAAT | AGGCCGAAAT | CGGCAAAATC | CCTTATAAAT | CAAAAGAATA | 1380 |
| GACCGAGATA | GGGTTGAGTG | TTGTTCCAGT | TTGGAACAAG | AGTCCACTAT | TAAAGAACGT | 1440 |
| GGACTCCAAC | GTCAAAGGGC | GAAAAACCGT | CTATCAGGGC | GATGGCCCAC | TACGTGAACC | 1500 |
| ATCACCCTAA | TCAAGTTTTT | TGGGGTCGAG | GTGCCGTAAA | GCACTAAATC | GGAACCCTAA | 1560 |
| AGGGAGCCCC | CGATTTAGAG | CTTGACGGGG | AAAGCCGGCG | AACGTGGCGA | GAAAGGAAGG | 1620 |

-continued

```
GAAGAAAGCG AAAGGAGCGG GCGCTAGGGC GCTGGCAAGT GTAGCGGTCA CGCTGCGCGT   1680
AACCACCACA CCCGCCGCGC TTAATGCGCC GCTACAGGGC GCGTCAGGTG GCACTTTTCG   1740
GGGAAATGTG CGCGGAACCC CTATTTGTTT ATTTTTCTAA ATACATTCAA ATATGTATCC   1800
GCTCATGAGA CAATAACCCT GATAAATGCT TCAATAATAT TGAAAAAGGA AGAGTATGAG   1860
TATTCAACAT TTCCGTGTCG CCCTTATTCC CTTTTTTGCG GCATTTTGCC TTCCTGTTTT   1920
TGCTCACCCA GAAACGCTGG TGAAAGTAAA AGATGCTGAA GATCAGTTGG GTGCACGAGT   1980
GGGTTACATC GAACTGGATC TCAACAGCGG TAAGATCCTT GAGAGTTTTC GCCCCGAAGA   2040
ACGTTTTCCA ATGATGAGCA CTTTTAAAGT TCTGCTATGT GGCGCGGTAT TATCCCGTGT   2100
TGACGCCGGG CAAGAGCAAC TCGGTCGCCG CATACACTAT TCTCAGAATG ACTTGGTTGA   2160
GTACTCACCA GTCACAGAAA AGCATCTTAC GGATGGCATG ACAGTAAGAG AATTATGCAG   2220
TGCTGCCATA ACCATGAGTG ATAACACTGC GGCCAACTTA CTTCTGACAA CGATCGGAGG   2280
ACCGAAGGAG CTAACCGCTT TTTTGCACAA CATGGGGGAT CATGTAACTC GCCTTGATCG   2340
TTGGGAACCG GAGCTGAATG AAGCCATACC AAACGACGAG CGTGACACCA CGATGCCTGC   2400
AGCAATGGCA ACAACGTTGC GCAAACTATT AACTGGCGAA CTACTTACTC TAGCTTCCCG   2460
GCAACAATTA ATAGACTGGA TGGAGGCGGA TAAAGTTGCA GGACCACTTC TGCGCTCGGC   2520
CCTTCCGGCT GGCTGGTTTA TTGCTGATAA ATCTGGAGCC GGTGAGCGTG GGTCTCGCGG   2580
TATCATTGCA GCACTGGGGC CAGATGGTAA GCCCTCCCGT ATCGTAGTTA TCTACACGAC   2640
GGGGAGTCAG GCAACTATGG ATGAACGAAA TAGACAGATC GCTGAGATAG GTGCCTCACT   2700
GATTAAGCAT TGGTAACTGT CAGACCAAGT TTACTCATAT ATACTTTAGA TTGATTTAAA   2760
ACTTCATTTT TAATTTAAAA GGATCTAGGT GAAGATCCTT TTTGATAATC TCATGACCAA   2820
AATCCCTTAA CGTGAGTTTT CGTTCCACTG AGCGTCAGAC CCCGTAGAAA AGATCAAAGG   2880
ATCTTCTTGA GATCCTTTTT TTCTGCGCGT AATCTGCTGC TTGCAAACAA AAAAACCACC   2940
GCTACCAGCG GTGGTTTGTT TGCCGGATCA AGAGCTACCA ACTCTTTTTC CGAAGGTAAC   3000
TGGCTTCAGC AGAGCGCAGA TACCAAATAC TGTCCTTCTA GTGTAGCCGT AGTTAGGCCA   3060
CCACTTCAAG AACTCTGTAG CACCGCCTAC ATACCTCGCT CTGCTAATCC TGTTACCAGT   3120
GGCTGCTGCC AGTGGCGATA AGTCGTGTCT TACCGGGTTG GACTCAAGAC GATAGTTACC   3180
GGATAAGGCG CAGCGGTCGG GCTGAACGGG GGGTTCGTGC ACACAGCCCA GCTTGGAGCG   3240
AACGACCTAC ACCGAACTGA GATACCTACA GCGTGAGCAT TGAGAAAGCG CCACGCTTCC   3300
CGAAGGGAGA AAGGCGGACA GGTATCCGGT AAGCGGCAGG GTCGGAACAG GAGAGCGCAC   3360
GAGGGAGCTT CCAGGGGGAA ACGCCTGGTA TCTTTATAGT CCTGTCGGGT TTCGCCACCT   3420
CTGACTTGAG CGTCGATTTT TGTGATGCTC GTCAGGGGGG CGGAGCCTAT GGAAAAACGC   3480
CAGCAACGCG GCCTTTTTAC GGTTCCTGGC CTTTTGCTGG CCTTTTGCTC ACATGTTCTT   3540
TCCTGCGTTA TCCCCTGATT CTGTGGATAA CCGTATTACC GCCTTTGAGT GAGCTGATAC   3600
CGCTCGCCGC AGCCGAACGA CCGAGCGCAG CGAGTCAGTG AGCGAGGAAG CGGAAG        3656
```

( 2 ) INFORMATION FOR SEQ ID NO:9:

( i ) SEQUENCE CHARACTERISTICS:
        ( A ) LENGTH: 3688 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pFS51

( x i ) SEQUENCE DESCRIPTION: SEQ ID NO:9:

| | | | | | |
|---|---|---|---|---|---|
| AGCGCCCAAT | ACGCAAACCG | CCTCTCCCCG | CGCGTTGGCC | GATTCATTAA | TGCAGAAAAA | 60
| ACTGTTAAC | AAGGTCCCTA | TTGTTACAGA | TGGAAGGGTC | AAACTTAATA | AAGGATATTT | 120
| GTTCGACTTT | GTGATTAGTT | TGATGCGATT | CAAAAAAGAA | TCCTCTCTAG | CTACCACCGC | 180
| AATAGATCCT | GTTAGATATC | ATAGATCCTC | GTCGCAATAT | CGCATTTTCT | AACGTGATGG | 240
| ATATATTAAA | GTCGAATAAA | GTGAACAATA | ATTAATTCTT | TATTGTCATC | ATGAACGGCG | 300
| GACATATTCA | GTTGATAATC | GGCCCCATGT | TTTCAGGTAA | AAGTACAGAA | TTAATTAGAC | 360
| GAGTTAGACG | TTATCAAATA | GCTCAATATA | AATGCGTGAC | TATAAAATAT | TCTAACGATA | 420
| ATAGATACGG | AACGGGACTA | TGGACGCATG | ATAAGAATAA | TTTTGAAGCA | TTGGAAGCAA | 480
| CTAAACTATG | TGATGTCTTG | GAATCAATTA | CAGATTTCTC | CGTGATAGGT | ATCGAGCAGC | 540
| TGCATATGAG | GCCTGGATCC | CGGGTCGACG | CGGCCGCTAA | CTGACTGATT | TTTCTCAATT | 600
| CTGTGAGCGT | ATGGCAAACG | AAGGAAAAAT | AGTTATAGTA | GCCGCACTCG | ATGGACATT | 660
| TCAACGTAAA | CCGTTAATA | ATATTTTGAA | TCTTATTCCA | TTATCTGAAA | TGGTGGTAAA | 720
| ACTAACTGCT | GTGTGTATGA | AATGCTTTAA | GGAGGCTTCC | TTTTCTAAAC | GATTGGGTGA | 780
| GGAAACCGAG | ATAGAAATAA | TAGGAGGTAA | TGATATGTAT | CAATCGGTGT | GTAGAAAGTG | 840
| TTACATCGAC | TCATAATATT | ATATTTTTA | TCTAAAAAAC | TAAAATAAA | CATTGATTAA | 900
| ATTTAATAT | AATACTTAAA | AATGGATGTT | GTGTCGTTAG | ATAAACCGTT | TATGTATTT | 960
| GAGGAAATTG | ATAATGAGTT | AGATTACGAA | CCAGAAAGTG | CAAATGAGGT | CGCAAAAAAA | 1020
| CTGCCGTATC | AAGGACAGTT | AAAACTATTA | CTAGGAGAAT | TATTTTTCT | TAGTAAGTTA | 1080
| CAGCGACACG | GTATATTAGA | TGGTGCCACC | GTAGTGTATA | TAGGATCTGC | TCCCGGTACA | 1140
| CATATACGTT | ATTGAGAGA | TCATTTCTAT | AATTTAGGAG | TGATCATCAA | ATGGATGCTA | 1200
| ATTGACGGCC | GCCATCATGA | TCCTATTTC | TGGCGTAATA | GCGAAGAGGC | CCGCACCGAT | 1260
| CGCCCTTCCC | AACAGTTGCG | CAGCCTGAAT | GGCGAATGGG | AAATTGTAAA | CGTTAATATT | 1320
| TTGTTAAAAT | TCGCGTTAAA | TTTTGTTAA | ATCAGCTCAT | TTTTTAACCA | ATAGGCCGAA | 1380
| ATCGGCAAAA | TCCCTTATAA | ATCAAAAGAA | TAGACCGAGA | TAGGGTTGAG | TGTTGTTCCA | 1440
| GTTTGGAACA | AGAGTCCACT | ATTAAAGAAC | GTGGACTCCA | ACGTCAAAGG | GCGAAAAACC | 1500
| GTCTATCAGG | GCGATGGCCC | ACTACGTGAA | CCATCACCCT | AATCAAGTTT | TTTGGGGTCG | 1560
| AGGTGCCGTA | AAGCACTAAA | TCGGAACCCT | AAAGGGAGCC | CCCGATTTAG | AGCTTGACGG | 1620
| GGAAAGCCGG | CGAACGTGGC | GAGAAAGGAA | GGGAAGAAAG | CGAAAGGAGC | GGGCGCTAGG | 1680
| GCGCTGGCAA | GTGTAGCGGT | CACGCTGCGC | GTAACCACCA | CACCCGCCGC | GCTTAATGCG | 1740
| CCGCTACAGG | GCGCGTCAGG | TGGCACTTTT | CGGGGAAATG | TGCGCGGAAC | CCCTATTTGT | 1800
| TTATTTTTCT | AAATACATTC | AAATATGTAT | CCGCTCATGA | GACAATAACC | CTGATAAATG | 1860
| CTTCAATAAT | ATTGAAAAAG | GAAGAGTATG | AGTATTCAAC | ATTTCCGTGT | CGCCCTTATT | 1920
| CCCTTTTTTG | CGGCATTTTG | CCTTCCTGTT | TTTGCTCACC | CAGAAACGCT | GGTGAAAGTA | 1980
| AAAGATGCTG | AAGATCAGTT | GGGTGCACGA | GTGGGTTACA | TCGAACTGGA | TCTCAACAGC | 2040
| GGTAAGATCC | TTGAGAGTTT | TCGCCCCGAA | GAACGTTTTC | CAATGATGAG | CACTTTTAAA | 2100
| GTTCTGCTAT | GTGGCGCGGT | ATTATCCCGT | GTTGACGCCG | GGCAAGAGCA | ACTCGGTCGC | 2160
| CGCATACACT | ATTCTCAGAA | TGACTTGGTT | GAGTACTCAC | CAGTCACAGA | AAAGCATCTT | 2220
| ACGGATGGCA | TGACAGTAAG | AGAATTATGC | AGTGCTGCCA | TAACCATGAG | TGATAACACT | 2280
| GCGGCCAACT | TACTTCTGAC | AACGATCGGA | GGACCGAAGG | AGCTAACCGC | TTTTTTGCAC | 2340

-continued

| | | | | | | |
|---|---|---|---|---|---|---|
| AACATGGGGG | ATCATGTAAC | TCGCCTTGAT | CGTTGGGAAC | CGGAGCTGAA | TGAAGCCATA | 2400 |
| CCAAACGACG | AGCGTGACAC | CACGATGCCT | GCAGCAATGG | CAACAACGTT | GCGCAAACTA | 2460 |
| TTAACTGGCG | AACTACTTAC | TCTAGCTTCC | CGGCAACAAT | TAATAGACTG | GATGGAGGCG | 2520 |
| GATAAAGTTG | CAGGACCACT | TCTGCGCTCG | GCCCTTCCGG | CTGGCTGGTT | TATTGCTGAT | 2580 |
| AAATCTGGAG | CCGGTGAGCG | TGGGTCTCGC | GGTATCATTG | CAGCACTGGG | GCCAGATGGT | 2640 |
| AAGCCCTCCC | GTATCGTAGT | TATCTACACG | ACGGGAGTC | AGGCAACTAT | GGATGAACGA | 2700 |
| AATAGACAGA | TCGCTGAGAT | AGGTGCCTCA | CTGATTAAGC | ATTGGTAACT | GTCAGACCAA | 2760 |
| GTTTACTCAT | ATATACTTTA | GATTGATTTA | AAACTTCATT | TTTAATTTAA | AAGGATCTAG | 2820 |
| GTGAAGATCC | TTTTTGATAA | TCTCATGACC | AAAATCCCTT | AACGTGAGTT | TTCGTTCCAC | 2880 |
| TGAGCGTCAG | ACCCCGTAGA | AAAGATCAAA | GGATCTTCTT | GAGATCCTTT | TTTTCTGCGC | 2940 |
| GTAATCTGCT | GCTTGCAAAC | AAAAAAACCA | CCGCTACCAG | CGGTGGTTTG | TTTGCCGGAT | 3000 |
| CAAGAGCTAC | CAACTCTTTT | TCCGAAGGTA | ACTGGCTTCA | GCAGAGCGCA | GATACCAAAT | 3060 |
| ACTGTCCTTC | TAGTGTAGCC | GTAGTTAGGC | CACCACTTCA | AGAACTCTGT | AGCACCGCCT | 3120 |
| ACATACCTCG | CTCTGCTAAT | CCTGTTACCA | GTGGCTGCTG | CCAGTGGCGA | TAAGTCGTGT | 3180 |
| CTTACCGGGT | TGGACTCAAG | ACGATAGTTA | CCGGATAAGG | CGCAGCGGTC | GGGCTGAACG | 3240 |
| GGGGGTTCGT | GCACACAGCC | CAGCTTGGAG | CGAACGACCT | ACACCGAACT | GAGATACCTA | 3300 |
| CAGCGTGAGC | ATTGAGAAAG | CGCCACGCTT | CCCGAAGGGA | GAAAGGCGGA | CAGGTATCCG | 3360 |
| GTAAGCGGCA | GGGTCGGAAC | AGGAGAGCGC | ACGAGGGAGC | TTCCAGGGGG | AAACGCCTGG | 3420 |
| TATCTTTATA | GTCCTGTCGG | GTTTCGCCAC | CTCTGACTTG | AGCGTCGATT | TTTGTGATGC | 3480 |
| TCGTCAGGGG | GGCGGAGCCT | ATGGAAAAAC | GCCAGCAACG | CGGCCTTTTT | ACGGTTCCTG | 3540 |
| GCCTTTTGCT | GGCCTTTTGC | TCACATGTTC | TTTCCTGCGT | TATCCCCTGA | TTCTGTGGAT | 3600 |
| AACCGTATTA | CCGCCTTTGA | GTGAGCTGAT | ACCGCTCGCC | GCAGCCGAAC | GACCGAGCGC | 3660 |
| AGCGAGTCAG | TGAGCGAGGA | AGCGGAAG | | | | 3688 |

( 2 ) INFORMATION FOR SEQ ID NO:10:

( i ) SEQUENCE CHARACTERISTICS:
        ( A ) LENGTH: 4659 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pFSgpt ( x i ) SEQUENCE DESCRIPTION: SEQ ID NO:10:

| | | | | | | |
|---|---|---|---|---|---|---|
| AGCGCCCAAT | ACGCAAACCG | CCTCTCCCCG | CGCGTTGGCC | GATTCATTAA | TGCAGAAAAA | 60 |
| ACTGTTTAAC | AAGGTCCCTA | TTGTTACAGA | TGGAAGGGTC | AAACTTAATA | AAGGATATTT | 120 |
| GTTCGACTTT | GTGATTAGTT | TGATGCGATT | CAAAAAAGAA | TCCTCTCTAG | CTACCACCGC | 180 |
| AATAGATCCT | GTTAGATATC | ATAGATCCTC | GTCGCAATAT | CGCATTTTCT | AACGTGATGG | 240 |
| ATATATTAAA | GTCGAATAAA | GTGAACAATA | ATTAATTCTT | TATTGTCATC | ATGAACGGCG | 300 |
| GACATATTCA | GTTGATAATC | GGCCCCATGT | TTTCAGGTAA | AAGTACAGAA | TTAATTAGAC | 360 |
| GAGTTAGACG | TTATCAAATA | GCTCAATATA | AATGCGTGAC | TATAAAATAT | TCTAACGATA | 420 |
| ATAGATACGG | AACGGGACTA | TGGACGCATG | ATAAGAATAA | TTTTGAAGCA | TTGGAAGCAA | 480 |
| CTAAACTATG | TGATGTCTTG | GAATCAATTA | CAGATTTCTC | CGTGATAGGT | ATCGAGCAGA | 540 |
| AAGCGGGGTT | TGAACAGGGT | TTCGCTCAGG | TTTGCCTGTG | TCATGGATGC | AGCCTCCAGA | 600 |

```
ATACTTACTG GAAACTATTG TAACCCGCCT GAAGTTAAAA AGAACAACGC CCGGCAGTGC    660
CAGGCGTTGA AAAGATTAGC GACCGGAGAT TGGCGGGACG AATACGACGC CCATATCCCA    720
CGGCTGTTCA ATCCAGGTAT CTTGCGGGAT ATCAACAACA TAGTCATCAA CCAGCGGACG    780
ACCAGCCGGT TTTGCGAAGA TGGTGACAAA GTGCGCTTTT GGATACATTT CACGAATCGC    840
AACCGCAGTA CCACCGGTAT CCACCAGGTC ATCAATAACG ATGAAGCCTT CGCCATCGCC    900
TTCTGCGCGT TTCAGCACTT TAAGCTCGCG CTGGTTGTCG TGATCGTAGC TGGAAATACA    960
AACGGTATCG ACATGACGAA TACCCAGTTC ACGCGCCAGT AACGCACCCG GTACCAGACC   1020
GCCACGGCTT ACGGCAATAA TGCCTTTCCA TTGTTCAGAA GGCATCAGTC GGCTTGCGAG   1080
TTTACGTGCA TGGATCTGCA ACATGTCCCA GGTGACGATG TATTTTCGC TCATGTGAAG    1140
TGTCCCAGCC TGTTTATCTA CGGCTTAAAA AGTGTTCGAG GGGAAAATAG GTTGCGCGAG   1200
ATTATAGAGA TCTGGCGCAC TAAAAACCAG TATTTCACAT GAGTCCGCGT CTTTTTACGC   1260
ACTGCCTCTC CCTGACGCGG GATAAAGTGG TATTCTCAAA CATATCTCGC AAGCCTGTCT   1320
TGTGTCCAAG CTTGGGGATC ATCCGTCACT GTTCTTATG ATTCTACTTC CTTACCGTGC    1380
AATAAATTAG AATATATTTT CTACTTTTAC GAGAAATTAA TTATTGTATT TATTATTTAT   1440
GGGTGAAAAA CTTACTATAA AAAGCGGGTG GGTTTGGAAT TAGTGATCAG TTTATGTATA   1500
TCGCAACTAC CGGCATATGA GGCCTGGATC CCGGGTCGAC GCGGCCGCTA ACTGACTGAT   1560
TTTTCTCAAT TCTGTGAGCG TATGGCAAAC GAAGGAAAAA TAGTTATAGT AGCCGCACTC   1620
GATGGGACAT TTCAACGTAA ACCGTTTAAT AATATTTTGA ATCTTATTCC ATTATCTGAA   1680
ATGGTGGTAA AACTAACTGC TGTGTGTATG AAATGCTTTA AGGAGGCTTC CTTTCTAAA    1740
CGATTGGGTG AGGAAACCGA GATAGAAATA ATAGGAGGTA ATGATATGTA TCAATCGGTG   1800
TGTAGAAAGT GTTACATCGA CTCATAATAT TATATTTTTT ATCTAAAAAA CTAAAAATAA   1860
ACATTGATTA AATTTTAATA TAATACTTAA AAATGGATGT TGTGTCGTTA GATAAACCGT   1920
TTATGTATTT TGAGGAAATT GATAATGAGT TAGATTACGA ACCAGAAAGT GCAAATGAGG   1980
TCGCAAAAAA ACTGCCGTAT CAAGGACAGT TAAAACTATT ACTAGGAGAA TTATTTTTTC   2040
TTAGTAAGTT ACAGCGACAC GGTATATTAG ATGGTGCCAC CGTAGTGTAT ATAGGATCTG   2100
CTCCCGGTAC ACATATACGT TATTTGAGAG ATCATTTCTA TAATTTAGGA GTGATCATCA   2160
AATGGATGCT AATTGACGGC CGCCATCATG ATCCTATTTT CTGGCGTAAT AGCGAAGAGG   2220
CCCGCACCGA TCGCCCTTCC CAACAGTTGC GCAGCCTGAA TGGCGAATGG AAATTGTAA    2280
ACGTTAATAT TTTGTTAAAA TTCGCGTTAA ATTTTGTTA AATCAGCTCA TTTTTTAACC    2340
AATAGGCCGA AATCGGCAAA ATCCCTTATA ATCAAAAGA ATAGACCGAG ATAGGGTTGA    2400
GTGTTGTTCC AGTTTGGAAC AAGAGTCCAC TATTAAAGAA CGTGGACTCC AACGTCAAAG   2460
GGCGAAAAAC CGTCTATCAG GGCGATGGCC CACTACGTGA ACCATCACCC TAATCAAGTT   2520
TTTTGGGGTC GAGGTGCCGT AAAGCACTAA ATCGGAACCC TAAAGGGAGC CCCCGATTTA   2580
GAGCTTGACG GGGAAAGCCG GCGAACGTGG CGAGAAAGGA AGGGAAGAAA GCGAAAGGAG   2640
CGGGCGCTAG GGCGCTGGCA AGTGTAGCGG TCACGCTGCG CGTAACCACC ACACCCGCCG   2700
CGCTTAATGC GCCGCTACAG GGCGCGTCAG GTGGCACTTT TCGGGGAAAT GTGCGCGGAA   2760
CCCCTATTTG TTTATTTTTC TAAATACATT CAAATATGTA TCCGCTCATG AGACAATAAC   2820
CCTGATAAAT GCTTCAATAA TATTGAAAAA GGAAGAGTAT GAGTATTCAA CATTTCCGTG   2880
TCGCCCTTAT TCCCTTTTTT GCGGCATTTT GCCTTCCTGT TTTTGCTCAC CCAGAAACGC   2940
TGGTGAAAGT AAAAGATGCT GAAGATCAGT TGGGTGCACG AGTGGGTTAC ATCGAACTGG   3000
```

| | | | | | |
|---|---|---|---|---|---|
| ATCTCAACAG | CGGTAAGATC | CTTGAGAGTT | TTCGCCCCGA | AGAACGTTTT | CCAATGATGA | 3060 |
| GCACTTTTAA | AGTTCTGCTA | TGTGGCGCGG | TATTATCCCG | TGTTGACGCC | GGGCAAGAGC | 3120 |
| AACTCGGTCG | CCGCATACAC | TATTCTCAGA | ATGACTTGGT | TGAGTACTCA | CCAGTCACAG | 3180 |
| AAAAGCATCT | TACGGATGGC | ATGACAGTAA | GAGAATTATG | CAGTGCTGCC | ATAACCATGA | 3240 |
| GTGATAACAC | TGCGGCCAAC | TTACTTCTGA | CAACGATCGG | AGGACCGAAG | GAGCTAACCG | 3300 |
| CTTTTTTGCA | CAACATGGGG | GATCATGTAA | CTCGCCTTGA | TCGTTGGGAA | CCGGAGCTGA | 3360 |
| ATGAAGCCAT | ACCAAACGAC | GAGCGTGACA | CCACGATGCC | TGCAGCAATG | GCAACAACGT | 3420 |
| TGCGCAAACT | ATTAACTGGC | GAACTACTTA | CTCTAGCTTC | CCGGCAACAA | TTAATAGACT | 3480 |
| GGATGGAGGC | GGATAAAGTT | GCAGGACCAC | TTCTGCGCTC | GGCCCTTCCG | GCTGGCTGGT | 3540 |
| TTATTGCTGA | TAAATCTGGA | GCCGGTGAGC | GTGGGTCTCG | CGGTATCATT | GCAGCACTGG | 3600 |
| GGCCAGATGG | TAAGCCCTCC | CGTATCGTAG | TTATCTACAC | GACGGGGAGT | CAGGCAACTA | 3660 |
| TGGATGAACG | AAATAGACAG | ATCGCTGAGA | TAGGTGCCTC | ACTGATTAAG | CATTGGTAAC | 3720 |
| TGTCAGACCA | AGTTACTCA | TATATACTTT | AGATTGATTT | AAAACTTCAT | TTTTAATTTA | 3780 |
| AAAGGATCTA | GGTGAAGATC | CTTTTTGATA | ATCTCATGAC | CAAAATCCCT | TAACGTGAGT | 3840 |
| TTTCGTTCCA | CTGAGCGTCA | GACCCCGTAG | AAAAGATCAA | AGGATCTTCT | TGAGATCCTT | 3900 |
| TTTTTCTGCG | CGTAATCTGC | TGCTTGCAAA | CAAAAAAACC | ACCGCTACCA | GCGGTGGTTT | 3960 |
| GTTTGCCGGA | TCAAGAGCTA | CCAACTCTTT | TTCCGAAGGT | AACTGGCTTC | AGCAGAGCGC | 4020 |
| AGATACCAAA | TACTGTCCTT | CTAGTGTAGC | CGTAGTTAGG | CCACCACTTC | AAGAACTCTG | 4080 |
| TAGCACCGCC | TACATACCTC | GCTCTGCTAA | TCCTGTTACC | AGTGGCTGCT | GCCAGTGGCG | 4140 |
| ATAAGTCGTG | TCTTACCGGG | TTGGACTCAA | GACGATAGTT | ACCGGATAAG | GCGCAGCGGT | 4200 |
| CGGGCTGAAC | GGGGGGTTCG | TGCACACAGC | CCAGCTTGGA | GCGAACGACC | TACACCGAAC | 4260 |
| TGAGATACCT | ACAGCGTGAG | CATTGAGAAA | GCGCCACGCT | TCCCGAAGGG | AGAAAGGCGG | 4320 |
| ACAGGTATCC | GGTAAGCGGC | AGGGTCGGAA | CAGGAGAGCG | CACGAGGGAG | CTTCCAGGGG | 4380 |
| GAAACGCCTG | GTATCTTTAT | AGTCCTGTCG | GGTTTCGCCA | CCTCTGACTT | GAGCGTCGAT | 4440 |
| TTTTGTGATG | CTCGTCAGGG | GGGCGGAGCC | TATGGAAAAA | CGCCAGCAAC | GCGGCCTTTT | 4500 |
| TACGGTTCCT | GGCCTTTTGC | TGGCCTTTTG | CTCACATGTT | CTTTCCTGCG | TTATCCCCTG | 4560 |
| ATTCTGTGGA | TAACCGTATT | ACCGCCTTTG | AGTGAGCTGA | TACCGCTCGC | CGCAGCCGAA | 4620 |
| CGACCGAGCG | CAGCGAGTCA | GTGAGCGAGG | AAGCGGAAG | | | 4659 |

( 2 ) INFORMATION FOR SEQ ID NO:11:

( i ) SEQUENCE CHARACTERISTICS:
        ( A ) LENGTH: 4818 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pP2m0gpt ( x i ) SEQUENCE DESCRIPTION: SEQ ID NO:11:

| | | | | | |
|---|---|---|---|---|---|
| AGCGCCCAAT | ACGCAAACCG | CCTCTCCCCG | CGCGTTGGCC | GATTCATTAA | TGCAGAAAAA | 60 |
| ACTGTTTAAC | AAGGTCCCTA | TTGTTACAGA | TGGAAGGGTC | AAACTTAATA | AAGGATATTT | 120 |
| GTTCGACTTT | GTGATTAGTT | TGATGCGATT | CAAAAAGAA | TCCTCTCTAG | CTACCACCGC | 180 |
| AATAGATCCT | GTTAGATATC | ATAGATCCTC | GTCGCAATAT | CGCATTTTCT | AACGTGATGG | 240 |
| ATATATTAAA | GTCGAATAAA | GTGAACAATA | ATTAATTCTT | TATTGTCATC | ATGAACGGCG | 300 |

```
GACATATTCA GTTGATAATC GGCCCCATGT TTTCAGGTAA AAGTACAGAA TTAATTAGAC     360
GAGTTAGACG TTATCAAATA GCTCAATATA AATGCGTGAC TATAAAATAT TCTAACGATA     420
ATAGATACGG AACGGGACTA TGGACGCATG ATAAGAATAA TTTTGAAGCA TTGGAAGCAA     480
CTAAACTATG TGATGTCTTG GAATCAATTA CAGATTTCTC CGTGATAGGT ATCGAGCAGA     540
AAGCGGGGTT TGAACAGGGT TTCGCTCAGG TTTGCCTGTG TCATGGATGC AGCCTCCAGA     600
ATACTTACTG GAAACTATTG TAACCCGCCT GAAGTTAAAA AGAACAACGC CCGGCAGTGC     660
CAGGCGTTGA AAAGATTAGC GACCGGAGAT TGGCGGGACG AATACGACGC CCATATCCCA     720
CGGCTGTTCA ATCCAGGTAT CTTGCGGGAT ATCAACAACA TAGTCATCAA CCAGCGGACG     780
ACCAGCCGGT TTTGCGAAGA TGGTGACAAA GTGCGCTTTT GGATACATTT CACGAATCGC     840
AACCGCAGTA CCACCGGTAT CCACCAGGTC ATCAATAACG ATGAAGCCTT CGCCATCGCC     900
TTCTGCGCGT TTCAGCACTT TAAGCTCGCG CTGGTTGTCG TGATCGTAGC TGGAAATACA     960
AACGGTATCG ACATGACGAA TACCCAGTTC ACGCGCCAGT AACGCACCCG GTACCAGACC    1020
GCCACGGCTT ACGGCAATAA TGCCTTTCCA TTGTTCAGAA GGCATCAGTC GGCTTGCGAG    1080
TTTACGTGCA TGGATCTGCA ACATGTCCCA GGTGACGATG TATTTTTCGC TCATGTGAAG    1140
TGTCCCAGCC TGTTTATCTA CGGCTTAAAA AGTGTTCGAG GGGAAAATAG GTTGCGCGAG    1200
ATTATAGAGA TCTGGCGCAC TAAAAACCAG TATTTCACAT GAGTCCGCGT CTTTTTACGC    1260
ACTGCCTCTC CCTGACGCGG GATAAAGTGG TATTCTCAAA CATATCTCGC AAGCCTGTCT    1320
TGTGTCCAAG CTTGGGGATC ATCCGTCACT GTTCTTTATG ATTCTACTTC CTTACCGTGC    1380
AATAAATTAG AATATATTTT CTACTTTTAC GAGAAATTAA TTATTGTATT TATTATTTAT    1440
GGGTGAAAAA CTTACTATAA AAAGCGGGTG GGTTTGGAAT TAGTGATCAG TTTATGTATA    1500
TCGCAACTAC CGGCATACGG CTTGGTATAG CGGACAACTA AGTAATTGTA AAGAAGAAAA    1560
CGAAACTATC AAAACCGTTT ATGAAATGAT AGAAAAAAGA ATATAAATAA TCCTGTATTT    1620
TAGTTTAAGT AACAGTAAAA TAATGAGTAG AAAATACTAT TTTTTATAGC CTATAAATGA    1680
ATTCGGATCC CGGGTCGACG CGGCCGCTAA CTGACTGATT TTTCTCAATT CTGTGAGCGT    1740
ATGGCAAACG AAGGAAAAAT AGTTATAGTA GCCGCACTCG ATGGGACATT TCAACGTAAA    1800
CCGTTTAATA ATATTTTGAA TCTTATTCCA TTATCTGAAA TGGTGGTAAA ACTAACTGCT    1860
GTGTGTATGA AATGCTTTAA GGAGGCTTCC TTTTCTAAAC GATTGGGTGA GGAAACCGAG    1920
ATAGAAATAA TAGGAGGTAA TGATATGTAT CAATCGGTGT GTAGAAAGTG TTACATCGAC    1980
TCATAATATT ATATTTTTA TCTAAAAAAC TAAAAATAAA CATTGATTAA ATTTAATAT     2040
AATACTTAAA AATGGATGTT GTGTCGTTAG ATAAACCGTT TATGTATTTT GAGGAAATTG    2100
ATAATGAGTT AGATTACGAA CCAGAAAGTG CAAATGAGGT CGCAAAAAAA CTGCCGTATC    2160
AAGGACAGTT AAAACTATTA CTAGGAGAAT TATTTTTTCT TAGTAAGTTA CAGCGACACG    2220
GTATATTAGA TGGTGCCACC GTAGTGTATA TAGGATCTGC TCCCGGTACA CATATACGTT    2280
ATTTGAGAGA TCATTTCTAT AATTTAGGAG TGATCATCAA ATGGATGCTA ATTGACGGCC    2340
GCCATCATGA TCCTATTTTC TGGCGTAATA GCGAAGAGGC CCGCACCGAT CGCCCTTCCC    2400
AACAGTTGCG CAGCCTGAAT GGCGAATGGG AAATTGTAAA CGTTAATATT TTGTTAAAAT    2460
TCGCGTTAAA TTTTTGTTAA ATCAGCTCAT TTTTTAACCA ATAGGCCGAA ATCGGCAAAA    2520
TCCCTTATAA ATCAAAAGAA TAGACCGAGA TAGGGTTGAG TGTTGTTCCA GTTTGGAACA    2580
AGAGTCCACT ATTAAAGAAC GTGGACTCCA ACGTCAAAGG GCGAAAAACC GTCTATCAGG    2640
GCGATGGCCC ACTACGTGAA CCATCACCCT AATCAAGTTT TTTGGGGTCG AGGTGCCGTA    2700
```

```
AAGCACTAAA TCGGAACCCT AAAGGGAGCC CCCGATTTAG AGCTTGACGG GGAAAGCCGG    2760
CGAACGTGGC GAGAAAGGAA GGGAAGAAAG CGAAAGGAGC GGGCGCTAGG GCGCTGGCAA    2820
GTGTAGCGGT CACGCTGCGC GTAACCACCA CACCCGCCGC GCTTAATGCG CCGCTACAGG    2880
GCGCGTCAGG TGGCACTTTT CGGGGAAATG TGCGCGGAAC CCTATTTGT TTATTTTTCT     2940
AAATACATTC AAATATGTAT CCGCTCATGA GACAATAACC CTGATAAATG CTTCAATAAT    3000
ATTGAAAAAG GAAGAGTATG AGTATTCAAC ATTTCCGTGT CGCCCTTATT CCCTTTTTG     3060
CGGCATTTTG CCTTCCTGTT TTTGCTCACC CAGAAACGCT GGTGAAAGTA AAAGATGCTG    3120
AAGATCAGTT GGGTGCACGA GTGGGTTACA TCGAACTGGA TCTCAACAGC GGTAAGATCC    3180
TTGAGAGTTT TCGCCCCGAA GAACGTTTTC CAATGATGAG CACTTTTAAA GTTCTGCTAT    3240
GTGGCGCGGT ATTATCCCGT GTTGACGCCG GGCAAGAGCA ACTCGGTCGC CGCATACACT    3300
ATTCTCAGAA TGACTTGGTT GAGTACTCAC CAGTCACAGA AAAGCATCTT ACGGATGGCA    3360
TGACAGTAAG AGAATTATGC AGTGCTGCCA TAACCATGAG TGATAACACT GCGGCCAACT    3420
TACTTCTGAC AACGATCGGA GGACCGAAGG AGCTAACCGC TTTTTTGCAC AACATGGGGG    3480
ATCATGTAAC TCGCCTTGAT CGTTGGGAAC CGGAGCTGAA TGAAGCCATA CCAAACGACG    3540
AGCGTGACAC CACGATGCCT GCAGCAATGG CAACAACGTT GCGCAAACTA TTAACTGGCG    3600
AACTACTTAC TCTAGCTTCC CGGCAACAAT TAATAGACTG GATGGAGGCG GATAAAGTTG    3660
CAGGACCACT TCTGCGCTCG GCCCTTCCGG CTGGCTGGTT TATTGCTGAT AAATCTGGAG    3720
CCGGTGAGCG TGGGTCTCGC GGTATCATTG CAGCACTGGG GCCAGATGGT AAGCCCTCCC    3780
GTATCGTAGT TATCTACACG ACGGGGAGTC AGGCAACTAT GGATGAACGA AATAGACAGA    3840
TCGCTGAGAT AGGTGCCTCA CTGATTAAGC ATTGGTAACT GTCAGACCAA GTTTACTCAT    3900
ATATACTTTA GATTGATTTA AAACTTCATT TTTAATTTAA AAGGATCTAG GTGAAGATCC    3960
TTTTTGATAA TCTCATGACC AAAATCCCTT AACGTGAGTT TTCGTTCCAC TGAGCGTCAG    4020
ACCCCGTAGA AAAGATCAAA GGATCTTCTT GAGATCCTTT TTTTCTGCGC GTAATCTGCT    4080
GCTTGCAAAC AAAAAAACCA CCGCTACCAG CGGTGGTTTG TTTGCCGGAT CAAGAGCTAC    4140
CAACTCTTTT TCCGAAGGTA ACTGGCTTCA GCAGAGCGCA GATACCAAAT ACTGTCCTTC    4200
TAGTGTAGCC GTAGTTAGGC CACCACTTCA AGAACTCTGT AGCACCGCCT ACATACCTCG    4260
CTCTGCTAAT CCTGTTACCA GTGGCTGCTG CCAGTGGCGA TAAGTCGTGT CTTACCGGGT    4320
TGGACTCAAG ACGATAGTTA CCGGATAAGG CGCAGCGGTC GGGCTGAACG GGGGGTTCGT    4380
GCACACAGCC CAGCTTGGAG CGAACGACCT ACACCGAACT GAGATACCTA CAGCGTGAGC    4440
ATTGAGAAAG CGCCACGCTT CCCGAAGGGA GAAAGGCGGA CAGGTATCCG GTAAGCGGCA    4500
GGGTCGGAAC AGGAGAGCGC ACGAGGGAGC TTCCAGGGGG AAACGCCTGG TATCTTTATA    4560
GTCCTGTCGG GTTTCGCCAC CTCTGACTTG AGCGTCGATT TTTGTGATGC TCGTCAGGGG    4620
GGCGGAGCCT ATGGAAAAAC GCCAGCAACG CGGCCTTTTT ACGGTTCCTG GCCTTTTGCT    4680
GGCCTTTTGC TCACATGTTC TTTCCTGCGT TATCCCCTGA TTCTGTGGAT AACCGTATTA    4740
CCGCCTTTGA GTGAGCTGAT ACCGCTCGCC GCAGCCGAAC GACCGAGCGC AGCGAGTCAG    4800
TGAGCGAGGA AGCGGAAG                                                  4818
```

( 2 ) INFORMATION FOR SEQ ID NO:12:

( i ) SEQUENCE CHARACTERISTICS:
        ( A ) LENGTH: 4821 base pairs
        ( B ) TYPE: nucleic acid
        ( C ) STRANDEDNESS: single ( D ) TOPOLOGY: linear ( v i i ) IMMEDIATE SOURCE:
  ( B ) CLONE: pP2m1gpt ( x i ) SEQUENCE DESCRIPTION: SEQ ID NO:12:

```
AGCGCCCAAT ACGCAAACCG CCTCTCCCCG CGCGTTGGCC GATTCATTAA TGCAGAAAAA        60
ACTGTTTAAC AAGGTCCCTA TTGTTACAGA TGGAAGGGTC AAACTTAATA AAGGATATTT       120
GTTCGACTTT GTGATTAGTT TGATGCGATT CAAAAAAGAA TCCTCTCTAG CTACCACCGC       180
AATAGATCCT GTTAGATATC ATAGATCCTC GTCGCAATAT CGCATTTTCT AACGTGATGG       240
ATATATTAAA GTCGAATAAA GTGAACAATA ATTAATTCTT TATTGTCATC ATGAACGGCG       300
GACATATTCA GTTGATAATC GGCCCCATGT TTTCAGGTAA AAGTACAGAA TTAATTAGAC       360
GAGTTAGACG TTATCAAATA GCTCAATATA AATGCGTGAC TATAAAATAT TCTAACGATA       420
ATAGATACGG AACGGGACTA TGGACGCATG ATAAGAATAA TTTTGAAGCA TTGGAAGCAA       480
CTAAACTATG TGATGTCTTG GAATCAATTA CAGATTTCTC CGTGATAGGT ATCGAGCAGA       540
AAGCGGGGTT TGAACAGGGT TTCGCTCAGG TTTGCCTGTG TCATGGATGC AGCCTCCAGA       600
ATACTTACTG GAAACTATTG TAACCCGCCT GAAGTTAAAA AGAACAACGC CCGGCAGTGC       660
CAGGCGTTGA AAAGATTAGC GACCGGAGAT TGGCGGGACG AATACGACGC CCATATCCCA       720
CGGCTGTTCA ATCCAGGTAT CTTGCGGGAT ATCAACAACA TAGTCATCAA CCAGCGGACG       780
ACCAGCCGGT TTGCGAAGA TGGTGACAAA GTGCGCTTTT GGATACATTT CACGAATCGC        840
AACCGCAGTA CCACCGGTAT CCACCAGGTC ATCAATAACG ATGAAGCCTT CGCCATCGCC       900
TTCTGCGCGT TCAGCACTT TAAGCTCGCG CTGGTTGTCG TGATCGTAGC TGGAAATACA        960
AACGGTATCG ACATGACGAA TACCCAGTTC ACGCGCCAGT AACGCACCCG GTACCAGACC      1020
GCCACGGCTT ACGGCAATAA TGCCTTTCCA TTGTTCAGAA GGCATCAGTC GGCTTGCGAG      1080
TTTACGTGCA TGGATCTGCA ACATGTCCCA GGTGACGATG TATTTTCGC TCATGTGAAG       1140
TGTCCCAGCC TGTTTATCTA CGGCTTAAAA AGTGTTCGAG GGGAAAATAG GTTGCGCGAG      1200
ATTATAGAGA TCTGGCGCAC TAAAAACCAG TATTTCACAT GAGTCCGCGT CTTTTACGC       1260
ACTGCCTCTC CCTGACGCGG GATAAAGTGG TATTCTCAAA CATATCTCGC AAGCCTGTCT      1320
TGTGTCCAAG CTTGGGGATC ATCCGTCACT GTTCTTTATG ATTCTACTTC CTTACCGTGC      1380
AATAAATTAG AATATATTTT CTACTTTTAC GAGAAATTAA TTATTGTATT TATTATTTAT      1440
GGGTGAAAAA CTTACTATAA AAAGCGGGTG GGTTTGGAAT TAGTGATCAG TTTATGTATA      1500
TCGCAACTAC CGGCATACGG CTTGGTATAG CGGACAACTA AGTAATTGTA AAGAAGAAAA      1560
CGAAACTATC AAAACCGTTT ATGAAATGAT AGAAAAAGA ATATAAATAA TCCTGTATTT       1620
TAGTTTAAGT AACAGTAAAA TAATGAGTAG AAAATACTAT TTTTATAGC CTATAAATCA       1680
TGAATTCGGA TCCCGGGTCG ACGCGGCCGC TAACTGACTG ATTTTTCTCA ATTCTGTGAG      1740
CGTATGGCAA ACGAAGGAAA AATAGTTATA GTAGCCGCAC TCGATGGGAC ATTTCAACGT      1800
AAACCGTTTA ATAATATTTT GAATCTTATT CCATTATCTG AAATGGTGGT AAAACTAACT      1860
GCTGTGTGTA TGAAATGCTT TAAGGAGGCT TCCTTTTCTA AACGATTGGG TGAGGAAACC      1920
GAGATAGAAA TAATAGGAGG TAATGATATG TATCAATCGG TGTGTAGAAA GTGTTACATC      1980
GACTCATAAT ATTATATTTT TTATCTAAAA AACTAAAAAT AAACATTGAT TAAATTTTAA      2040
TATAATACTT AAAAATGGAT GTTGTGTCGT TAGATAAACC GTTTATGTAT TTTGAGGAAA      2100
TTGATAATGA GTTAGATTAC GAACCAGAAA GTGCAAATGA GGTCGCAAAA AAACTGCCGT      2160
ATCAAGGACA GTTAAAACTA TTACTAGGAG AATTATTTTT TCTTAGTAAG TTACAGCGAC      2220
```

```
ACGGTATATT AGATGGTGCC ACCGTAGTGT ATATAGGATC TGCTCCCGGT ACACATATAC   2280
GTTATTTGAG AGATCATTTC TATAATTTAG GAGTGATCAT CAAATGGATG CTAATTGACG   2340
GCCGCCATCA TGATCCTATT TTCTGGCGTA ATAGCGAAGA GGCCCGCACC GATCGCCCTT   2400
CCCAACAGTT GCGCAGCCTG AATGGCGAAT GGGAAATTGT AAACGTTAAT ATTTTGTTAA   2460
AATTCGCGTT AAATTTTTGT TAAATCAGCT CATTTTTTAA CCAATAGGCC GAAATCGGCA   2520
AAATCCCTTA TAAATCAAAA GAATAGACCG AGATAGGGTT GAGTGTTGTT CCAGTTTGGA   2580
ACAAGAGTCC ACTATTAAAG AACGTGGACT CCAACGTCAA AGGGCGAAAA ACCGTCTATC   2640
AGGGCGATGG CCCACTACGT GAACCATCAC CCTAATCAAG TTTTTTGGGG TCGAGGTGCC   2700
GTAAAGCACT AAATCGGAAC CCTAAAGGGA GCCCCGATT TAGAGCTTGA CGGGGAAAGC   2760
CGGCGAACGT GGCGAGAAAG GAAGGGAAGA AAGCGAAAGG AGCGGGCGCT AGGGCGCTGG   2820
CAAGTGTAGC GGTCACGCTG CGCGTAACCA CCACACCCGC CGCGCTTAAT GCGCCGCTAC   2880
AGGGCGCGTC AGGTGGCACT TTTCGGGGAA ATGTGCGCGG AACCCCTATT TGTTTATTTT   2940
TCTAAATACA TTCAAATATG TATCCGCTCA TGAGACAATA ACCCTGATAA ATGCTTCAAT   3000
AATATTGAAA AAGGAAGAGT ATGAGTATTC AACATTTCCG TGTCGCCCTT ATTCCCTTTT   3060
TTGCGGCATT TTGCCTTCCT GTTTTGCTC ACCCAGAAAC GCTGGTGAAA GTAAAAGATG   3120
CTGAAGATCA GTTGGGTGCA CGAGTGGGTT ACATCGAACT GGATCTCAAC AGCGGTAAGA   3180
TCCTTGAGAG TTTTCGCCCC GAAGAACGTT TTCCAATGAT GAGCACTTTT AAAGTTCTGC   3240
TATGTGGCGC GGTATTATCC CGTGTTGACG CCGGGCAAGA GCAACTCGGT CGCCGCATAC   3300
ACTATTCTCA GAATGACTTG GTTGAGTACT CACCAGTCAC AGAAAAGCAT CTTACGGATG   3360
GCATGACAGT AAGAGAATTA TGCAGTGCTG CCATAACCAT GAGTGATAAC ACTGCGGCCA   3420
ACTTACTTCT GACAACGATC GGAGGACCGA AGGAGCTAAC CGCTTTTTTG CACAACATGG   3480
GGGATCATGT AACTCGCCTT GATCGTTGGG AACCGGAGCT GAATGAAGCC ATACCAAACG   3540
ACGAGCGTGA CACCACGATG CCTGCAGCAA TGGCAACAAC GTTGCGCAAA CTATTAACTG   3600
GCGAACTACT TACTCTAGCT TCCCGGCAAC AATTAATAGA CTGGATGGAG GCGGATAAAG   3660
TTGCAGGACC ACTTCTGCGC TCGGCCCTTC CGGCTGGCTG GTTTATTGCT GATAAATCTG   3720
GAGCCGGTGA GCGTGGGTCT CGCGGTATCA TTGCAGCACT GGGGCCAGAT GGTAAGCCCT   3780
CCCGTATCGT AGTTATCTAC ACGACGGGGA GTCAGGCAAC TATGGATGAA CGAAATAGAC   3840
AGATCGCTGA GATAGGTGCC TCACTGATTA AGCATTGGTA ACTGTCAGAC CAAGTTTACT   3900
CATATATACT TTAGATTGAT TTAAAACTTC ATTTTTAATT TAAAAGGATC TAGGTGAAGA   3960
TCCTTTTTGA TAATCTCATG ACCAAAATCC CTTAACGTGA GTTTCGTTC CACTGAGCGT   4020
CAGACCCCGT AGAAAAGATC AAAGGATCTT CTTGAGATCC TTTTTTTCTG CGCGTAATCT   4080
GCTGCTTGCA AACAAAAAAA CCACCGCTAC CAGCGGTGGT TTGTTTGCCG GATCAAGAGC   4140
TACCAACTCT TTTTCCGAAG GTAACTGGCT TCAGCAGAGC GCAGATACCA AATACTGTCC   4200
TTCTAGTGTA GCCGTAGTTA GGCCACCACT TCAAGAACTC TGTAGCACCG CCTACATACC   4260
TCGCTCTGCT AATCCTGTTA CCAGTGGCTG CTGCCAGTGG CGATAAGTCG TGTCTTACCG   4320
GGTTGGACTC AAGACGATAG TTACCGGATA AGGCGCAGCG GTCGGGCTGA ACGGGGGGTT   4380
CGTGCACACA GCCCAGCTTG GAGCGAACGA CCTACACCGA ACTGAGATAC CTACAGCGTG   4440
AGCATTGAGA AAGCGCCACG CTTCCCGAAG GGAGAAAGGC GGACAGGTAT CCGGTAAGCG   4500
GCAGGGTCGG AACAGGAGAG CGCACGAGGG AGCTTCCAGG GGGAAACGCC TGGTATCTTT   4560
ATAGTCCTGT CGGGTTTCGC CACCTCTGAC TTGAGCGTCG ATTTTTGTGA TGCTCGTCAG   4620
```

-continued

```
GGGGGCGGAG CCTATGGAAA AACGCCAGCA ACGCGGCCTT TTTACGGTTC CTGGCCTTTT    4680
GCTGGCCTTT TGCTCACATG TTCTTTCCTG CGTTATCCCC TGATTCTGTG GATAACCGTA    4740
TTACCGCCTT TGAGTGAGCT GATACCGCTC GCCGCAGCCG AACGACCGAG CGCAGCGAGT    4800
CAGTGAGCGA GGAAGCGGAA G                                              4821
```

( 2 ) INFORMATION FOR SEQ ID NO:13:

( i ) SEQUENCE CHARACTERISTICS:
        ( A ) LENGTH: 4824 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pP2m2gpt ( x i ) SEQUENCE DESCRIPTION: SEQ ID NO:13:

```
AGCGCCCAAT ACGCAAACCG CCTCTCCCCG CGCGTTGGCC GATTCATTAA TGCAGAAAAA      60
ACTGTTTAAC AAGGTCCCTA TTGTTACAGA TGGAAGGGTC AAACTTAATA AAGGATATTT     120
GTTCGACTTT GTGATTAGTT TGATGCGATT CAAAAAAGAA TCCTCTCTAG CTACCACCGC     180
AATAGATCCT GTTAGATATC ATAGATCCTC GTCGCAATAT CGCATTTTCT AACGTGATGG     240
ATATATTAAA GTCGAATAAA GTGAACAATA ATTAATTCTT TATTGTCATC ATGAACGGCG     300
GACATATTCA GTTGATAATC GGCCCCATGT TTTCAGGTAA AAGTACAGAA TTAATTAGAC     360
GAGTTAGACG TTATCAAATA GCTCAATATA AATGCGTGAC TATAAAATAT CTAACGATA      420
ATAGATACGG AACGGGACTA TGGACGCATG ATAAGAATAA TTTTGAAGCA TTGGAAGCAA     480
CTAAACTATG TGATGTCTTG GAATCAATTA CAGATTTCTC CGTGATAGGT ATCGAGCAGA     540
AAGCGGGGTT TGAACAGGGT TTCGCTCAGG TTTGCCTGTG TCATGGATGC AGCCTCCAGA     600
ATACTTACTG GAAACTATTG TAACCCGCCT GAAGTAAAA AGAACAACGC CCGGCAGTGC     660
CAGGCGTTGA AAAGATTAGC GACCGGAGAT TGGCGGGACG AATACGACGC CCATATCCCA     720
CGGCTGTTCA ATCCAGGTAT CTTGCGGGAT ATCAACAACA TAGTCATCAA CCAGCGGACG     780
ACCAGCCGGT TTTGCGAAGA TGGTGACAAA GTGCGCTTTT GGATACATTT CACGAATCGC     840
AACCGCAGTA CCACCGGTAT CCACCAGGTC ATCAATAACG ATGAAGCCTT CGCCATCGCC     900
TTCTGCGCGT TCAGCACTT TAAGCTCGCG CTGGTTGTCG TGATCGTAGC TGGAAATACA     960
AACGGTATCG ACATGACGAA TACCCAGTTC ACGCGCCAGT AACGCACCCG GTACCAGACC    1020
GCCACGGCTT ACGGCAATAA TGCCTTTCCA TTGTTCAGAA GGCATCAGTC GGCTTGCGAG    1080
TTTACGTGCA TGGATCTGCA ACATGTCCCA GGTGACGATG TATTTTTCGC TCATGTGAAG    1140
TGTCCCAGCC TGTTTATCTA CGGCTTAAAA AGTGTTCGAG GGGAAAATAG GTTGCGCGAG    1200
ATTATAGAGA TCTGGCGCAC TAAAAACCAG TATTTCACAT GAGTCCGCGT CTTTTTACGC    1260
ACTGCCTCTC CCTGACGCGG GATAAAGTGG TATTCTCAAA CATATCTCGC AAGCCTGTCT    1320
TGTGTCCAAG CTTGGGGATC ATCCGTCACT GTTCTTTATG ATTCTACTTC CTTACCGTGC    1380
AATAAATTAG AATATATTTT CTACTTTTAC GAGAAATTAA TTATTGTATT TATTATTTAT    1440
GGGTGAAAAA CTTACTATAA AAAGCGGGTG GGTTTGGAAT TAGTGATCAG TTTATGTATA    1500
TCGCAACTAC CGGCATACGG CTTGGTATAG CGGACAACTA AGTAATTGTA AAGAAGAAAA    1560
CGAAACTATC AAAACCGTTT ATGAAATGAT AGAAAAAAGA ATATAAATAA TCCTGTATTT    1620
TAGTTTAAGT AACAGTAAAA TAATGAGTAG AAAATACTAT TTGTTTTAT AGCCTATAAA     1680
TCATGAATTC GGATCCCGGG TCGACGCGGC CGCTAACTGA CTGATTTTTC TCAATTCTGT    1740
```

```
GAGCGTATGG CAAACGAAGG AAAAATAGTT ATAGTAGCCG CACTCGATGG GACATTTCAA    1800
CGTAAACCGT TTAATAATAT TTTGAATCTT ATTCCATTAT CTGAAATGGT GGTAAAACTA    1860
ACTGCTGTGT GTATGAAATG CTTTAAGGAG GCTTCCTTTT CTAAACGATT GGGTGAGGAA    1920
ACCGAGATAG AAATAATAGG AGGTAATGAT ATGTATCAAT CGGTGTGTAG AAAGTGTTAC    1980
ATCGACTCAT AATATTATAT TTTTATCTA AAAAACTAAA AATAAACATT GATTAAATTT     2040
TAATATAATA CTTAAAAATG GATGTTGTGT CGTTAGATAA ACCGTTTATG TATTTTGAGG    2100
AAATTGATAA TGAGTTAGAT TACGAACCAG AAAGTGCAAA TGAGGTCGCA AAAAAACTGC    2160
CGTATCAAGG ACAGTTAAAA CTATTACTAG GAGAATTATT TTTTCTTAGT AAGTTACAGC    2220
GACACGGTAT ATTAGATGGT GCCACCGTAG TGTATATAGG ATCTGCTCCC GGTACACATA    2280
TACGTTATTT GAGAGATCAT TTCTATAATT TAGGAGTGAT CATCAAATGG ATGCTAATTG    2340
ACGGCCGCCA TCATGATCCT ATTTCTGGC GTAATAGCGA AGAGGCCCGC ACCGATCGCC     2400
CTTCCCAACA GTTGCGCAGC CTGAATGGCG AATGGGAAAT TGTAAACGTT AATATTTTGT    2460
TAAAATTCGC GTTAAATTTT TGTTAAATCA GCTCATTTTT TAACCAATAG GCCGAAATCG    2520
GCAAAATCCC TTATAAATCA AAAGAATAGA CCGAGATAGG GTTGAGTGTT GTTCCAGTTT    2580
GGAACAAGAG TCCACTATTA AAGAACGTGG ACTCCAACGT CAAAGGGCGA AAAACCGTCT    2640
ATCAGGGCGA TGGCCCACTA CGTGAACCAT CACCCTAATC AAGTTTTTG GGGTCGAGGT     2700
GCCGTAAAGC ACTAAATCGG AACCCTAAAG GGAGCCCCCG ATTAGAGCT TGACGGGGAA     2760
AGCCGGCGAA CGTGGCGAGA AAGGAAGGGA AGAAAGCGAA AGGAGCGGGC GCTAGGGCGC    2820
TGGCAAGTGT AGCGGTCACG CTGCGCGTAA CCACCACACC CGCCGCGCTT AATGCGCCGC    2880
TACAGGGCGC GTCAGGTGGC ACTTTTCGGG GAAATGTGCG CGGAACCCCT ATTTGTTTAT    2940
TTTTCTAAAT ACATTCAAAT ATGTATCCGC TCATGAGACA ATAACCCTGA TAAATGCTTC    3000
AATAATATTG AAAAGGAAG AGTATGAGTA TTCAACATTT CCGTGTCGCC CTTATTCCCT     3060
TTTTTGCGGC ATTTTGCCTT CCTGTTTTTG CTCACCCAGA AACGCTGGTG AAAGTAAAAG    3120
ATGCTGAAGA TCAGTTGGGT GCACGAGTGG GTTACATCGA ACTGGATCTC AACAGCGGTA    3180
AGATCCTTGA GAGTTTTCGC CCCGAAGAAC GTTTTCCAAT GATGAGCACT TTTAAAGTTC    3240
TGCTATGTGG CGCGGTATTA TCCCGTGTTG ACGCCGGGCA AGAGCAACTC GGTCGCCGCA    3300
TACACTATTC TCAGAATGAC TTGGTTGAGT ACTCACCAGT CACAGAAAAG CATCTTACGG    3360
ATGGCATGAC AGTAAGAGAA TTATGCAGTG CTGCCATAAC CATGAGTGAT AACACTGCGG    3420
CCAACTTACT TCTGACAACG ATCGGAGGAC CGAAGGAGCT AACCGCTTTT TTGCACAACA    3480
TGGGGGATCA TGTAACTCGC CTTGATCGTT GGGAACCGGA GCTGAATGAA GCCATACCAA    3540
ACGACGAGCG TGACACCACG ATGCCTGCAG CAATGGCAAC AACGTTGCGC AAACTATTAA    3600
CTGGCGAACT ACTTACTCTA GCTTCCCGGC AACAATTAAT AGACTGGATG GAGGCGGATA    3660
AAGTTGCAGG ACCACTTCTG CGCTCGGCCC TTCCGGCTGG CTGGTTTATT GCTGATAAAT    3720
CTGGAGCCGG TGAGCGTGGG TCTCGCGGTA TCATTGCAGC ACTGGGGCCA GATGGTAAGC    3780
CCTCCCGTAT CGTAGTTATC TACACGACGG GGAGTCAGGC AACTATGGAT GAACGAAATA    3840
GACAGATCGC TGAGATAGGT GCCTCACTGA TTAAGCATTG GTAACTGTCA GACCAAGTTT    3900
ACTCATATAT ACTTTAGATT GATTTAAAAC TTCATTTTTA ATTTAAAAGG ATCTAGGTGA    3960
AGATCCTTTT TGATAATCTC ATGACCAAAA TCCCTTAACG TGAGTTTTCG TTCCACTGAG    4020
CGTCAGACCC CGTAGAAAAG ATCAAAGGAT CTTCTTGAGA TCCTTTTTTT CTGCGCGTAA    4080
TCTGCTGCTT GCAAACAAAA AAACCACCGC TACCAGCGGT GGTTTGTTTG CCGGATCAAG    4140
```

| | | | | | |
|---|---|---|---|---|---|
| AGCTACCAAC | TCTTTTTCCG | AAGGTAACTG | GCTTCAGCAG | AGCGCAGATA | CCAAATACTG | 4200 |
| TCCTTCTAGT | GTAGCCGTAG | TTAGGCCACC | ACTTCAAGAA | CTCTGTAGCA | CCGCCTACAT | 4260 |
| ACCTCGCTCT | GCTAATCCTG | TTACCAGTGG | CTGCTGCCAG | TGGCGATAAG | TCGTGTCTTA | 4320 |
| CCGGGTTGGA | CTCAAGACGA | TAGTTACCGG | ATAAGGCGCA | GCGGTCGGGC | TGAACGGGGG | 4380 |
| GTTCGTGCAC | ACAGCCCAGC | TTGGAGCGAA | CGACCTACAC | CGAACTGAGA | TACCTACAGC | 4440 |
| GTGAGCATTG | AGAAAGCGCC | ACGCTTCCCG | AAGGGAGAAA | GGCGGACAGG | TATCCGGTAA | 4500 |
| GCGGCAGGGT | CGGAACAGGA | GAGCGCACGA | GGGAGCTTCC | AGGGGGAAAC | GCCTGGTATC | 4560 |
| TTTATAGTCC | TGTCGGGTTT | CGCCACCTCT | GACTTGAGCG | TCGATTTTTG | TGATGCTCGT | 4620 |
| CAGGGGGGCG | GAGCCTATGG | AAAAACGCCA | GCAACGCGGC | CTTTTTACGG | TTCCTGGCCT | 4680 |
| TTTGCTGGCC | TTTTGCTCAC | ATGTTCTTTC | CTGCGTTATC | CCCTGATTCT | GTGGATAACC | 4740 |
| GTATTACCGC | CTTTGAGTGA | GCTGATACCG | CTCGCCGCAG | CCGAACGACC | GAGCGCAGCG | 4800 |
| AGTCAGTGAG | CGAGGAAGCG | GAAG | | | | 4824 |

( 2 ) INFORMATION FOR SEQ ID NO:14:

( i ) SEQUENCE CHARACTERISTICS:
        ( A ) LENGTH: 7218 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pTZgpt-F1s ( x i ) SEQUENCE DESCRIPTION: SEQ ID NO:14:

| | | | | | |
|---|---|---|---|---|---|
| CAGCTGGCGA | AAGGGGGATG | TGCTGCAAGG | CGATTAAGTT | GGGTAACGCC | AGGGTTTTCC | 60 |
| CAGTCACGAC | GTTGTAAAAC | GACGGCCCTG | AATATGAAGG | AGCAAAAGGT | TGTAACATTT | 120 |
| TATTACCGTG | TGGGATATAA | AAGTCCTTGA | TCCATTGATC | TGGAAACGGG | CATCTCCATT | 180 |
| TAAGACTAGA | CGCCACGGGG | TTTAAAATAC | TAATCATGAC | ATTTGTAGA | GCGTAATTAC | 240 |
| TTAGTAAATC | CGCCGTACTA | GGTTCATTTC | CTCCTCGTTT | GGATCTCACA | TCAGAAATTA | 300 |
| AAATAATCTT | AGAAGGATGC | AGTTGTTTTT | TGATGGATCG | TAGATATTCC | TCATCAACGA | 360 |
| ACCGAGTCAC | TAGAGTCACA | TCACGCAATC | CATTTAAAAT | AGGATCATGA | TGGCGGCCGT | 420 |
| CAATTAGCAT | CCATTTGATG | ATCACTCCTA | AATTATAGAA | ATGATCTCTC | AAATAACGTA | 480 |
| TATGTGTACC | GGGAGCAGAT | CCTATATACA | CTACGGTGGC | ACCATCTAAT | ATACCGTGTC | 540 |
| GCTGTAACTT | ACTAAGAAAA | ATAATTCTC | CTAGTAATAG | TTTAACTGT | CCTTGATACG | 600 |
| GCAGTTTTTT | TGCGACCTCA | TTTGCACTTT | CTGGTTCGTA | ATCTAACTCA | TTATCAATTT | 660 |
| CCTCAAAATA | CATAAACGGT | TTATCTAACG | ACACAACATC | CATTTTAAG | TATTATATTA | 720 |
| AAATTTAATC | AATGTTTATT | TTAGTTTTT | TAGATAAAAA | ATATAATATT | ATGAGTCGAT | 780 |
| GTAACACTTT | CTACACACCG | ATTGATACAT | ATCATTACCT | CCTATTATTT | CTATCTCGGT | 840 |
| TTCCTCACCC | AATCGTTTAG | AAAAGGAAGC | CTCCTTAAAG | CATTTCATAC | ACACAGCAGT | 900 |
| TAGTTTTACC | ACCATTTCAG | ATAATGGAAT | AAGATTCAAA | ATATTATTAA | ACGGTTTACG | 960 |
| TTGAAATGTC | CCATCGAGTG | CGGCTACTAT | AACTATTTTT | CCTTCGTTTG | CCATACGCTC | 1020 |
| ACAGAATTAA | TTCCGAGCTT | GGCTGCAGGT | CGAGGGAGCT | TGCGATYYYY | YYYYYYYYYY | 1080 |
| YYYYYYYYYY | YYYYYYYYYY | YYYYYYYYYY | YYYYYYYYYY | YYYYYYYYYY | YYYYYYYYYY | 1140 |
| YYYYYYYYYY | YYYYYYYYYY | YYYYYYYYYY | YYYYYYYYYY | YYYYYYYYYY | YYYYYYYYYY | 1200 |
| YYYYYYYYYY | YYYYYYYYYY | YYYYYYYYYY | YYYYYYYYYY | YYYYYYYYYY | YYYYYYYYYY | 1260 |

| | | | | | | |
|---|---|---|---|---|---|---|
| YYYYYYYYYY | YYYYYYYYYY | YYYYYYYYYY | YYYYYYYYYY | YYYYYYYYYY | YYYYYYYYYY | 1320 |
| YYYYYYYYYY | YYYYYYYYYY | YYYYYYYYYY | YYYYYYYYYY | YYYYYYYYYY | YYYYYYYYYY | 1380 |
| YYYYYYYYYY | YYYYYYYYYY | YYYYYYYYYY | YYYYYYYYYY | YYYYYYYYYY | YYYYGTACCA | 1440 |
| AATTCTTCTA | TCTCTTTAAC | TACTTGCATA | GATAGGTAAT | TACAGTGATG | CCTACATGCC | 1500 |
| GTTTTTTGAA | ACTGAATAGA | TGCGTCTAGA | AGCGATGCTA | CGCTAGTCAC | AATCACCACT | 1560 |
| TTCATATTTA | GAATATATGT | ATGTAAAAAT | ATAGTAGAAT | TCATTTGT | TTTTTCTAT | 1620 |
| GCTATAAATG | AATTCCTGCA | GGTCGACTCT | AGAGGATCCC | CTTAAGTTAA | CTTAAGGGTA | 1680 |
| CCGCCTCGAC | ATCTATATAC | TATATAGTAA | TACCAATACT | CAAGACTACG | AAACTGATAC | 1740 |
| AATCTCTTAT | CATGTGGGTA | ATGTTCTCGA | TGTCGAATAG | CCATATGCCG | GTAGTTGCGA | 1800 |
| TATACATAAA | CTGATCACTA | ATTCCAAACC | CACCCGCTTT | TTATAGTAAG | TTTTTCACCC | 1860 |
| ATAAATAATA | AATACAATAA | TTAATTTCTC | GTAAAAGTAG | AAAATATATT | CTAATTTATT | 1920 |
| GCACGGTAAG | GAAGTAGAAT | CATAAAGAAC | AGTGACGGAT | GATCCCCAAG | CTTGGACACA | 1980 |
| AGACAGGCTT | GCGAGATATG | TTTGAGAATA | CCACTTTATC | CCGCGTCAGG | GAGAGGCAGT | 2040 |
| GCGTAAAAAG | ACGCGGACTC | ATGTGAAATA | CTGGTTTTTA | GTGCGCCAGA | TCTCTATAAT | 2100 |
| CTCGCGCAAC | CTATTTTCCC | CTCGAACACT | TTTTAAGCCG | TAGATAAACA | GGCTGGGACA | 2160 |
| CTTCACATGA | GCGAAAAATA | CATCGTCACC | TGGGACATGT | TGCAGATCCA | TGCACGTAAA | 2220 |
| CTCGCAAGCC | GACTGATGCC | TTCTGAACAA | TGGAAAGGCA | TTATTGCCGT | AAGCCGTGGC | 2280 |
| GGTCTGGTAC | CGGGTGCGTT | ACTGGCGCGT | GAACTGGGTA | TTCGTCATGT | CGATACCGTT | 2340 |
| TGTATTTCCA | GCTACGATCA | CGACAACCAG | CGCGAGCTTA | AAGTGCTGAA | ACGCGCAGAA | 2400 |
| GGCGATGGCG | AAGGCTTCAT | CGTTATTGAT | GACCTGGTGG | ATACCGGTGG | TACTGCGGTT | 2460 |
| GCGATTCGTG | AAATGTATCC | AAAAGCGCAC | TTTGTCACCA | TCTTCGCAAA | ACCGGCTGGT | 2520 |
| CGTCCGCTGG | TTGATGACTA | TGTTGTTGAT | ATCCCGCAAG | ATACCTGGAT | TGAACAGCCG | 2580 |
| TGGGATATGG | GCGTCGTATT | CGTCCCGCCA | ATCTCCGGTC | GCTAATCTTT | CAACGCCTG | 2640 |
| GCACTGCCGG | GCGTTGTTCT | TTTTAACTTC | AGGCGGGTTA | CAATAGTTTC | CAGTAAGTAT | 2700 |
| TCTGGAGGCT | GCATCCATGA | CACAGGCAAA | CCTGAGCGAA | ACCCTGTTCA | AACCCCGCTT | 2760 |
| TAAACATCCT | GAAACCTCGA | CGCTAGTCCG | CCGCTTTAAT | CACGGCGCAC | AACCGCCTGT | 2820 |
| GCAGTCGGCC | CTTGATGGTA | AAACCATCCC | TCACTGGTAT | CGCATGATTA | ACCGTCTGAT | 2880 |
| GTGGATCTGG | CGCGGCATTG | ACCCACGCGA | AATCCTCGAC | GTCCAGGCAC | GTATTGTGAT | 2940 |
| GAGCGATGCC | GAACGTACCG | ACGATGATTT | ATACGATACG | GTGATTGGCT | ACCGTGGCGG | 3000 |
| CAACTGGATT | TATGAGTGGG | CCCCGGATCT | TTGTGAAGGA | ACCTTACTTC | TGTGGTGTGA | 3060 |
| CATAATTGGA | CAAACTACCT | ACAGAGATTT | AAAGCTCTAA | GGTAAATATA | AAATTTTTAA | 3120 |
| GTGTATAATG | TGTTAAACTA | CTGATTCTAA | TTGTTTGTGT | ATTTAGATT | CCAACCTATG | 3180 |
| GAACTGATGA | ATGGGAGCAG | TGGTGGAATG | CCTTTAATGA | GGAAAACCTG | TTTTGCTCAG | 3240 |
| AAGAAATGCC | ATCTAGTGAT | GATGAGGCTA | CTGCTGACTC | TCAACATTCT | ACTCCTCCAA | 3300 |
| AAAAGAAGAG | AAAGGTAGAA | GACCCCAAGG | ACTTTCCTTC | AGAATTGCTA | AGTTTTTGA | 3360 |
| GTCATGCTGT | GTTTAGTAAT | AGAACTCTTG | CTTGCTTTGC | TATTTACACC | ACAAAGGAAA | 3420 |
| AAGCTGCACT | GCTATACAAG | AAAATTATGG | AAAAATATTC | TGTAACCTTT | ATAAGTAGGC | 3480 |
| ATAACAGTTA | TAATCATAAC | ATACTGTTTT | TTCTTACTCC | ACACAGGCAT | AGAGTGTCTG | 3540 |
| CTATTAATAA | CTATGCTCAA | AAATTGTGTA | CCTTTAGCTT | TTAATTTGT | AAAGGGGTTA | 3600 |
| ATAAGGAATA | TTTGATGTAT | AGTGCCTTGA | CTAGAGATCA | TAATCAGCCA | TACCACATTT | 3660 |

```
GTAGAGGTTT TACTTGCTTT AAAAAACCTC CCACACCTCC CCCTGAACCT GAAACATAAA    3720
ATGAATGCAA TTGTTGTTGT TAAGCTTGGG GGAATTAATT CAACAATGTC TGGAAAGAAC    3780
TGTCCTTCAT CGATACCTAT CACGGAGAAA TCTGTAATTG ATTCCAAGAC ATCACATAGT    3840
TTAGTTGCTT CCAATGCTTC AAAATTATTC TTATCATGCG TCCATAGTCC CGTTCCGTAT    3900
CTATTATCGT TAGAATATTT TATAGTCACG CATTTATATT GAGCTATTTG ATAACGTCTA    3960
ACTCGTCTAA TTAATTCTGT ACTTTTACCT GAAACATGG GGCCGATTAT CAACTGAATA    4020
TGTCCGCCGT TCATGATGAC AATAAAGAAT TAATTATTGT TCACTTTATT CGACTTTAAT    4080
ATATCCATCA CGTTAGAAAA TGCGATATTG CGACGAGGAT CTATGTATCT AACAGGATCT    4140
ATTGCGGTGG TAGCTAGAGA GGATTCTTTT TTGAATCGCA TCAAACTAAT CACAAAGTCG    4200
AACAAATATC CTTTATTAAG TTTGACCCTT CCATCTGTAA CAATAGGGAC CTTGTTAAAC    4260
AGTTTTTTAA AATCTTGAAA GTCTGTGAAT TTGTCAATT GTCTGTATTC CTCTGAAAGA    4320
GATTCATAAC AATGACCCAC GGCTTCTAAT TTATTTTTG ATTGGATCAA TAATAATAAC    4380
AGAAAGTCTA GATATTGAGT GATTTGCAAT ATATCAGATA ATGAAGATTC ATCATCTTGA    4440
CTAGCCAAAT ACTTAAAAAA TGAATCATCA TCTGCGAAGA ACATCGTTAA GAGATACTGG    4500
TTGTGATCCA TTTATTGATC GCAAAGCTT GGCGTAATCA TGGTCATAGC TGTTTCCTGT    4560
GTGAAATTGT TATCCGCTCA CAATTCCACA CAACATACGA GCCGGAAGCA TAAAGTGTAA    4620
AGCCTGGGGT GCCTAATGAG TGAGCTAACT CACATTAATT GCGTTGCGCT CACTGCCCGC    4680
TTTCCAGTCG GGAAACCTGT CGTGCCAGCT GGCGTAATAG CGAAGAGGCC CGCACCGATC    4740
GCCCTTCCCA ACAGTTGCGC AGCCTGAATG GCGAATGGGA AATTGTAAAC GTTAATATTT    4800
TGTTAAAATT CGCGTTAAAT TTTTGTTAAA TCAGCTCATT TTTTAACCAA TAGGCCGAAA    4860
TCGGCAAAAT CCCTTATAAA TCAAAAGAAT AGACCGAGAT AGGGTTGAGT GTTGTTCCAG    4920
TTTGGAACAA GAGTCCACTA TTAAAGAACG TGGACTCCAA CGTCAAAGGG CGAAAAACCG    4980
TCTATCAGGG CGATGGCCCA CTACGTGAAC CATCACCCTA ATCAAGTTTT TGGGGTCGA    5040
GGTGCCGTAA AGCACTAAAT CGGAACCCTA AAGGGAGCCC CCGATTTAGA GCTTGACGGG    5100
GAAAGCCGGC GAACGTGGCG AGAAAGGAAG GGAAGAAAGC GAAAGGAGCG GCGCTAGGG    5160
CGCTGGCAAG TGTAGCGGTC ACGCTGCGCG TAACCACCAC ACCCGCCGCG CTTAATGCGC    5220
CGCTACAGGG CGCGTCAGGT GGCACTTTTC GGGGAAATGT GCGCGGAACC CCTATTTGTT    5280
TATTTTTCTA AATACATTCA AATATGTATC CGCTCATGAG ACAATAACCC TGATAAATGC    5340
TTCAATAATA TTGAAAAAGG AAGAGTATGA GTATTCAACA TTTCCGTGTC GCCCTTATTC    5400
CCTTTTTTGC GGCATTTTGC CTTCCTGTTT TTGCTCACCC AGAAACGCTG GTGAAAGTAA    5460
AAGATGCTGA AGATCAGTTG GGTGCACGAG TGGGTTACAT CGAACTGGAT CTCAACAGCG    5520
GTAAGATCCT TGAGAGTTTT CGCCCCGAAG AACGTTTTCC AATGATGAGC ACTTTTAAAG    5580
TTCTGCTATG TGGCGCGGTA TTATCCCGTG TTGACGCCGG GCAAGAGCAA CTCGGTCGCC    5640
GCATACACTA TTCTCAGAAT GACTTGGTTG AGTACTCACC AGTCACAGAA AAGCATCTTA    5700
CGGATGGCAT GACAGTAAGA GAATTATGCA GTGCTGCCAT AACCATGAGT GATAACACTG    5760
CGGCCAACTT ACTTCTGACA ACGATCGGAG GACCGAAGGA GCTAACCGCT TTTTTGCACA    5820
ACATGGGGGA TCATGTAACT CGCCTTGATC GTTGGGAACC GGAGCTGAAT GAAGCCATAC    5880
CAAACGACGA GCGTGACACC ACGATGCCTC AGCAATGGCA ACAACGTTGC GCAAACTATT    5940
AACTGGCGAA CTACTTACTC TAGCTTCCCG GCAACAATTA ATAGACTGGA TGGAGGCGGA    6000
TAAAGTTGCA GGACCACTTC TGCGCTCGGC CCTTCCGGCT GGCTGGTTTA TTGCTGATAA    6060
```

-continued

| | | | | | |
|---|---|---|---|---|---|
| ATCTGGAGCC | GGTGAGCGTG | GGTCTCGCGG | TATCATTGCA | GCACTGGGGC | CAGATGGTAA | 6120 |
| GCCCTCCCGT | ATCGTAGTTA | TCTACACGAC | GGGGAGTCAG | GCAACTATGG | ATGAACGAAA | 6180 |
| TAGACAGATC | GCTGAGATAG | GTGCCTCACT | GATTAAGCAT | TGGTAACTGT | CAGACCAAGT | 6240 |
| TTACTCATAT | ATACTTTAGA | TTGATTTAAA | ACTTCATTTT | TAATTTAAAA | GGATCTAGGT | 6300 |
| GAAGATCCTT | TTTGATAATC | TCATGACCAA | AATCCCTTAA | CGTGAGTTTT | CGTTCCACTG | 6360 |
| AGCGTCAGAC | CCCGTAGAAA | AGATCAAAGG | ATCTTCTTGA | GATCCTTTTT | TTCTGCGCGT | 6420 |
| AATCTGCTGC | TTGCAAACAA | AAAAACCACC | GCTACCAGCG | GTGGTTTGTT | TGCCGGATCA | 6480 |
| AGAGCTACCA | ACTCTTTTTC | CGAAGGTAAC | TGGCTTCAGC | AGAGCGCAGA | TACCAAATAC | 6540 |
| TGTCCTTCTA | GTGTAGCCGT | AGTTAGGCCA | CCACTTCAAG | AACTCTGTAG | CACCGCCTAC | 6600 |
| ATACCTCGCT | CTGCTAATCC | TGTTACCAGT | GGCTGCTGCC | AGTGGCGATA | AGTCGTGTCT | 6660 |
| TACCGGGTTG | GACTCAAGAC | GATAGTTACC | GGATAAGGCG | CAGCGGTCGG | GCTGAACGGG | 6720 |
| GGGTTCGTGC | ACACAGCCCA | GCTTGGAGCG | AACGACCTAC | ACCGAACTGA | GATACCTACA | 6780 |
| GCGTGAGCAT | TGAGAAAGCG | CCACGCTTCC | CGAAGGGAGA | AAGGCGGACA | GGTATCCGGT | 6840 |
| AAGCGGCAGG | GTCGGAACAG | GAGAGCGCAC | GAGGGAGCTT | CCAGGGGGAA | ACGCCTGGTA | 6900 |
| TCTTTATAGT | CCTGTCGGGT | TTCGCCACCT | CTGACTTGAG | CGTCGATTTT | TGTGATGCTC | 6960 |
| GTCAGGGGGG | CGGAGCCTAT | GGAAAAACGC | CAGCAACGCG | GCCTTTTTAC | GGTTCCTGGC | 7020 |
| CTTTTGCTGG | CCTTTTGCTC | ACATGTTCTT | TCCTGCGTTA | TCCCCTGATT | CTGTGGATAA | 7080 |
| CCGTATTACC | GCCTTTGAGT | GAGCTGATAC | CGCTCGCCGC | AGCCGAACGA | CCGAGCGCAG | 7140 |
| CGAGTCAGTG | AGCGAGGAAG | CGGAAGAGCG | CCCAATACGC | AAACCGCCTC | TCCCCGCGCG | 7200 |
| TTGGCCGATT | CATTAATG | | | | | 7218 |

(2) INFORMATION FOR SEQ ID NO:15:

(i) SEQUENCE CHARACTERISTICS:
    (A) LENGTH: 6601 base pairs
    (B) TYPE: nucleic acid
    (C) STRANDEDNESS: single
    (D) TOPOLOGY: linear (vii) IMMEDIATE SOURCE:
    (B) CLONE: pTZgpt-dp (xi) SEQUENCE DESCRIPTION: SEQ ID NO:15:

| | | | | | |
|---|---|---|---|---|---|
| CAGCTGGCGA | AAGGGGGATG | TGCTGCAAGG | CGATTAAGTT | GGGTAACGCC | AGGGTTTTCC | 60 |
| CAGTCACGAC | GTTGTAAAAC | GACGGCCCTG | AATATGAAGG | AGCAAAAGGT | TGTAACATTT | 120 |
| TATTACCGTG | TGGGATATAA | AAGTCCTTGA | TCCATTGATC | TGGAAACGGG | CATCTCCATT | 180 |
| TAAGACTAGA | CGCCACGGGG | TTTAAAATAC | TAATCATGAC | ATTTTGTAGA | GCGTAATTAC | 240 |
| TTAGTAAATC | CGCCGTACTA | GGTTCATTTC | CTCCTCGTTT | GGATCTCACA | TCAGAAATTA | 300 |
| AAATAATCTT | AGAAGGATGC | AGTTGTTTTT | TGATGGATCG | TAGATATTCC | TCATCAACGA | 360 |
| ACCGAGTCAC | TAGAGTCACA | TCACGCAATC | CATTTAAAAT | AGGATCATGA | TGGCGGCCGT | 420 |
| CAATTAGCAT | CCATTTGATG | ATCACTCCTA | AATTATAGAA | ATGATCTCTC | AAATAACGTA | 480 |
| TATGTGTACC | GGGAGCAGAT | CCTATATACA | CTACGGTGGC | ACCATCTAAT | ATACCGTGTC | 540 |
| GCTGTAACTT | ACTAAGAAAA | AATAATTCTC | CTAGTAATAG | TTTAACTGT | CCTTGATACG | 600 |
| GCAGTTTTTT | TGCGACCTCA | TTTGCACTTT | CTGGTTCGTA | ATCTAACTCA | TTATCAATTT | 660 |
| CCTCAAAATA | CATAAACGGT | TTATCTAACG | ACACAACATC | CATTTTTAAG | TATTATATTA | 720 |
| AAATTTAATC | AATGTTTATT | TTTAGTTTTT | TAGATAAAAA | ATATAATATT | ATGAGTCGAT | 780 |

```
GTAACACTTT CTACACACCG ATTGATACAT ATCATTACCT CCTATTATTT CTATCTCGGT      840
TTCCTCACCC AATCGTTTAG AAAAGGAAGC CTCCTTAAAG CATTTCATAC ACACAGCAGT      900
TAGTTTTACC ACCATTTCAG ATAATGGAAT AAGATTCAAA ATATTATTAA ACGGTTTACG      960
TTGAAATGTC CCATCGAGTG CGGCTACTAT AACTATTTTT CCTTCGTTTG CCATACGCTC     1020
ACAGAATTAA TTCCGAGCTT GGCGGTTAAC CAACTTAAGG GTACCGCCTC GACATCTATA     1080
TACTATATAG TAATACCAAT ACTCAAGACT ACGAAACTGA TACAATCTCT TATCATGTGG     1140
GTAATGTTCT CGATGTCGAA TAGCCATATG CCGGTAGTTG CGATATACAT AAACTGATCA     1200
CTAATTCCAA ACCCACCCGC TTTTTATAGT AAGTTTTTCA CCCATAAATA ATAAATACAA     1260
TAATTAATTT CTCGTAAAAG TAGAAAATAT ATTCTAATTT ATTGCACGGT AAGGAAGTAG     1320
AATCATAAAG AACAGTGACG GATGATCCCC AAGCTTGGAC ACAAGACAGG CTTGCGAGAT     1380
ATGTTTGAGA ATACCACTTT ATCCCGCGTC AGGGAGAGGC AGTGCGTAAA AAGACGCGGA     1440
CTCATGTGAA ATACTGGTTT TTAGTGCGCC AGATCTCTAT AATCTCGCGC AACCTATTTT     1500
CCCCTCGAAC ACTTTTTAAG CCGTAGATAA ACAGGCTGGG ACACTTCACA TGAGCGAAAA     1560
ATACATCGTC ACCTGGGACA TGTTGCAGAT CCATGCACGT AAACTCGCAA GCCGACTGAT     1620
GCCTTCTGAA CAATGGAAAG GCATTATTGC CGTAAGCCGT GGCGGTCTGG TACCGGGTGC     1680
GTTACTGGCG CGTGAACTGG GTATTCGTCA TGTCGATACC GTTTGTATTT CCAGCTACGA     1740
TCACGACAAC CAGCGCGAGC TTAAAGTGCT GAAACGCGCA GAAGGCGATG GCGAAGGCTT     1800
CATCGTTATT GATGACCTGG TGGATACCGG TGGTACTGCG GTTGCGATTC GTGAAATGTA     1860
TCCAAAAGCG CACTTTGTCA CCATCTTCGC AAAACCGGCT GGTCGTCCGC TGGTTGATGA     1920
CTATGTTGTT GATATCCCGC AAGATACCTG GATTGAACAG CCGTGGGATA TGGGCGTCGT     1980
ATTCGTCCCG CCAATCTCCG GTCGCTAATC TTTTCAACGC CTGGCACTGC CGGGCGTTGT     2040
TCTTTTTAAC TTCAGGCGGG TTACAATAGT TTCCAGTAAG TATTCTGGAG GCTGCATCCA     2100
TGACACAGGC AAACCTGAGC GAAACCCTGT TCAAACCCCG CTTTAAACAT CCTGAAACCT     2160
CGACGCTAGT CCGCCGCTTT AATCACGGCG CACAACCGCC TGTGCAGTCG GCCCTTGATG     2220
GTAAAACCAT CCCTCACTGG TATCGCATGA TTAACCGTCT GATGTGGATC TGGCGCGGCA     2280
TTGACCCACG CGAAATCCTC GACGTCCAGG CACGTATTGT GATGAGCGAT GCCGAACGTA     2340
CCGACGATGA TTTATACGAT ACGGTGATTG GCTACCGTGG CGGCAACTGG ATTTATGAGT     2400
GGGCCCCGGA TCTTTGTGAA GGAACCTTAC TTCTGTGGTG TGACATAATT GGACAAACTA     2460
CCTACAGAGA TTTAAAGCTC TAAGGTAAAT ATAAAATTTT TAAGTGTATA ATGTGTTAAA     2520
CTACTGATTC TAATTGTTTG TGTATTTTAG ATTCCAACCT ATGGAACTGA TGAATGGGAG     2580
CAGTGGTGGA ATGCCTTTAA TGAGGAAAAC CTGTTTTGCT CAGAAGAAAT GCCATCTAGT     2640
GATGATGAGG CTACTGCTGA CTCTCAACAT TCTACTCCTC CAAAAAAGAA GAGAAAGGTA     2700
GAAGACCCCA AGGACTTTCC TTCAGAATTG CTAAGTTTTT TGAGTCATGC TGTGTTTAGT     2760
AATAGAACTC TTGCTTGCTT TGCTATTTAC ACCACAAAGG AAAAGCTGC ACTGCTATAC     2820
AAGAAAATTA TGGAAAAATA TTCTGTAACC TTTATAAGTA GGCATAACAG TTATAATCAT     2880
AACATACTGT TTTTTCTTAC TCCACACAGG CATAGAGTGT CTGCTATTAA TAACTATGCT     2940
CAAAAATTGT GTACCTTTAG CTTTTTAATT TGTAAAGGGG TTAATAAGGA ATATTTGATG     3000
TATAGTGCCT TGACTAGAGA TCATAATCAG CCATACCACA TTTGTAGAGG TTTTACTTGC     3060
TTTAAAAAAC CTCCCACACC TCCCCCTGAA CCTGAAACAT AAAATGAATG CAATTGTTGT     3120
TGTTAAGCTT GGGGGAATTA ATTCAACAAT GTCTGGAAAG AACTGTCCTT CATCGATACC     3180
```

```
TATCACGGAG  AAATCTGTAA  TTGATTCCAA  GACATCACAT  AGTTTAGTTG  CTTCCAATGC    3240
TTCAAAATTA  TTCTTATCAT  GCGTCCATAG  TCCCGTTCCG  TATCTATTAT  CGTTAGAATA    3300
TTTTATAGTC  ACGCATTTAT  ATTGAGCTAT  TTGATAACGT  CTAACTCGTC  TAATTAATTC    3360
TGTACTTTTA  CCTGAAAACA  TGGGGCCGAT  TATCAACTGA  ATATGTCCGC  CGTTCATGAT    3420
GACAATAAAG  AATTAATTAT  TGTTCACTTT  ATTCGACTTT  AATATATCCA  TCACGTTAGA    3480
AAATGCGATA  TTGCGACGAG  GATCTATGTA  TCTAACAGGA  TCTATTGCGG  TGGTAGCTAG    3540
AGAGGATTCT  TTTTGAATC   GCATCAAACT  AATCACAAAG  TCGAACAAAT  ATCCTTTATT    3600
AAGTTTGACC  CTTCCATCTG  TAACAATAGG  GACCTTGTTA  AACAGTTTTT  TAAAATCTTG    3660
AAAGTCTGTG  AATTTGTCA   ATTGTCTGTA  TTCCTCTGAA  AGAGATTCAT  AACAATGACC    3720
CACGGCTTCT  AATTTATTTT  TTGATTGGAT  CAATAATAAT  AACAGAAAGT  CTAGATATTG    3780
AGTGATTTGC  AATATATCAG  ATAATGAAGA  TTCATCATCT  TGACTAGCCA  AATACTTAAA    3840
AAATGAATCA  TCATCTGCGA  AGAACATCGT  TAAGAGATAC  TGGTTGTGAT  CCATTTATTG    3900
ATCGCAAAAG  CTTGGCGTAA  TCATGGTCAT  AGCTGTTTCC  TGTGTGAAAT  TGTTATCCGC    3960
TCACAATTCC  ACACAACATA  CGAGCCGGAA  GCATAAAGTG  TAAAGCCTGG  GGTGCCTAAT    4020
GAGTGAGCTA  ACTCACATTA  ATTGCGTTGC  GCTCACTGCC  CGCTTTCCAG  TCGGGAAACC    4080
TGTCGTGCCA  GCTGGCGTAA  TAGCGAAGAG  GCCCGCACCG  ATCGCCCTTC  CAACAGTTG    4140
CGCAGCCTGA  ATGGCGAATG  GGAAATTGTA  ACGTTAATA   TTTGTTAAA   ATTCGCGTTA    4200
AATTTTTGTT  AAATCAGCTC  ATTTTTTAAC  CAATAGGCCG  AAATCGGCAA  AATCCCTTAT    4260
AAATCAAAAG  AATAGACCGA  GATAGGGTTG  AGTGTTGTTC  CAGTTTGGAA  CAAGAGTCCA    4320
CTATTAAAGA  ACGTGGACTC  CAACGTCAAA  GGGCGAAAAA  CCGTCTATCA  GGGCGATGGC    4380
CCACTACGTG  AACCATCACC  CTAATCAAGT  TTTTTGGGGT  CGAGGTGCCG  TAAAGCACTA    4440
AATCGGAACC  CTAAAGGGAG  CCCCCGATTT  AGAGCTTGAC  GGGGAAAGCC  GGCGAACGTG    4500
GCGAGAAAGG  AAGGGAAGAA  AGCGAAAGGA  GCGGGCGCTA  GGGCGCTGGC  AAGTGTAGCG    4560
GTCACGCTGC  GCGTAACCAC  CACACCCGCC  GCGCTTAATG  CGCCGCTACA  GGGCGCGTCA    4620
GGTGGCACTT  TTCGGGGAAA  TGTGCGCGGA  ACCCCTATTT  GTTTATTTTT  CTAAATACAT    4680
TCAAATATGT  ATCCGCTCAT  GAGACAATAA  CCCTGATAAA  TGCTTCAATA  ATATTGAAAA    4740
AGGAAGAGTA  TGAGTATTCA  ACATTTCCGT  GTCGCCCTTA  TTCCCTTTTT  TGCGGCATTT    4800
TGCCTTCCTG  TTTTTGCTCA  CCCAGAAACG  CTGGTGAAAG  TAAAAGATGC  TGAAGATCAG    4860
TTGGGTGCAC  GAGTGGGTTA  CATCGAACTG  GATCTCAACA  GCGGTAAGAT  CCTTGAGAGT    4920
TTTCGCCCCG  AAGAACGTTT  TCCAATGATG  AGCACTTTTA  AAGTTCTGCT  ATGTGGCGCG    4980
GTATTATCCC  GTGTTGACGC  CGGGCAAGAG  CAACTCGGTC  GCCGCATACA  CTATTCTCAG    5040
AATGACTTGG  TTGAGTACTC  ACCAGTCACA  GAAAAGCATC  TTACGGATGG  CATGACAGTA    5100
AGAGAATTAT  GCAGTGCTGC  CATAACCATG  AGTGATAACA  CTGCGGCCAA  CTTACTTCTG    5160
ACAACGATCG  GAGGACCGAA  GGAGCTAACC  GCTTTTTGC   ACAACATGGG  GGATCATGTA    5220
ACTCGCCTTG  ATCGTTGGGA  ACCGGAGCTG  AATGAAGCCA  TACCAAACGA  CGAGCGTGAC    5280
ACCACGATGC  CTCAGCAATG  GCAACAACGT  TGCGCAAACT  ATTAACTGGC  GAACTACTTA    5340
CTCTAGCTTC  CCGGCAACAA  TTAATAGACT  GGATGGAGGC  GGATAAAGTT  GCAGGACCAC    5400
TTCTGCGCTC  GGCCCTTCCG  GCTGGCTGGT  TTATTGCTGA  TAAATCTGGA  GCCGGTGAGC    5460
GTGGGTCTCG  CGGTATCATT  GCAGCACTGG  GGCCAGATGG  TAAGCCCTCC  CGTATCGTAG    5520
TTATCTACAC  GACGGGGAGT  CAGGCAACTA  TGGATGAACG  AAATAGACAG  ATCGCTGAGA    5580
```

|  |  |  |  |  |  |
|---|---|---|---|---|---|
| TAGGTGCCTC | ACTGATTAAG | CATTGGTAAC | TGTCAGACCA | AGTTACTCA | TATATACTTT | 5640 |
| AGATTGATTT | AAAACTTCAT | TTTTAATTTA | AAAGGATCTA | GGTGAAGATC | CTTTTTGATA | 5700 |
| ATCTCATGAC | CAAAATCCCT | TAACGTGAGT | TTTCGTTCCA | CTGAGCGTCA | GACCCCGTAG | 5760 |
| AAAAGATCAA | AGGATCTTCT | TGAGATCCTT | TTTTCTGCG | CGTAATCTGC | TGCTTGCAAA | 5820 |
| CAAAAAAACC | ACCGCTACCA | GCGGTGGTTT | GTTTGCCGGA | TCAAGAGCTA | CCAACTCTTT | 5880 |
| TTCCGAAGGT | AACTGGCTTC | AGCAGAGCGC | AGATACCAAA | TACTGTCCTT | CTAGTGTAGC | 5940 |
| CGTAGTTAGG | CCACCACTTC | AAGAACTCTG | TAGCACCGCC | TACATACCTC | GCTCTGCTAA | 6000 |
| TCCTGTTACC | AGTGGCTGCT | GCCAGTGGCG | ATAAGTCGTG | TCTTACCGGG | TTGGACTCAA | 6060 |
| GACGATAGTT | ACCGGATAAG | GCGCAGCGGT | CGGGCTGAAC | GGGGGGTTCG | TGCACACAGC | 6120 |
| CCAGCTTGGA | GCGAACGACC | TACACCGAAC | TGAGATACCT | ACAGCGTGAG | CATTGAGAAA | 6180 |
| GCGCCACGCT | TCCCGAAGGG | AGAAAGGCGG | ACAGGTATCC | GGTAAGCGGC | AGGGTCGGAA | 6240 |
| CAGGAGAGCG | CACGAGGGAG | CTTCCAGGGG | GAAACGCCTG | GTATCTTTAT | AGTCCTGTCG | 6300 |
| GGTTTCGCCA | CCTCTGACTT | GAGCGTCGAT | TTTTGTGATG | CTCGTCAGGG | GGGCGGAGCC | 6360 |
| TATGGAAAAA | CGCCAGCAAC | GCGGCCTTTT | TACGGTTCCT | GGCCTTTTGC | TGGCCTTTTG | 6420 |
| CTCACATGTT | CTTTCCTGCG | TTATCCCCTG | ATTCTGTGGA | TAACCGTATT | ACCGCCTTTG | 6480 |
| AGTGAGCTGA | TACCGCTCGC | CGCAGCCGAA | CGACCGAGCG | CAGCGAGTCA | GTGAGCGAGG | 6540 |
| AAGCGGAAGA | GCGCCCAATA | CGCAAACCGC | CTCTCCCCGC | GCGTTGGCCG | ATTCATTAAT | 6600 |
| G |  |  |  |  |  | 6601 |

( 2 ) INFORMATION FOR SEQ ID NO:16:

( i ) SEQUENCE CHARACTERISTICS:
        ( A ) LENGTH: 9917 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pTZgpt-sP11

( x i ) SEQUENCE DESCRIPTION: SEQ ID NO:16:

|  |  |  |  |  |  |
|---|---|---|---|---|---|
| CAGCTGGCGA | AAGGGGGATG | TGCTGCAAGG | CGATTAAGTT | GGGTAACGCC | AGGGTTTTCC | 60 |
| CAGTCACGAC | GTTGTAAAAC | GACGGCCCTG | AATATGAAGG | AGCAAAAGGT | TGTAACATTT | 120 |
| TATTACCGTG | TGGGATATAA | AAGTCCTTGA | TCCATTGATC | TGGAAACGGG | CATCTCCATT | 180 |
| TAAGACTAGA | CGCCACGGGG | TTTAAAATAC | TAATCATGAC | ATTTTGTAGA | GCGTAATTAC | 240 |
| TTAGTAAATC | CGCCGTACTA | GGTTCATTTC | CTCCTCGTTT | GGATCTCACA | TCAGAAATTA | 300 |
| AAATAATCTT | AGAAGGATGC | AGTTGTTTTT | TGATGGATCG | TAGATATTCC | TCATCAACGA | 360 |
| ACCGAGTCAC | TAGAGTCACA | TCACGCAATC | CATTTAAAAT | AGGATCATGA | TGGCGGCCGT | 420 |
| CAATTAGCAT | CCATTTGATG | ATCACTCCTA | AATTATAGAA | ATGATCTCTC | AAATAACGTA | 480 |
| TATGTGTACC | GGGAGCAGAT | CCTATATACA | CTACGGTGGC | ACCATCTAAT | ATACCGTGTC | 540 |
| GCTGTAACTT | ACTAAGAAAA | ATAATTCTC | CTAGTAATAG | TTTAACTGT | CCTTGATACG | 600 |
| GCAGTTTTTT | TGCGACCTCA | TTTGCACTTT | CTGGTTCGTA | ATCTAACTCA | TTATCAATTT | 660 |
| CCTCAAAATA | CATAAACGGT | TTATCTAACG | ACACAACATC | CATTTTAAG | TATTATATTA | 720 |
| AAATTTAATC | AATGTTTATT | TTTAGTTTTT | TAGATAAAAA | ATATAATATT | ATGAGTCGAT | 780 |
| GTAACACTTT | CTACACACCG | ATTGATACAT | ATCATTACCT | CCTATTATTT | CTATCTCGGT | 840 |
| TTCCTCACCC | AATCGTTTAG | AAAAGGAAGC | CTCCTTAAAG | CATTTCATAC | ACACAGCAGT | 900 |

```
TAGTTTTACC ACCATTTCAG ATAATGGAAT AAGATTCAAA ATATTATTAA ACGGTTTACG    960
TTGAAATGTC CCATCGAGTG CGGCTACTAT AACTATTTTT CCTTCGTTTG CCATACGCTC   1020
ACAGAATTAA TTCCGAGCTT GGCGGTTCCA GGATCCGTCG ACAGGCCTAT CGATGAAGGA   1080
CAGTTCTTTC CAGACATTGT TGGATTAAAT AGTACATAAT GGATTTCCTT ACGCGAAATA   1140
CGGGCAGACA TGGCCTGCCC GGTTATTATT ATTTTGACA CCAGACCAAC TGGTAATGGT    1200
AGCGACCGGC GCTCAGCTGT AATTCCGCCG ATACTGACGG GCTCCAGGAG TCGTCGCCAC   1260
CAATCCCCAT ATGGAAACCG TCGATATTCA GCCATGTGCC TTCTTCCGCG TGCAGCAGAT   1320
GGCGATGGCT GGTTTCCATC AGTTGCTGTT GACTGTAGCG GCTGATGTTG AACTGGAAGT   1380
CGCCGCGCCA CTGGTGTGGG CCATAATTCA ATTCGCGCGT CCCGCAGCGC AGACCGTTTT   1440
CGCTCGGGAA GACGTACGGG GTATACATGT CTGACAATGG CAGATCCCAG CGGTCAAAAC   1500
AGGCGGCAGT AAGGCGGTCG GGATAGTTTT CTTGCGGCCC TAATCCGAGC CAGTTTACCC   1560
GCTCTGCTAC CTGCGCCAGC TGGCAGTTCA GGCCAATCCG CGCCGGATGC GGTGTATCGC   1620
TCGCCACTTC AACATCAACG GTAATCGCCA TTTGACCACT ACCATCAATC CGGTAGGTTT   1680
TCCGGCTGAT AAATAAGGTT TTCCCCTGAT GCTGCCACGC GTGAGCGGTC GTAATCAGCA   1740
CCGCATCAGC AAGTGTATCT GCCGTGCACT GCAACAACGC TGCTTCGGCC TGGTAATGGC   1800
CCGCCGCCTT CCAGCGTTCG ACCCAGGCGT TAGGGTCAAT GCGGGTCGCT TCACTTACGC   1860
CAATGTCGTT ATCCAGCGGT GCACGGGTGA ACTGATCGCG CAGCGGCGTC AGCAGTTGTT   1920
TTTTATCGCC AATCCACATC TGTGAAAGAA AGCCTGACTG GCGGTTAAAT TGCCAACGCT   1980
TATTACCCAG CTCGATGCAA AAATCCATTT CGCTGGTGGT CAGATGCGGG ATGGCGTGGG   2040
ACGCGGCGGG GAGCGTCACA CTGAGGTTTT CCGCCAGACG CCACTGCTGC CAGGCGCTGA   2100
TGTGCCCGGC TTCTGACCAT GCGGTCGCGT TCGGTTGCAC TACGCGTACT GTGAGCCAGA   2160
GTTGCCCGGC GCTCTCCGGC TGCGGTAGTT CAGGCAGTTC AATCAACTGT TTACCTTGTG   2220
GAGCGACATC CAGAGGCACT TCACCGCTTG CCAGCGGCTT ACCATCCAGC GCCACCATCC   2280
AGTGCAGGAG CTCGTTATCG CTATGACGGA ACAGGTATTC GCTGGTCACT TCGATGGTTT   2340
GCCCGGATAA ACGGAACTGG AAAAACTGCT GCTGGTGTTT TGCTTCCGTC AGCGCTGGAT   2400
GCGGCGTGCG GTCGGCAAAG ACCAGACCGT TCATACAGAA CTGGCGATCG TTCGGCGTAT   2460
CGCCAAAATC ACCGCCGTAA GCCGACCACG GGTTGCCGTT TTCATCATAT TTAATCAGCG   2520
ACTGATCCAC CCAGTCCCAG ACGAAGCCGC CCTGTAAACG GGATACTGA CGAAACGCCT    2580
GCCAGTATTT AGCGAAACCG CCAAGACTGT TACCCATCGC GTGGGCGTAT TCGCAAAGGA   2640
TCAGCGGGCG CGTCTCTCCA GGTAGCGAAA GCCATTTTTT GATGGACCAT TTCGGCACAG   2700
CCGGGAAGGG CTGGTCTTCA TCCACGCGCG CGTACATCGG GCAAATAATA TCGGTGGCCG   2760
TGGTGTCGGC TCCGCCGCCT TCATACTGCA CCGGGCGGGA AGGATCGACA GATTTGATCC   2820
AGCGATACAG CGCGTCGTGA TTAGCGCCGT GGCCTGATTC ATTCCCAGC GACCAGATGA    2880
TCACACTCGG GTGATTACGA TCGCGCTGCA CCATTCGCGT TACGCGTTCG CTCATCGCCG   2940
GTAGCCAGCG CGGATCATCG GTCAGACGAT TCATTGGCAC CATGCCGTGG GTTTCAATAT   3000
TGGCTTCATC CACCACATAC AGGCCGTAGC GGTCGCACAG CGTGTACCAC AGCGGATGGT   3060
TCGGATAATG CGAACAGCGC ACGGCGTTAA AGTTGTTCTG CTTCATCAGC AGGATATCCT   3120
GCACCATCGT CTGCTCATCC ATGACCTGAC CATGCAGAGG ATGATGCTCG TGACGGTTAA   3180
CGCCTCGAAT CAGCAACGGC TTGCCGTTCA GCAGCAGCAG ACCATTTTCA ATCCGCACCT   3240
CGCGGAAACC GACATCGCAG GCTTCTGCTT CAATCAGCGT GCCGTCGGCG GTGTGCAGTT   3300
```

```
CAACCACCGC ACGATAGAGA TTCGGGATTT CGGCGCTCCA CAGTTTCGGG TTTTCGACGT    3360
TCAGACGTAG TGTGACGCGA TCGGCATAAC CACCACGCTC ATCGATAATT TCACCGCCGA    3420
AAGGCGCGGT GCCGCTGGCG ACCTGCGTTT CACCCTGCCA TAAAGAAACT GTTACCCGTA    3480
GGTAGTCACG CAACTCGCCG CACATCTGAA CTTCAGCCTC CAGTACAGCG CGGCTGAAAT    3540
CATCATTAAA GCGAGTGGCA ACATGGAAAT CGCTGATTTG TGTAGTCGGT TTATGCAGCA    3600
ACGAGACGTC ACGGAAAATG CCGCTCATCC GCCACATATC CTGATCTTCC AGATAACTGC    3660
CGTCACTCCA ACGCAGCACC ATCACCGCGA GGCGGTTTTC TCCGGCGCGT AAAAATGCGC    3720
TCAGGTCAAA TTCAGACGGC AAACGACTGT CCTGGCCGTA ACCGACCCAG CGCCCGTTGC    3780
ACCACAGATG AAACGCCGAG TTAACGCCAT CAAAATAAT TCGCGTCTGG CCTTCCTGTA     3840
GCCAGCTTTC ATCAACATTA AATGTGAGCG AGTAACAACC CGTCGGATTC TCCGTGGGAA    3900
CAAACGGCGG ATTGACCGTA ATGGGATAGG TTACGTTGGT GTAGATGGGC GCATCGTAAC    3960
CGTGCATCTG CCAGTTTGAG GGGACGACGA CAGTATCGGC CTCAGGAAGA TCGCACTCCA    4020
GCCAGCTTTC CGGCACCGCT TCTGGTGCCG GAAACCAGGC AAAGCGCCAT TCGCCATTCA    4080
GGCTGCGCAA CTGTTGGGAA GGGCGATCGG TGCGGGCCTC TTCGCTATTA CGCCAGCTGG    4140
CGAAAGGGGG ATGTGCTGCA AGGCGATTAA GTTGGGTAAC GCCAGGGTTT TCCCAGTCAC    4200
GACGTTGTAA AACGACGGGA TCGCGGCCGC GATCCCCGAT TCGTAGAGCC TCGTTGCGTT    4260
TGTTAGCACG AACCATATGT AAGGAATTCC TGCAGCCTAT TTATAGCATA GAAAAAAACA    4320
AAATGAAATT CTACTATATT TTTACATACA TATATTCTAA CCCAACCAAC TTAAGGGTAC    4380
CGCCTCGACA TCTATATACT ATATAGTAAT ACCAATACTC AAGACTACGA AACTGATACA    4440
ATCTCTTATC ATGTGGGTAA TGTTCTCGAT GTCGAATAGC CATATGCCGG TAGTTGCGAT    4500
ATACATAAAC TGATCACTAA TTCCAAACCC ACCCGCTTTT TATAGTAAGT TTTTCACCCA    4560
TAAATAATAA ATACAATAAT TAATTTCTCG TAAAAGTAGA AAATATATTC TAATTTATTG    4620
CACGGTAAGG AAGTAGAATC ATAAAGAACA GTGACGGATG ATCCCCAAGC TTGGACACAA    4680
GACAGGCTTG CGAGATATGT TTGAGAATAC CACTTTATCC CGCGTCAGGG AGAGGCAGTG    4740
CGTAAAAAGA CGCGGACTCA TGTGAAATAC TGGTTTTTAG TGCGCCAGAT CTCTATAATC    4800
TCGCGCAACC TATTTTCCCC TCGAACACTT TTTAAGCCGT AGATAAACAG GCTGGGACAC    4860
TTCACATGAG CGAAAAATAC ATCGTCACCT GGGACATGTT GCAGATCCAT GCACGTAAAC    4920
TCGCAAGCCG ACTGATGCCT TCTGAACAAT GGAAAGGCAT TATTGCCGTA AGCCGTGGCG    4980
GTCTGGTACC GGGTGCGTTA CTGGCGCGTG AACTGGGTAT TCGTCATGTC GATACCGTTT    5040
GTATTTCCAG CTACGATCAC GACAACCAGC GCGAGCTTAA AGTGCTGAAA CGCGCAGAAG    5100
GCGATGGCGA AGGCTTCATC GTTATTGATG ACCTGGTGGA TACCGGTGGT ACTGCGGTTG    5160
CGATTCGTGA AATGTATCCA AAAGCGCACT TTGTCACCAT CTTCGCAAAA CCGGCTGGTC    5220
GTCCGCTGGT TGATGACTAT GTTGTTGATA TCCCGCAAGA TACCTGGATT GAACAGCCGT    5280
GGGATATGGG CGTCGTATTC GTCCCGCCAA TCTCCGGTCG CTAATCTTTT CAACGCCTGG    5340
CACTGCCGGG CGTTGTTCTT TTTAACTTCA GGCGGGTTAC AATAGTTTCC AGTAAGTATT    5400
CTGGAGGCTG CATCCATGAC ACAGGCAAAC CTGAGCGAAA CCCTGTTCAA ACCCCGCTTT    5460
AAACATCCTG AAACCTCGAC GCTAGTCCGC CGCTTTAATC ACGGCGCACA ACCGCCTGTG    5520
CAGTCGGCCC TTGATGGTAA AACCATCCCT CACTGGTATC GCATGATTAA CCGTCTGATG    5580
TGGATCTGGC GCGGCATTGA CCCACGCGAA ATCCTCGACG TCCAGGCACG TATTGTGATG    5640
AGCGATGCCG AACGTACCGA CGATGATTTA TACGATACGG TGATTGGCTA CCGTGGCGGC    5700
```

```
AACTGGATTT ATGAGTGGGC CCCGGATCTT TGTGAAGGAA CCTTACTTCT GTGGTGTGAC  5760
ATAATTGGAC AAACTACCTA CAGAGATTTA AAGCTCTAAG GTAAATATAA AATTTTTAAG  5820
TGTATAATGT GTTAAACTAC TGATTCTAAT TGTTTGTGTA TTTAGATTC  CAACCTATGG  5880
AACTGATGAA TGGGAGCAGT GGTGGAATGC CTTTAATGAG GAAAACCTGT TTTGCTCAGA  5940
AGAAATGCCA TCTAGTGATG ATGAGGCTAC TGCTGACTCT CAACATTCTA CTCCTCCAAA  6000
AAAGAAGAGA AAGGTAGAAG ACCCCAAGGA CTTTCCTTCA GAATTGCTAA GTTTTTGAG   6060
TCATGCTGTG TTTAGTAATA GAACTCTTGC TTGCTTTGCT ATTTACACCA CAAAGGAAAA  6120
AGCTGCACTG CTATACAAGA AAATTATGGA AAAATATTCT GTAACCTTTA TAAGTAGGCA  6180
TAACAGTTAT AATCATAACA TACTGTTTTT TCTTACTCCA CACAGGCATA GAGTGTCTGC  6240
TATTAATAAC TATGCTCAAA AATTGTGTAC CTTTAGCTTT TTAATTTGTA AAGGGGTTAA  6300
TAAGGAATAT TTGATGTATA GTGCCTTGAC TAGAGATCAT AATCAGCCAT ACCACATTTG  6360
TAGAGGTTTT ACTTGCTTTA AAAACCTCC  CACACCTCCC CCTGAACCTG AAACATAAAA  6420
TGAATGCAAT TGTTGTTGTT AAGCTTGGGG GAATTAATTC AACAATGTCT GGAAAGAACT  6480
GTCCTTCATC GATACCTATC ACGGAGAAAT CTGTAATTGA TTCCAAGACA TCACATAGTT  6540
TAGTTGCTTC CAATGCTTCA AAATTATTCT TATCATGCGT CCATAGTCCC GTTCCGTATC  6600
TATTATCGTT AGAATATTTT ATAGTCACGC ATTTATATTG AGCTATTTGA TAACGTCTAA  6660
CTCGTCTAAT TAATTCTGTA CTTTTACCTG AAAACATGGG GCCGATTATC AACTGAATAT  6720
GTCCGCCGTT CATGATGACA ATAAAGAATT AATTATTGTT CACTTTATTC GACTTTAATA  6780
TATCCATCAC GTTAGAAAAT GCGATATTGC GACGAGGATC TATGTATCTA ACAGGATCTA  6840
TTGCGGTGGT AGCTAGAGAG GATTCTTTTT TGAATCGCAT CAAACTAATC ACAAAGTCGA  6900
ACAAATATCC TTTATTAAGT TTGACCCTTC CATCTGTAAC AATAGGGACC TTGTTAAACA  6960
GTTTTTTAAA ATCTTGAAAG TCTGTGAATT TTGTCAATTG TCTGTATTCC TCTGAAAGAG  7020
ATTCATAACA ATGACCCACG GCTTCTAATT TATTTTTTGA TTGGATCAAT AATAATAACA  7080
GAAAGTCTAG ATATTGAGTG ATTTGCAATA TATCAGATAA TGAAGATTCA TCATCTTGAC  7140
TAGCCAAATA CTTAAAAAAT GAATCATCAT CTGCGAAGAA CATCGTTAAG AGATACTGGT  7200
TGTGATCCAT TTATTGATCG CAAAAGCTTG GCGTAATCAT GGTCATAGCT GTTTCCTGTG  7260
TGAAATTGTT ATCCGCTCAC AATTCCACAC AACATACGAG CCGGAAGCAT AAAGTGTAAA  7320
GCCTGGGGTG CCTAATGAGT GAGCTAACTC ACATTAATTG CGTTGCGCTC ACTGCCCGCT  7380
TTCCAGTCGG GAAACCTGTC GTGCCAGCTG GCGTAATAGC GAAGAGGCCC GCACCGATCG  7440
CCCTTCCCAA CAGTTGCGCA GCCTGAATGG CGAATGGGAA ATTGTAAACG TTAATATTTT  7500
GTTAAAATTC GCGTTAAATT TTTGTTAAAT CAGCTCATTT TTTAACCAAT AGGCCGAAAT  7560
CGGCAAAATC CCTTATAAAT CAAAAGAATA GACCGAGATA GGGTTGAGTG TTGTTCCAGT  7620
TTGGAACAAG AGTCCACTAT TAAAGAACGT GGACTCCAAC GTCAAAGGGC GAAAACCGT   7680
CTATCAGGGC GATGGCCCAC TACGTGAACC ATCACCCTAA TCAAGTTTTT TGGGGTCGAG  7740
GTGCCGTAAA GCACTAAATC GGAACCCTAA AGGGAGCCCC CGATTTAGAG CTTGACGGGG  7800
AAAGCCGGCG AACGTGGCGA GAAAGGAAGG GAAGAAAGCG AAAGGAGCGG GCGCTAGGGC  7860
GCTGGCAAGT GTAGCGGTCA CGCTGCGCGT AACCACCACA CCCGCCGCGC TTAATGCGCC  7920
GCTACAGGGC GCGTCAGGTG GCACTTTTCG GGGAAATGTG CGCGGAACCC CTATTTGTTT  7980
ATTTTTCTAA ATACATTCAA ATATGTATCC GCTCATGAGA CAATAACCCT GATAAATGCT  8040
TCAATAATAT TGAAAAAGGA AGAGTATGAG TATTCAACAT TTCCGTGTCG CCCTTATTCC  8100
```

| | | | | | |
|---|---|---|---|---|---|
| CTTTTTTGCG | GCATTTTGCC | TTCCTGTTTT | TGCTCACCCA | GAAACGCTGG | TGAAAGTAAA | 8160
| AGATGCTGAA | GATCAGTTGG | GTGCACGAGT | GGGTTACATC | GAACTGGATC | TCAACAGCGG | 8220
| TAAGATCCTT | GAGAGTTTTC | GCCCCGAAGA | ACGTTTTCCA | ATGATGAGCA | CTTTTAAAGT | 8280
| TCTGCTATGT | GGCGCGGTAT | TATCCCGTGT | TGACGCCGGG | CAAGAGCAAC | TCGGTCGCCG | 8340
| CATACACTAT | TCTCAGAATG | ACTTGGTTGA | GTACTCACCA | GTCACAGAAA | AGCATCTTAC | 8400
| GGATGGCATG | ACAGTAAGAG | AATTATGCAG | TGCTGCCATA | ACCATGAGTG | ATAACACTGC | 8460
| GGCCAACTTA | CTTCTGACAA | CGATCGGAGG | ACCGAAGGAG | CTAACCGCTT | TTTTGCACAA | 8520
| CATGGGGGAT | CATGTAACTC | GCCTTGATCG | TTGGGAACCG | GAGCTGAATG | AAGCCATACC | 8580
| AAACGACGAG | CGTGACACCA | CGATGCCTCA | GCAATGGCAA | CAACGTTGCG | CAAACTATTA | 8640
| ACTGGCGAAC | TACTTACTCT | AGCTTCCCGG | CAACAATTAA | TAGACTGGAT | GGAGGCGGAT | 8700
| AAAGTTGCAG | GACCACTTCT | GCGCTCGGCC | CTTCCGGCTG | GCTGGTTTAT | TGCTGATAAA | 8760
| TCTGGAGCCG | GTGAGCGTGG | GTCTCGCGGT | ATCATTGCAG | CACTGGGGCC | AGATGGTAAG | 8820
| CCCTCCCGTA | TCGTAGTTAT | CTACACGACG | GGGAGTCAGG | CAACTATGGA | TGAACGAAAT | 8880
| AGACAGATCG | CTGAGATAGG | TGCCTCACTG | ATTAAGCATT | GGTAACTGTC | AGACCAAGTT | 8940
| TACTCATATA | TACTTTAGAT | TGATTTAAAA | CTTCATTTTT | AATTTAAAAG | GATCTAGGTG | 9000
| AAGATCCTTT | TTGATAATCT | CATGACCAAA | ATCCCTTAAC | GTGAGTTTTC | GTTCCACTGA | 9060
| GCGTCAGACC | CCGTAGAAAA | GATCAAAGGA | TCTTCTTGAG | ATCCTTTTTT | TCTGCGCGTA | 9120
| ATCTGCTGCT | TGCAAACAAA | AAAACCACCG | CTACCAGCGG | TGGTTTGTTT | GCCGGATCAA | 9180
| GAGCTACCAA | CTCTTTTTCC | GAAGGTAACT | GGCTTCAGCA | GAGCGCAGAT | ACCAAATACT | 9240
| GTCCTTCTAG | TGTAGCCGTA | GTTAGGCCAC | CACTTCAAGA | ACTCTGTAGC | ACCGCCTACA | 9300
| TACCTCGCTC | TGCTAATCCT | GTTACCAGTG | GCTGCTGCCA | GTGGCGATAA | GTCGTGTCTT | 9360
| ACCGGGTTGG | ACTCAAGACG | ATAGTTACCG | GATAAGGCGC | AGCGGTCGGG | CTGAACGGGG | 9420
| GGTTCGTGCA | CACAGCCCAG | CTTGGAGCGA | ACGACCTACA | CCGAACTGAG | ATACCTACAG | 9480
| CGTGAGCATT | GAGAAAGCGC | CACGCTTCCC | GAAGGGAGAA | AGGCGGACAG | GTATCCGGTA | 9540
| AGCGGCAGGG | TCGGAACAGG | AGAGCGCACG | AGGGAGCTTC | CAGGGGGAAA | CGCCTGGTAT | 9600
| CTTTATAGTC | CTGTCGGGTT | TCGCCACCTC | TGACTTGAGC | GTCGATTTTT | GTGATGCTCG | 9660
| TCAGGGGGGC | GGAGCCTATG | GAAAAACGCC | AGCAACGCGG | CCTTTTTACG | GTTCCTGGCC | 9720
| TTTTGCTGGC | CTTTTGCTCA | CATGTTCTTT | CCTGCGTTAT | CCCCTGATTC | TGTGGATAAC | 9780
| CGTATTACCG | CCTTTGAGTG | AGCTGATACC | GCTCGCCGCA | GCCGAACGAC | CGAGCGCAGC | 9840
| GAGTCAGTGA | GCGAGGAAGC | GGAAGAGCGC | CCAATACGCA | AACCGCCTCT | CCCCGCGCGT | 9900
| TGGCCGATTC | ATTAATG | | | | | 9917

( 2 ) INFORMATION FOR SEQ ID NO:17:

( i ) SEQUENCE CHARACTERISTICS:
        ( A ) LENGTH: 9916 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pTZgpt-s4b ( x i ) SEQUENCE DESCRIPTION: SEQ ID NO:17:

| | | | | | |
|---|---|---|---|---|---|
| CAGCTGGCGA | AAGGGGGATG | TGCTGCAAGG | CGATTAAGTT | GGGTAACGCC | AGGGTTTTCC | 60
| CAGTCACGAC | GTTGTAAAAC | GACGGCCCTG | AATATGAAGG | AGCAAAAGGT | TGTAACATTT | 120

| | | | | | |
|---|---|---|---|---|---|
|TATTACCGTG|TGGGATATAA|AAGTCCTTGA|TCCATTGATC|TGGAAACGGG|CATCTCCATT|180|
|TAAGACTAGA|CGCCACGGGG|TTTAAAATAC|TAATCATGAC|ATTTTGTAGA|GCGTAATTAC|240|
|TTAGTAAATC|CGCCGTACTA|GGTTCATTTC|CTCCTCGTTT|GGATCTCACA|TCAGAAATTA|300|
|AAATAATCTT|AGAAGGATGC|AGTTGTTTTT|TGATGGATCG|TAGATATTCC|TCATCAACGA|360|
|ACCGAGTCAC|TAGAGTCACA|TCACGCAATC|CATTTAAAAT|AGGATCATGA|TGGCGGCCGT|420|
|CAATTAGCAT|CCATTTGATG|ATCACTCCTA|AATTATAGAA|ATGATCTCTC|AAATAACGTA|480|
|TATGTGTACC|GGGAGCAGAT|CCTATATACA|CTACGGTGGC|ACCATCTAAT|ATACCGTGTC|540|
|GCTGTAACTT|ACTAAGAAAA|AATAATTCTC|CTAGTAATAG|TTTTAACTGT|CCTTGATACG|600|
|GCAGTTTTTT|TGCGACCTCA|TTTGCACTTT|CTGGTTCGTA|ATCTAACTCA|TTATCAATTT|660|
|CCTCAAAATA|CATAAACGGT|TTATCTAACG|ACACAACATC|CATTTTAAG|TATTATATTA|720|
|AAATTTAATC|AATGTTTATT|TTTAGTTTTT|TAGATAAAAA|ATATAATATT|ATGAGTCGAT|780|
|GTAACACTTT|CTACACACCG|ATTGATACAT|ATCATTACCT|CCTATTATTT|CTATCTCGGT|840|
|TTCCTCACCC|AATCGTTTAG|AAAAGGAAGC|CTCCTTAAAG|CATTTCATAC|ACACAGCAGT|900|
|TAGTTTTACC|ACCATTTCAG|ATAATGGAAT|AAGATTCAAA|ATATTATTAA|ACGGTTTACG|960|
|TTGAAATGTC|CCATCGAGTG|CGGCTACTAT|AACTATTTTT|CCTTCGTTTG|CCATACGCTC|1020|
|ACAGAATTAA|TTCGAGCTT|GGCGGTTCCA|GGATCCGTCG|ACAGGCCTAT|CGATGAAGGA|1080|
|CAGTTCTTTC|CAGACATTGT|TGGATTAAAT|AGTACATAAT|GGATTTCCTT|ACGCGAAATA|1140|
|CGGGCAGACA|TGGCCTGCCC|GGTTATTATT|ATTTTTGACA|CCAGACCAAC|TGGTAATGGT|1200|
|AGCGACCGGC|GCTCAGCTGT|AATTCCGCCG|ATACTGACGG|GCTCCAGGAG|TCGTCGCCAC|1260|
|CAATCCCCAT|ATGGAAACCG|TCGATATTCA|GCCATGTGCC|TTCTTCCGCG|TGCAGCAGAT|1320|
|GGCGATGGCT|GGTTTCCATC|AGTTGCTGTT|GACTGTAGCG|GCTGATGTTG|AACTGGAAGT|1380|
|CGCCGCGCCA|CTGGTGTGGG|CCATAATTCA|ATTCGCGCGT|CCCGCAGCGC|AGACCGTTTT|1440|
|CGCTCGGGAA|GACGTACGGG|GTATACATGT|CTGACAATGG|CAGATCCCAG|CGGTCAAAAC|1500|
|AGGCGGCAGT|AAGGCGGTCG|GGATAGTTTT|CTTGCGGCCC|TAATCCGAGC|CAGTTTACCC|1560|
|GCTCTGCTAC|CTGCGCCAGC|TGGCAGTTCA|GGCCAATCCG|CGCCGGATGC|GGTGTATCGC|1620|
|TCGCCACTTC|AACATCAACG|GTAATCGCCA|TTTGACCACT|ACCATCAATC|CGGTAGGTTT|1680|
|TCCGGCTGAT|AAATAAGGTT|TTCCCCTGAT|GCTGCCACGC|GTGAGCGGTC|GTAATCAGCA|1740|
|CCGCATCAGC|AAGTGTATCT|GCCGTGCACT|GCAACAACGC|TGCTTCGGCC|TGGTAATGGC|1800|
|CCGCCGCCTT|CCAGCGTTCG|ACCCAGGCGT|TAGGGTCAAT|GCGGGTCGCT|TCACTTACGC|1860|
|CAATGTCGTT|ATCCAGCGGT|GCACGGGTGA|ACTGATCGCG|CAGCGGCGTC|AGCAGTTGTT|1920|
|TTTTATCGCC|AATCCACATC|TGTGAAAGAA|AGCCTGACTG|GCGGTTAAAT|TGCCAACGCT|1980|
|TATTACCCAG|CTCGATGCAA|AAATCCATTT|CGCTGGTGGT|CAGATGCGGG|ATGGCGTGGG|2040|
|ACGCGGCGGG|GAGCGTCACA|CTGAGGTTTT|CCGCCAGACG|CCACTGCTGC|CAGGCGCTGA|2100|
|TGTGCCCGGC|TTCTGACCAT|GCGGTCGCGT|TCGGTTGCAC|TACGCGTACT|GTGAGCCAGA|2160|
|GTTGCCCGGC|GCTCTCCGGC|TGCGGTAGTT|CAGGCAGTTC|AATCAACTGT|TTACCTTGTG|2220|
|GAGCGACATC|CAGAGGCACT|TCACCGCTTG|CCAGCGGCTT|ACCATCCAGC|GCCACCATCC|2280|
|AGTGCAGGAG|CTCGTTATCG|CTATGACGGA|ACAGGTATTC|GCTGGTCACT|TCGATGGTTT|2340|
|GCCCGGATAA|ACGGAACTGG|AAAAACTGCT|GCTGGTGTTT|TGCTTCCGTC|AGCGCTGGAT|2400|
|GCGGCGTGCG|GTCGGCAAAG|ACCAGACCGT|TCATACAGAA|CTGGCGATCG|TTCGGCGTAT|2460|
|CGCCAAAATC|ACCGCCGTAA|GCCGACCACG|GGTTGCCGTT|TTCATCATAT|TTAATCAGCG|2520|

```
ACTGATCCAC CCAGTCCCAG ACGAAGCCGC CCTGTAAACG GGGATACTGA CGAAACGCCT   2580
GCCAGTATTT AGCGAAACCG CCAAGACTGT TACCCATCGC GTGGGCGTAT TCGCAAAGGA   2640
TCAGCGGGCG CGTCTCTCCA GGTAGCGAAA GCCATTTTTT GATGGACCAT TTCGGCACAG   2700
CCGGGAAGGG CTGGTCTTCA TCCACGCGCG CGTACATCGG GCAAATAATA TCGGTGGCCG   2760
TGGTGTCGGC TCCGCCGCCT TCATACTGCA CCGGGCGGGA AGGATCGACA GATTTGATCC   2820
AGCGATACAG CGCGTCGTGA TTAGCGCCGT GGCCTGATTC ATTCCCCAGC GACCAGATGA   2880
TCACACTCGG GTGATTACGA TCGCGCTGCA CCATTCGCGT TACGCGTTCG CTCATCGCCG   2940
GTAGCCAGCG CGGATCATCG GTCAGACGAT TCATTGGCAC CATGCCGTGG GTTTCAATAT   3000
TGGCTTCATC CACCACATAC AGGCCGTAGC GGTCGCACAG CGTGTACCAC AGCGGATGGT   3060
TCGGATAATG CGAACAGCGC ACGGCGTTAA AGTTGTTCTG CTTCATCAGC AGGATATCCT   3120
GCACCATCGT CTGCTCATCC ATGACCTGAC CATGCAGAGG ATGATGCTCG TGACGGTTAA   3180
CGCCTCGAAT CAGCAACGGC TTGCCGTTCA GCAGCAGCAG ACCATTTTCA ATCCGCACCT   3240
CGCGGAAACC GACATCGCAG GCTTCTGCTT CAATCAGCGT GCCGTCGGCG GTGTGCAGTT   3300
CAACCACCGC ACGATAGAGA TTCGGGATTT CGGCGCTCCA CAGTTTCGGG TTTTCGACGT   3360
TCAGACGTAG TGTGACGCGA TCGGCATAAC CACCACGCTC ATCGATAATT TCACCGCCGA   3420
AAGGCGCGGT GCCGCTGGCG ACCTGCGTTT CACCCTGCCA TAAAGAAACT GTTACCCGTA   3480
GGTAGTCACG CAACTCGCCG CACATCTGAA CTTCAGCCTC CAGTACAGCG CGGCTGAAAT   3540
CATCATTAAA GCGAGTGGCA ACATGGAAAT CGCTGATTTG TGTAGTCGGT TTATGCAGCA   3600
ACGAGACGTC ACGGAAAATG CCGCTCATCC GCCACATATC CTGATCTTCC AGATAACTGC   3660
CGTCACTCCA ACGCAGCACC ATCACCGCGA GGCGGTTTTC TCCGGCGCGT AAAAATGCGC   3720
TCAGGTCAAA TTCAGACGGC AAACGACTGT CCTGGCCGTA ACCGACCCAG CGCCCGTTGC   3780
ACCACAGATG AAACGCCGAG TTAACGCCAT CAAAAATAAT TCGCGTCTGG CCTTCCTGTA   3840
GCCAGCTTTC ATCAACATTA AATGTGAGCG AGTAACAACC CGTCGGATTC TCCGTGGGAA   3900
CAAACGGCGG ATTGACCGTA ATGGGATAGG TTACGTTGGT GTAGATGGGC GCATCGTAAC   3960
CGTGCATCTG CCAGTTTGAG GGGACGACGA CAGTATCGGC CTCAGGAAGA TCGCACTCCA   4020
GCCAGCTTTC CGGCACCGCT TCTGGTGCCG GAAACCAGGC AAAGCGCCAT TCGCCATTCA   4080
GGCTGCGCAA CTGTTGGGAA GGGCGATCGG TGCGGGCCTC TTCGCTATTA CGCCAGCTGG   4140
CGAAAGGGGG ATGTGCTGCA AGGCGATTAA GTTGGGTAAC GCCAGGGTTT TCCCAGTCAC   4200
GACGTTGTAA AACGACGGGA TCGCGGCCGC GATCCCCGAT TCGTAGAGCC TCGTTGCGTT   4260
TGTTAGCACG AACCATATGT AAGGAATTCC TGCAGCCTAT TTATATTTGA TAGTTTTTTA   4320
CTTGTAACGT ATCAAAATAA GTACCTAAAG AGACCTAACC CCAACCAACT TAAGGGTACC   4380
GCCTCGACAT CTATATACTA TATAGTAATA CCAATACTCA AGACTACGAA ACTGATACAA   4440
TCTCTTATCA TGTGGGTAAT GTTCTCGATG TCGAATAGCC ATATGCCGGT AGTTGCGATA   4500
TACATAAACT GATCACTAAT TCCAAACCCA CCCGCTTTTT ATAGTAAGTT TTTCACCCAT   4560
AAATAATAAA TACAATAATT AATTTCTCGT AAAAGTAGAA AATATATTCT AATTTATTGC   4620
ACGGTAAGGA AGTAGAATCA TAAAGAACAG TGACGGATGA TCCCAAGCT TGGACACAAG   4680
ACAGGCTTGC GAGATATGTT TGAGAATACC ACTTTATCCC GCGTCAGGGA GAGGCAGTGC   4740
GTAAAAAGAC GCGGACTCAT GTGAAATACT GGTTTTTAGT GCGCCAGATC TCTATAATCT   4800
CGCGCAACCT ATTTTCCCCT CGAACACTTT TTAAGCCGTA GATAAACAGG CTGGGACACT   4860
TCACATGAGC GAAAAATACA TCGTCACCTG GGACATGTTG CAGATCCATG CACGTAAACT   4920
```

```
CGCAAGCCGA CTGATGCCTT CTGAACAATG GAAAGGCATT ATTGCCGTAA GCCGTGGCGG    4980
TCTGGTACCG GGTGCGTTAC TGGCGCGTGA ACTGGGTATT CGTCATGTCG ATACCGTTTG    5040
TATTTCCAGC TACGATCACG ACAACCAGCG CGAGCTTAAA GTGCTGAAAC GCGCAGAAGG    5100
CGATGGCGAA GGCTTCATCG TTATTGATGA CCTGGTGGAT ACCGGTGGTA CTGCGGTTGC    5160
GATTCGTGAA ATGTATCCAA AAGCGCACTT TGTCACCATC TTCGCAAAAC CGGCTGGTCG    5220
TCCGCTGGTT GATGACTATG TTGTTGATAT CCCGCAAGAT ACCTGGATTG AACAGCCGTG    5280
GGATATGGGC GTCGTATTCG TCCCGCCAAT CTCCGGTCGC TAATCTTTTC AACGCCTGGC    5340
ACTGCCGGGC GTTGTTCTTT TTAACTTCAG GCGGGTTACA ATAGTTTCCA GTAAGTATTC    5400
TGGAGGCTGC ATCCATGACA CAGGCAAACC TGAGCGAAAC CCTGTTCAAA CCCCGCTTTA    5460
AACATCCTGA AACCTCGACG CTAGTCCGCC GCTTTAATCA CGGCGCACAA CCGCCTGTGC    5520
AGTCGGCCCT TGATGGTAAA ACCATCCCTC ACTGGTATCG CATGATTAAC CGTCTGATGT    5580
GGATCTGGCG CGGCATTGAC CCACGCGAAA TCCTCGACGT CCAGGCACGT ATTGTGATGA    5640
GCGATGCCGA ACGTACCGAC GATGATTTAT ACGATACGGT GATTGGCTAC CGTGGCGGCA    5700
ACTGGATTTA TGAGTGGGCC CCGGATCTTT GTGAAGGAAC CTTACTTCTG TGGTGTGACA    5760
TAATTGGACA AACTACCTAC AGAGATTTAA AGCTCTAAGG TAAATATAAA ATTTTTAAGT    5820
GTATAATGTG TTAAACTACT GATTCTAATT GTTTGTGTAT TTTAGATTCC AACCTATGGA    5880
ACTGATGAAT GGGAGCAGTG GTGGAATGCC TTTAATGAGG AAAACCTGTT TTGCTCAGAA    5940
GAAATGCCAT CTAGTGATGA TGAGGCTACT GCTGACTCTC AACATTCTAC TCCTCCAAAA    6000
AAGAAGAGAA AGGTAGAAGA CCCCAAGGAC TTTCCTTCAG AATTGCTAAG TTTTTTGAGT    6060
CATGCTGTGT TTAGTAATAG AACTCTTGCT TGCTTTGCTA TTTACACCAC AAAGGAAAAA    6120
GCTGCACTGC TATACAAGAA AATTATGGAA AAATATTCTG TAACCTTTAT AAGTAGGCAT    6180
AACAGTTATA ATCATAACAT ACTGTTTTTT CTTACTCCAC ACAGGCATAG AGTGTCTGCT    6240
ATTAATAACT ATGCTCAAAA ATTGTGTACC TTTAGCTTTT TAATTTGTAA AGGGGTTAAT    6300
AAGGAATATT TGATGTATAG TGCCTTGACT AGAGATCATA ATCAGCCATA CCACATTTGT    6360
AGAGGTTTTA CTTGCTTTAA AAAACCTCCC ACACCTCCCC CTGAACCTGA AACATAAAAT    6420
GAATGCAATT GTTGTTGTTA ACTTGGGGG AATTAATTCA ACAATGTCTG GAAAGAACTG    6480
TCCTTCATCG ATACCTATCA CGGAGAAATC TGTAATTGAT CCAAGACAT CACATAGTTT    6540
AGTTGCTTCC AATGCTTCAA AATTATTCTT ATCATGCGTC CATAGTCCCG TTCCGTATCT    6600
ATTATCGTTA GAATATTTTA TAGTCACGCA TTTATATTGA GCTATTTGAT AACGTCTAAC    6660
TCGTCTAATT AATTCTGTAC TTTTACCTGA AAACATGGGG CCGATTATCA ACTGAATATG    6720
TCCGCCGTTC ATGATGACAA TAAAGAATTA ATTATTGTTC ACTTTATTCG ACTTTAATAT    6780
ATCCATCACG TTAGAAAATG CGATATTGCG ACGAGGATCT ATGTATCTAA CAGGATCTAT    6840
TGCGGTGGTA GCTAGAGAGG ATTCTTTTTT GAATCGCATC AAACTAATCA CAAAGTCGAA    6900
CAAATATCCT TTATTAAGTT TGACCCTTCC ATCTGTAACA ATAGGGACCT TGTTAAACAG    6960
TTTTTTAAAA TCTTGAAAGT CTGTGAATTT TGTCAATTGT CTGTATTCCT CTGAAAGAGA    7020
TTCATAACAA TGACCCACGG CTTCTAATTT ATTTTTTGAT TGGATCAATA ATAATAACAG    7080
AAAGTCTAGA TATTGAGTGA TTTGCAATAT ATCAGATAAT GAAGATTCAT CATCTTGACT    7140
AGCCAAATAC TTAAAAAATG AATCATCATC TGCGAAGAAC ATCGTTAAGA GATACTGGTT    7200
GTGATCCATT TATTGATCGC AAAAGCTTGG CGTAATCATG GTCATAGCTG TTTCCTGTGT    7260
GAAATTGTTA TCCGCTCACA ATTCCACACA ACATACGAGC CGGAAGCATA AAGTGTAAAG    7320
```

```
CCTGGGGTGC CTAATGAGTG AGCTAACTCA CATTAATTGC GTTGCGCTCA CTGCCCGCTT    7380
TCCAGTCGGG AAACCTGTCG TGCCAGCTGG CGTAATAGCG AAGAGGCCCG CACCGATCGC    7440
CCTTCCCAAC AGTTGCGCAG CCTGAATGGC GAATGGGAAA TTGTAAACGT TAATATTTTG    7500
TTAAAATTCG CGTTAAATTT TTGTTAAATC AGCTCATTTT TTAACCAATA GGCCGAAATC    7560
GGCAAAATCC CTTATAAATC AAAAGAATAG ACCGAGATAG GGTTGAGTGT TGTTCCAGTT    7620
TGGAACAAGA GTCCACTATT AAAGAACGTG GACTCCAACG TCAAAGGGCG AAAAACCGTC    7680
TATCAGGGCG ATGGCCCACT ACGTGAACCA TCACCCTAAT CAAGTTTTTT GGGGTCGAGG    7740
TGCCGTAAAG CACTAAATCG GAACCCTAAA GGGAGCCCCC GATTTAGAGC TTGACGGGGA    7800
AAGCCGGCGA ACGTGGCGAG AAAGGAAGGG AAGAAAGCGA AAGGAGCGGG CGCTAGGGCG    7860
CTGGCAAGTG TAGCGGTCAC GCTGCGCGTA ACCACCACAC CCGCCGCGCT TAATGCGCCG    7920
CTACAGGGCG CGTCAGGTGG CACTTTTCGG GGAAATGTGC GCGGAACCCC TATTTGTTTA    7980
TTTTTCTAAA TACATTCAAA TATGTATCCG CTCATGAGAC AATAACCCTG ATAAATGCTT    8040
CAATAATATT GAAAAAGGAA GAGTATGAGT ATTCAACATT TCCGTGTCGC CCTTATTCCC    8100
TTTTTGCGG CATTTGCCT TCCTGTTTTT GCTCACCCAG AAACGCTGGT GAAAGTAAAA    8160
GATGCTGAAG ATCAGTTGGG TGCACGAGTG GGTTACATCG AACTGGATCT CAACAGCGGT    8220
AAGATCCTTG AGAGTTTTCG CCCCGAAGAA CGTTTTCCAA TGATGAGCAC TTTTAAAGTT    8280
CTGCTATGTG GCGCGGTATT ATCCCGTGTT GACGCCGGGC AAGAGCAACT CGGTCGCCGC    8340
ATACACTATT CTCAGAATGA CTTGGTTGAG TACTCACCAG TCACAGAAAA GCATCTTACG    8400
GATGGCATGA CAGTAAGAGA ATTATGCAGT GCTGCCATAA CCATGAGTGA TAACACTGCG    8460
GCCAACTTAC TTCTGACAAC GATCGGAGGA CCGAAGGAGC TAACCGCTTT TTTGCACAAC    8520
ATGGGGGATC ATGTAACTCG CCTTGATCGT TGGGAACCGG AGCTGAATGA AGCCATACCA    8580
AACGACGAGC GTGACACCAC GATGCCTCAG CAATGGCAAC AACGTTGCGC AAACTATTAA    8640
CTGGCGAACT ACTTACTCTA GCTTCCCGGC AACAATTAAT AGACTGGATG GAGGCGGATA    8700
AAGTTGCAGG ACCACTTCTG CGCTCGGCCC TTCCGGCTGG CTGGTTTATT GCTGATAAAT    8760
CTGGAGCCGG TGAGCGTGGG TCTCGCGGTA TCATTGCAGC ACTGGGGCCA GATGGTAAGC    8820
CCTCCCGTAT CGTAGTTATC TACACGACGG GGAGTCAGGC AACTATGGAT GAACGAAATA    8880
GACAGATCGC TGAGATAGGT GCCTCACTGA TTAAGCATTG GTAACTGTCA GACCAAGTTT    8940
ACTCATATAT ACTTTAGATT GATTTAAAAC TTCATTTTTA ATTTAAAAGG ATCTAGGTGA    9000
AGATCCTTTT TGATAATCTC ATGACCAAAA TCCCTTAACG TGAGTTTTCG TTCCACTGAG    9060
CGTCAGACCC CGTAGAAAAG ATCAAAGGAT CTTCTTGAGA TCCTTTTTTT CTGCGCGTAA    9120
TCTGCTGCTT GCAAACAAAA AAACCACCGC TACCAGCGGT GGTTTGTTTG CCGGATCAAG    9180
AGCTACCAAC TCTTTTTCCG AAGGTAACTG GCTTCAGCAG AGCGCAGATA CCAAATACTG    9240
TCCTTCTAGT GTAGCCGTAG TTAGGCCACC ACTTCAAGAA CTCTGTAGCA CCGCCTACAT    9300
ACCTCGCTCT GCTAATCCTG TTACCAGTGG CTGCTGCCAG TGGCGATAAG TCGTGTCTTA    9360
CCGGGTTGGA CTCAAGACGA TAGTTACCGG ATAAGGCGCA GCGGTCGGGC TGAACGGGGG    9420
GTTCGTGCAC ACAGCCCAGC TTGGAGCGAA CGACCTACAC CGAACTGAGA TACCTACAGC    9480
GTGAGCATTG AGAAAGCGCC ACGCTTCCCG AAGGGAGAAA GGCGGACAGG TATCCGGTAA    9540
GCGGCAGGGT CGGAACAGGA GAGCGCACGA GGGAGCTTCC AGGGGGAAAC GCCTGGTATC    9600
TTTATAGTCC TGTCGGGTTT CGCCACCTCT GACTTGAGCG TCGATTTTTG TGATGCTCGT    9660
CAGGGGGGCG GAGCCTATGG AAAAACGCCA GCAACGCGGC CTTTTTACGG TTCCTGGCCT    9720
```

```
TTTGCTGGCC TTTTGCTCAC ATGTTCTTTC CTGCGTTATC CCCTGATTCT GTGGATAACC    9780
GTATTACCGC CTTTGAGTGA GCTGATACCG CTCGCCGCAG CCGAACGACC GAGCGCAGCG    9840
AGTCAGTGAG CGAGGAAGCG GAAGAGCGCC CAATACGCAA ACCGCCTCTC CCCGCGCGTT    9900
GGCCGATTCA TTAATG                                                    9916
```

( 2 ) INFORMATION FOR SEQ ID NO:18:

( i ) SEQUENCE CHARACTERISTICS:
        ( A ) LENGTH: 9890 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: pTZgpt-sart ( x i ) SEQUENCE DESCRIPTION: SEQ ID NO:18:

```
CAGCTGGCGA AAGGGGGATG TGCTGCAAGG CGATTAAGTT GGGTAACGCC AGGGTTTTCC     60
CAGTCACGAC GTTGTAAAAC GACGGCCCTG AATATGAAGG AGCAAAAGGT TGTAACATTT    120
TATTACCGTG TGGGATATAA AAGTCCTTGA TCCATTGATC TGGAAACGGG CATCTCCATT    180
TAAGACTAGA CGCCACGGGG TTTAAAATAC TAATCATGAC ATTTTGTAGA GCGTAATTAC    240
TTAGTAAATC CGCCGTACTA GGTTCATTTC CTCCTCGTTT GGATCTCACA TCAGAAATTA    300
AAATAATCTT AGAAGGATGC AGTTGTTTTT TGATGGATCG TAGATATTCC TCATCAACGA    360
ACCGAGTCAC TAGAGTCACA TCACGCAATC CATTTAAAAT AGGATCATGA TGGCGGCCGT    420
CAATTAGCAT CCATTTGATG ATCACTCCTA AATTATAGAA ATGATCTCTC AAATAACGTA    480
TATGTGTACC GGGAGCAGAT CCTATATACA CTACGGTGGC ACCATCTAAT ATACCGTGTC    540
GCTGTAACTT ACTAAGAAAA AATAATTCTC CTAGTAATAG TTTAACTGT  CCTTGATACG    600
GCAGTTTTTT TGCGACCTCA TTTGCACTTT CTGGTTCGTA ATCTAACTCA TTATCAATTT    660
CCTCAAAATA CATAAACGGT TTATCTAACG ACACAACATC CATTTTAAG  TATTATATTA    720
AAATTTAATC AATGTTTATT TTTAGTTTTT TAGATAAAAA ATATAATATT ATGAGTCGAT    780
GTAACACTTT CTACACACCG ATTGATACAT ATCATTACCT CCTATTATTT CTATCTCGGT    840
TTCCTCACCC AATCGTTTAG AAAAGGAAGC CTCCTTAAAG CATTTCATAC ACACAGCAGT    900
TAGTTTTACC ACCATTTCAG ATAATGGAAT AAGATTCAAA ATATTATTAA ACGGTTTACG    960
TTGAAATGTC CCATCGAGTG CGGCTACTAT AACTATTTTT CCTTCGTTTG CCATACGCTC   1020
ACAGAATTAA TTCCGAGCTT GGCGGTTCCA GGATCCGTCG ACAGGCCTAT CGATGAAGGA   1080
CAGTTCTTTC CAGACATTGT TGGATTAAAT AGTACATAAT GGATTCCTT  ACGCGAAATA   1140
CGGGCAGACA TGGCCTGCCC GGTTATTATT ATTTTGACA  CCAGACCAAC TGGTAATGGT   1200
AGCGACCGGC GCTCAGCTGT AATTCCGCCG ATACTGACGG GCTCCAGGAG TCGTCGCCAC   1260
CAATCCCCAT ATGGAAACCG TCGATATTCA GCCATGTGCC TTCTTCCGCG TGCAGCAGAT   1320
GGCGATGGCT GGTTTCCATC AGTTGCTGTT GACTGTAGCG GCTGATGTTG AACTGGAAGT   1380
CGCCGCGCCA CTGGTGTGGG CCATAATTCA ATTCGCGCGT CCCGCAGCGC AGACCGTTTT   1440
CGCTCGGGAA GACGTACGGG GTATACATGT CTGACAATGG CAGATCCCAG CGGTCAAAAC   1500
AGGCGGCAGT AAGGCGGTCG GGATAGTTTT CTTGCGGCCC TAATCCGAGC CAGTTTACCC   1560
GCTCTGCTAC CTGCGCCAGC TGGCAGTTCA GGCCAATCCG CGCCGGATGC GGTGTATCGC   1620
TCGCCACTTC AACATCAACG GTAATCGCCA TTTGACCACT ACCATCAATC CGTAGGTTT    1680
TCCGGCTGAT AAATAAGGTT TTCCCCTGAT GCTGCCACGC GTGAGCGGTC GTAATCAGCA   1740
```

```
CCGCATCAGC AAGTGTATCT GCCGTGCACT GCAACAACGC TGCTTCGGCC TGGTAATGGC    1800
CCGCCGCCTT CCAGCGTTCG ACCCAGGCGT TAGGGTCAAT GCGGGTCGCT TCACTTACGC    1860
CAATGTCGTT ATCCAGCGGT GCACGGGTGA ACTGATCGCG CAGCGGCGTC AGCAGTTGTT    1920
TTTTATCGCC AATCCACATC TGTGAAAGAA AGCCTGACTG GCGGTTAAAT TGCCAACGCT    1980
TATTACCCAG CTCGATGCAA AAATCCATTT CGCTGGTGGT CAGATGCGGG ATGGCGTGGG    2040
ACGCGGCGGG GAGCGTCACA CTGAGGTTTT CCGCCAGACG CCACTGCTGC CAGGCGCTGA    2100
TGTGCCCGGC TTCTGACCAT GCGGTCGCGT TCGGTTGCAC TACGCGTACT GTGAGCCAGA    2160
GTTGCCCGGC GCTCTCCGGC TGCGGTAGTT CAGGCAGTTC AATCAACTGT TTACCTTGTG    2220
GAGCGACATC CAGAGGCACT TCACCGCTTG CCAGCGGCTT ACCATCCAGC GCCACCATCC    2280
AGTGCAGGAG CTCGTTATCG CTATGACGGA ACAGGTATTC GCTGGTCACT TCGATGGTTT    2340
GCCCGGATAA ACGGAACTGG AAAAACTGCT GCTGGTGTTT TGCTTCCGTC AGCGCTGGAT    2400
GCGGCGTGCG GTCGGCAAAG ACCAGACCGT TCATACAGAA CTGGCGATCG TTCGGCGTAT    2460
CGCCAAAATC ACCGCCGTAA GCCGACCACG GGTTGCCGTT TTCATCATAT TTAATCAGCG    2520
ACTGATCCAC CCAGTCCCAG ACGAAGCCGC CCTGTAAACG GGGATACTGA CGAAACGCCT    2580
GCCAGTATTT AGCGAAACCG CCAAGACTGT TACCCATCGC GTGGGCGTAT TCGCAAAGGA    2640
TCAGCGGGCG CGTCTCTCCA GGTAGCGAAA GCCATTTTTT GATGGACCAT TTCGGCACAG    2700
CCGGGAAGGG CTGGTCTTCA TCCACGCGCG CGTACATCGG GCAAATAATA TCGGTGGCCG    2760
TGGTGTCGGC TCCGCCGCCT TCATACTGCA CCGGGCGGGA AGGATCGACA GATTTGATCC    2820
AGCGATACAG CGCGTCGTGA TTAGCGCCGT GGCCTGATTC ATTCCCCAGC GACCAGATGA    2880
TCACACTCGG GTGATTACGA TCGCGCTGCA CCATTCGCGT TACGCGTTCG CTCATCGCCG    2940
GTAGCCAGCG CGGATCATCG GTCAGACGAT TCATTGGCAC CATGCCGTGG GTTTCAATAT    3000
TGGCTTCATC CACCACATAC AGGCCGTAGC GGTCGCACAG CGTGTACCAC AGCGGATGGT    3060
TCGGATAATG CGAACAGCGC ACGGCGTTAA AGTTGTTCTG CTTCATCAGC AGGATATCCT    3120
GCACCATCGT CTGCTCATCC ATGACCTGAC CATGCAGAGG ATGATGCTCG TGACGGTTAA    3180
CGCCTCGAAT CAGCAACGGC TTGCCGTTCA GCAGCAGCAG ACCATTTTCA ATCCGCACCT    3240
CGCGGAAACC GACATCGCAG GCTTCTGCTT CAATCAGCGT GCCGTCGGCG GTGTGCAGTT    3300
CAACCACCGC ACGATAGAGA TTCGGGATTT CGGCGCTCCA CAGTTTCGGG TTTTCGACGT    3360
TCAGACGTAG TGTGACGCGA TCGGCATAAC CACCACGCTC ATCGATAATT TCACCGCCGA    3420
AAGGCGCGGT GCCGCTGGCG ACCTGCGTTT CACCCTGCCA TAAAGAAACT GTTACCCGTA    3480
GGTAGTCACG CAACTCGCCG CACATCTGAA CTTCAGCCTC CAGTACAGCG CGGCTGAAAT    3540
CATCATTAAA GCGAGTGGCA ACATGGAAAT CGCTGATTTG TGTAGTCGGT TTATGCAGCA    3600
ACGAGACGTC ACGGAAAATG CCGCTCATCC GCCACATATC CTGATCTTCC AGATAACTGC    3660
CGTCACTCCA ACGCAGCACC ATCACCGCGA GGCGGTTTTC TCCGGCGCGT AAAAATGCGC    3720
TCAGGTCAAA TTCAGACGGC AAACGACTGT CCTGGCCGTA ACCGACCCAG CGCCCGTTGC    3780
ACCACAGATG AAACGCCGAG TTAACGCCAT CAAAAATAAT TCGCGTCTGG CCTTCCTGTA    3840
GCCAGCTTTC ATCAACATTA AATGTGAGCG AGTAACAACC CGTCGGATTC TCCGTGGGAA    3900
CAAACGGCGG ATTGACCGTA ATGGGATAGG TTACGTTGGT GTAGATGGGC GCATCGTAAC    3960
CGTGCATCTG CCAGTTTGAG GGGACGACGA CAGTATCGGC CTCAGGAAGA TCGCACTCCA    4020
GCCAGCTTTC CGGCACCGCT TCTGGTGCCG GAAACCAGGC AAAGCGCCAT TCGCCATTCA    4080
GGCTGCGCAA CTGTTGGGAA GGGCGATCGG TGCGGGCCTC TTCGCTATTA CGCCAGCTGG    4140
```

```
CGAAAGGGGG ATGTGCTGCA AGGCGATTAA GTTGGGTAAC GCCAGGGTTT TCCCAGTCAC   4200
GACGTTGTAA AACGACGGGA TCGCGGCCGC GATCCCCGAT TCGTAGAGCC TCGTTGCGTT   4260
TGTTAGCACG AACCATATGT AAGGAATTCC TGCAGCCTAT TTATATGCCA AAAAAAAAA   4320
AAAAAAAAG CTTCCCAACC AACTTAAGGG TACCGCCTCG ACATCTATAT ACTATATAGT   4380
AATACCAATA CTCAAGACTA CGAAACTGAT ACAATCTCTT ATCATGTGGG TAATGTTCTC   4440
GATGTCGAAT AGCCATATGC CGGTAGTTGC GATATACATA AACTGATCAC TAATTCCAAA   4500
CCCACCCGCT TTTTATAGTA AGTTTTTCAC CCATAAATAA TAAATACAAT AATTAATTTC   4560
TCGTAAAAGT AGAAAATATA TTCTAATTTA TTGCACGGTA AGGAAGTAGA ATCATAAAGA   4620
ACAGTGACGG ATGATCCCCA AGCTTGGACA CAAGACAGGC TTGCGAGATA TGTTTGAGAA   4680
TACCACTTTA TCCCGCGTCA GGGAGAGGCA GTGCGTAAAA AGACGCGGAC TCATGTGAAA   4740
TACTGGTTTT TAGTGCGCCA GATCTCTATA ATCTCGCGCA ACCTATTTC CCCTCGAACA   4800
CTTTTTAAGC CGTAGATAAA CAGGCTGGGA CACTTCACAT GAGCGAAAAA TACATCGTCA   4860
CCTGGGACAT GTTGCAGATC CATGCACGTA AACTCGCAAG CCGACTGATG CCTTCTGAAC   4920
AATGGAAAGG CATTATTGCC GTAAGCCGTG GCGGTCTGGT ACCGGGTGCG TTACTGGCGC   4980
GTGAACTGGG TATTCGTCAT GTCGATACCG TTTGTATTTC CAGCTACGAT CACGACAACC   5040
AGCGCGAGCT TAAAGTGCTG AAACGCGCAG AAGGCGATGG CGAAGGCTTC ATCGTTATTG   5100
ATGACCTGGT GGATACCGGT GGTACTGCGG TTGCGATTCG TGAAATGTAT CCAAAAGCGC   5160
ACTTTGTCAC CATCTTCGCA AAACCGGCTG GTCGTCCGCT GGTTGATGAC TATGTTGTTG   5220
ATATCCCGCA AGATACCTGG ATTGAACAGC CGTGGGATAT GGGCGTCGTA TTCGTCCCGC   5280
CAATCTCCGG TCGCTAATCT TTTCAACGCC TGGCACTGCC GGGCGTTGTT CTTTTTAACT   5340
TCAGGCGGGT TACAATAGTT TCCAGTAAGT ATTCTGGAGG CTGCATCCAT GACACAGGCA   5400
AACCTGAGCG AAACCCTGTT CAAACCCCGC TTTAAACATC CTGAAACCTC GACGCTAGTC   5460
CGCCGCTTTA ATCACGGCGC ACAACCGCCT GTGCAGTCGG CCCTTGATGG TAAAACCATC   5520
CCTCACTGGT ATCGCATGAT TAACCGTCTG ATGTGGATCT GGCGCGGCAT TGACCCACGC   5580
GAAATCCTCG ACGTCCAGGC ACGTATTGTG ATGAGCGATG CCGAACGTAC CGACGATGAT   5640
TTATACGATA CGGTGATTGG CTACCGTGGC GGCAACTGGA TTTATGAGTG GGCCCCGGAT   5700
CTTTGTGAAG GAACCTTACT TCTGTGGTGT GACATAATTG GACAAACTAC CTACAGAGAT   5760
TTAAAGCTCT AAGGTAAATA TAAAATTTTT AAGTGTATAA TGTGTTAAAC TACTGATTCT   5820
AATTGTTTGT GTATTTAGA TTCCAACCTA TGGAACTGAT GAATGGGAGC AGTGGTGGAA   5880
TGCCTTTAAT GAGGAAAACC TGTTTTGCTC AGAAGAAATG CCATCTAGTG ATGATGAGGC   5940
TACTGCTGAC TCTCAACATT CTACTCCTCC AAAAAAGAAG AGAAAGGTAG AAGACCCCAA   6000
GGACTTTCCT TCAGAATTGC TAAGTTTTTT GAGTCATGCT GTGTTTAGTA ATAGAACTCT   6060
TGCTTGCTTT GCTATTTACA CCACAAAGGA AAAAGCTGCA CTGCTATACA AGAAAATTAT   6120
GGAAAAATAT TCTGTAACCT TTATAAGTAG GCATAACAGT TATAATCATA ACATACTGTT   6180
TTTTCTTACT CCACACAGGC ATAGAGTGTC TGCTATTAAT AACTATGCTC AAAAATTGTG   6240
TACCTTTAGC TTTTTAATTT GTAAAGGGGT TAATAAGGAA TATTTGATGT ATAGTGCCTT   6300
GACTAGAGAT CATAATCAGC CATACCACAT TTGTAGAGGT TTTACTTGCT TTAAAAAACC   6360
TCCCACACCT CCCCCTGAAC CTGAAACATA AAATGAATGC AATTGTTGTT GTTAAGCTTG   6420
GGGGAATTAA TTCAACAATG TCTGGAAAGA ACTGTCCTTC ATCGATACCT ATCACGGAGA   6480
AATCTGTAAT TGATTCCAAG ACATCACATA GTTAGTTGC TTCCAATGCT TCAAAATTAT   6540
```

```
TCTTATCATG CGTCCATAGT CCCGTTCCGT ATCTATTATC GTTAGAATAT TTTATAGTCA    6600
CGCATTTATA TTGAGCTATT TGATAACGTC TAACTCGTCT AATTAATTCT GTACTTTTAC    6660
CTGAAAACAT GGGGCCGATT ATCAACTGAA TATGTCCGCC GTTCATGATG ACAATAAAGA    6720
ATTAATTATT GTTCACTTTA TTCGACTTTA ATATATCCAT CACGTTAGAA AATGCGATAT    6780
TGCGACGAGG ATCTATGTAT CTAACAGGAT CTATTGCGGT GGTAGCTAGA GAGGATTCTT    6840
TTTTGAATCG CATCAAACTA ATCACAAAGT CGAACAAATA TCCTTTATTA AGTTTGACCC    6900
TTCCATCTGT AACAATAGGG ACCTTGTTAA ACAGTTTTT AAAATCTTGA AAGTCTGTGA    6960
ATTTGTCAA TTGTCTGTAT TCCTCTGAAA GAGATTCATA ACAATGACCC ACGGCTTCTA    7020
ATTTATTTTT TGATTGGATC AATAATAATA ACAGAAAGTC TAGATATTGA GTGATTTGCA    7080
ATATATCAGA TAATGAAGAT TCATCATCTT GACTAGCCAA ATACTTAAAA AATGAATCAT    7140
CATCTGCGAA GAACATCGTT AAGAGATACT GGTTGTGATC CATTTATTGA TCGCAAAAGC    7200
TTGGCGTAAT CATGGTCATA GCTGTTTCCT GTGTGAAATT GTTATCCGCT CACAATTCCA    7260
CACAACATAC GAGCCGGAAG CATAAAGTGT AAAGCCTGGG GTGCCTAATG AGTGAGCTAA    7320
CTCACATTAA TTGCGTTGCG CTCACTGCCC GCTTTCCAGT CGGGAAACCT GTCGTGCCAG    7380
CTGGCGTAAT AGCGAAGAGG CCCGCACCGA TCGCCCTTCC CAACAGTTGC GCAGCCTGAA    7440
TGGCGAATGG GAAATTGTAA ACGTTAATAT TTTGTTAAAA TTCGCGTTAA ATTTTTGTTA    7500
AATCAGCTCA TTTTTTAACC AATAGGCCGA AATCGGCAAA ATCCCTTATA AATCAAAAGA    7560
ATAGACCGAG ATAGGGTTGA GTGTTGTTCC AGTTTGGAAC AAGAGTCCAC TATTAAAGAA    7620
CGTGGACTCC AACGTCAAAG GGCGAAAAAC CGTCTATCAG GGCGATGGCC CACTACGTGA    7680
ACCATCACCC TAATCAAGTT TTTTGGGGTC GAGGTGCCGT AAAGCACTAA ATCGGAACCC    7740
TAAAGGGAGC CCCCGATTTA GAGCTTGACG GGGAAAGCCG GCGAACGTGG CGAGAAAGGA    7800
AGGGAAGAAA GCGAAAGGAG CGGGCGCTAG GGCGCTGGCA AGTGTAGCGG TCACGCTGCG    7860
CGTAACCACC ACACCCGCCG CGCTTAATGC GCCGCTACAG GGCGCGTCAG GTGGCACTTT    7920
TCGGGGAAAT GTGCGCGGAA CCCCTATTTG TTTATTTTTC TAAATACATT CAAATATGTA    7980
TCCGCTCATG AGACAATAAC CCTGATAAAT GCTTCAATAA TATTGAAAAA GGAAGAGTAT    8040
GAGTATTCAA CATTTCCGTG TCGCCCTTAT TCCCTTTTTT GCGGCATTTT GCCTTCCTGT    8100
TTTTGCTCAC CCAGAAACGC TGGTGAAAGT AAAAGATGCT GAAGATCAGT TGGGTGCACG    8160
AGTGGGTTAC ATCGAACTGG ATCTCAACAG CGGTAAGATC CTTGAGAGTT TTCGCCCCGA    8220
AGAACGTTTT CCAATGATGA GCACTTTTAA AGTTCTGCTA TGTGGCGCGG TATTATCCCG    8280
TGTTGACGCC GGGCAAGAGC AACTCGGTCG CCGCATACAC TATTCTCAGA ATGACTTGGT    8340
TGAGTACTCA CCAGTCACAG AAAAGCATCT TACGGATGGC ATGACAGTAA GAGAATTATG    8400
CAGTGCTGCC ATAACCATGA GTGATAACAC TGCGGCCAAC TTACTTCTGA CAACGATCGG    8460
AGGACCGAAG GAGCTAACCG CTTTTTTGCA CAACATGGGG GATCATGTAA CTCGCCTTGA    8520
TCGTTGGGAA CCGGAGCTGA ATGAAGCCAT ACCAAACGAC GAGCGTGACA CCACGATGCC    8580
TCAGCAATGG CAACAACGTT GCGCAAACTA TTAACTGGCG AACTACTTAC TCTAGCTTCC    8640
CGGCAACAAT TAATAGACTG GATGGAGGCG GATAAAGTTG CAGGACCACT TCTGCGCTCG    8700
GCCCTTCCGG CTGGCTGGTT TATTGCTGAT AAATCTGGAG CCGGTGAGCG TGGGTCTCGC    8760
GGTATCATTG CAGCACTGGG GCCAGATGGT AAGCCCTCCC GTATCGTAGT TATCTACACG    8820
ACGGGGAGTC AGGCAACTAT GGATGAACGA AATAGACAGA TCGCTGAGAT AGGTGCCTCA    8880
CTGATTAAGC ATTGGTAACT GTCAGACCAA GTTTACTCAT ATATACTTTA GATTGATTTA    8940
```

-continued

```
AAACTTCATT TTTAATTTAA AAGGATCTAG GTGAAGATCC TTTTTGATAA TCTCATGACC      9000
AAAATCCCTT AACGTGAGTT TTCGTTCCAC TGAGCGTCAG ACCCCGTAGA AAAGATCAAA      9060
GGATCTTCTT GAGATCCTTT TTTTCTGCGC GTAATCTGCT GCTTGCAAAC AAAAAAACCA      9120
CCGCTACCAG CGGTGGTTTG TTTGCCGGAT CAAGAGCTAC CAACTCTTTT TCCGAAGGTA      9180
ACTGGCTTCA GCAGAGCGCA GATACCAAAT ACTGTCCTTC TAGTGTAGCC GTAGTTAGGC      9240
CACCACTTCA AGAACTCTGT AGCACCGCCT ACATACCTCG CTCTGCTAAT CCTGTTACCA      9300
GTGGCTGCTG CCAGTGGCGA TAAGTCGTGT CTTACCGGGT TGGACTCAAG ACGATAGTTA      9360
CCGGATAAGG CGCAGCGGTC GGGCTGAACG GGGGGTTCGT GCACACAGCC CAGCTTGGAG      9420
CGAACGACCT ACACCGAACT GAGATACCTA CAGCGTGAGC ATTGAGAAAG CGCCACGCTT      9480
CCCGAAGGGA GAAAGGCGGA CAGGTATCCG GTAAGCGGCA GGGTCGGAAC AGGAGAGCGC      9540
ACGAGGGAGC TTCCAGGGGG AAACGCCTGG TATCTTTATA GTCCTGTCGG GTTTCGCCAC      9600
CTCTGACTTG AGCGTCGATT TTTGTGATGC TCGTCAGGGG GGCGGAGCCT ATGGAAAAAC      9660
GCCAGCAACG CGGCCTTTTT ACGGTTCCTG GCCTTTTGCT GGCCTTTTGC TCACATGTTC      9720
TTTCCTGCGT TATCCCCTGA TTCTGTGGAT AACCGTATTA CCGCCTTTGA GTGAGCTGAT      9780
ACCGCTCGCC GCAGCCGAAC GACCGAGCGC AGCGAGTCAG TGAGCGAGGA AGCGGAAGAG      9840
CGCCCAATAC GCAAACCGCC TCTCCCCGCG CGTTGGCCGA TTCATTAATG                9890
```

( 2 ) INFORMATION FOR SEQ ID NO:19:

( i ) SEQUENCE CHARACTERISTICS:
        ( A ) LENGTH: 991 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: FPV P2-promoter and P2- gene ( x i ) SEQUENCE DESCRIPTION: SEQ ID NO:19:

```
ATGCATTTGT TAGAGCTTGG TATAGCGGAC AACTAAGTAA TTGTAAAGAA GAAAACGAAA       60
CTATCAAAAC CGTTTATGAA ATGATAGAAA AAGAATATA  AATAATCCTG TATTTTAGTT      120
TAAGTAACAG TAAAATAATG AGTAGAAAAT ACTATTTTT  ATAGCCTATA AATCATGGAA      180
AAGAAACTGA TTCAAGAGTA TGAAAAACTC AAAGGCCAAG AGGCCAAAGA TGTCTTTACC      240
AGGCAGCTAC TTATCTGCCA CGAAGATATG CGTGGCAGAA TGGACAACAT GACTAAGTTA      300
ATTAGTGACG TATTTAGAAC ATTGGCTGGA GGTAGTAGCA AAGCACCCAC GAGAAGTCG       360
GATATTGATA CGATGCCTCC TTCTAATGAT GCTGGTTCTG AGCCACAGCC CAACCTAGC       420
GAAAGTAAAC CACCCGAGCA ACCCTCTCCC GAACCCGAAA AAGACTCTTC TAGTAAACCA      480
TCAGATCAAC CTACTCCCGA ACCCGAAAAA GGCTCTTCTA GCAAACCCCG TACAGATATC      540
TTAGTGGTT  TACGTAATAA AGAAATTAAT TTTGAAAGA  ACTGTTGGAG CATTTATCCA      600
ATATTATTAT TTAATTTAAA TCAATTGAGT TAATGTAATA ACTTTTTACA TATATTTTGC      660
TCTAGTCCGA AATAGGAAAT TAGCAAAAAA TAATGATTAT TATATATTAA TGTTTTAACT      720
TAATAATTAA TTTATAAAAT ATTTATTGTC ACATCCGTTC TTTATCACGT TATCGTACGT      780
GGTAGGTAGT TATGGATGTT TTTATCATTA CTTTTGTAA  TGATAGTAAA TAGTATCACA      840
GCAGATTTAA TTACTTCTGT GATATACAAT ACATGTATTA AGGATTACCC GCACCCAAAA      900
ATAATATCGT GATCTGTAAT ATATAAAAAT AAATACCATA CTATATGTTT ATATCACCAA      960
TCATGGTAAA AATAGTGTTT GTGATGAATT C                                    991
```

( 2 ) INFORMATION FOR SEQ ID NO:20:

( i ) SEQUENCE CHARACTERISTICS:
    ( A ) LENGTH: 112 base pairs
    ( B ) TYPE: nucleic acid
    ( C ) STRANDEDNESS: single
    ( D ) TOPOLOGY: linear ( v i i ) IMMEDIATE SOURCE:
    ( B ) CLONE: FPV enlarged intergenic seqeunce ( x i ) SEQUENCE DESCRIPTION: SEQ ID NO:20:

```
AGTAATTAAG GTTTTTATCG ATCCCGGGTA CCGGTTTAGT GTAATAAATT TAATAAAATA     60
TTGACAAAAT AGTTAAATGA ATATATGAAA GTACATTATA CACGGAATGG AG            112
```

( 2 ) INFORMATION FOR SEQ ID NO:21:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( v i i ) IMMEDIATE SOURCE:
    ( B ) CLONE: m0

( x i ) SEQUENCE DESCRIPTION: SEQ ID NO:21:

```
TAAATGAATT CC                                                         12
```

( 2 ) INFORMATION FOR SEQ ID NO:22:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( v i i ) IMMEDIATE SOURCE:
    ( B ) CLONE: m1

( x i ) SEQUENCE DESCRIPTION: SEQ ID NO:22:

```
TAAACATGAA TTCC                                                       14
```

( 2 ) INFORMATION FOR SEQ ID NO:23:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( v i i ) IMMEDIATE SOURCE:
    ( B ) CLONE: p11 late promoter consensus region ( x i ) SEQUENCE DESCRIPTION: SEQ ID NO:23:

```
TAAATGAATT C                                                          11
```

( 2 ) INFORMATION FOR SEQ ID NO:24:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( v i i ) IMMEDIATE SOURCE:
    ( B ) CLONE: mutated p11 late promoter consensus region ( x i ) SEQUENCE DESCRIPTION: SEQ ID NO:24:

TAAATAAAGA ATTC 14

( 2 ) INFORMATION FOR SEQ ID NO:25:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: oligonucleotide probe ( x i ) SEQUENCE DESCRIPTION: SEQ ID NO:25:

CAGTTATTGT GGCCGCGCTT AACGGTGA 28

( 2 ) INFORMATION FOR SEQ ID NO:26:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: mutagenic primer ( x i ) SEQUENCE DESCRIPTION: SEQ ID NO:26:

TTACACTAAA CCGGTACCCG GGATCGATAA AAACCTTAAT TACTA 45

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: primer ( x i ) SEQUENCE DESCRIPTION: SEQ ID NO:27:

CCATTCCGTG TATAATGTAC 20

( 2 ) INFORMATION FOR SEQ ID NO:28:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: oligonucleotide I ( x i ) SEQUENCE DESCRIPTION: SEQ ID NO:28:

GCCTATTTAT AGCATAGAAA AAAACAAAAT GAAATTTTAC TATATTTTA TATACATATA 60

TTCTAACCC 69

( 2 ) INFORMATION FOR SEQ ID NO:29:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (genomic)

(v i i) IMMEDIATE SOURCE:
        (B) CLONE: oligonucleotide II (x i) SEQUENCE DESCRIPTION: SEQ ID NO:29:

GGGTTAGAAT ATATGTATGT AAAAATATAG TAGAATTTCA TTTTGTTTTT TTCTATGCTA    60

TAAATAGGCT GCA    73

(2) INFORMATION FOR SEQ ID NO:30:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (v i i) IMMEDIATE SOURCE:
        (B) CLONE: mutagenic primer (x i) SEQUENCE DESCRIPTION: SEQ ID NO:30:

ACCATATGTA AGGAATTCCT TAGATAA    27

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (v i i) IMMEDIATE SOURCE:
        (B) CLONE: synthetic linker sequence (x i) SEQUENCE DESCRIPTION: SEQ ID NO:31:

CGATTGGCCA GGATCCGTCG ACAGGCCTAT    30

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i v) ANTI-SENSE: YES (v i i) IMMEDIATE SOURCE:
        (B) CLONE: complementary strand of synthetic linker
              sequence (x i) SEQUENCE DESCRIPTION: SEQ ID NO:32:

CGATAGGCCT GTCGACGGAT CCTGGCCAAT    30

(2) INFORMATION FOR SEQ ID NO:33:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (v i i) IMMEDIATE SOURCE:
        (B) CLONE: P-MCS2

(x i) SEQUENCE DESCRIPTION: SEQ ID NO:33:

AATTGAGAAA AATCAGTCAG TTAGCGGCCG CGTCGACCCG GGATCCAGGC CTCATATGCA    60

GCTGCT    66

(2) INFORMATION FOR SEQ ID NO:34:

( i ) SEQUENCE CHARACTERISTICS:
    ( A ) LENGTH: 172 base pairs
    ( B ) TYPE: nucleic acid
    ( C ) STRANDEDNESS: single
    ( D ) TOPOLOGY: linear ( v i i ) IMMEDIATE SOURCE:
    ( B ) CLONE: m0.2

( x i ) SEQUENCE DESCRIPTION: SEQ ID NO:34:

```
GATCCGAATT CATTTATAGG CTATAAAAAA TAGTATTTTC TACTCATTAT TTTACTGTTA      60
CTTAAACTAA AATACAGGAT TATTTATATT CTTTTTCTA  TCATTCATA  AACGGTTTTG     120
ATAGTTTCGT TTTCTTCTTT ACAATTACTT AGTTGTCCGC TATACCAAGC CG             172
```

( 2 ) INFORMATION FOR SEQ ID NO:35:

( i ) SEQUENCE CHARACTERISTICS:
        ( A ) LENGTH: 175 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: m1.2

( x i ) SEQUENCE DESCRIPTION: SEQ ID NO:35:

```
GATCCGAATT CATGATTTAT AGGCTATAAA AAATAGTATT TTCTACTCAT TATTTTACTG      60
TTACTTAAAC TAAAATACAG GATTATTTAT ATTCTTTTT  CTATCATTTC ATAAACGGTT     120
TTGATAGTTT CGTTTCTTC  TTTACAATTA CTTAGTTGTC CGCTATACCA AGCCG          175
```

( 2 ) INFORMATION FOR SEQ ID NO:36:

( i ) SEQUENCE CHARACTERISTICS:
        ( A ) LENGTH: 178 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: m2.2

( x i ) SEQUENCE DESCRIPTION: SEQ ID NO:36:

```
GATCCGAATT CATGATTTAT AGGCTATAAA ACAAATAGT  ATTTCTACT  CATTATTTA       60
CTGTTACTTA AACTAAAATA CAGGATTATT TATATTCTTT TTCTATCAT  TTCATAAACG     120
GTTTGATAG  TTTCGTTTTC TTCTTTACAA TTACTTAGTT GTCCGCTATA CCAAGCCG       178
```

( 2 ) INFORMATION FOR SEQ ID NO:37:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: oligonucleotide ( x i ) SEQUENCE DESCRIPTION: SEQ ID NO:37:

```
TAGCTATAAA TAAAGAATTC CTGCAG                                           26
```

( 2 ) INFORMATION FOR SEQ ID NO:38:

( i ) SEQUENCE CHARACTERISTICS:
        ( A ) LENGTH: 73 base pairs
        ( B ) TYPE: nucleic acid (C) STRANDEDNESS: single
(D) TOPOLOGY: linear (vii) IMMEDIATE SOURCE:
(B) CLONE: sp11(4)

(xi) SEQUENCE DESCRIPTION: SEQ ID NO:38:

GGGTTAGAAT ATATGTATGT AAAAATATAG TAGAATTTCA TTTTGTTTTT TTCTATGCTA    60

TAAATAGGCT GCA    73

(2) INFORMATION FOR SEQ ID NO:39:

(i) SEQUENCE CHARACTERISTICS:
(A) LENGTH: 72 base pairs
(B) TYPE: nucleic acid
(C) STRANDEDNESS: single
(D) TOPOLOGY: linear (vii) IMMEDIATE SOURCE:
(B) CLONE: s4b(4)

(xi) SEQUENCE DESCRIPTION: SEQ ID NO:39:

GGGGTTACGT CTCTTTAGGT ACTTATTTTG ATACGTTACA AGTAAAAAAC TATCAAATAT    60

AAATAGGCTG CA    72

(2) INFORMATION FOR SEQ ID NO:40:

(i) SEQUENCE CHARACTERISTICS:
(A) LENGTH: 46 base pairs
(B) TYPE: nucleic acid
(C) STRANDEDNESS: single
(D) TOPOLOGY: linear (vii) IMMEDIATE SOURCE:
(B) CLONE: sart(4)

(xi) SEQUENCE DESCRIPTION: SEQ ID NO:40:

GGGAAGCTTT TTTTTTTTT TTTTTTGGC ATATAAATAG GCTGCA    46

(2) INFORMATION FOR SEQ ID NO:41:

(i) SEQUENCE CHARACTERISTICS:
(A) LENGTH: 45 base pairs
(B) TYPE: nucleic acid
(C) STRANDEDNESS: single
(D) TOPOLOGY: linear (vii) IMMEDIATE SOURCE:
(B) CLONE: primer sequence (xi) SEQUENCE DESCRIPTION: SEQ ID NO:41:

TTACACTAAA TCGGTACCCG GGATCGATAA AAACCTTAAT TACTA    45

(2) INFORMATION FOR SEQ ID NO:42:

(i) SEQUENCE CHARACTERISTICS:
(A) LENGTH: 91 base pairs
(B) TYPE: nucleic acid
(C) STRANDEDNESS: single
(D) TOPOLOGY: linear (vii) IMMEDIATE SOURCE:
(B) CLONE: FPV wildtype intergenic seqeunce (xi) SEQUENCE DESCRIPTION: SEQ ID NO:42:

AGTAATTAAG GGGTTTAGTG TAATAAATTT AATAAAATAT TGACAAAATA GTTAAATGAA    60

TATATGAAAG TACATTATAC ACGGAATGGA G    91

( 2 ) INFORMATION FOR SEQ ID NO:43:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: P11wt ( x i ) SEQUENCE DESCRIPTION: SEQ ID NO:43:

```
GAATATATGT ATGTAAAAAT ATAGTAGAAT TTCATTTTGT TTTTTCTAT GCTATAAATG      60
AATTCCTGCA GGTCGACTCT AGAGGATCCC GTC                                 93
```

( 2 ) INFORMATION FOR SEQ ID NO:44:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: P11m ( x i ) SEQUENCE DESCRIPTION: SEQ ID NO:44:

```
ATTTAGAATA TATGTATGTA AAAATATAGT AGAATTTCAT TTTGTTTTT TCTATGCTAT      60
AAATAAAGAA TTCCTGCAGG T                                              81
```

( 2 ) INFORMATION FOR SEQ ID NO:45:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: sP11

( x i ) SEQUENCE DESCRIPTION: SEQ ID NO:45:

```
GGGTTAGAAT ATATGTATGT AAAAATATAG TAGAATTTCA TTTTGTTTTT TTCTATGCTA    60
TAAATAGGCT GCAGGAATTC CTTACATATG                                    90
```

( 2 ) INFORMATION FOR SEQ ID NO:46:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: s4b ( x i ) SEQUENCE DESCRIPTION: SEQ ID NO:46:

```
GGGGTTACGT CTCTTTAGGT ACTTATTTTG ATACGTTACA AGTAAAAAAC TATCAAATAT    60
AAATAGGCTG CAGGAATTCC TTACATATG                                     89
```

( 2 ) INFORMATION FOR SEQ ID NO:47:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( v i i ) IMMEDIATE SOURCE:
    ( B ) CLONE: sart ( x i ) SEQUENCE DESCRIPTION: SEQ ID NO:47:

GGGAAGCTTT TTTTTTTTT TTTTTTGGC ATATAAATAG GCTGCAGGAA TTCCTTACAT    60

ATG    63

( 2 ) INFORMATION FOR SEQ ID NO:48:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: P2 promoter wildtype sequence in plasmid
            pTZgpt- P2a ( x i ) SEQUENCE DESCRIPTION: SEQ ID NO:48:

AATGAGTAGA AAATACTATT TTTATAGCC TATAAATCAT GGAAAAG    47

( 2 ) INFORMATION FOR SEQ ID NO:49:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: P2 promoter wildtype sequence in plasmid
            pTZgpt- P2a ( x i ) SEQUENCE DESCRIPTION: SEQ ID NO:49:

TCCTTACATA TGGTTCGT    18

( 2 ) INFORMATION FOR SEQ ID NO:50:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: P2 promoter mutant m0 in plasmid
            pP2m0gpt- lacZ ( x i ) SEQUENCE DESCRIPTION: SEQ ID NO:50:

AATGAGTAGA AAATACTATT TTTATAGCC TATAAATGAA TTCCGTTCGT    50

( 2 ) INFORMATION FOR SEQ ID NO:51:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: P2 promoter mutant m1 in plasmid
            pP2m1gpt- lacZ ( x i ) SEQUENCE DESCRIPTION: SEQ ID NO:51:

AATGAGTAGA AAATACTATT TTTATAGCC TATAAATCAT GAATTCCGTT CGT    53

( 2 ) INFORMATION FOR SEQ ID NO:52:

( i ) SEQUENCE CHARACTERISTICS:
   ( A ) LENGTH: 56 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:52:

```
AATGAGTAGA AAATACTATT TTGTTTTATA GCCTATAAAT CATGAATTCC GTTCGT         56
```